US008980280B2

(12) United States Patent
Poulet et al.

(10) Patent No.: US 8,980,280 B2
(45) **Date of Patent: *Mar. 17, 2015**

(54) RECOMBINANT FELINE LEUKEMIA VIRUS VACCINE CONTAINING OPTIMIZED FELINE LEUKEMIA VIRUS ENVELOPE GENE

(75) Inventors: Herve Poulet, Sainte Foy-Les (FR); Thierry Heidmann, Paris (FR)

(73) Assignees: Merial, Inc., Duluth, GA (US); Centre National de la Recherche Scientifique (FR); Institut Gustave Roussy (FR); Universite Paris-Sud (FR)

( * ) Notice: Subject to any disclaimer, the term of this patent is extended or adjusted under 35 U.S.C. 154(b) by 0 days.

This patent is subject to a terminal disclaimer.

(21) Appl. No.: 13/365,018

(22) Filed: Feb. 2, 2012

(65) Prior Publication Data

US 2012/0183569 A1 Jul. 19, 2012

Related U.S. Application Data

(63) Continuation-in-part of application No. 11/547,399, filed on Aug. 20, 2007, now Pat. No. 8,178,657.

(60) Provisional application No. 61/509,912, filed on Jul. 20, 2011.

(51) Int. Cl.

| | |
|---|---|
| ***A61K 39/21*** | (2006.01) |
| *C12N 15/00* | (2006.01) |
| *A61K 39/00* | (2006.01) |

(52) U.S. Cl.

CPC ............ *A61K 39/21* (2013.01); *A61K 2039/53* (2013.01); *A61K 2039/552* (2013.01); *C12N 2710/24043* (2013.01); *C12N 2740/13034* (2013.01)

USPC .................. 424/207.1; 424/199.1; 424/232.1; 435/320.1; 536/23.72; 530/350; 530/395

(58) Field of Classification Search

None

See application file for complete search history.

(56) References Cited

PUBLICATIONS

Arjona A. et al., "Seroepidemiological survey of infection by feline leukemia virus and immunodeficiency virus in Madrid and correlation with some clinical aspects", Journal of Clinical Microbiology, 2000, 38, 3448-3449.

Braley J., "FeLV and FIV: survey shows prevalence in the United States and Europe", Feline Practice, 1994, 22, 25-29.

DeNoronha, F., et al., "Influence of antisera to oncornavirus glycoprotein (gp71) on infections of cats with feline leukemia virus", 1978, Virology 85:617-621.

Flynn, J.N., et al., "Longitudinal analysis of feline leukemia virus-specific cytotoxic T lymphocytes: correlation with recovery from infection", 2002, J. Virol, p. 2306-2315.

Hosie M.J. et al., "Prevalence of feline leukaemia virus and antibodies to feline immunodeficiency virus in cats in the United Kingdom", Veterinary Records, 1989, 125, 293-297.

Malik R. et al., "Prevalences of feline leukaemia virus and feline immunodeficiency virus infections in cats in Sydney", Australian Veterinary Journal, 1997, 75, 323-327.

Mathes, L.E. et al., "Abrogation of lymphocyte blastogenesis by a feline leukaemia virus protein", 1978, Nature, vol. 274, p. 687-689.

Nunberg, J.H., et al., "Method to map antigenic determinants recognized by monoclonal antibodies: localization of a determinant of virus neutralization on the feline leukemia virus envelope protein gp70", 1983, PNAS 81:3675-3679.

Poulet H. et al., "Efficacy of a canarypox virus-vectored vaccine against feline leukaemia", Veterinary Record, 2003, 153, 141-145.

Sparkes A.H., "Feline leukaemia virus: a review of immunity and vaccination", Journal of Small Animal Practice, 1997, 38, 187-194.

Tartaglia J. et al.,"protection of cats against feline leukemia virus by vaccination with a canarypox virus recombinant, ALVAC-FL", Journal of Virology, 1993, 67, 2370-2375.

Thomsen D.R., et al., "Expression of feline leukaemia virus gp85 and gag proteins and assembly into virus-like particles using the baculovirus expression vector system", Journal of General Virology, 73, 1819-1824, 1992.

*Primary Examiner* — Bao Li

(74) *Attorney, Agent, or Firm* — Judy Jarecki-Black; Ruoying Chen; Merial, Inc.

(57) ABSTRACT

The present invention provides vectors that contain and express in vivo or in vitro FeLV antigens that elicit an immune response in animal or human against FeLV, compositions comprising said vectors and/or FeLV polypeptides, methods of vaccination against FeLV, and kits for use with such methods and compositions.

12 Claims, 57 Drawing Sheets

Figure 1A

| SEQ ID NO: | type | Description |
|---|---|---|
| 1 | DNA | Full-length ENV mutated (2 mutations) DNA (pPB713) |
| 2 | Protein | Full-length ENV mutated (2 mutations) protein (pPB713) |
| 3 | DNA | Full-length ENV mutated (1 mutation) DNA |
| 4 | Protein | Full-length ENV mutated (1 mutation) protein |
| 5 | DNA | Full-length ENV (no mutation) DNA (in vCP2295) |
| 6 | Protein | Full-length ENV (no mutation) protein |
| 7 | Protein | Full-length FeLV ENV mutant protein from plasmid pHCMV-ENV FeLV |
| 8 | DNA | vCP2295 vector sequence |
| 9 | DNA | plasmid pJY1874.1 |
| 10 | DNA | GAG-PRO codon-optimized DNA |
| 11 | DNA | GAG-PRO wild type DNA |
| 12 | Protein | GAG-PRO protein |
| 13 | DNA | Primer forward 13301JY |
| 14 | DNA | Primer reverse 13302JY |
| 15 | DNA | H6P promoter |
| 16 | DNA | vCP2294 |
| 17 | DNA | 11369JY primer |
| 18 | DNA | 11377JY primer |
| 19 | DNA | 8103JY primer |
| 20 | DNA | 8104JY primer |
| 21 | DNA | 7900CXL primer |
| 22 | DNA | 7934CXL primer |
| 23 | DNA | 7931DC primer |
| 24 | DNA | 7932DC primer |
| 25 | DNA | 7862CXL primer |
| 26 | DNA | 7847CXL primer |
| 27 | Protein | pPB179 |
| 28 | Protein | 1_Glasgow-1 (Genbank accession No. AAA43053) |
| 29 | Protein | 3_Glasgow-1 |
| 30 | Protein | Rickard (NP_047256) |
| 31 | Protein | NP_047256 |
| 32 | Protein | AAA43051 |
| 33 | Protein | FAIDS (Genbank accession No. AAA93093) |
| 34 | Protein | 82K (Genbank accession No. AAA43050) |
| 35 | DNA | Glasgow (Genbank accession No. M12500) |
| 36 | DNA | plasmid pCXL208.2 (pH6C5env) fragment containing FeLV ENV DNA and left and right arms |
| 37 | DNA | Plasmid pPB713 sequence |
| 38 | DNA | pJY1874.1 DNA fragment containing the left and right arms and insert |

Figure 1B

| | | |
|---|---|---|
| 39 | DNA | 3' end FeLV ENV mutated (2 mutations) DNA |
| 40 | Protein | C-terminus FeLV ENV mutated (2 mutations) protein |
| 41 | DNA | 3'end FeLV ENV mutated (1 mutation) DNA |
| 42 | Protein | C-terminus FeLV ENV mutated (1 mutation) protein |
| 43 | Protein | Full-length FeLV ENV mutant protein |

Plasmid Diagram:

Figure 3A

Nucleotide sequence containing Env (with translation) and left and right arms for plasmid pCXL208.2 (pH6C5env) (SEQ ID NO:36)

```
      PstI
   1 GGCTGCAGGTATTCTAAACTAGGAATAGATGAAATTATGTGCAAAGGAGATACCTTTAGATATGGATCTGATTTATT
     CCGACGTCCATAAGATTTGATCCTTATCTACTTTAATACACGTTTCCTCTATGGAAATCTATACCTAGACTAAATAA
  78 TGGTTTTTCATAATCATAATCTAACAACATTTTCACTATACTATACCTTCTTGCACAAGTCGCCATTAGTAGTATAG
     ACCAAAAAGTATTAGTATTAGATTGTTGTAAAAGTGATATGATATGGAAGAACGTGTTCAGCGGTAATCATCATATC
 155 ACTTATACTTTGTAACCATAGTATACTTTAGCGCGTCATCTTCTTCATCTAAAACAGATTTACAACAATAATCATCG
     TGAATATGAAACATTGGTATCATATGAAATCGCGCAGTAGAAGAAGTAGATTTTGTCTAAATGTTGTTATTAGTAGC
 232 TCGTCATCTTCATCTTCATTAAAGTTTTCATATTCAATAACTTTCTTTTCTAAAACATCATCTGAATCAATAAACAT
     AGCAGTAGAAGTAGAAGTAATTTCAAAAGTATAAGTTATTGAAAGAAAAGATTTTGTAGTAGACTTAGTTATTTGTA
 309 AGAACGGTATAGAGCGTTAATCTCCATTGTAAAATATACTAACGCGTTGCTCATGATGTACTTTTTTTCATTATTTA
     TCTTGCCATATCTCGCAATTAGAGGTAACATTTTATATGATTGCGCAACGAGTACTACATGAAAAAAAGTAATAAAT
                                                                    ⇐Left arm     XhoI
 386 GAAATTATGCATTTTAGATCTTTATAAGCGGCCGTGATTAACTAGTCATAAAAACCCGGGATCGATTCTAGACTCGA
     CTTTAATACGTAAAATCTAGAAATATTCGCCGGCACTAATTGATCAGTATTTTTGGGCCCTAGCTAAGATCTGAGCT
             H6p⇒
 463 GCGGGGA TCTCTTTATTCTATACTTAAAAAGTGAAAATAAATACAAAGGTTCTTGAGGGTTGTGTTAAATTGAAAGC
     CGCCCCT AGAGAAATAAGATATGAATTTTTCACTTTTATTTATGTTTCCAAGAACTCCCAACACAATTTAACTTTCG
                                                                   Env⇒
 540 GAGAAATAATCATAAATTATTTCATTATCGCGATATCCGTTAAGTTTGTATCGTA ATGGAAAGTCCAACGCACCCAA
     CTCTTTATTAGTATTTAATAAAGTAATAGCGCTATAGGCAATTCAAACATAGCAT TACCTTTCAGGTTGCGTGGGTT
                                                             > M  E  S  P  T  H  P
 617 AACCCTCTAAAGATAAGACTCTCTCGTGGAACTTAGCGTTTCTGGTGGGGATCTTATTTACAATAGACATAGGAATG
     TTGGGAGATTTCTATTCTGAGAGAGCACCTTGAATCGCAAAGACCACCCCTAGAATAAATGTTATCTGTATCCTTAC
    >K  P  S  K  D  K  T  L  S  W  N  L  A  F  L  V  G  I  L  F  T  I  D  I  G  M
 694 GCCAATCCTAGTCCACACCAAATATATAATGTAACTTGGGTAATAACCAATGTACAAACTAACACCCAAGCTAACGC
     CGGTTAGGATCAGGTGTGGTTTATATATTACATTGAACCCATTATTGGTTACATGTTTGATTGTGGGTTCGATTGCG
    > A  N  P  S  P  H  Q  I  Y  N  V  T  W  V  I  T  N  V  Q  T  N  T  Q  A  N  A
 771 CACCTCTATGTTAGGAACCTTAACCGATGCCTACCCTACCCTACATGTTGACTTATGTGACCTAGTGGGAGACACCT
     GTGGAGATACAATCCTTGGAATTGGCTACGGATGGGATGGGATGTACAACTGAATACACTGGATCACCCTCTGTGGA
    >  T  S  M  L  G  T  L  T  D  A  Y  P  T  L  H  V  D  L  C  D  L  V  G  D  T
 848 GGGAACCTATAGTCCTAAACCCAACCAATGTAAAACACGGGGCACGTTACTCCTCCTCAAAATATGGATGTAAAACT
     CCCTTGGATATCAGGATTTGGGTTGGTTACATTTTGTGCCCCGTGCAATGAGGAGGAGTTTTATACCTACATTTTGA
    >W  E  P  I  V  L  N  P  T  N  V  K  H  G  A  R  Y  S  S  S  K  Y  G  C  K  T
 925 ACAGATAGAAAAAAACAGCAACAGACATACCCCTTTTACGTCTGCCCCGGACATGCCCCCTCGTTGGGGCCAAAGGG
     TGTCTATCTTTTTTTGTCGTTGTCTGTATGGGGAAAATGCAGACGGGGCCTGTACGGGGGAGCAACCCCGGTTTCCC
    > T  D  R  K  K  Q  Q  Q  T  Y  P  F  Y  V  C  P  G  H  A  P  S  L  G  P  K  G
1002 AACACATTGTGGAGGGGCACAAGATGGGTTTTGTGCCGCATGGGGATGTGAGACCACCGGAGAAGCTTGGTGGAAGC
     TTGTGTAACACCTCCCCGTGTTCTACCCAAAACACGGCGTACCCCTACACTCTGGTGGCCTCTTCGAACCACCTTCG
    >  T  H  C  G  G  A  Q  D  G  F  C  A  A  W  G  C  E  T  T  G  E  A  W  W  K
1079 CCACCTCCTCATGGGACTATATCACAGTAAAAAGAGGGAGTAGTCAGGACAATAGCTGTGAGGGAAAATGCAACCCC
     GGTGGAGGAGTACCCTGATATAGTGTCATTTTTCTCCCTCATCAGTCCTGTTATCGACACTCCCTTTTACGTTGGGG
    >P  T  S  S  W  D  Y  I  T  V  K  R  G  S  S  Q  D  N  S  C  E  G  K  C  N  P
1156 CTGGTTTTGCAGTTCACCCAGAAGGGAAGACAAGCCTCTTGGGACGGACCTAAGATGTGGGGATTGCGACTATACCG
     GACCAAAACGTCAAGTGGGTCTTCCCTTCTGTTCGGAGAACCCTGCCTGGATTCTACACCCCTAACGCTGATATGGC
    > L  V  L  Q  F  T  Q  K  G  R  Q  A  S  W  D  G  P  K  M  W  G  L  R  L  Y  R
1233 TACAGGATATGACCCTATCGCTTTATTCACGGTGTCCCGGCAGGTATCAACCATTACGCCGCCTCAGGCAATGGGAC
     ATGTCCTATACTGGGATAGCGAAATAAGTGCCACAGGGCCGTCCATAGTTGGTAATGCGGCGGAGTCCGTTACCCTG
    >  T  G  Y  D  P  I  A  L  F  T  V  S  R  Q  V  S  T  I  T  P  P  Q  A  M  G
1310 CAAACCTAGTCTTACCTGATCAAAAACCCCCATCCCGACAATCTCAAACAGGGTCCAAAGTGGCGACCCAGAGGCCC
     GTTTGGATCAGAATGGACTAGTTTTTGGGGGTAGGGCTGTTAGAGTTTGTCCCAGGTTTCACCGCTGGGTCTCCGGG
    >P  N  L  V  L  P  D  Q  K  P  P  S  R  Q  S  Q  T  G  S  K  V  A  T  Q  R  P
1387 CAAACGAATGAAAGCGCCCCAAGGTCTGTTGCCCCCACCACCATGGGTCCCAAACGGATTGGGACCGGAGATAGGTT
     GTTTGCTTACTTTCGCGGGGTTCCAGACAACGGGGGTGGTGGTACCCAGGGTTTGCCTAACCCTGGCCTCTATCCAA
    > Q  T  N  E  S  A  P  R  S  V  A  P  T  T  M  G  P  K  R  I  G  T  G  D  R  L
1464 AATAAATTTAGTACAAGGGACATACCTAGCCTTAAATGCCACCGACCCCAACAAAACTAAAGACTGTTGGCTCTGCC
     TTATTTAAATCATGTTCCCTGTATGGATCGGAATTTACGGTGGCTGGGGTTGTTTTGATTTCTGACAACCGAGACGG
    >  I  N  L  V  Q  G  T  Y  L  A  L  N  A  T  D  P  N  K  T  K  D  C  W  L  C
1541 TGGTTTCTCGACCACCCTATTACGAAGGGATTGCAATCTTAGGTAACTACAGCAACCAAACAAACCCCCCCCCATCC
     ACCAAAGAGCTGGTGGGATAATGCTTCCCTAACGTTAGAATCCATTGATGTCGTTGGTTTGTTTGGGGGGGGGTAGG
    >L  V  S  R  P  P  Y  Y  E  G  I  A  I  L  G  N  Y  S  N  Q  T  N  P  P  P  S
1618 TGCCTATCTACTCCGCAACACAAACTAACTATATCTGAAGTATCAGGGCAAGGAATGTGCATAGGGACTGTTCCTAA
     ACGGATAGATGAGGCGTTGTGTTTGATTGATATAGACTTCATAGTCCCGTTCCTTACACGTATCCCTGACAAGGATT
    > C  L  S  T  P  Q  H  K  L  T  I  S  E  V  S  G  Q  G  M  C  I  G  T  V  P  K
```

Figure 3B

```
1695 AACCCACCAGGCTTTGTGCAATAAGACACAACAGGGACATACAGGGGCGCACTATCTAGCCGCCCCCAACGGCACCT
     TTGGGTGGTCCGAAACACGTTATTCTGTGTTGTCCCTGTATGTCCCCGCGTGATAGATCGGCGGGGGTTGCCGTGGA
    >  T  H  Q  A  L  C  N  K  T  Q  Q  G  H  T  G  A  H  Y  L  A  A  P  N  G  T
1772 ATTGGGCCTGTAACACTGGACTCACCCCATGCATTTCCATGGCGGTGCTCAATTGGACCTCTGAATTCTGTGTCTTA
     TAACCCGGACATTGTGACCTGAGTGGGGTACGTAAAGGTACCGCCACGAGTTAACCTGGAGACTTAAGACACAGAAT
    >Y  W  A  C  N  T  G  L  T  P  C  I  S  M  A  V  L  N  W  T  S  E  F  C  V  L
1849 ATCGAATTATGGCCCAGAGTGACTTACCATCAACCCGAATATGTGTACACACATTTTGCCAAAGCTGTCAGGTTCCG
     TAGCTTAATACCGGGTCTCACTGAATGGTAGTTGGGCTTATACACATGTGTGTAAAACGGTTTCGACAGTCCAAGGC
    > I  E  L  W  P  R  V  T  Y  H  Q  P  E  Y  V  Y  T  H  F  A  K  A  V  R  F  R
1926 AAGAGAACCAATATCACTAACGGTTGCCCTTATGTTGGGAGGACTTACTGTAGGGGGCATAGCCGCGGGGGTCGGAA
     TTCTCTTGGTTATAGTGATTGCCAACGGGAATACAACCCTCCTGAATGACATCCCCCGTATCGGCGCCCCCAGCCTT
    >  R  E  P  I  S  L  T  V  A  L  M  L  G  G  L  T  V  G  G  I  A  A  G  V  G
2003 CAGGGACTAAAGCCCTCCTTGAAACAGCCCAGTTTAGACAACTACAAATGGCCATGCACACAGACATCCAGGCCCTA
     GTCCCTGATTTCGGGAGGAACTTTGTCGGGTCAAATCTGTTGATGTTTACCGGTACGTGTGTCTGTAGGTCCGGGAT
    >T  G  T  K  A  L  L  E  T  A  Q  F  R  Q  L  Q  M  A  M  H  T  D  I  Q  A  L
2080 GAAGAATCAATTAGTGCCTTAGAAAAGTCCCTGACCTCCCTTTCTGAAGTAGTCTTACAAAACAGACGGGGCCTAGA
     CTTCTTAGTTAATCACGGAATCTTTTCAGGGACTGGAGGGAAAGACTTCATCAGAATGTTTTGTCTGCCCCGGATCT
    > E  E  S  I  S  A  L  E  K  S  L  T  S  L  S  E  V  V  L  Q  N  R  R  G  L  D
2157 TATTCTATTCTTACAAGAGGGAGGGCTCTGTGCCGCATTGAAAGAAGAATGTTGCTTCTATGCGGATCACACCGGAC
     ATAAGATAAGAATGTTCTCCCTCCCGAGACACGGCGTAACTTTCTTCTTACAACGAAGATACGCCTAGTGTGGCCTG
    >  I  L  F  L  Q  E  G  G  L  C  A  A  L  K  E  E  C  C  F  Y  A  D  H  T  G
2234 TCGTCCGAGACAATATGGCCAAATTAAGAGAAAGACTAAAACAGCGGCAACAATTGTTTGACTCCCAACAGGGATGG
     AGCAGGCTCTGTTATACCGGTTTAATTCTCTTTCTGATTTTGTCGCCGTTGTTAACAAACTGAGGGTTGTCCCTACC
    >L  V  R  D  N  M  A  K  L  R  E  R  L  K  Q  R  Q  Q  L  F  D  S  Q  Q  G  W
2311 TTTGAAGGATGGTTCAACAAGTCCCCCTGGTTTACAACCCTAATTTCCTCCATTATGGGCCCCTTACTAATCCTACT
     AAACTTCCTACCAAGTTGTTCAGGGGGACCAAATGTTGGGATTAAAGGAGGTAATACCCGGGGAATGATTAGGATGA
    > F  E  G  W  F  N  K  S  P  W  F  T  T  L  I  S  S  I  M  G  P  L  L  I  L  L
2388 CCTAATTCTCCTCTTCGGCCCATGCATCCTTAACCGATTAGTACAATTCGTAAAAGACAGAATATCTGTGGTACAGG
     GGATTAAGAGGAGAAGCCGGGTACGTAGGAATTGGCTAATCATGTTAAGCATTTTCTGTCTTATAGACACCATGTCC
    >  L  I  L  L  F  G  P  C  I  L  N  R  L  V  Q  F  V  K  D  R  I  S  V  V  Q
                                                                          BamHI
2465 CTTTAATTTTAACCCAACAGTACCAACAGATAAAGCAATACGATCCGGACCGACCATGATTTTTCTGGATCCTTTTT
     GAAATTAAAATTGGGTTGTCATGGTTGTCTATTTCGTTATGCTAGGCCTGGCTGGTACTAAAAAGACCTAGGAAAAA
    >A  L  I  L  T  Q  Q  Y  Q  Q  I  K  Q  Y  D  P  D  R  P
2542 ATAGCTAATTAGTCACGTACCTTTGAGAGTACCACTTCAGCTACCTCTTTTGTGTCTCAGAGTAACTTTCTTTAATC
     TATCGATTAATCAGTGCATGGAAACTCTCATGGTGAAGTCGATGGAGAAAACACAGAGTCTCATTGAAAGAAATTAG
2619 AATTCCAAAACAGTATATGATTTTCCATTTCTTTCAAAGATGTAGTTTACATCTGCTCCTTTGTTGAAAAGTAGCCT
     TTAAGGTTTTGTCATATACTAAAAGGTAAAGAAAGTTTCTACATCAAATGTAGACGAGGAAACAACTTTTCATCGGA
2696 GAGCACTTCTTTTCTACCATGAATTACAGCTGGCAAGATCAATTTTTCCCAGTTCTGGACATTTTATTTTTTTTAAG
     CTCGTGAAGAAAAGATGGTACTTAATGTCGACCGTTCTAGTTAAAAAGGGTCAAGACCTGTAAAATAAAAAAAATTC
2773 TAGTGTGCTACATATTTCAATATTTCCAGATTGTACAGCGATCATTAAAGGAGTACGTCCCATGTTATCCAGCAAGT
     ATCACACGATGTATAAAGTTATAAAGGTCTAACATGTCGCTAGTAATTTCCTCATGCAGGGTACAATAGGTCGTTCA
2850 CAGTATCAGCACCTTTGTTCAATAGAAGTTTAACCATTGTTAAATTTTTATTTGATACGGCTATATGTAGAGGAGTT
     GTCATAGTCGTGGAAACAAGTTATCTTCAAATTGGTAACAATTTAAAAATAAACTATGCCGATATACATCTCCTCAA
2927 AACCGATCCGTGTTTGAAATATCTACATCCGCCGAATGAGCCAATAGAAGTTTAACCAAATTAACTTTGTTAAGGTA
     TTGGCTAGGCACAAACTTTATAGATGTAGGCGGCTTACTCGGTTATCTTCAAATTGGTTTAATTGAAACAATTCCAT
3004 AGCTGCCAAACACAAAGGAGTAAAGCCTCCGCTGTAAAGAACATTGTTTACATAGTTATTCTTCAACAGATCTTTCA
     TCGACGGTTTGTGTTTCCTCATTTCGGAGGCGACATTTCTTGTAACAAATGTATCAATAAGAAGTTGTCTAGAAAGT
3081 CTATTTTGTAGTCGTCTCTCAACACCGCATCATGCAGACAAGAAGTTGTGCATTCAGTAACTACAGGTTTAGCTCCA
     GATAAAACATCAGCAGAGAGTTGTGGCGTAGTACGTCTGTTCTTCAACACGTAAGTCATTGATGTCCAAATCGAGGT
3158 TACCTCATCAAGATTTTTATAGCCTCGGTATTCTTGAACATTACAGCCATTTCAAGAGGAGATTGTAGAGTACCATA
     ATGGAGTAGTTCTAAAAATATCGGAGCCATAAGAACTTGTAATGTCGGTAAAGTTCTCCTCTAACATCTCATGGTAT
3235 TTCCGTGTTAGGGTCGAATCCATTGTCCAAAAACCTATTTAGAGATGCATTGTCATTATCCATGATAGCCTCACAGA
     AAGGCACAATCCCAGCTTAGGTAACAGGTTTTTGGATAAATCTCTACGTAACAGTAATAGGTACTATCGGAGTGTCT
3312 CGTATATGTAAGCCATCTTGAATGTATAATTTTGTTGTTTTCAACAACCGCTCGTGAACAGCTTCTATACTTTTTCA
     GCATATACATTCGGTAGAACTTACATATTAAAACAACAAAAGTTGTTGGCGAGCACTTGTCGAAGATATGAAAAAGT
3389 TTTTCTTCATGATTAATATAGTTTACGGAATATAAGTATACAAAAAGTTTATAGTAATCTCATAATATCTGAAACAC
     AAAAGAAGTACTAATTATATCAAATGCCTTATATTCATATGTTTTTCAAATATCATTAGAGTATTATAGACTTTGTG
3466 ATACATAAAACATGGAAGAATTACACGATGTCGTTGAGATAAATGGCTTTTTATTGTCATAGTTTACAAATTCGCAG
     TATGTATTTTGTACCTTCTTAATGTGCTACAGCAACTCTATTTACCGAAAAATAACAGTATCAAATGTTTAAGCGTC
3543 TAATCTTCATCTTTTACGAATATTGCAGAATCTGTTTTATCCAACCAGTGATTTTTGTATAATATAACTGGTATCCT
     ATTAGAAGTAGAAAATGCTTATAACGTCTTAGACAAAATAGGTTGGTCACTAAAAACATATTATATTGACCATAGGA
3620 ATCTTCCGATAGAATGCTGTTATTTAACATTTTTGCACCTATTAAGTTACATCTGTCAAATCCATCTTTCCAACTGA
     TAGAAGGCTATCTTACGACAATAAATTGTAAAAACGTGGATAATTCAATGTAGACAGTTTAGGTAGAAAGGTTGACT
3697 CTTTATGTAACGATGCGAAATAGCATTTATCACTATGTCGTACCCAATTATCATGACAAGATTCTCTTAAATACGTA
     GAAATACATTGCTACGCTTTATCGTAAATAGTGATACAGCATGGGTTAATAGTACTGTTCTAAGAGAATTTATGCAT
3774 ATCTTATTATCTCTTGCATATTCGTAATAGTAATTGTAAAGAGTATACGATAACAGTATAGATATACACGTGATATA
```

Figure 3C

```
     TAGAATAATAGAGAACGTATAAGCATTATCATTAACATTTCTCATATGCTATTGTCATATCTATATGTGCACTATAT
3851 AATATTTAACCCCATTCCTGAGTAAAATAATTACGATATTACATTTCCTTTTATTATTTTTATGTTTTAGTTATTTG
     TTATAAATTGGGGTAAGGACTCATTTTATTAATGCTATAATGTAAAGGAAAATAATAAAAATACAAAATCAATAAAC
3928 TTAGGTTATACAAAAATTATGTTTATTTGTGTATATTTAAAGCGTCGTTAAGAATAAGCTTAGTTAACATATTATCG
     AATCCAATATGTTTTTAATACAAATAAACACATATAAATTTCGCAGCAATTCTTATTCGAATCAATTGTATAATAGC
4005 CTTAGGTTTTGTAGTATTTGAATCCTTTCTTTAAATGGATTATTTTTCCAATGCATATTTATAGCTTCATCCAAAGT
     GAATCCAAAACATCATAAACTTAGGAAAGAAATTTACCTAATAAAAAGGTTACGTATAAATATCGAAGTAGGTTTCA
               ⇐Right arm  NotI
4082 ATAACATTTAACATTCAGAATTGCGGCCGC
     TATTGTAAATTGTAAGTCTTAACGCCGGCG
```

FeLV ENV mutant protein sequence (SEQ ID NO:7) from plasmid pHCMV-ENV FeLV

| Type | From | To | Length | Description | Feature ID |
|---|---|---|---|---|---|
| SIGNAL | 1 | 33 | 33 | Potential. | |
| CHAIN | 34 | 445 | 412 | glycoprotein gp70 | |
| CHAIN | 446 | 642 | 197 | protein p15E. (underlined) | |

| | |
|---|---|
| Length | 642 AA |
| Molecular weight | 71080 Da |
| STRAIN=82K | |

---------+---------+---------+---------+---------+

MESPTHPKPS KDKTLSWNLV FLVGILFTID IGMANPSPPQ MYNVTWVITN 50

VQTNTQANAT SMLGTLTDVY PTLHVDLCDL VGDTWEPMVL SPTGYPPSKY 100

GCKTTDRKKQ QQTYPFYVCP GHRPSLGPKG THCGGAQDGF CAAWGCETTG 150

EAWWKPSSSW DYITVKRGSS QNNNCEGKCN PLILQFTQKG KQASWDGPKM 200

WGLRLYRTGY DPIALFTVSR RVSTITPPQA MGPDLVLPDQ KPPSRQSQTG 250

SKVATQRPQT NESAPRSVAP TTVGPKRIGT GDRLINLVQG AYLALNATDP 300

NKTKDCWLCL VSRPPYYEGI AILGNYSNQT NPPPSCLSIP PHKLTISKVS 350

GQGLCIGTVP KTHQALCNKT HQGHTGADYR AAPRYLAAPN GTYWACNTGL 400

TPCISMAVLN LTSDFCVLIE LWPRVTYHQP EYVYTHFAKA GRFRREPISL 450

TVALMLGGLT VGGIAAGVGT GTKALLETAQ FRQLQMAMHT DIQALEESIS 500

ALEKSLTSLS EVVLQNRRGL DILFLQ*R*GGL CAALKEECCF YADHTGLVRD 550

NMAKLRERLK QRQQLFDSQQ GWFEGWFNRS PWFTTLISSI MGPLLILLLI 600

LLFGPYILNR LVQFVKDRIS VVQALILTQQ YQQIKQYDPD RP 642

Note: R in italic is the mutation site, substitution of R (Arg) for E (Glu)

pPB713 plasmid restriction map

FeLV ENV protein sequence alignment

Figure 5B
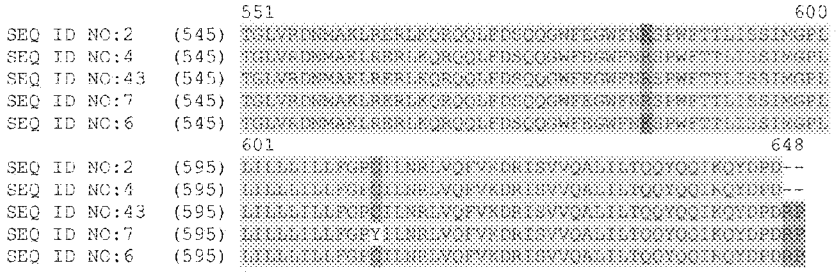
FeLV ENV protein sequence alignment
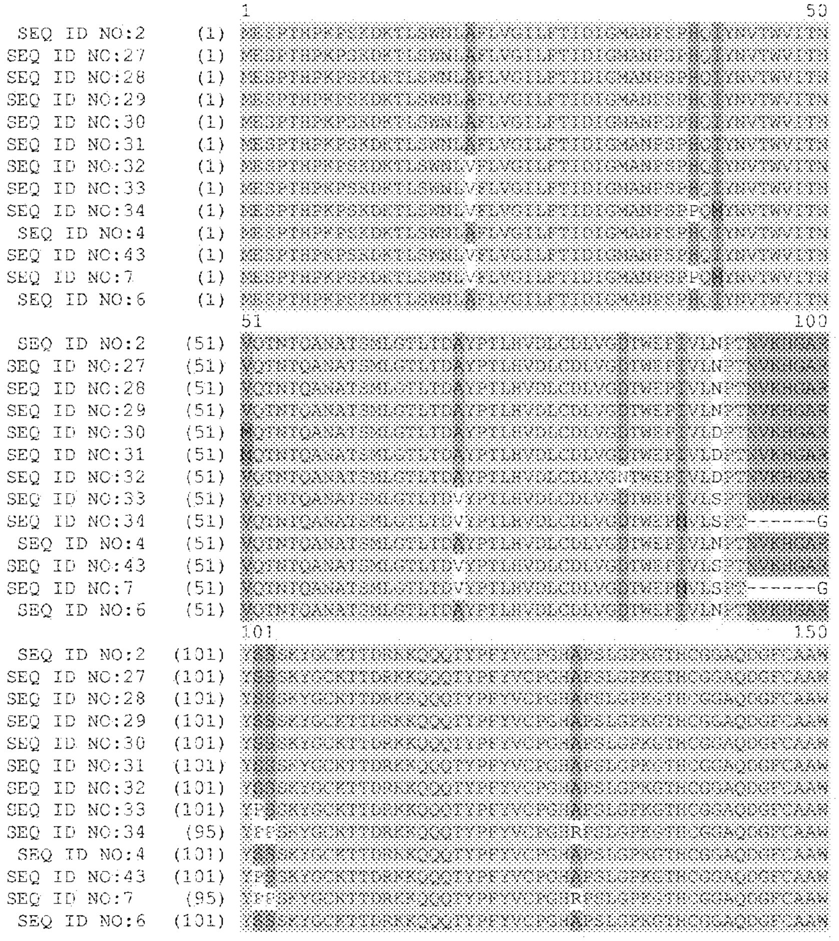

Figure 5E
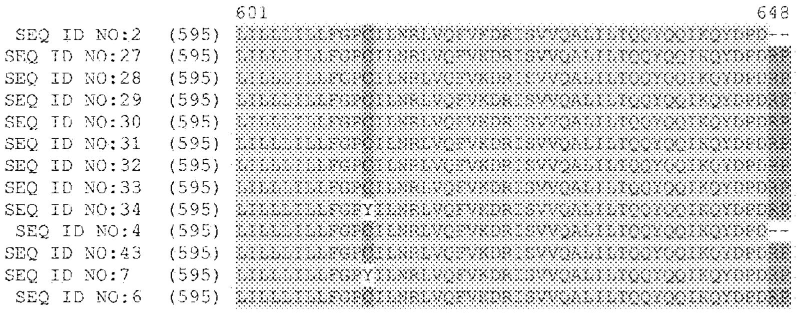
Sequence identity percentage at protein level:
| SEQ ID | 2 | 4 | 6 | 7 | 43 | 27 | 28 | 29 | 30 | 31 | 32 | 33 | 34 |
|---|---|---|---|---|---|---|---|---|---|---|---|---|---|
| 2 | 100 | 99 | 99 | 99 | 98 | 99 | 99 | 99 | 98 | 98 | 98 | 98 | 95 |
| 4 | | 100 | 99 | 93 | 98 | 99 | 99 | 99 | 97 | 97 | 97 | 98 | 93 |
| 6 | | | 100 | 93 | 97 | 99 | 99 | 99 | 97 | 97 | 97 | 98 | 93 |
| 7 | | | | 100 | 95 | 93 | 93 | 93 | 92 | 92 | 93 | 95 | 99 |
| 43 | | | | | 100 | 97 | 98 | 97 | 97 | 97 | 98 | 99 | 95 |
| 27 | | | | | | 100 | 99 | 99 | 98 | 98 | 98 | 98 | 93 |
| 28 | | | | | | | 100 | 99 | 98 | 98 | 98 | 98 | 93 |
| 29 | | | | | | | | 100 | 98 | 98 | 98 | 98 | 93 |
| 30 | | | | | | | | | 100 | 100 | 98 | 97 | 93 |
| 31 | | | | | | | | | | 100 | 98 | 97 | 93 |
| 32 | | | | | | | | | | | 100 | 98 | 93 |
| 33 | | | | | | | | | | | | 100 | 95 |
| 34 | | | | | | | | | | | | | 100 |
FeLV ENV DNA sequence alignment
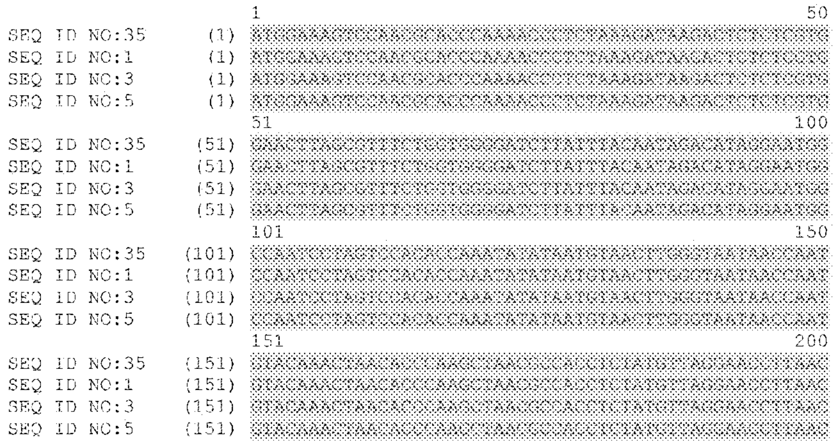

Figure 5F

| | | |
|---|---|---|
| | | 201 … 250 |
| SEQ ID NO:35 | (201) | GGATGCCTACCCTACCCTACATGTTGACTTATGTGACCTAGTGGAAGACA |
| SEQ ID NO:1 | (201) | GGATGCCTACCCTACCCTACATGTTGACTTATGTGACCTAGTGGAAGACA |
| SEQ ID NO:3 | (201) | GGATGCCTACCCTACCCTACATGTTGACTTATGTGACCTAGTGGAAGACA |
| SEQ ID NO:5 | (201) | GGATGCCTACCCTACCCTACATGTTGACTTATGTGACCTAGTGGAAGACA |
| | | 251 … 300 |
| SEQ ID NO:35 | (251) | CCTGGGAACCTATAGTCCTAAACCCAACCAATGTAAAACACGGGGCACCT |
| SEQ ID NO:1 | (251) | CCTGGGAACCTATAGTCCTAAACCCAACCAATGTAAAACACGGGGCACCT |
| SEQ ID NO:3 | (251) | CCTGGGAACCTATAGTCCTAAACCCAACCAATGTAAAACACGGGGCACCT |
| SEQ ID NO:5 | (251) | CCTGGGAACCTATAGTCCTAAACCCAACCAATGTAAAACACGGGGCACCT |
| | | 301 … 350 |
| SEQ ID NO:35 | (301) | TACTCCTCCTCAAAATATGGATGTAAAACTACAGATAGAAAAAAACAGCA |
| SEQ ID NO:1 | (301) | TACTCCTCCTCAAAATATGGATGTAAAACTACAGATAGAAAAAAACAGCA |
| SEQ ID NO:3 | (301) | TACTCCTCCTCAAAATATGGATGTAAAACTACAGATAGAAAAAAACAGCA |
| SEQ ID NO:5 | (301) | TACTCCTCCTCAAAATATGGATGTAAAACTACAGATAGAAAAAAACAGCA |
| | | 351 … 400 |
| SEQ ID NO:35 | (351) | ACAGACATACCCCTTTTACGTCTGCCCCGGACATGCCCCCTCGTTGGGGC |
| SEQ ID NO:1 | (351) | ACAGACATACCCCTTTTACGTCTGCCCCGGACATGCCCCCTCGTTGGGGC |
| SEQ ID NO:3 | (351) | ACAGACATACCCCTTTTACGTCTGCCCCGGACATGCCCCCTCGTTGGGGC |
| SEQ ID NO:5 | (351) | ACAGACATACCCCTTTTACGTCTGCCCCGGACATGCCCCCTCGTTGGGGC |
| | | 401 … 450 |
| SEQ ID NO:35 | (401) | CAAAGGGAACACATTGTGGACGGGCACAAGATGGGTTTTGTCCCGCATGG |
| SEQ ID NO:1 | (401) | CAAAGGGAACACATTGTGGACGGGCACAAGATGGGTTTTGTCCCGCATGG |
| SEQ ID NO:3 | (401) | CAAAGGGAACACATTGTGGACGGGCACAAGATGGGTTTTGTCCCGCATGG |
| SEQ ID NO:5 | (401) | CAAAGGGAACACATTGTGGACGGGCACAAGATGGGTTTTGTCCCGCATGG |
| | | 451 … 500 |
| SEQ ID NO:35 | (451) | GGATGTGAGACCACCGGACAAGCTTGGTGGAAGCCCACCTCCTCATGGGA |
| SEQ ID NO:1 | (451) | GGATGTGAGACCACCGGACAAGCTTGGTGGAAGCCCACCTCCTCATGGGA |
| SEQ ID NO:3 | (451) | GGATGTGAGACCACCGGACAAGCTTGGTGGAAGCCCACCTCCTCATGGGA |
| SEQ ID NO:5 | (451) | GGATGTGAGACCACCGGACAAGCTTGGTGGAAGCCCACCTCCTCATGGGA |
| | | 501 … 550 |
| SEQ ID NO:35 | (501) | CTATATCACACTAAAAAGAGCGAGTAGTCAGGACAATAGCTCTGAGGCAA |
| SEQ ID NO:1 | (501) | CTATATCACACTAAAAAGAGCGAGTAGTCAGGACAATAGCTCTGAGGCAA |
| SEQ ID NO:3 | (501) | CTATATCACACTAAAAAGAGCGAGTAGTCAGGACAATAGCTCTGAGGCAA |
| SEQ ID NO:5 | (501) | CTATATCACACTAAAAAGAGCGAGTAGTCAGGACAATAGCTCTGAGGCAA |
| | | 551 … 600 |
| SEQ ID NO:35 | (551) | AATGCAACCCCCTGGTTTTGCAGTTCACCCAGAAGGGAAGACAAGCCTCT |
| SEQ ID NO:1 | (551) | AATGCAACCCCCTGGTTTTGCAGTTCACCCAGAAGGGAAGACAAGCCTCT |
| SEQ ID NO:3 | (551) | AATGCAACCCCCTGGTTTTGCAGTTCACCCAGAAGGGAAGACAAGCCTCT |
| SEQ ID NO:5 | (551) | AATGCAACCCCCTGGTTTTGCAGTTCACCCAGAAGGGAAGACAAGCCTCT |
| | | 601 … 650 |
| SEQ ID NO:35 | (601) | TGGGACGGACCTAAGATGTGCGGATTGCGACTATACCGTACAGGATATGA |
| SEQ ID NO:1 | (601) | TGGGACGGACCTAAGATGTGCGGATTGCGACTATACCGTACAGGATATGA |
| SEQ ID NO:3 | (601) | TGGGACGGACCTAAGATGTGCGGATTGCGACTATACCGTACAGGATATGA |
| SEQ ID NO:5 | (601) | TGGGACGGACCTAAGATGTGCGGATTGCGACTATACCGTACAGGATATGA |
| | | 651 … 700 |
| SEQ ID NO:35 | (651) | CCCTATCGCTTTATTCACGGTGTCCCGGCAGGTATCAACCATTACGCCGC |
| SEQ ID NO:1 | (651) | CCCTATCGCTTTATTCACGGTGTCCCGGCAGGTATCAACCATTACGCCGC |
| SEQ ID NO:3 | (651) | CCCTATCGCTTTATTCACGGTGTCCCGGCAGGTATCAACCATTACGCCGC |
| SEQ ID NO:5 | (651) | CCCTATCGCTTTATTCACGGTGTCCCGGCAGGTATCAACCATTACGCCGC |
| | | 701 … 750 |
| SEQ ID NO:35 | (701) | CTCAGGCAATGGGACCAAACCTAGTCTTACCTGATCAAAAACCCCCATCC |
| SEQ ID NO:1 | (701) | CTCAGGCAATGGGACCAAACCTAGTCTTACCTGATCAAAAACCCCCATCC |
| SEQ ID NO:3 | (701) | CTCAGGCAATGGGACCAAACCTAGTCTTACCTGATCAAAAACCCCCATCC |
| SEQ ID NO:5 | (701) | CTCAGGCAATGGGACCAAACCTAGTCTTACCTGATCAAAAACCCCCATCC |
| | | 751 … 800 |
| SEQ ID NO:35 | (751) | CGACAATCTCAAACAGGGTCCAAAGTGGCGACCCAGAGCCCCAAACCGAA |
| SEQ ID NO:1 | (751) | CGACAATCTCAAACAGGGTCCAAAGTGGCGACCCAGAGCCCCAAACCGAA |
| SEQ ID NO:3 | (751) | CGACAATCTCAAACAGGGTCCAAAGTGGCGACCCAGAGCCCCAAACCGAA |
| SEQ ID NO:5 | (751) | CGACAATCTCAAACAGGGTCCAAAGTGGCGACCCAGAGCCCCAAACCGAA |
| | | 801 … 850 |
| SEQ ID NO:35 | (801) | TGAAAGCGCCCCAAGGTCTGTTGCCCCCACCACCATGGGTCCCAAACCGA |
| SEQ ID NO:1 | (801) | TGAAAGCGCCCCAAGGTCTGTTGCCCCCACCACCATGGGTCCCAAACCGA |
| SEQ ID NO:3 | (801) | TGAAAGCGCCCCAAGGTCTGTTGCCCCCACCACCATGGGTCCCAAACCGA |
| SEQ ID NO:5 | (801) | TGAAAGCGCCCCAAGGTCTGTTGCCCCCACCACCATGGGTCCCAAACCGA |

Figure 5G

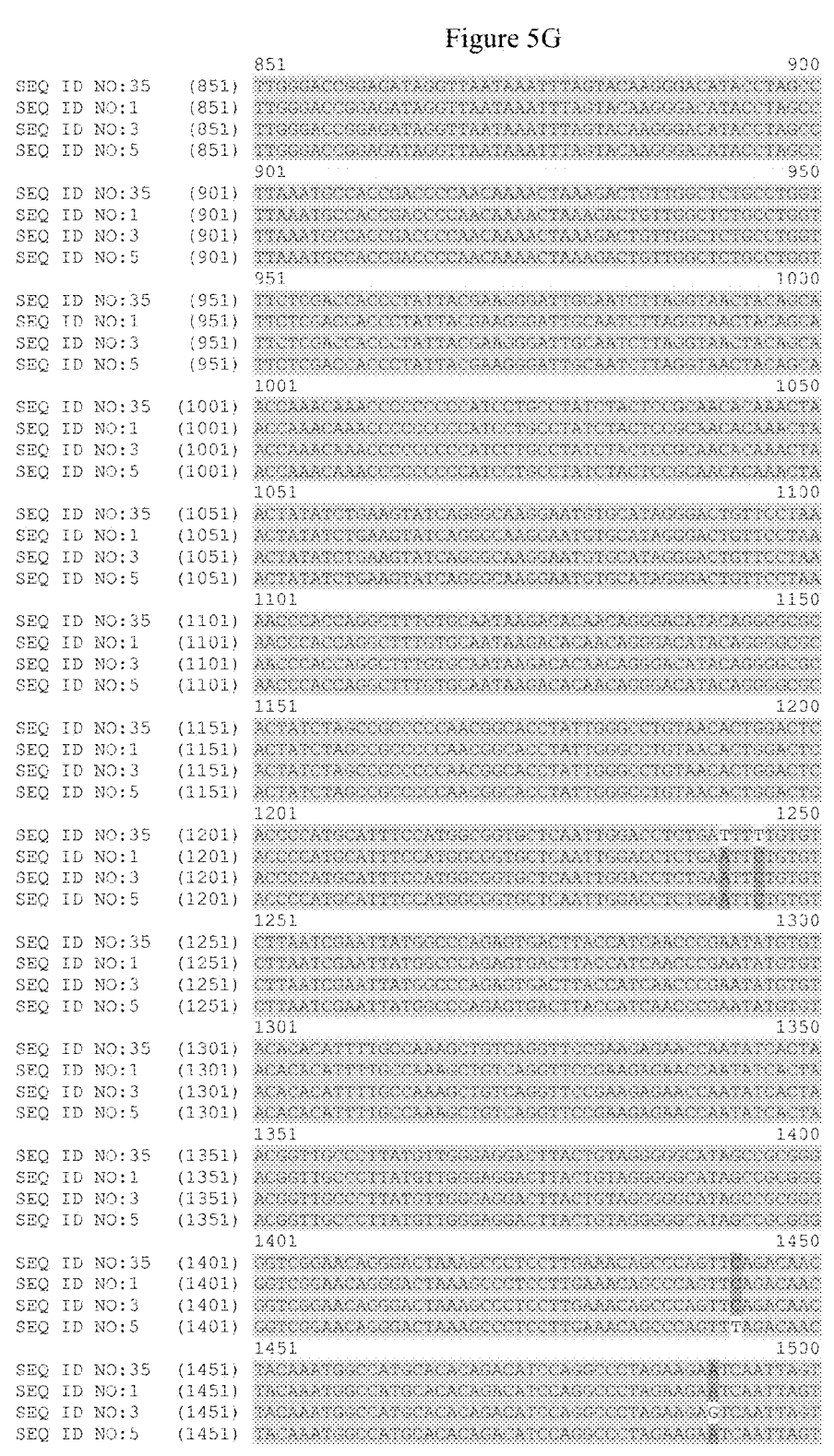

| | | |
|---|---|---|
| | | 851 900 |
| SEQ ID NO:35 | (851) | TTGGGACCGGAGATAGGTTAATAAATTTAGTACAAGGGACATACCTAGCC |
| SEQ ID NO:1 | (851) | TTGGGACCGGAGATAGGTTAATAAATTTAGTACAAGGGACATACCTAGCC |
| SEQ ID NO:3 | (851) | TTGGGACCGGAGATAGGTTAATAAATTTAGTACAAGGGACATACCTAGCC |
| SEQ ID NO:5 | (851) | TTGGGACCGGAGATAGGTTAATAAATTTAGTACAAGGGACATACCTAGCC |
| | | 901 950 |
| SEQ ID NO:35 | (901) | TTAAATGCCACCGACCCCAACAAAACTAAAGACTGTTGGCTCTGCCTGGT |
| SEQ ID NO:1 | (901) | TTAAATGCCACCGACCCCAACAAAACTAAAGACTGTTGGCTCTGCCTGGT |
| SEQ ID NO:3 | (901) | TTAAATGCCACCGACCCCAACAAAACTAAAGACTGTTGGCTCTGCCTGGT |
| SEQ ID NO:5 | (901) | TTAAATGCCACCGACCCCAACAAAACTAAAGACTGTTGGCTCTGCCTGGT |
| | | 951 1000 |
| SEQ ID NO:35 | (951) | TTCTCGACCACCCTATTACGAAGGGATTGCAATCTTAGGTAACTACAGCA |
| SEQ ID NO:1 | (951) | TTCTCGACCACCCTATTACGAAGGGATTGCAATCTTAGGTAACTACAGCA |
| SEQ ID NO:3 | (951) | TTCTCGACCACCCTATTACGAAGGGATTGCAATCTTAGGTAACTACAGCA |
| SEQ ID NO:5 | (951) | TTCTCGACCACCCTATTACGAAGGGATTGCAATCTTAGGTAACTACAGCA |
| | | 1001 1050 |
| SEQ ID NO:35 | (1001) | ACCAAACAAACCTCCTCCCATCCTGCCTATCTACTCCGCAACACAAACTA |
| SEQ ID NO:1 | (1001) | ACCAAACAAACCTCCTCCCATCCTGCCTATCTACTCCGCAACACAAACTA |
| SEQ ID NO:3 | (1001) | ACCAAACAAACCTCCTCCCATCCTGCCTATCTACTCCGCAACACAAACTA |
| SEQ ID NO:5 | (1001) | ACCAAACAAACCTCCTCCCATCCTGCCTATCTACTCCGCAACACAAACTA |
| | | 1051 1100 |
| SEQ ID NO:35 | (1051) | ACTATATCTGAAGTATCAGGCCAAGGAATGTGCATAGGGACTGTTCCTAA |
| SEQ ID NO:1 | (1051) | ACTATATCTGAAGTATCAGGCCAAGGAATGTGCATAGGGACTGTTCCTAA |
| SEQ ID NO:3 | (1051) | ACTATATCTGAAGTATCAGGCCAAGGAATGTGCATAGGGACTGTTCCTAA |
| SEQ ID NO:5 | (1051) | ACTATATCTGAAGTATCAGGCCAAGGAATGTGCATAGGGACTGTTCCTAA |
| | | 1101 1150 |
| SEQ ID NO:35 | (1101) | AACCCACCAGCCTTTCTGCAATAAGACACAACAGGGACATACAGGCGCGC |
| SEQ ID NO:1 | (1101) | AACCCACCAGCCTTTCTGCAATAAGACACAACAGGGACATACAGGCGCGC |
| SEQ ID NO:3 | (1101) | AACCCACCAGCCTTTCTGCAATAAGACACAACAGGGACATACAGGCGCGC |
| SEQ ID NO:5 | (1101) | AACCCACCAGCCTTTCTGCAATAAGACACAACAGGGACATACAGGCGCGC |
| | | 1151 1200 |
| SEQ ID NO:35 | (1151) | ACTATCTAGCCGCCCCCAACGCCACCTATTGGGCCTGTAACACTGGACTC |
| SEQ ID NO:1 | (1151) | ACTATCTAGCCGCCCCCAACGCCACCTATTGGGCCTGTAACACTGGACTC |
| SEQ ID NO:3 | (1151) | ACTATCTAGCCGCCCCCAACGCCACCTATTGGGCCTGTAACACTGGACTC |
| SEQ ID NO:5 | (1151) | ACTATCTAGCCGCCCCCAACGCCACCTATTGGGCCTGTAACACTGGACTC |
| | | 1201 1250 |
| SEQ ID NO:35 | (1201) | ACCCCATGCATTTCCATGGCCGTGCTCAATTGGACCTCTGATTTTTGTGT |
| SEQ ID NO:1 | (1201) | ACCCCATGCATTTCCATGGCCGTGCTCAATTGGACCTCTGA[illegible]TT[illegible]TGTGT |
| SEQ ID NO:3 | (1201) | ACCCCATGCATTTCCATGGCCGTGCTCAATTGGACCTCTGA[illegible]TT[illegible]TGTGT |
| SEQ ID NO:5 | (1201) | ACCCCATGCATTTCCATGGCCGTGCTCAATTGGACCTCTGA[illegible]TT[illegible]TGTGT |
| | | 1251 1300 |
| SEQ ID NO:35 | (1251) | CTTAATCCAATTATGCCCCAGACTGACTTACCATCAACCCGAATATGTGT |
| SEQ ID NO:1 | (1251) | CTTAATCCAATTATGCCCCAGACTGACTTACCATCAACCCGAATATGTGT |
| SEQ ID NO:3 | (1251) | CTTAATCCAATTATGCCCCAGACTGACTTACCATCAACCCGAATATGTGT |
| SEQ ID NO:5 | (1251) | CTTAATCCAATTATGCCCCAGACTGACTTACCATCAACCCGAATATGTGT |
| | | 1301 1350 |
| SEQ ID NO:35 | (1301) | ACACACATTTTGCCAAAGCTGTCAGGTTCCGAAGAGAACCAATATCACTA |
| SEQ ID NO:1 | (1301) | ACACACATTTTGCCAAAGCTGTCAGGTTCCGAAGAGAACCAATATCACTA |
| SEQ ID NO:3 | (1301) | ACACACATTTTGCCAAAGCTGTCAGGTTCCGAAGAGAACCAATATCACTA |
| SEQ ID NO:5 | (1301) | ACACACATTTTGCCAAAGCTGTCAGGTTCCGAAGAGAACCAATATCACTA |
| | | 1351 1400 |
| SEQ ID NO:35 | (1351) | ACGGTTGCCCTTATGTTGGGAGGACTTACTGTAGGGGGCATAGCCGCGGC |
| SEQ ID NO:1 | (1351) | ACGGTTGCCCTTATGTTGGGAGGACTTACTGTAGGGGGCATAGCCGCGGC |
| SEQ ID NO:3 | (1351) | ACGGTTGCCCTTATGTTGGGAGGACTTACTGTAGGGGGCATAGCCGCGGC |
| SEQ ID NO:5 | (1351) | ACGGTTGCCCTTATGTTGGGAGGACTTACTGTAGGGGGCATAGCCGCGGC |
| | | 1401 1450 |
| SEQ ID NO:35 | (1401) | GGTCGCAACACGGACTAAAGCCCTCCTTGAAACAGCCCAGTT[illegible]AGACAAC |
| SEQ ID NO:1 | (1401) | GGTCGCAACACGGACTAAAGCCCTCCTTGAAACAGCCCAGTT[illegible]AGACAAC |
| SEQ ID NO:3 | (1401) | GGTCGCAACACGGACTAAAGCCCTCCTTGAAACAGCCCAGTT[illegible]AGACAAC |
| SEQ ID NO:5 | (1401) | GGTCGCAACACGGACTAAAGCCCTCCTTGAAACAGCCCAGTTTAGACAAC |
| | | 1451 1500 |
| SEQ ID NO:35 | (1451) | TACAAATGGCCATGCACACAGACATTCAGGCCCTAGAAGA[illegible]TCAATTAGT |
| SEQ ID NO:1 | (1451) | TACAAATGGCCATGCACACAGACATTCAGGCCCTAGAAGA[illegible]TCAATTAGT |
| SEQ ID NO:3 | (1451) | TACAAATGGCCATGCACACAGACATTCAGGCCCTAGAAGAGTCAATTAGT |
| SEQ ID NO:5 | (1451) | TACAAATGGCCATGCACACAGACATTCAGGCCCTAGAAGA[illegible]TCAATTAGT |

Sequence identity percentage

| | SEQ ID NIO:35 | SEQ ID NO:1 | SEQ ID NO:3 | SEQ ID NO:5 |
|---|---|---|---|---|
| SEQ ID NO:35 | | 99 | 99 | 100 |
| SEQ ID NO:1 | | | 99 | 99 |
| SEQ ID NO:3 | | | | 99 |
| SEQ ID NO:5 | | | | |

Figure 5I

Sequence comparison (nucleotides) between FeLV env in pPB712 and FeLV env in pHCMV-Env FeLV

```
ClustalW (v1.4) multiple sequence alignment

2 Sequences Aligned           Alignment Score = 3444
Gaps Inserted = 0             Conserved Identities = 521

Pairwise Alignment Mode: Fast
Pairwise Alignment Parameters:
    ktup = 2   Gap Penalty = 5   Top Diagonals = 4   Window Size = 4

Multiple Alignment Parameters:
    Open Gap Penalty = 10.0   Extend Gap Penalty = 5.0
    Delay Divergent = 10%     Transitions: Weighted

Processing time: 0.2 seconds


SEQ ID NO:41      1 CCGCGGGGGTCGGAACAGGGACTAAAGCCCTCCTTGAAACAGCCCAGTTC  50
SEQ ID NO:39      1 CCGCGGGGGTCGGAACAGGGACTAAAGCCCTCCTTGAAACAGCCCAGTTC  50

SEQ ID NO:41     51 AGACAACTACAAATGGCCATGCACACAGACATCCAGGCCCTAGAAGAGTC 100
SEQ ID NO:39     51 AGACAACTACAAATGGCCATGCACACAGACATCCAGGCCCTAGAAGAATC 100

SEQ ID NO:41    101 AATTAGTGCCTTAGAAAAGTCCCTGACCTCCCTTTCTGAAGTAGTCTTAC 150
SEQ ID NO:39    101 AATTAGTGCCTTAGAAAAGTCCCTGACCTCCCTTTCTGAAGTAGTCTTAC 150

SEQ ID NO:41    151 AAAACAGACGGGGCCTAGATATTCTATTCCTACAACGGGGAGGGCTCTGC 200
SEQ ID NO:39    151 AAAACAGACGGGGCCTAGATATTCTATTCTTACAACGGGGAGGGCTCTGC 200

SEQ ID NO:41    201 GCAGCATTAAAAGAAGAATGTTGCTTCTATGCGGATCACACCGGACTCGT 250
SEQ ID NO:39    201 GCAGCATTAAAAGAAGAATGTTGCTTCTATGCGGATCACACCGGACTCGT 250

SEQ ID NO:41    251 CCGAGACAATATGGCTAAATTAAGAGAAAGACTAAAACAGCGGCAACAAC 300
SEQ ID NO:39    251 CCGAGACAATATGGCCAAATTAAGAGAAAGACTAAAACAGCGGCAACAAC 300

SEQ ID NO:41    301 TGTTTGACTCCCAACAGGGATGGTTTGAAGGATGGTTCAACAGGTCCCCC 350
SEQ ID NO:39    301 TGTTTGACTCCCAACAGGGATGGTTTGAAGGATGGTTCAACAAGTCCCCC 350

SEQ ID NO:41    351 TGGTTTACAACCCTAATTTCCTCCATTATGGGCCCCTTACTAATCCTACT 400
SEQ ID NO:39    351 TGGTTTACAACCCTAATTTCCTCCATTATGGGCCCCTTACTAATCCTACT 400

SEQ ID NO:41    401 CCTAATTCTCCTCTTCGGCCCATGCATCCTTAACAGATTAGTACAATTCG 450
SEQ ID NO:39    401 CCTAATTCTCCTCTTCGGCCCATGCATCCTTAACCGATTAGTACAGTTCG 450

SEQ ID NO:41    451 TAAAAGACAGAATATCTGTGGTACAAGCCTTAATTTTAACCCAACAGTAC 500
SEQ ID NO:39    451 TAAAAGACAGAATATCTGTGGTACAGGCTTTAATTTTAACCCAACAGTAC 500

SEQ ID NO:41    501 CAACAGATAAAGCAATACGATCCGGACCG 529
SEQ ID NO:39    501 CAACAGATAAAGCAATACGATCCGGACCG 529
```

SEQ ID NO:39: FeLV env DNA from pPB712 plasmid
SEQ ID NO:41: FeLV env DNA from pHCMV-Env FeLV plasmid

Figure 5J

Sequence comparison (amino-acids) between FeLV env in pPB712 and FeLV env in pHCMV-Env FeLV

```
ClustalW (v1.4) multiple sequence alignment

2 Sequences Aligned           Alignment Score = 1074
Gaps Inserted = 0             Conserved Identities = 174

Pairwise Alignment Mode: Fast
Pairwise Alignment Parameters:
    ktup = 1   Gap Penalty = 3   Top Diagonals = 5   Window Size = 5

Multiple Alignment Parameters:
    Open Gap Penalty = 10.0   Extend Gap Penalty = 0.1
    Delay Divergent = 10%     Gap Distance = 8
    Similarity Matrix: blosum

Processing time: 0.1 seconds


SEQ ID NO:40       1 AGVGTGTKALLETAQFRQLQMAMHTDIQALEESISALEKSLTSLSEVVLQ  50
SEQ ID NO:42       1 AGVGTGTKALLETAQFRQLQMAMHTDIQALEESISALEKSLTSLSEVVLQ  50

SEQ ID NO:40      51 NRRGLDILFLQRGGLCAALKEECCFYADHTGLVRDNMAKLRERLKQRQQL 100
SEQ ID NO:42      51 NRRGLDILFLQRGGLCAALKEECCFYADHTGLVRDNMAKLRERLKQRQQL 100

SEQ ID NO:40     101 FDSQQGWFEGWFNKSPWFTTLISSIMGPLLILLLILLFGPCILNRLVQFV 150
SEQ ID NO:42     101 FDSQQGWFEGWFNRSPWFTTLISSIMGPLLILLLILLFGPCILNRLVQFV 150

SEQ ID NO:40     151 KDRISVVQALILTQQYQQIKQYDPD 175
SEQ ID NO:42     151 KDRISVVQALILTQQYQQIKQYDPD 175
```

SEQ ID NO:40: FeLV env protein (double-mutation) from pPB712 plasmid
SEQ ID NO:42: FeLV env protein (single-mutation) from pHCMV-Env FeLV plasmid

Sequence comparison (amino-acids) of FeLV env from different strains and sequence from pHCMV-Env FeLV (single FeLV mutation)

```
pPB179         MESPTHPKPSKDKTLSWNLAFLVGILFTIDIGMANPSPHQIYNVTWVITNVQTNTQANAT
1_Glasgow-1    MESPTHPKPSKDKTLSWNLAFLVGILFTIDIGMANPSPHQIYNVTWVITNVQTNTQANAT
3_Glasgow-1    MESPTHPKPSKDKTLSWNLAFLVGILFTIDIGMANPSPHQIYNVTWVITNVQTNTQANAT
Rickard        MESPTHPKPSKDKTLSWNLAFLVGILFTIDIGMANPSPHQIYNVTWVITNMQTNTQANAT
NP_047256      MESPTHPKPSKDKTLSWNLAFLVGILFTIDIGMANPSPHQIYNVTWVITNMQTNTQANAT
AAA43051       MESPTHPKPSKDKTLSWNLVFLVGILFTIDIGMANPSPHQIYNVTWVITNVQTNTQANAT
FeLV mut       MESPTHPKPSKDKTLSWNLVFLVGILFTIDIGMANPSPHQIYNVTWVITNVQTNTQANAT
FAIDS          MESPTHPKPSKDKTLSWNLVFLVGILFTIDIGMANPSPHQIYNVTWVITNVQTNTQANAT
82K            MESPTHPKPSKDKTLSWNLVFLVGILFTIDIGMANPSPPQMYNVTWVITNVQTNTQANAT
               *****************.**************** *:*******:******* pPB179         SMLGTLTDAYPTLHVDLCDLVGDTWEPIVLNPTNVKHGARYSSSKYGCKTTDRKKQQQTY
1_Glasgow-1    SMLGTLTDAYPTLHVDLCDLVGDTWEPIVLNPTNVKHGARYSSSKYGCKTTDRKKQQQTY
3_Glasgow-1    SMLGTLTDAYPTLHVDLCDLVGDTWEPIVLNPTNVKHGARYSSSKYGCKTTDRKKQQQTY
Rickard        SMLGTLTDAYPTLHVDLCDLVGDTWEPIVLDPTNVKHGARYSSSKYGCKTTDRKKQQQTY
NP_047256      SMLGTLTDAYPTLHVDLCDLVGDTWEPIVLDPTNVKHGARYSSSKYGCKTTDRKKQQQTY
AAA43051       SMLGTLTDAYPTLHVDLCDLVGNTWEPIVLDPTNVKHGARYSSSKYGCKTTDRKKQQQTY
FeLV mut       SMLGTLTDVYPTLHVDLCDLVGDTWEPIVLSPTNVKHGARYPSSKYGCKTTDRKKQQQTY
FAIDS          SMLGTLTDVYPTLHVDLCDLVGDTWEPIVLSPTNVKHGARYPSSKYGCKTTDRKKQQQTY
82K            SMLGTLTDVYPTLHVDLCDLVGDTWEPMVLSPTGYPP------SKYGCKTTDRKKQQQTY
               ******.*********::..          **************
```

Figure 5K

```
pPB179          PFYVCPGHAPSLGPKGTHCGGAQDGFCAAWGCETTGEAWWKPTSSWDYITVKRGSSQDNS
1_Glasgow-1     PFYVCPGHAPSLGPKGTHCGGAQDGFCAAWGCETTGEAWWKPTSSWDYITVKRGSSQDNS
3_Glasgow-1     PFYVCPGHAPSLGPKGTHCGGAQDGFCAAWGCETTGEAWWKPTSSWDYITVKRGSSQDNS
Rickard         PFYVCPGHAPSLGPKGTHCGGAQDGFCAAWGCETTGEAWWKPSSSWDYITVKRGSSQDNS
NP_047256       PFYVCPGHAPSLGPKGTHCGGAQDGFCAAWGCETTGEAWWKPSSSWDYITVKRGSSQDNS
AAA43051        PFYVCPGHAPSLGPKGTHCGGAQDGFCAAWGCETTGEAWWKPSSSWDYITVKRGSSQDNS
FeLV mut        PFYVCPGHAPSLGPKGTHCGGAQDGFCAAWGCETTGEAWWKPSSSWDYITVKRGSSQDNN
FAIDS           PFYVCPGHAPSLGPKGTHCGGAQDGFCAAWGCETTGEAWWKPSSSWDYITVKRGSSQDNN
82K             PFYVCPGHRPSLGPKGTHCGGAQDGFCAAWGCETTGEAWWKPSSSWDYITVKRGSSQNNN
                ****** *****************************:************:*.

pPB179          CEGKCNPLVLQFTQKGRQASWDGPKMWGLRLYRTGYDPIALFTVSRQVSTITPPQAMGPN
1_Glasgow-1     CEGKCNPLVLQFTQKGRQASWDGPKMWGLRLYRTGYDPIALFTVSRQVSTITPPQAMGPN
3_Glasgow-1     CEGKCNPLVLQFTQKGRQASWDGPKMWGLRLYRTGYDPIALFTVSRQVSTITPPQAMGPN
Rickard         CEGKCNPLILQFTQKGRQASWDGPKIWGLRLYRTGYDPIALFTVSRQVSAITPPQAMGPN
NP_047256       CEGKCNPLILQFTQKGRQASWDGPKIWGLRLYRTGYDPIALFTVSRQVSAITPPQAMGPN
AAA43051        CEGKCNPLILQFTQKGRQASWDGPKMWGLRLYRTGYDPIALFTVSRQVSTITPPQAMGPN
FeLV mut        CEGKCNPLILQFTQKGKQASWDGPKMWGLRLYRTGYDPIALFTVSRQVSTITPPQAMGPN
FAIDS           CEGKCNPLILQFTQKGKQASWDGPKMWGLRLYRTGYDPIALFTVSRQVSTITPPQAMGPN
82K             CEGKCNPLILQFTQKGKQASWDGPKMWGLRLYRTGYDPIALFTVSRKVSTITPPQAMGPD
                ******:***:*****:***************::*********:

pPB179          LVLPDQKPPSRQSQTGSKVATQRPQTNESAPRSVAPTTMGPKRIGTGDRLINLVQGTYLA
1_Glasgow-1     LVLPDQKPPSRQSQTGSKVATQRPQTNESAPRSVAPTTMGPKRIGTGDRLINLVQGTYLA
3_Glasgow-1     LVLPDQKPPSRQSQTGSKVATQRPQTNESAPRSVAPTTMGPKRIGTGDRLINLVQGTYLA
Rickard         LVLPDQKPPSRQSQTGSKVATQRLQTTESAPRSVAPTTVGPKRIGTGDRLINLVQGTYLA
NP_047256       LVLPDQKPPSRQSQTGSKVATQRLQTTESAPRSVAPTTVGPKRIGTGDRLINLVQGTYLA
AAA43051        LVLPDQKPPSRQSQTGSKVATQRLQTNESASRSVAPTTVVPKRIGTGDRLINLVQGTYLA
FeLV mut        LVLPDQKPPSRQSQTGSKVATQRPQTNESAPRSVAPTTVGPKRIGTGDRLINLVQGTYLA
FAIDS           LVLPDQKPPSRQSQTGSKVATQRPQTNESAPRSVAPTTVGPKRIGTGDRLINLVQGTYLA
82K             LVLPDQKPPSRQSQTGSKVATQRPQTNESAPRSVAPTTVGPKRIGTGDRLINLVQGAYLA
                ********************* .*.***: ************:* pPB179          LNATDPNKTKDCWLCLVSRPPYYEGIAILGNYSNQTNPPPSCLSTPQHKLTISEVSGQGM
1_Glasgow-1     LNATDPNKTKDCWLCLVSRPPYYEGIAILGNYSNQTNPPPSCLSTPQHKLTISEVSGQGM
3_Glasgow-1     LNATDPNKTKDCWLCLVSRPPYYEGIAILGTYSNQTNPPPSCLSTPQHKLTISEVSGQGM
Rickard         LNATDPNKTKDCWLCLVSRPPYYEGIAILGNYSNQTNPPPSCLSTPQHKLTISEVSGQGL
NP_047256       LNATDPNKTKDCWLCLVSRPPYYEGIAILGNYSNQTNPPPSCLSTPQHKLTISEVSGQGL
AAA43051        LNATDPNKTKDCWLCLVSRPPYYEGIAILGNYSNQTNPPPSCLSTPQHKLTISEVSGQGL
FeLV mut        LNATDPNKTKDCWLCLVSRPPYYEGIAILGNYSNQTNPPPSCLSIPQHKLTISEVSGQGL
FAIDS           LNATDPNKTKDCWLCLVSRPPYYEGIAILGNYSNQTNPPPSCLSIPQHKLTISEVSGQGL
82K             LNATDPNKTKDCWLCLVSRPPYYEGIAILGNYSNQTNPPPSCLSIPPHKLTISKVSGQGL
                ****************************.*********** * ****:***:

pPB179          CIGTVPKTHQALCNKTQQGHTGAHYLAAP------NGTYWACNTGLTPCISMAVLNWTSE
1_Glasgow-1     CIGTVPKTHQALCNKTQQGHTGAHYLAAP------NGTYWACNTGLTPCISMAVLNWTSD
3_Glasgow-1     CIGTVPKTHQALCNKTQQGHTGAHYLAAP------NGTYWACNTGLTPCISMAVLNWTSD
Rickard         CIGTVPKTHQALCNETQQGHTGAHYLAAP------NGAYWACNTGLTPCISMAVLNWTSD
NP_047256       CIGTVPKTHQALCNETQQGHTGAHYLAAP------NGAYWACNTGLTPCISMAVLNWTSD
AAA43051        CIGTVPKTHQALCNETQQGHTGAHYLAAP------NGTYWACNTGLTPCISMAVLNWTSD
FeLV mut        CIGTVPKTHQALCNKTQQGHTGAHYLAAP------NGTYWACNTGLTPCISMAVLNWTSD
FAIDS           CIGTVPKTHQALCNKTQQGHTGAHYLAAP------NGTYWACNTGLTPCISMAVLNWTSD
82K             CIGTVPKTHQALCNKTHQGHTGADYRAAPRYLAAPNGTYWACNTGLTPCISMAVLNLTSD
                **************:*:******.* *      :**************** :

pPB179          FCVLIELWPRVTYHQPEYVYTHFAKAVRFRREPISLTVALMLGGLTVGGIAAGVGTGTKA
1_Glasgow-1     FCVLIELWPRVTYHQPEYVYTHFAKAVRFRREPISLTVALMLGGLTVGGIAAGVGTGTKA
3_Glasgow-1     FCVLIELWPRVTYHQPEYVYTHFAKAVRFRREPISLTVALMLGGLTVGGIAAGVGTGTKA
Rickard         FCVLIELWPRVTYHQPEYVYTHFAKAVRFRREPISLTVALMLGGLTVGGIAAGVGTGTKA
NP_047256       FCVLIELWPRVTYHQPEYVYTHFAKAVRFRREPISLTVALMLGGLTVGGIAAGVGTGTKA
AAA43051        FCVLIELWPRVTYHQPEYVYTHFAKAVRFRREPISLTVALMLGGLTVGGIAAGVGTGTKA
FeLV mut        FCVLIELWPRVTYHQPEYVYTHFAKAVRFRREPISLTVALMLGGLTVGGIAAGVGTGTKA
FAIDS           FCVLIELWPRVTYHQPEYVYTHFAKAVRFRREPISLTVALMLGGLTVGGIAAGVGTGTKA
82K             FCVLIELWPRVTYHQPEYVYTHFAKAGRFRREPISLTVALMLGGLTVGGIAAGVGTGTKA
                ************************ *******************************
```

Figure 5L

```
pPB179          LLETAQFRQLQMAMHTDIQALEESISALEKSLTSLSEVVLQNRRGLDILFLQEGGLCAAL
1_Glasgow-1     LLETAQFRQLQMAMHTDIQALEESISALEKSLTSLSEVVLQNRRGLDILFLQEGGLCAAL
3_Glasgow-1     LLETAQFRQLQMAMHTDIQALEESISALEKSLTSLSEVVLQNRRGLDILFLQEGGLCAAL
Rickard         LLETAQFRQLQMAMHTDIQALEESISALEKSLTSLSEVVLQNRRGLDILFLQEGGLCAAL
NP_047256       LLETAQFRQLQMAMHTDIQALEESISALEKSLTSLSEVVLQNRRGLDILFLQEGGLCAAL
AAA43051        LLETAQFRQLQMAMHTDIQALEESISALEKSLTSLSEVVLQNRRGLDILFLQEGGLCAAL
FeLV mut        LLETAQFRQLQMAMHTDIQALEESISALEKSLTSLSEVVLQNRRGLDILFLQRGGLCAAL
FAIDS           LLETAQFRQLQMAMHTDIQALEESISALEKSLTSLSEVVLQNRRGLDILFLQEGGLCAAL
82K             LLETAQFRQLQMAMHTDIQALEESISALEKSLTSLSEVVLQNRRGLDILFLQEGGLCAAL
                ****************************************************.*******

pPB179          KEECCFYADHTGLVRDNMAKLRERLKQRQQLFDSQQGWFEGWFNKSPWFTTLISSIMGPL
1_Glasgow-1     KEECCFYADHTGLVRDNMAKLRERLKQRQQLFDSQQGWFEGWFNKSPWFTTLISSIMGPL
3_Glasgow-1     KEECCFYADHTGLVRDNMAKLRERLKQRQQLFDSQQGWFEGWFNKSPWFTTLISSIMGPL
Rickard         KEECCFYADHTGLVRDNMAKLRERLKQRQQLFDSQQGWFEGWFNKSPWFTTLISSIMGPL
NP_047256       KEECCFYADHTGLVRDNMAKLRERLKQRQQLFDSQQGWFEGWFNKSPWFTTLISSIMGPL
AAA43051        KEECCFYADHTGLVRDNMAKLRERLKQRQQLFDSQQGWFEGWFNKSPWFTTLISSIMGPL
FeLV mut        KEECCFYADHTGLVRDNMAKLRERLKQRQQLFDSQQGWFEGWFNRSPWFTTLISSIMGPL
FAIDS           KEECCFYADHTGLVRDNMAKLRERLKQRQQLFDSQQGWFEGWFNRSPWFTTLISSIMGPL
82K             KEECCFYADHTGLVRDNMAKLRERLKQRQQLFDSQQGWFEGWFNRSPWFTTLISSIMGPL
                ********************************************:***************

pPB179          LILLLILLFGPCILNRLVQFVKDRISVVQALILTQQYQQIKQYDPDRP
1_Glasgow-1     LILLLILLFGPCILNRLVQFVKDRISVVQALILTQQYQQIKQYDPDRP
3_Glasgow-1     LILLLILLFGPCILNRLVQFVKDRISVVQALILTQQYQQIKQYDPDRP
Rickard         LILLLILLFGPCILNRLVQFVKDRISVVQALILTQQYQQIKQYDPDRP
NP_047256       LILLLILLFGPCILNRLVQFVKDRISVVQALILTQQYQQIKQYDPDRP
AAA43051        LILLLILLFGPCILNRLVQFVKDRISVVQALILTQQYQQIKQYDPDRP
FeLV mut        LILLLILLFGPCILNRLVQFVKDRISVVQALILTQQYQQIKQYDPDRP
FAIDS           LILLLILLFGPCILNRLVQFVKDRISVVQALILTQQYQQIKQYDPDRP
82K             LILLLILLFGPYILNRLVQFVKDRISVVQALILTQQYQQIKQYDPDRP
                *********** ************************************
```

Single Mutation of FeLV

Second mutation position of FeLV in pPB712 where it is K in SEQ ID NOs :2 and 40.

SEQ ID NO:27: pPB179
SEQ ID NO:28: 1_Glasgow-1
SEQ ID NO:29: 3_Glasgow-1
SEQ ID NO:30: Rickard
SEQ ID NO:31: NP_047256
SEQ ID NO:32: AAA43051
SEQ ID NO:33: FAIDS
SEQ ID NO:34: 82K
SEQ ID NO:43: FeLV mut (single mutation)

pPB712 plasmid restriction map gap-pro: SEQ ID NO:11 (Genbank accession No. M18247)
codon optimized gap-pro: SEQ ID NO:10

Sequence identity percentage between SEQ ID NO:10 and SEQ ID NO:11 is 76.6% pC3 H6p-FeLV codon optimized gag-pro (pJY1874.1)

Feature Map

CDS (2 total)

FeLV codon optimized gag-pro
Start: 1153 End: 3039

Amp R
Start: 6243 End: 7099

Misc. Feature (2 total)

C3L
Start: 3 End: 942

C3R
Start: 3070 End: 5632

Promoter Eukaryotic (1 total)

H6p
Start: 967 End: 1152

Figure 10

Predicted amino acid sequence of product(s): GAG-PRO (SEQ ID NO: 12)

FeLV GAG
PRO

GAG Start with the second Met-G76

1 MGQTITTPLS LTLDHWSEVR ARAHNQGVEV RKKKWITLCE AEWVMMNVGW
51 PREGTFSLDS ISQVEKKIFA PGPYGHPDQV PYITTWRSLA TDPPSWVRPF
101 LPPPKPPTPL PQPLSPQPSA PLTSSLYPVL PKPDPPKPPV LPPDPSSPLI
151 DLLTEEPPPY PGGHGPPPSG PRTPTASPIA SRLRERRENP AEESQALPLR
201 EGPNNRPQYW PFSASDLYNW KSHNPPFSQD PVALTNLIES ILVTHQPTWD
251 DCQQLLQALL TGEERQRVLL EARKQVPGED GRPTQLPNVI DETFPLTRPN
301 WDFATPAGRE HLRLYRQLLL AGLRGAARRP TNLAQVKQVV QGKEETPAAF
351 LERLKEAYRM YTPYDPEDPG QAASVILSFI YQSSPDIRNK LQRLEGLQGF
401 TLSDLLKEAE KIYNKRETPE EREERLWQRQ EERDKKRHKE MTKVLATVVA
451 QNRDKDREES KLGDQRKIPL GKDQCAYCKE KGHWVRDCPK RPRKKPANST
501 LLNLGD*ESQ GQDPPPEPRI TLKIGGQPVT FLVDTGAQHS VLTRPDGPLS
551 DRTALVQGAT GSKNYRWTTD RRVQLATGKV THSFLYVPEC PYPLLGRDLL
601 TKLKAQIHFT GEGANVVGPR GLPLQVL*

Figure 11A

Nucleotide sequence of arms and insert with translation (plasmid pJY1874.1) (SEQ ID NO:38)

Color code: C3L; H6p; FeLV gag-pro; C3R

```
      C3L
1     TGCGGCCGCG TCGACATGCA TTGTTAGTTC TGTAGATCAG TAACGTATAG CATACGAGTA TAATTATCGT
      ACGCCGGCGC AGCTGTACGT AACAATCAAG ACATCTAGTC ATTGCATATC GTATGCTCAT ATTAATAGCA

71    AGGTAGTAGG TATCCTAAAA TAAATCTGAT ACAGATAATA ACTTTGTAAA TCAATTCAGC AATTTCTCTA
      TCCATCATCC ATAGGATTTT ATTTAGACTA TGTCTATTAT TGAAACATTT AGTTAAGTCG TTAAAGAGAT

141   TTATCATGAT AATGATTAAT ACACAGCGTG TCGTTATTTT TTGTTACGAT AGTATTTCTA AAGTAAAGAG
      AATAGTACTA TTACTAATTA TGTGTCGCAC AGCAATAAAA AACAATGCTA TCATAAAGAT TTCATTTCTC

211   CAGGAATCCC TAGTATAATA GAAATAATCC ATATGAAAAA TATAGTAATG TACATATTTC TAATGTTAAC
      GTCCTTAGGG ATCATATTAT CTTTATTAGG TATACTTTTT ATATCATTAC ATGTATAAAG ATTACAATTG
                     8231SL
281   ATATTTATAG GTAAATCCAG GAAGGGTAAT TTTTACATAT CTATATACGC TTATTACAGT TATTAAAAAT
      TATAAATATC CATTTAGGTC CTTCCCATTA AAAATGTATA GATATATGCG AATAATGTCA ATAATTTTTA

351   ATACTTGCAA ACATGTTAGA AGTAAAAAAG AAAGAACTAA TTTTACAAAG TGCTTTACCA AAATGCCAAT
      TATGAACGTT TGTACAATCT TCATTTTTTC TTTCTTGATT AAAATGTTTC ACGAAATGGT TTTACGGTTA

421   GGAAATTACT TAGTATGTAT ATAATGTATA AAGGTATGAA TATCACAAAC AGCAAATCGG CTATTCCCAA
      CCTTTAATGA ATCATACATA TATTACATAT TTCCATACTT ATAGTGTTTG TCGTTTAGCC GATAAGGGTT

491   GTTGAGAAAC GGTATAATAG ATATATTTCT AGATACCATT AATAACCTTA TAAGCTTGAC GTTTCCTATA
      CAACTCTTTG CCATATTATC TATATAAAGA TCTATGGTAA TTATTGGAAT ATTCGAACTG CAAAGGATAT

561   ATGCCTACTA AGAAAACTAG AAGATACATA CATACTAACG CCATACGAGA GTAACTACTC ATCGTATAAC
      TACGGATGAT TCTTTTGATC TTCTATGTAT GTATGATTGC GGTATGCTCT CATTGATGAG TAGCATATTG
                8232SL
631   TACTGTTGCT AACAGTGACA CTGATGTTAT AACTCATCTT TGATGTGGTA TAAATGTATA ATAACTATAT
      ATGACAACGA TTGTCACTGT GACTACAATA TTGAGTAGAA ACTACACCAT ATTTACATAT TATTGATATA
                                                8253SL
701   TACACTGGTA TTTTATTTCA GTTATATACT ATATAGTATT AAAAATTATA TTTGTATAAT TATATTATTA
      ATGTGACCAT AAAATAAAGT CAATATATGA TATATCATAA TTTTTAATAT AAACATATTA ATATAATAAT

771   TATTCAGTGT AGAAAGTAAA ATACTATAAA TATGTATCTC TTATTTATAA CTTATTAGTA AAGTATGTAC
      ATAAGTCACA TCTTTCATTT TATGATATTT ATACATAGAG AATAAATATT GAATAATCAT TTCATACATG

841   TATTCAGTTA TATTGTTTTA TAAAAGCTAA ATGCTACTAG ATTGATATAA ATGAATATGT AATAAATTAG
      ATAAGTCAAT ATAACAAAAT ATTTTCGATT TACGATGATC TAACTATATT TACTTATACA TTATTTAATC
                                                           H6p
911   TAATGTAGTA TACTAATATT AACTCACATT TGACTAATTA GCTATAAAAA CCCGGGTTAA TTAATTAGTC
      ATTACATCAT ATGATTATAA TTGAGTGTAA ACTGATTAAT CGATATTTTT GGGCCCAATT AATTAATCAG

981   ATCAGGCAGG GCGAGAACGA GACTATCTGC TCGTTAATTA ATTAGAGCTT CTTTATTCTA TACTTAAAAA
      TAGTCCGTCC CGCTCTTGCT CTGATAGACG AGCAATTAAT TAATCTCGAA GAAATAAGAT ATGAATTTTT
1051  GTGAAAATAA ATACAAAGGT TCTTGAGGGT TGTGTTAAAT TGAAAGCGAG AAATAATCAT AAATTATTTC
      CACTTTTATT TATGTTTCCA AGAACTCCCA ACACAATTTA ACTTTCGCTC TTTATTAGTA TTTAATAAAG
                                        Gag
                13229SL                 M  G  Q   T  I  T   T  P  L  S   L  T  L ·
1121  ATTATCGCGA TATCCGTTAA GTTTGTATCG TAATGGGACA GACCATCACC ACCCCCCTGT CTCTCACCCT
      TAATAGCGCT ATAGGCAATT CAAACATAGC ATTACCCTGT CTGGTAGTGG TGGGGGGACA GAGAGTGGGA

·D  H  W   S  E  V  R   A  R  A   H  N  Q   G  V  E  V   R  K  K   K  W  I
1191  GGACCACTGG TCTGAGGTGA GAGCCAGAGC CCACAACCAG GGCGTGGAGG TGAGGAAGAA GAAGTGGATC
      CCTGGTGACC AGACTCCACT CTCGGTCTCG GGTGTTGGTC CCGCACCTCC ACTCCTTCTT CTTCACCTAG
                                        11369JY
       T  L  C  E   A  E  W   V  M  M   N  V  G  W   P  R  E   G  T  F   S  L  D ·
1261  ACCCTGTGTG AGGCCGAGTG GGTGATGATG AACGTGGGCT GGCCTAGAGA GGGCACCTTC TCCCTGGACT
      TGGGACACAC TCCGGCTCAC CCACTACTAC TTGCACCCGA CCGGATCTCT CCCGTGGAAG AGGGACCTGA
```

Figure 11B

```
      · I  S  Q   V  E  K   K  I  F  A   P  G  P   Y  G  H   P  D  Q  V   P  Y  I
1331  CCATCTCCCA GGTGGAGAAG AAGATCTTCG CCCCTGGCCC TTACGGCCAC CCCGATCAGG TGCCCTACAT
      GGTAGAGGGT CCACCTCTTC TTCTAGAAGC GGGGACCGGG AATGCCGGTG GGGCTAGTCC ACGGGATGTA
                 11370JY
      · T  T  W   R  S  L  A   T  D  P   P  S  W   V  R  P  F   L  P  P   P  K  P
1401  CACCACCTGG AGATCTCTGG CCACCGACCC TCCTAGCTGG GTGAGACCCT TCCTGCCCCC TCCCAAACCT
      GTGGTGGACC TCTAGAGACC GGTGGCTGGG AGGATCGACC CACTCTGGGA AGGACGGGGG AGGGTTTGGA

P  T  P  L   P  Q  P   L  S  P   Q  P  S  A   P  L  T   S  S  L   Y  P  V  L
1471  CCTACCCCTC TGCCTCAGCC TCTGTCTCCT CAGCCTTCTG CCCCCCTCAC CTCTTCTCTG TACCCCGTGC
      GGATGGGGAG ACGGAGTCGG AGACAGAGGA GTCGGAAGAC GGGGGGAGTG GAGAAGAGAC ATGGGGCACG

· P  K  P   D  P  P   K  P  P  V   L  P  P   D  P  S   S  P  L  I   D  L  L
1541  TGCCCAAACC CGACCCCCCT AAACCTCCTG TGCTGCCCCC CGACCCCTCT TCTCCCCTCA TCGACCTGCT
      ACGGGTTTGG GCTGGGGGGA TTTGGAGGAC ACGACGGGGG GCTGGGGAGA AGAGGGGAGT AGCTGGACGA

· T  E  E   P  P  P  Y   P  G  G   H  G  P   P  P  S  G   P  R  T   P  T  A
1611  CACCGAGGAG CCCCCTCCTT ACCCTGGCGG ACACGGCCCT CCTCCCTCTG GACCCCGGAC CCCTACCGCC
      GTGGCTCCTC GGGGGAGGAA TGGGACCGCC TGTGCCGGGA GGAGGGAGAC CTGGGGCCTG GGGATGGCGG
                 11371JY
       S  P  I  A   S  R  L   R  E  R   R  E  N  P   A  E  E   S  Q  A   L  P  L  R
1681  TCTCCTATCG CCTCCAGGCT GAGGGAGAGA AGGGAGAACC CCGCCGAGGA ATCTCAGGCC CTGCCTCTGA
      AGAGGATAGC GGAGGTCCGA CTCCCTCTCT TCCCTCTTGG GGCGGCTCCT TAGAGTCCGG GACGGAGACT
                 11372JY
      · E  G  P   N  N  R   P  Q  Y  W   P  F  S   A  S  D   L  Y  N  W   K  S  H
1751  GAGAGGGCCC CAACAACAGG CCCCAGTACT GGCCTTTCTC TGCCTCCGAC CTGTACAACT GGAAGTCCCA
      CTCTCCCGGG GTTGTTGTCC GGGGTCATGA CCGGAAAGAG ACGGAGGCTG GACATGTTGA CCTTCAGGGT

· N  P  P   F  S  Q  D   P  V  A   L  T  N   L  I  E  S   I  L  V   T  H  Q
1821  CAACCCCCCA TTCTCTCAGG ACCCCGTGGC CCTCACCAAC CTCATCGAGT CCATCCTGGT GACCCATCAG
      GTTGGGGGGT AAGAGAGTCC TGGGGCACCG GGAGTGGTTG GAGTAGCTCA GGTAGGACCA CTGGGTAGTC

P  T  W  D   D  C  Q   Q  L  L   Q  A  L  L   T  G  E   E  R  Q   R  V  L  L
1891  CCCACCTGGG ACGACTGTCA GCAACTGCTG CAGGCTCTGC TCACCGGCGA GGAGAGACAG AGAGTGCTGC
      GGGTGGACCC TGCTGACAGT CGTTGACGAC GTCCGAGACG AGTGGCCGCT CCTCTCTGTC TCTCACGACG

· E  A  R   K  Q  V   P  G  E  D   G  R  P   T  Q  L   P  N  V  I   D  E  T
1961  TGGAGGCCAG AAAACAGGTG CCCGGCGAGG ATGGCAGACC TACCCAGCTG CCCAACGTGA TCGACGAGAC
      ACCTCCGGTC TTTTGTCCAC GGGCCGCTCC TACCGTCTGG ATGGGTCGAC GGGTTGCACT AGCTGCTCTG
                 11373JY
      · F  P  L   T  R  P  N   W  D  F   A  T  P   A  G  R  E   H  L  R   L  Y  R
2031  CTTCCCACTC ACCAGACCCA ACTGGGACTT CGCCACCCCT GCCGGCAGAG AGCACCTGAG GCTGTACAGA
      GAAGGGTGAG TGGTCTGGGT TGACCCTGAA GCGGTGGGGA CGGCCGTCTC TCGTGGACTC CGACATGTCT
                 11374JY
       Q  L  L  L   A  G  L   R  G  A   A  R  R  P   T  N  L   A  Q  V   K  Q  V  V
2101  CAGCTGCTGC TGGCCGGACT GAGAGGAGCC GCCAGGAGAC CTACCAACCT GGCCCAGGTG AAGCAGGTGG
      GTCGACGACG ACCGGCCTGA CTCTCCTCGG CGGTCCTCTG GATGGTTGGA CCGGGTCCAC TTCGTCCACC

· Q  G  K   E  E  T   P  A  A  F   L  E  R   L  K  E   A  Y  R  M   Y  T  P
2171  TGCAGGGCAA AGAGGAAACC CCTGCCGCCT TCCTGGAGAG ACTGAAGGAA GCCTACCGGA TGTACACCCC
      ACGTCCCGTT TCTCCTTTGG GGACGGCGGA AGGACCTCTC TGACTTCCTT CGGATGGCCT ACATGTGGGG
                                                         11375JY
      · Y  D  P   E  D  P  G   Q  A  A   S  V  I   L  S  F  I   Y  Q  S   S  P  D
2241  CTACGACCCT GAGGATCCTG GACAGGCCGC CTCTGTGATC CTGTCCTTCA TCTACCAGTC CAGCCCCGAC
      GATGCTGGGA CTCCTAGGAC CTGTCCGGCG GAGACACTAG GACAGGAAGT AGATGGTCAG GTCGGGGCTG
                                                         11376JY
       I  R  N  K   L  Q  R   L  E  G   L  Q  G  F   T  L  S   D  L  L   K  E  A  E
2311  ATCAGGAACA AGCTGCAGAG ACTGGAGGGC CTGCAGGGCT TCACCCTGTC CGACCTGCTG AAGGAGGCCG
      TAGTCCTTGT TCGACGTCTC TGACCTCCCG GACGTCCCGA AGTGGGACAG GCTGGACGAC TTCCTCCGGC

· K  I  Y   N  K  R   E  T  P  E   E  R  E   E  R  L   W  Q  R  Q   E  E  R
2381  AGAAGATCTA CAACAAGCGG GAGACCCCCG AGGAGAGAGA GGAAAGGCTG TGGCAGAGAC AGGAGGAGAG
      TCTTCTAGAT GTTGTTCGCC CTCTGGGGGC TCCTCTCTCT CCTTTCCGAC ACCGTCTCTG TCCTCCTCTC

· D  K  K   R  H  K  E   M  T  K   V  L  A   T  V  V  A   Q  N  R   D  K  D
2451  GGACAAGAAG CGGCACAAGG AGATGACCAA GGTGCTGGCC ACCGTGGTGG CCCAGAACAG GGACAAGGAC
      CCTGTTCTTC GCCGTGTTCC TCTACTGGTT CCACGACCGG TGGCACCACC GGGTCTTGTC CCTGTTCCTG
```

Figure 11C

```
      R  E  E  S   K  L  G   D  Q  R   K  I  P  L   G  K  D   Q  C  A   Y  C  K  E
2521  AGGGAGGAGT CTAAGCTGGG CGACCAGAGG AAAATCCCCC TGGGCAAGGA CCAGTGCGCC TACTGTAAGG
      TCCCTCCTCA GATTCGACCC GCTGGTCTCC TTTTAGGGGG ACCCGTTCCT GGTCACGCGG ATGACATTCC
                                                                        11509JY
      · K  G  H   W  V  R   D  C  P  K   R  P  R   K  K  P   A  N  S  T   L  L  N
2591  AGAAGGGCCA CTGGGTGAGA GATTGCCCCA AGAGGCCCAG GAAGAAGCCC GCCAACTCCA CCCTGCTCAA
      TCTTCCCGGT GACCCACTCT CTAACGGGGT TCTCCGGGTC CTTCTTCGGG CGGTTGAGGT GGGACGAGTT
                                                                        11377JY
      11509JY       pro
      ·L  G  D   *  E  S  Q   G  Q  D   P  P  P   E  P  R  I   T  L  K   I  G  G
2661  CTTAGGAGAT TAGGAGAGTC AGGGCCAGGA CCCTCCACCT GAGCCCAGAA TCACCCTGAA GATCGGCGGC
      GAATCCTCTA ATCCTCTCAG TCCCGGTCCT GGGAGGTGGA CTCGGGTCTT AGTGGGACTT CTAGCCGCCG
      11377JY
      Q  P  V  T   F  L  V   D  T  G   A  Q  H  S   V  L  T   R  P  D   G  P  L  S
2731  CAGCCCGTGA CCTTCCTGGT GGACACCGGA GCCCAGCACT CTGTGCTCAC AAGACCCGAC GGCCCCCTGT
      GTCGGGCACT GGAAGGACCA CCTGTGGCCT CGGGTCGTGA GACACGAGTG TTCTGGGCTG CCGGGGGACA · D  R  T   A  L  V   Q  G  A  T   G  S  K   N  Y  R   W  T  T  D   R  R  V
2801  CGGATAGAAC CGCCCTGGTG CAGGGAGCCA CCGGCTCCAA GAACTACAGG TGGACCACCG ACAGAAGGGT
      GCCTATCTTG GCGGGACCAC GTCCCTCGGT GGCCGAGGTT CTTGATGTCC ACCTGGTGGC TGTCTTCCCA ·Q  L  A   T  G  K  V   T  H  S   F  L  Y   V  P  E  C   P  Y  P   L  L  G
2871  GCAGCTGGCC ACAGGAAAGG TGACCCACTC CTTCCTGTAC GTGCCCGAGT GTCCCTACCC TCTGCTGGGC
      CGTCGACCGG TGTCCTTTCC ACTGGGTGAG GAAGGACATG CACGGGCTCA CAGGGATGGG AGACGACCCG R  D  L  L   T  K  L   K  A  Q   I  H  F  T   G  E  G   A  N  V   V  G  P  R
2941  AGAGATCTGC TCACCAAGCT GAAGGCCCAG ATCCACTTCA CCGGCGAAGG CGCCAATGTG GTGGGCCCCA
      TCTCTAGACG AGTGGTTCGA CTTCCGGGTC TAGGTGAAGT GGCCGCTTCC GCGGTTACAC CACCCGGGGT · G  L  P   L  Q  V   L  *  *                                    C3R
3011  GAGGACTGCC CCTGCAGGTG CTGTAATGAT TTTTCTTGAC TAGTTAATCA AATAAAAAGC ATACAAGCTA
      CTCCTGACGG GGACGTCCAC GACATTACTA AAAAGAACTG ATCAATTAGT TTATTTTTCG TATGTTCGAT 3081  TTGCTTCGCT ATCGTTACAA AATGGCAGGA ATTTTGTGTA AACTAAGCCA CATACTTGCC AATGAAAAAA
      AACGAAGCGA TAGCAATGTT TTACCGTCCT TAAAACACAT TTGATTCGGT GTATGAACGG TTACTTTTTT
                                       8249SL
3151  ATAGTAGAAA GGATACTATT TTAATGGGAT TAGATGTTAA GGTTCCTTGG GATTATAGTA ACTGGGCATC
      TATCATCTTT CCTATGATAA AATTACCCTA ATCTACAATT CCAAGGAACC CTAATATCAT TGACCCGTAG 3221  TGTTAACTTT TAGGACGTTA GGTTAGATAC TGATGTTACA GATTATAATA ATGTTACAAT AAAATACATG
      ACAATTGAAA ATCCTGCAAT CCAATCTATG ACTACAATGT CTAATATTAT TACAATGTTA TTTTATGTAC 3291  ACAGGATGTG ATATTTTTCC TCATATAACT CTTGGAATAG CAAATATGGA TCAATGTGAT AGATTTGAAA
      TGTCCTACAC TATAAAAAGG AGTATATTGA GAACCTTATC GTTTATACCT AGTTACACTA TCTAAACTTT 3361  ATTTCAAAAA GCAAATAACT GATCAAGATT TACAGACTAT TTCTATAGTC TGTAAAGAAG AGATGTGTTT
      TAAAGTTTTT CGTTTATTGA CTAGTTCTAA ATGTCTGATA AAGATATCAG ACATTTCTTC TCTACACAAA
                                                                          8236SL
3431  TCCTCAGAGT AACGCCTCTA AACAGTTGGG AGCGAAAGGA TGCCCTGTAG TTATGAAACT GGAGGTATCT
      AGGAGTCTCA TTGCGGAGAT TTGTCAACCC TCGCTTTCCT ACGGGACATC AATACTTTGA CCTCCATAGA
         8236SL
3501  GATGAACTTA GAGCCGTAAG AAATGTTCTG CTGAATGCGG TACCCTGTTC GAAGGACGTG TTTGGTGATA
      CTACTTGAAT CTCGGCATTC TTTACAAGAC GACTTACGCC ATGGGACAAG CTTCCTGCAC AAACCACTAT 3571  TCACAGTAGA TAATCCGTGG AATCCTCACA TAACAGTAGG ATATGTTAAG GAGGACGATG TCGAAAACAA
      AGTGTCATCT ATTAGGCACC TTAGGAGTGT ATTGTCATCC TATACAATTC CTCCTGCTAC AGCTTTTGTT
                                                        8248SL
3641  GAAACGCCTA ATGGAGTGCA TGTCCAAGTT TAGGGGGCAA GAAATACAAG TTCTAGGATG GTATTAATAA
      CTTTGCGGAT TACCTCACGT ACAGGTTCAA ATCCCCCGTT CTTTATGTTC AAGATCCTAC CATAATTATT 3711  GTATCTAAGT ATTTGGTATA ATTTATTAAA TAGTATAATT ATAACAAATA ATAAATAACA TGATAACGGT
      CATAGATTCA TAAACCATAT TAAATAATTT ATCATATTAA TATTGTTTAT TATTTATTGT ACTATTGCCA 3781  TTTTATTAGA ATAAAATAGA GATAATATCA TAATGATATA TAATACTTCA TTACCAGAAA TGAGTAATGG
      AAAATAATCT TATTTTATCT CTATTATAGT ATTACTATAT ATTATGAAGT AATGGTCTTT ACTCATTACC
```

Figure 11D

```
3851 AAGACTTATA AATGAACTGC ATAAAGCTAT AAGGTATAGA GATATAAATT TAGTAAGGTA TATACTTAAA
     TTCTGAATAT TTACTTGACG TATTTCGATA TTCCATATCT CTATATTTAA ATCATTCCAT ATATGAATTT
                                      8239SL
3921 AAATGCAAAT ACAATAACGT AAATATACTA TCAACGTCTT TGTATTTAGC CGTAAGTATT TCTGATATAG
     TTTACGTTTA TGTTATTGCA TTTATATGAT AGTTGCAGAA ACATAAATCG GCATTCATAA AGACTATATC

3991 AAATGGTAAA ATTATTACTA GAACACGGTG CCGATATTTT AAAATGTAAA AATCCTCCTC TTCATAAAGC
     TTTACCATTT TAATAATGAT CTTGTGCCAC GGCTATAAAA TTTTACATTT TTAGGAGGAG AAGTATTTCG
                       8247SL
4061 TGCTAGTTTA GATAATACAG AAATTGCTAA ACTACTAATA GATTCTGGCG CTGACATAGA ACAGATACAT
     ACGATCAAAT CTATTATGTC TTTAACGATT TGATGATTAT CTAAGACCGC GACTGTATCT TGTCTATGTA

4131 TCTGGAAATA GTCCGTTATA TATTTCTGTA TATAGAAACA ATAAGTCATT AACTAGATAT TTATTAAAAA
     AGACCTTTAT CAGGCAATAT ATAAAGACAT ATATCTTTGT TATTCAGTAA TTGATCTATA AATAATTTTT

4201 AAGGTGTTAA TTGTAATAGA TTCTTTCTAA ATTATTACGA TGTACTGTAT GATAAGATAT CTGATGATAT
     TTCCACAATT AACATTATCT AAGAAAGATT TAATAATGCT ACATGACATA CTATTCTATA GACTACTATA
                                                                     8240SL
4271 GTATAAAATA TTTATAGATT TTAATATTGA TCTTAATATA CAAACTAGAA ATTTTGAAAC TCCGTTACAT
     CATATTTTAT AAATATCTAA AATTATAACT AGAATTATAT GTTTGATCTT TAAAACTTTG AGGCAATGTA
      8240SL
4341 TACGCTATAA AGTATAAGAA TATAGATTTA ATTAGGATAT TGTTAGATAA TAGTATTAAA ATAGATAAAA
     ATGCGATATT TCATATTCTT ATATCTAAAT TAATCCTATA ACAATCTATT ATCATAATTT TATCTATTTT

4411 GTTTATTTTT GCATAAACAG TATCTCATAA AGGCACTTAA AAATAATTGT AGTTACGATA TAATAGCGTT
     CAAATAAAAA CGTATTTGTC ATAGAGTATT TCCGTGAATT TTTATTAACA TCAATGCTAT ATTATCGCAA
                      8246SL
4481 ACTTATAAAT CACGGAGTGC CTATAAACGA ACAAGATGAT TTAGGTAAAA CCCCATTACA TCATTCGGTA
     TGAATATTTA GTGCCTCACG GATATTTGCT TGTTCTACTA AATCCATTTT GGGGTAATGT AGTAAGCCAT

4551 ATTAATAGAA GAAAAGATGT AACAGCACTT CTGTTAAATC TAGGAGCTGA TATAAACGTA ATAGATGACT
     TAATTATCTT CTTTTCTACA TTGTCGTGAA GACAATTTAG ATCCTCGACT ATATTTGCAT TATCTACTGA

4621 GTATGGGCAG TCCCTTACAT TACGCTGTTT CACGTAACGA TATCGAAACA ACAAAGACAC TTTTAGAAAG
     CATACCCGTC AGGGAATGTA ATGCGACAAA GTGCATTGCT ATAGCTTTGT TGTTTCTGTG AAAATCTTTC

4691 AGGATCTAAT GTTAATGTGG TTAATAATCA TATAGATACC GTTCTAAATA TAGCTGTTGC ATCTAAAAAC
     TCCTAGATTA CAATTACACC AATTATTAGT ATATCTATGG CAAGATTTAT ATCGACAACG TAGATTTTTG
                                           8241SL
4761 AAAACTATAG TAAACTTATT ACTGAAGTAC GGTACTGATA CAAAGTTGGT AGGATTAGAT AAACATGTTA
     TTTTGATATC ATTTGAATAA TGACTTCATG CCATGACTAT GTTTCAACCA TCCTAATCTA TTTGTACAAT

4831 TTCACATAGC TATAGAAATG AAAGATATTA ATATACTGAA TGCGATCTTA TTATATGGTT GCTATGTAAA
     AAGTGTATCG ATATCTTTAC TTTCTATAAT TATATGACTT ACGCTAGAAT AATATACCAA CGATACATTT
                                                  8245SL
4901 CGTCTATAAT CATAAAGGTT TCACTGCTGT ATACATGGCA GTTAGTTCTA TGAAAACAGA ATTTGTTAAA
     GCAGATATTA GTATTTCCAA AGTGACGACA TATGTACCGT CAATCAAGAT ACTTTTGTCT TAAACAATTT

4971 CTCTTACTTG ACCACGGTGC TTACGTAAAT GCTAAAGCTA AGTTATCTGG AAATACTCCT TTACATAAAG
     GAGAATGAAC TGGTGCCACG AATGCATTTA CGATTTCGAT TCAATAGACC TTTATGAGGA AATGTATTTC

5041 CTATGTTATC TAATAGTTTT AATAATATAA AATTACTTTT ATCTTATAAC GCCGACTATA ATTCTCTAAA
     GATACAATAG ATTATCAAAA TTATTATATT TTAATGAAAA TAGAATATTG CGGCTGATAT TAAGAGATTT

5111 TAATCACGGT AATACGCCTC TAACTTGTGT TAGCTTTTTA GATGACAAGA TAGCTATTAT GATAATATCT
     ATTAGTGCCA TTATGCGGAG ATTGAACACA ATCGAAAAAT CTACTGTTCT ATCGATAATA CTATTATAGA

8242SL
5181 AAAATGATGT TAGAAATATC TAAAAATCCT GAAATAGCTA ATTCAGAAGG TTTTATAGTA AACATGGAAC
     TTTTACTACA ATCTTTATAG ATTTTTAGGA CTTTATCGAT TAAGTCTTCC AAAATATCAT TTGTACCTTG

5251 ATATAAACAG TAATAAAAGA CTACTATCTA TAAAAGAATC ATGCGAAAAA GAACTAGATG TTATAACACA
     TATATTTGTC ATTATTTTCT GATGATAGAT ATTTTCTTAG TACGCTTTTT CTTGATCTAC AATATTGTGT
                                                  8244SL
5321 TATAAAGTTA AATTCTATAT ATTCTTTTAA TATCTTTCTT GACAATAACA TAGATCTTAT GGTAAAGTTC
     ATATTTCAAT TTAAGATATA TAAGAAAATT ATAGAAAGAA CTGTTATTGT ATCTAGAATA CCATTTCAAG
```

Figure 11E

```
5391  GTAACTAATC CTAGAGTTAA TAAGATACCT GCATGTATAC GTATATATAG GGAATTAATA CGGAAAAATA
      CATTGATTAG GATCTCAATT ATTCTATGGA CGTACATATG CATATATATC CCTTAATTAT GCCTTTTTAT

5461  AATCATTAGC TTTTCATAGA CATCAGCTAA TAGTTAAAGC TGTAAAAGAG AGTAAGAATC TAGGAATAAT
      TTAGTAATCG AAAAGTATCT GTAGTCGATT ATCAATTTCG ACATTTTCTC TCATTCTTAG ATCCTTATTA

5531  AGGTAGGTTA CCTATAGATA TCAAACATAT AATAATGGAA CTATTAAGTA ATAATGATTT ACATTCTGTT
      TCCATCCAAT GGATATCTAT AGTTTGTATA TTATTACCTT GATAATTCAT TATTACTAAA TGTAAGACAA

5601  ATCACCAGCT GTTGTAACCC AGTAGTATAA AG
      TAGTGGTCGA CAACATTGGG TCATCATATT TC
```

Figure 12 Generation of vCP2294
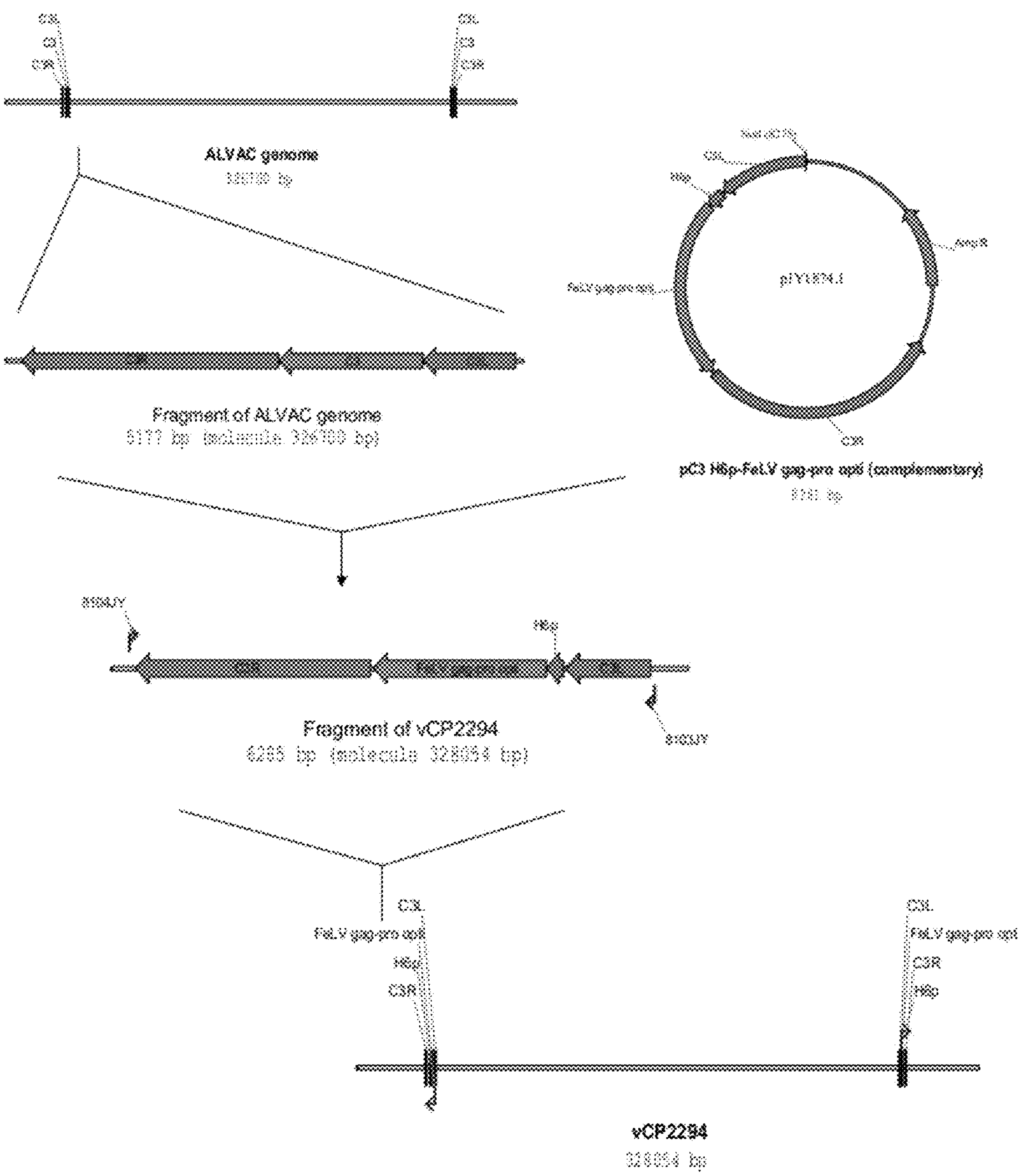

vCP2294 C3 region map showing primer locations:

Fragment of vCP2294

6791 bp (molecule 328054 bp)

Figure 14A vCP2294 sequence (SEQ ID NO:16)

Colour Key:
Sequencing Primers
C3 Arms
FeLV gag-pro
Promoter

```
                         8103JY
     ~~~~~~~~~~~~~~~~~~~~~~~~~~~~~~~~~~~~~
   1 GAGGCATCCA ACATATAAAG AAGACTAAAG CTGTAGAAGC TGTTATGAAG
     CTCCGTAGGT TGTATATTTC TTCTGATTTC GACATCTTCG ACAATACTTC
  51 AATATCTTAT CAGATATATT AGATGCATTG TTAGTTCTGT AGATCAGTAA
     TTATAGAATA GTCTATATAA TCTACGTAAC AATCAAGACA TCTAGTCATT
 101 CGTATAGCAT ACGAGTATAA TTATCGTAGG TAGTAGGTAT CCTAAAATAA
     GCATATCGTA TGCTCATATT AATAGCATCC ATCATCCATA GGATTTTATT
 151 ATCTGATACA GATAATAACT TTGTAAATCA ATTCAGCAAT TTCTCTATTA
     TAGACTATGT CTATTATTGA AACATTTAGT TAAGTCGTTA AAGAGATAAT
 201 TCATGATAAT GATTAATACA CAGCGTGTCG TTATTTTTTG TTACGATAGT
     AGTACTATTA CTAATTATGT GTCGCACAGC AATAAAAAAC AATGCTATCA
 251 ATTTCTAAAG TAAAGAGCAG GAATCCCTAG TATAATAGAA ATAATCCATA
     TAAAGATTTC ATTTCTCGTC CTTAGGGATC ATATTATCTT TATTAGGTAT
 301 TGAAAAATAT AGTAATGTAC ATATTTCTAA TGTTAACATA TTTATAGGTA
     ACTTTTTATA TCATTACATG TATAAAGATT ACAATTGTAT AAATATCCAT
 351 AATCCAGGAA GGGTAATTTT TACATATCTA TATACGCTTA TTACAGTTAT
     TTAGGTCCTT CCCATTAAAA ATGTATAGAT ATATGCGAAT AATGTCAATA
 401 TAAAAATATA CTTGCAAACA TGTTAGAAGT AAAAAAGAAA GAACTAATTT
     ATTTTTATAT GAACGTTTGT ACAATCTTCA TTTTTTCTTT CTTGATTAAA
 451 TACAAAGTGC TTTACCAAAA TGCCAATGGA AATTACTTAG TATGTATATA
     ATGTTTCACG AAATGGTTTT ACGGTTACCT TTAATGAATC ATACATATAT
 501 ATGTATAAAG GTATGAATAT CACAAACAGC AAATCGGCTA TTCCCAAGTT
     TACATATTTC CATACTTATA GTGTTTGTCG TTTAGCCGAT AAGGGTTCAA
 551 GAGAAACGGT ATAATAGATA TATTTCTAGA TACCATTAAT AACCTTATAA
     CTCTTTGCCA TATTATCTAT ATAAAGATCT ATGGTAATTA TTGGAATATT
 601 GCTTGACGTT TCCTATAATG CCTACTAAGA AAACTAGAAG ATACATACAT
     CGAACTGCAA AGGATATTAC GGATGATTCT TTTGATCTTC TATGTATGTA
 651 ACTAACGCCA TACGAGAGTA ACTACTCATC GTATAACTAC TGTTGCTAAC
     TGATTGCGGT ATGCTCTCAT TGATGAGTAG CATATTGATG ACAACGATTG
 701 AGTGACACTG ATGTTATAAC TCATCTTTGA TGTGGTATAA ATGTATAATA
     TCACTGTGAC TACAATATTG AGTAGAAACT ACACCATATT TACATATTAT
 751 ACTATATTAC ACTGGTATTT TATTTCAGTT ATATACTATA TAGTATTAAA
     TGATATAATG TGACCATAAA ATAAAGTCAA TATATGATAT ATCATAATTT
 801 AATTATATTT GTATAATTAT ATTATTATAT TCAGTGTAGA AAGTAAAATA
     TTAATATAAA CATATTAATA TAATAATATA AGTCACATCT TTCATTTTAT
 851 CTATAAATAT GTATCTCTTA TTTATAACTT ATTAGTAAAG TATGTACTAT
     GATATTTATA CATAGAGAAT AAATATTGAA TAATCATTTC ATACATGATA
 901 TCAGTTATAT TGTTTTATAA AAGCTAAATG CTACTAGATT GATATAAATG
     AGTCAATATA ACAAAATATT TTCGATTTAC GATGATCTAA CTATATTTAC
 951 AATATGTAAT AAATTAGTAA TGTAGTATAC TAATATTAAC TCACATTTGA
     TTATACATTA TTTAATCATT ACATCATATG ATTATAATTG AGTGTAAACT
1001 CTAATTAGCT ATAAAAACCC GGGTTAATTA ATTAGTCATC AGGCAGGGCG
     GATTAATCGA TATTTTTGGG CCCAATTAAT TAATCAGTAG TCCGTCCCGC
1051 AGAACGAGAC TATCTGCTCG TTAATTAATT AGAGCTTCTT TATTCTATAC
     TCTTGCTCTG ATAGACGAGC AATTAATTAA TCTCGAAGAA ATAAGATATG
1101 TTAAAAAGTG AAAATAAATA CAAAGGTTCT TGAGGGTTGT GTTAAATTGA
     AATTTTTCAC TTTTATTTAT GTTTCCAAGA ACTCCCAACA CAATTTAACT
1151 AAGCGAGAAA TAATCATAAA TTATTTCATT ATCGCGATAT CCGTTAAGTT
     TTCGCTCTTT ATTAGTATTT AATAAAGTAA TAGCGCTATA GGCAATTCAA
                   M  G  Q  T   I  T  T   P  L  S  L   T  L  D ·
1201 TGTATCGTAA TGGGACAGAC CATCACCACC CCCCTGTCTC TCACCCTGGA
     ACATAGCATT ACCCTGTCTG GTAGTGGTGG GGGGACAGAG AGTGGGACCT
```

Figure 14B

```
      .H  W  S   E  V  R  A   R  A  H   N  Q  G   V  E  V  R ·
1251  CCACTGGTCT GAGGTGAGAG CCAGAGCCCA CAACCAGGGC GTGGAGGTGA
      GGTGACCAGA CTCCACTCTC GGTCTCGGGT GTTGGTCCCG CACCTCCACT
                                                 11369JY
                                                ~~~~~~~~~~
      ..K  K  K   W  I  T   L  C  E  A   E  W  V   M  M  N
1301  GGAAGAAGAA GTGGATCACC CTGTGTGAGG CCGAGTGGGT GATGATGAAC
      CCTTCTTCTT CACCTAGTGG GACACACTCC GGCTCACCCA CTACTACTTG
        11369JY
      ~~~~~~~~~~~~~~
       V  G  W  P   R  E  G   T  F  S   L  D  S  I   S  Q  V ·
1351  GTGGGCTGGC CTAGAGAGGG CACCTTCTCC CTGGACTCCA TCTCCCAGGT
      CACCCGACCG GATCTCTCCC GTGGAAGAGG GACCTGAGGT AGAGGGTCCA
      .E  K  K   I  F  A  P   G  P  Y   G  H  P   D  Q  V  P ·
1401  GGAGAAGAAG ATCTTCGCCC CTGGCCCTTA CGGCCACCCC GATCAGGTGC
      CCTCTTCTTC TAGAAGCGGG GACCGGGAAT GCCGGTGGGG CTAGTCCACG
      ..Y  I  T   T  W  R   S  L  A  T   D  P  P   S  W  V
1451  CCTACATCAC CACCTGGAGA TCTCTGGCCA CCGACCCTCC TAGCTGGGTG
      GGATGTAGTG GTGGACCTCT AGAGACCGGT GGCTGGGAGG ATCGACCCAC
       R  P  F  L   P  P  P   K  P  P   T  P  L  P   Q  P  L ·
1501  AGACCCTTCC TGCCCCCTCC CAAACCTCCT ACCCCTCTGC CTCAGCCTCT
      TCTGGGAAGG ACGGGGGAGG GTTTGGAGGA TGGGGAGACG GAGTCGGAGA
      .S  P  Q   P  S  A  P   L  T  S   S  L  Y   P  V  L  P ·
1551  GTCTCCTCAG CCTTCTGCCC CCCTCACCTC TTCTCTGTAC CCCGTGCTGC
      CAGAGGAGTC GGAAGACGGG GGGAGTGGAG AAGAGACATG GGGCACGACG
      ..K  P  D   P  P  K   P  P  V  L   P  P  D   P  S  S
1601  CCAAACCCGA CCCCCCTAAA CCTCCTGTGC TGCCCCCCGA CCCCTCTTCT
      GGTTTGGGCT GGGGGGATTT GGAGGACACG ACGGGGGGCT GGGGAGAAGA
       P  L  I  D   L  L  T   E  E  P   P  P  Y  P   G  G  H ·
1651  CCCCTCATCG ACCTGCTCAC CGAGGAGCCC CCTCCTTACC CTGGCGGACA
      GGGGAGTAGC TGGACGAGTG GCTCCTCGGG GGAGGAATGG GACCGCCTGT
      .G  P  P   P  S  G  P   R  T  P   T  A  S   P  I  A  S ·
1701  CGGCCCTCCT CCCTCTGGAC CCCGGACCCC TACCGCCTCT CCTATCGCCT
      GCCGGGAGGA GGGAGACCTG GGGCCTGGGG ATGGCGGAGA GGATAGCGGA
      ..R  L  R   E  R  R   E  N  P  A   E  E  S   Q  A  L
1751  CCAGGCTGAG GGAGAGAAGG GAGAACCCCG CCGAGGAATC TCAGGCCCTG
      GGTCCGACTC CCTCTCTTCC CTCTTGGGGC GGCTCCTTAG AGTCCGGGAC
       P  L  R  E   G  P  N   N  R  P   Q  Y  W  P   F  S  A ·
1801  CCTCTGAGAG AGGGCCCCAA CAACAGGCCC CAGTACTGGC CTTTCTCTGC
      GGAGACTCTC TCCCGGGGTT GTTGTCCGGG GTCATGACCG GAAAGAGACG
      .S  D  L   Y  N  W  K   S  H  N   P  P  F   S  Q  D  P ·
1851  CTCCGACCTG TACAACTGGA AGTCCCACAA CCCCCCATTC TCTCAGGACC
      GAGGCTGGAC ATGTTGACCT TCAGGGTGTT GGGGGGTAAG AGAGTCCTGG
      ..V  A  L   T  N  L   I  E  S  I   L  V  T   H  Q  P
1901  CCGTGGCCCT CACCAACCTC ATCGAGTCCA TCCTGGTGAC CCATCAGCCC
      GGCACCGGGA GTGGTTGGAG TAGCTCAGGT AGGACCACTG GGTAGTCGGG
       T  W  D  D   C  Q  Q   L  L  Q   A  L  L  T   G  E  E ·
1951  ACCTGGGACG ACTGTCAGCA ACTGCTGCAG GCTCTGCTCA CCGGCGAGGA
      TGGACCCTGC TGACAGTCGT TGACGACGTC CGAGACGAGT GGCCGCTCCT
      .R  Q  R   V  L  L  E   A  R  K   Q  V  P   G  E  D  G ·
2001  GAGACAGAGA GTGCTGCTGG AGGCCAGAAA ACAGGTGCCC GGCGAGGATG
      CTCTGTCTCT CACGACGACC TCCGGTCTTT TGTCCACGGG CCGCTCCTAC
      ..R  P  T   Q  L  P   N  V  I  D   E  T  F   P  L  T
2051  GCAGACCTAC CCAGCTGCCC AACGTGATCG ACGAGACCTT CCCACTCACC
      CGTCTGGATG GGTCGACGGG TTGCACTAGC TGCTCTGGAA GGGTGAGTGG
       R  P  N  W   D  F  A   T  P  A   G  R  E  H   L  R  L ·
2101  AGACCCAACT GGGACTTCGC CACCCCTGCC GGCAGAGAGC ACCTGAGGCT
      TCTGGGTTGA CCCTGAAGCG GTGGGGACGG CCGTCTCTCG TGGACTCCGA
```

Figure 14C

.Y R Q L L L A G L R G A A R R P T ·
2151 GTACAGACAG CTGCTGCTGG CCGGACTGAG AGGAGCCGCC AGGAGACCTA
CATGTCTGTC GACGACGACC GGCCTGACTC TCCTCGGCGG TCCTCTGGAT
..N L A Q V K Q V V Q G K E E T P
2201 CCAACCTGGC CCAGGTGAAG CAGGTGGTGC AGGGCAAAGA GGAAACCCCT
GGTTGGACCG GGTCCACTTC GTCCACCACG TCCCGTTTCT CCTTTGGGGA
A A F L E R L K E A Y R M Y T P Y ·
2251 GCCGCCTTCC TGGAGAGACT GAAGGAAGCC TACCGGATGT ACACCCCCTA
CGGCGGAAGG ACCTCTCTGA CTTCCTTCGG ATGGCCTACA TGTGGGGGAT
.D P E D P G Q A A S V I L S F I Y ·
2301 CGACCCTGAG GATCCTGGAC AGGCCGCCTC TGTGATCCTG TCCTTCATCT
GCTGGGACTC CTAGGACCTG TCCGGCGGAG ACACTAGGAC AGGAAGTAGA
..Q S S P D I R N K L Q R L E G L
2351 ACCAGTCCAG CCCCGACATC AGGAACAAGC TGCAGAGACT GGAGGGCCTG
TGGTCAGGTC GGGGCTGTAG TCCTTGTTCG ACGTCTCTGA CCTCCCGGAC
Q G F T L S D L L K E A E K I Y N ·
2401 CAGGGCTTCA CCCTGTCCGA CCTGCTGAAG GAGGCCGAGA AGATCTACAA
GTCCCGAAGT GGGACAGGCT GGACGACTTC CTCCGGCTCT TCTAGATGTT
.K R E T P E E R E E R L W Q R Q E ·
2451 CAAGCGGGAG ACCCCCGAGG AGAGAGAGGA AAGGCTGTGG CAGAGACAGG
GTTCGCCCTC TGGGGGCTCC TCTCTCTCCT TTCCGACACC GTCTCTGTCC
..E R D K K R H K E M T K V L A T
2501 AGGAGAGGGA CAAGAAGCGG CACAAGGAGA TGACCAAGGT GCTGGCCACC
TCCTCTCCCT GTTCTTCGCC GTGTTCCTCT ACTGGTTCCA CGACCGGTGG
V V A Q N R D K D R E E S K L G D ·
2551 GTGGTGGCCC AGAACAGGGA CAAGGACAGG GAGGAGTCTA AGCTGGGCGA
CACCACCGGG TCTTGTCCCT GTTCCTGTCC CTCCTCAGAT TCGACCCGCT
.Q R K I P L G K D Q C A Y C K E K ·
2601 CCAGAGGAAA ATCCCCCTGG GCAAGGACCA GTGCGCCTAC TGTAAGGAGA
GGTCTCCTTT TAGGGGGACC CGTTCCTGGT CACGCGGATG ACATTCCTCT
..G H W V R D C P K R P R K K P A
2651 AGGGCCACTG GGTGAGAGAT TGCCCCAAGA GGCCCAGAAA GAAGCCCGCC
TCCCGGTGAC CCACTCTCTA ACGGGGTTCT CCGGGTCTTT CTTCGGGCGG
N S T L L N L G D * E S Q G Q D P ·
2701 AACTCCACCC TGCTCAACTT AGGAGATTAG GAGAGTCAGG GCCAGGACCC
TTGAGGTGGG ACGAGTTGAA TCCTCTAATC CTCTCAGTCC CGGTCCTGGG
~~~~~~~~~~~~~~~~~~~~~~~
11377JY
.P P E P R I T L K I G G Q P V T F ·
2751 TCCACCTGAG CCCAGAATCA CCCTGAAGAT CGGCGGCCAG CCCGTGACCT
AGGTGGACTC GGGTCTTAGT GGGACTTCTA GCCGCCGGTC GGGCACTGGA
..L V D T G A Q H S V L T R P D G
2801 TCCTGGTGGA CACCGGAGCC CAGCACTCTG TGCTCACAAG ACCCGACGGC
AGGACCACCT GTGGCCTCGG GTCGTGAGAC ACGAGTGTTC TGGGCTGCCG
P L S D R T A L V Q G A T G S K N ·
2851 CCCCTGTCCG ATAGAACCGC CCTGGTGCAG GGAGCCACCG GCTCCAAGAA
GGGGACAGGC TATCTTGGCG GGACCACGTC CCTCGGTGGC CGAGGTTCTT
.Y R W T T D R R V Q L A T G K V T ·
2901 CTACAGGTGG ACCACCGACA GAAGGGTGCA GCTGGCCACA GGAAAGGTGA
GATGTCCACC TGGTGGCTGT CTTCCCACGT CGACCGGTGT CCTTTCCACT
..H S F L Y V P E C P Y P L L G R
2951 CCCACTCCTT CCTGTACGTG CCCGAGTGTC CCTACCCTCT GCTGGGCAGA
GGGTGAGGAA GGACATGCAC GGGCTCACAG GGATGGGAGA CGACCCGTCT
D L L T K L K A Q I H F T G E G A ·
3001 GATCTGCTCA CCAAGCTGAA GGCCCAGATC CACTTCACCG GCGAAGGCGC
CTAGACGAGT GGTTCGACTT CCGGGTCTAG GTGAAGTGGC CGCTTCCGCG
.N V V G P R G L P L Q V L * *
3051 CAATGTGGTG GGCCCCAGAG GACTGCCCCT GCAGGTGCTG TAATGATTTT
GTTACACCAC CCGGGGTCTC CTGACGGGGA CGTCCACGAC ATTACTAAAA
~~~~~~~~~~~~~~~~~~~~~~~

Figure 14D

3101 TCTTGACTAG TTAATCAAAT AAAAAGCATA CAAGCTATTG CTTCGCTATC
AGAACTGATC AATTAGTTTA TTTTTCGTAT GTTCGATAAC GAAGCGATAG
3151 GTTACAAAAT GGCAGGAATT TTGTGTAAAC TAAGCCACAT ACTTGCCAAT
CAATGTTTTA CCGTCCTTAA AACACATTTG ATTCGGTGTA TGAACGGTTA
3201 GAAAAAAATA GTAGAAAGGA TACTATTTTA ATGGGATTAG ATGTTAAGGT
CTTTTTTTAT CATCTTTCCT ATGATAAAAT TACCCTAATC TACAATTCCA
3251 TCCTTGGGAT TATAGTAACT GGGCATCTGT TAACTTTTAC GACGTTAGGT
AGGAACCCTA ATATCATTGA CCCGTAGACA ATTGAAAATG CTGCAATCCA
3301 TAGATACTGA TGTTACAGAT TATAATAATG TTACAATAAA ATACATGACA
ATCTATGACT ACAATGTCTA ATATTATTAC AATGTTATTT TATGTACTGT
3351 GGATGTGATA TTTTTCCTCA TATAACTCTT GGAATAGCAA ATATGGATCA
CCTACACTAT AAAAAGGAGT ATATTGAGAA CCTTATCGTT TATACCTAGT
3401 ATGTGATAGA TTTGAAAATT TCAAAAAGCA AATAACTGAT CAAGATTTAC
TACACTATCT AAACTTTTAA AGTTTTTCGT TTATTGACTA GTTCTAAATG
3451 AGACTATTTC TATAGTCTGT AAAGAAGAGA TGTGTTTTCC TCAGAGTAAC
TCTGATAAAG ATATCAGACA TTTCTTCTCT ACACAAAAGG AGTCTCATTG
3501 GCCTCTAAAC AGTTGGGAGC GAAAGGATGC GCTGTAGTTA TGAAACTGGA
CGGAGATTTG TCAACCCTCG CTTTCCTACG CGACATCAAT ACTTTGACCT
3551 GGTATCTGAT GAACTTAGAG CCCTAAGAAA TGTTCTGCTG AATGCGGTAC
CCATAGACTA CTTGAATCTC GGGATTCTTT ACAAGACGAC TTACGCCATG
3601 CCTGTTCGAA GGACGTGTTT GGTGATATCA CAGTAGATAA TCCGTGGAAT
GGACAAGCTT CCTGCACAAA CCACTATAGT GTCATCTATT AGGCACCTTA
3651 CCTCACATAA CAGTAGGATA TGTTAAGGAG GACGATGTCG AAAACAAGAA
GGAGTGTATT GTCATCCTAT ACAATTCCTC CTGCTACAGC TTTTGTTCTT
3701 ACGCCTAATG GAGTGCATGT CCAAGTTTAG GGGGCAAGAA ATACAAGTTC
TGCGGATTAC CTCACGTACA GGTTCAAATC CCCCGTTCTT TATGTTCAAG
3751 TAGGATGGTA TTAATAAGTA TCTAAGTATT TGGTATAATT TATTAAATAG
ATCCTACCAT AATTATTCAT AGATTCATAA ACCATATTAA ATAATTTATC
3801 TATAATTATA ACAAATAATA AATAACATGA TAACGGTTTT TATTAGAATA
ATATTAATAT TGTTTATTAT TTATTGTACT ATTGCCAAAA ATAATCTTAT
3851 AAATAGAGAT AATATCATAA TGATATATAA TACTTCATTA CCAGAAATGA
TTTATCTCTA TTATAGTATT ACTATATATT ATGAAGTAAT GGTCTTTACT
3901 GTAATGGAAG ACTTATAAAT GAACTGCATA AAGCTATAAG GTATAGAGAT
CATTACCTTC TGAATATTTA CTTGACGTAT TTCGATATTC CATATCTCTA
3951 ATAAATTTAG TAAGGTATAT ACTTAAAAAA TGCAAATACA ATAACGTAAA
TATTTAAATC ATTCCATATA TGAATTTTTT ACGTTTATGT TATTGCATTT
4001 TATACTATCA ACGTCTTTGT ATTTAGCCGT AAGTATTTCT GATATAGAAA
ATATGATAGT TGCAGAAACA TAAATCGGCA TTCATAAAGA CTATATCTTT
4051 TGGTAAAATT ATTACTAGAA CACGGTGCCG ATATTTTAAA ATGTAAAAAT
ACCATTTTAA TAATGATCTT GTGCCACGGC TATAAAATTT TACATTTTTA
4101 CCTCCTCTTC ATAAAGCTGC TAGTTTAGAT AATACAGAAA TTGCTAAACT
GGAGGAGAAG TATTTCGACG ATCAAATCTA TTATGTCTTT AACGATTTGA
4151 ACTAATAGAT TCTGGCGCTG ACATAGAACA GATACATTCT GGAAATAGTC
TGATTATCTA AGACCGCGAC TGTATCTTGT CTATGTAAGA CCTTTATCAG
4201 CGTTATATAT TTCTGTATAT AGAAACAATA AGTCATTAAC TAGATATTTA
GCAATATATA AAGACATATA TCTTTGTTAT TCAGTAATTG ATCTATAAAT
4251 TTAAAAAAAG GTGTTAATTG TAATAGATTC TTTCTAAATT ATTACGATGT
AATTTTTTTC CACAATTAAC ATTATCTAAG AAAGATTTAA TAATGCTACA
4301 ACTGTATGAT AAGATATCTG ATGATATGTA TAAAATATTT ATAGATTTTA
TGACATACTA TTCTATAGAC TACTATACAT ATTTTATAAA TATCTAAAAT
4351 ATATTGATCT TAATATACAA ACTAGAAATT TTGAAACTCC GTTACATTAC
TATAACTAGA ATTATATGTT TGATCTTTAA AACTTTGAGG CAATGTAATG
4401 GCTATAAAGT ATAAGAATAT AGATTTAATT AGGATATTGT TAGATAATAG
CGATATTTCA TATTCTTATA TCTAAATTAA TCCTATAACA ATCTATTATC
4451 TATTAAAATA GATAAAAGTT TATTTTTGCA TAAACAGTAT CTCATAAAGG
ATAATTTTAT CTATTTTCAA ATAAAAACGT ATTTGTCATA GAGTATTTCC
4501 CACTTAAAAA TAATTGTAGT TACGATATAA TAGCGTTACT TATAAATCAC
GTGAATTTTT ATTAACATCA ATGCTATATT ATCGCAATGA ATATTTAGTG
4551 GGAGTGCCTA TAAACGAACA AGATGATTTA GGTAAAACCC CATTACATCA
CCTCACGGAT ATTTGCTTGT TCTACTAAAT CCATTTTGGG GTAATGTAGT

Figure 14E

```
4601   TTCGGTAATT AATAGAAGAA AAGATGTAAC AGCACTTCTG TTAAATCTAG
       AAGCCATTAA TTATCTTCTT TTCTACATTG TCGTGAAGAC AATTTAGATC
4651   GAGCTGATAT AAACGTAATA GATGACTGTA TGGGCAGTCC CTTACATTAC
       CTCGACTATA TTTGCATTAT CTACTGACAT ACCCGTCAGG GAATGTAATG
4701   GCTGTTTCAC GTAACGATAT CGAAACAACA AAGACACTTT TAGAAAGAGG
       CGACAAAGTG CATTGCTATA GCTTTGTTGT TTCTGTGAAA ATCTTTCTCC
4751   ATCTAATGTT AATGTGGTTA ATAATCATAT AGATACCGTT CTAAATATAG
       TAGATTACAA TTACACCAAT TATTAGTATA TCTATGGCAA GATTTATATC
4801   CTGTTGCATC TAAAAACAAA ACTATAGTAA ACTTATTACT GAAGTACGGT
       GACAACGTAG ATTTTTGTTT TGATATCATT TGAATAATGA CTTCATGCCA
4851   ACTGATACAA AGTTGGTAGG ATTAGATAAA CATGTTATTC ACATAGCTAT
       TGACTATGTT TCAACCATCC TAATCTATTT GTACAATAAG TGTATCGATA
4901   AGAAATGAAA GATATTAATA TACTGAATGC GATCTTATTA TATGGTTGCT
       TCTTTACTTT CTATAATTAT ATGACTTACG CTAGAATAAT ATACCAACGA
4951   ATGTAAACGT CTATAATCAT AAAGGTTTCA CTCCTCTATA CATGGCAGTT
       TACATTTGCA GATATTAGTA TTTCCAAAGT GAGGAGATAT GTACCGTCAA
5001   AGTTCTATGA AAACAGAATT TGTTAAACTC TTACTTGACC ACGGTGCTTA
       TCAAGATACT TTTGTCTTAA ACAATTTGAG AATGAACTGG TGCCACGAAT
5051   CGTAAATGCT AAAGCTAAGT TATCTGGAAA TACTCCTTTA CATAAAGCTA
       GCATTTACGA TTTCGATTCA ATAGACCTTT ATGAGGAAAT GTATTTCGAT
5101   TGTTATCTAA TAGTTTTAAT AATATAAAAT TACTTTTATC TTATAACGCC
       ACAATAGATT ATCAAAATTA TTATATTTTA ATGAAAATAG AATATTGCGG
5151   GACTATAATT CTCTAAATAA TCACGGTAAT ACGCCTCTAA CTTGTGTTAG
       CTGATATTAA GAGATTTATT AGTGCCATTA TGCGGAGATT GAACACAATC
5201   CTTTTTAGAT GACAAGATAG CTATTATGAT AATATCTAAA ATGATGTTAG
       GAAAAATCTA CTGTTCTATC GATAATACTA TTATAGATTT TACTACAATC
5251   AAATATCTAA AAATCCTGAA ATAGCTAATT CAGAAGGTTT TATAGTAAAC
       TTTATAGATT TTTAGGACTT TATCGATTAA GTCTTCCAAA ATATCATTTG
5301   ATGGAACATA TAAACAGTAA TAAAAGACTA CTATCTATAA AAGAATCATG
       TACCTTGTAT ATTTGTCATT ATTTTCTGAT GATAGATATT TTCTTAGTAC
5351   CGAAAAAGAA CTAGATGTTA TAACACATAT AAAGTTAAAT TCTATATATT
       GCTTTTTCTT GATCTACAAT ATTGTGTATA TTTCAATTTA AGATATATAA
5401   CTTTTAATAT CTTTCTTGAC AATAACATAG ATCTTATGGT AAAGTTCGTA
       GAAAATTATA GAAAGAACTG TTATTGTATC TAGAATACCA TTTCAAGCAT
5451   ACTAATCCTA GAGTTAATAA GATACCTGCA TGTATACGTA TATATAGGGA
       TGATTAGGAT CTCAATTATT CTATGGACGT ACATATGCAT ATATATCCCT
5501   ATTAATACGG AAAAATAAAT CATTAGCTTT TCATAGACAT CAGCTAATAG
       TAATTATGCC TTTTTATTTA GTAATCGAAA AGTATCTGTA GTCGATTATC
5551   TTAAAGCTGT AAAAGAGAGT AAGAATCTAG GAATAATAGG TAGGTTACCT
       AATTTCGACA TTTTCTCTCA TTCTTAGATC CTTATTATCC ATCCAATGGA
5601   ATAGATATCA AACATATAAT AATGGAACTA TTAAGTAATA ATGATTTACA
       TATCTATAGT TTGTATATTA TTACCTTGAT AATTCATTAT TACTAAATGT
5651   TTCTGTTATC ACCAGCTGTT GTAACCCAGT AGTATAAAGT GATTTTATTC
       AAGACAATAG TGGTCGACAA CATTGGGTCA TCATATTTCA CTAAAATAAG
5701   AATTACGAAG ATAAACATTA AATTTGTTAA CAGATATGAG TTATGAGTAT
       TTAATGCTTC TATTTGTAAT TTAAACAATT GTCTATACTC AATACTCATA
                                        ~~~~~~~~~~~~~~~~~~~~~
                                               8104JY

5751   TTAACTA
       AATTGAT
       .......
``` vCP2296 C5 region map showing primer locations:

Fragment of vCP2296

4675 bp (molecule 331774 bp)

Figure 18A vCP2295 annotated sequence (SEQ ID NO:8)

Color Key: Sequencing Primers; C5 Arms; FeLV ENV; Promoter

```
                7932DC
        ~~~~~~~~~~~~~~~~~~~~~~~~~~~~~
   1    TGATTATAGC TATTATCACA GACTCATTCA ATTTCATCTT ATTAGCAGAG
        ACTAATATCG ATAATAGTGT CTGAGTAAGT TAAAGTAGAA TAATCGTCTC
  51    TTAACATAAT CTTCTATTAT CGATATATTT TTTTCGTCTT CAGCTGTAAA
        AATTGTATTA GAAGATAATA GCTATATAAA AAAAGCAGAA GTCGACATTT
 101    CAAATATAAT GAAAAGTATT CTAAACTAGG AATAGATGAA ATTATGTGCA
        GTTTATATTA CTTTTCATAA GATTTGATCC TTATCTACTT TAATACACGT
 151    AAGGAGATAC CTTTAGATAT GGATCTGATT TATTTGGTTT TTCATAATCA
        TTCCTCTATG GAAATCTATA CCTAGACTAA ATAAACCAAA AAGTATTAGT
 201    TAATCTAACA ACATTTTCAC TATACTATAC CTTCTTGCAC AAGTCGCCAT
        ATTAGATTGT TGTAAAAGTG ATATGATATG GAAGAACGTG TTCAGCGGTA
 251    TAGTAGTATA GACTTATACT TTGTAACCAT AGTATACTTT AGCGCGTCAT
        ATCATCATAT CTGAATATGA AACATTGGTA TCATATGAAA TCGCGCAGTA
 301    CTTCTTCATC TAAAACAGAT TTACAACAAT AATCATCGTC GTCATCTTCA
        GAAGAAGTAG ATTTTGTCTA AATGTTGTTA TTAGTAGCAG CAGTAGAAGT
 351    TCTTCATTAA AGTTTTCATA TTCAATAACT TTCTTTTCTA AAACATCATC
        AGAAGTAATT TCAAAAGTAT AAGTTATTGA AAGAAAAGAT TTTGTAGTAG
 401    TGAATCAATA AACATAGAAC GGTATAGAGC GTTAATCTCC ATTGTAAAAT
        ACTTAGTTAT TTGTATCTTG CCATATCTCG CAATTAGAGG TAACATTTTA
 451    ATACTAACGC GTTGCTCATG ATGTACTTTT TTTCATTATT TAGAAATTAT
        TATGATTGCG CAACGAGTAC TACATGAAAA AAAGTAATAA ATCTTTAATA
 501    GCATTTTAGA TCTTTATAAG CGGCCGTGAT TAACTAGTCA TAAAAACCCG
        CGTAAAATCT AGAAATATTC GCCGGCACTA ATTGATCAGT ATTTTTGGGC
 551    GGATCGATTC TAGACTCGAG CGGGGATCTC TTTATTCTAT ACTTAAAAAG
        CCTAGCTAAG ATCTGAGCTC GCCCCTAGAG AAATAAGATA TGAATTTTTC
 601    TGAAAATAAA TACAAAGGTT CTTGAGGGTT GTGTTAAATT GAAAGCGAGA
        ACTTTTATTT ATGTTTCCAA GAACTCCCAA CACAATTTAA CTTTCGCTCT
 651    AATAATCATA AATTATTTCA TTATCGCGAT ATCCGTTAAG TTTGTATCGT
        TTATTAGTAT TTAATAAAGT AATAGCGCTA TAGGCAATTC AAACATAGCA
 701    AATGGAAAGT CCAACGCACC CAAAACCCTC TAAAGATAAG ACTCTCTCGT
        TTACCTTTCA GGTTGCGTGG GTTTTGGGAG ATTTCTATTC TGAGAGAGCA
 751    GGAACTTAGC GTTTCTGGTG GGGATCTTAT TTACAATAGA CATAGGAATG
        CCTTGAATCG CAAAGACCAC CCCTAGAATA AATGTTATCT GTATCCTTAC
 801    GCCAATCCTA GTCCACACCA AATATATAAT GTAACTTGGG TAATAACCAA
        CGGTTAGGAT CAGGTGTGGT TTATATATTA CATTGAACCC ATTATTGGTT
 851    TGTACAAACT AACACCCAAG CTAACGCCAC CTCTATGTTA GGAACCTTAA
        ACATGTTTGA TTGTGGGTTC GATTGCGGTG GAGATACAAT CCTTGGAATT
 901    CCGATGCCTA CCCTACCCTA CATGTTGACT TATGTGACCT AGTGGGAGAC
        GGCTACGGAT GGGATGGGAT GTACAACTGA ATACACTGGA TCACCCTCTG
 951    ACCTGGGAAC CTATAGTCCT AAACCCAACC AATGTAAAAC ACGGGGCACG
        TGGACCCTTG GATATCAGGA TTTGGGTTGG TTACATTTTG TGCCCCGTGC
1001    TTACTCCTCC TCAAAATATG GATGTAAAAC TACAGATAGA AAAAAACAGC
        AATGAGGAGG AGTTTTATAC CTACATTTTG ATGTCTATCT TTTTTTGTCG
1051    AACAGACATA CCCCTTTTAC GTCTGCCCCG GACATGCCCC CTCGTTGGGG
        TTGTCTGTAT GGGGAAAATG CAGACGGGGC CTGTACGGGG GAGCAACCCC
1101    CCAAAGGGAA CACATTGTGG AGGGGCACAA GATGGGTTTT GTGCCGCATG
        GGTTTCCCTT GTGTAACACC TCCCCGTGTT CTACCCAAAA CACGGCGTAC
1151    GGGATGTGAG ACCACCGGAG AAGCTTGGTG GAAGCCCACC TCCTCATGGG
        CCCTACACTC TGGTGGCCTC TTCGAACCAC CTTCGGGTGG AGGAGTACCC
```

Figure 18B

| | | | | | |
|---|---|---|---|---|---|
| 1201 | ACTATATCAC | AGTAAAAAGA | GGGAGTAGTC | AGGACAATAG | CTGTGAGGGA |
| | TGATATAGTG | TCATTTTTCT | CCCTCATCAG | TCCTGTTATC | GACACTCCCT |
| 1251 | AAATGCAACC | CCCTGGTTTT | GCAGTTCACC | CAGAAGGGAA | GACAAGCCTC |
| | TTTACGTTGG | GGGACCAAAA | CGTCAAGTGG | GTCTTCCCTT | CTGTTCGGAG |
| 1301 | TTGGGACGGA | CCTAAGATGT | GGGGATTGCG | ACTATACCGT | ACAGGATATG |
| | AACCCTGCCT | GGATTCTACA | CCCCTAACGC | TGATATGGCA | TGTCCTATAC |
| 1351 | ACCCTATCGC | TTTATTCACG | GTGTCCCGGC | AGGTATCAAC | CATTACGCCG |
| | TGGGATAGCG | AAATAAGTGC | CACAGGGCCG | TCCATAGTTG | GTAATGCGGC |
| 1401 | CCTCAGGCAA | TGGGACCAAA | CCTAGTCTTA | CCTGATCAAA | AACCCCCATC |
| | GGAGTCCGTT | ACCCTGGTTT | GGATCAGAAT | GGACTAGTTT | TTGGGGGTAG |
| 1451 | CCGACAATCT | CAAACAGGGT | CCAAAGTGGC | GACCCAGAGG | CCCCAAACGA |
| | GGCTGTTAGA | GTTTGTCCCA | GGTTTCACCG | CTGGGTCTCC | GGGGTTTGCT |
| 1501 | ATGAAAGCGC | CCCAAGGTCT | GTTGCCCCCA | CCACCATGGG | TCCCAAACGG |
| | TACTTTCGCG | GGGTTCCAGA | CAACGGGGGT | GGTGGTACCC | AGGGTTTGCC |
| 1551 | ATTGGGACCG | GAGATAGGTT | AATAAATTTA | GTACAAGGGA | CATACCTAGC |
| | TAACCCTGGC | CTCTATCCAA | TTATTTAAAT | CATGTTCCCT | GTATGGATCG |
| 1601 | CTTAAATGCC | ACCGACCCCA | ACAAAACTAA | AGACTGTTGG | CTCTGCCTGG |
| | GAATTTACGG | TGGCTGGGGT | TGTTTTGATT | TCTGACAACC | GAGACGGACC |
| 1651 | TTTCTCGACC | ACCCTATTAC | GAAGGGATTG | CAATCTTAGG | TAACTACAGC |
| | AAAGAGCTGG | TGGGATAATG | CTTCCCTAAC | GTTAGAATCC | ATTGATGTCG |
| 1701 | AACCAAACAA | ACCCCCCCCC | ATCCTGCCTA | TCTACTCCGC | AACACAAACT |
| | TTGGTTTGTT | TGGGGGGGGG | TAGGACGGAT | AGATGAGGCG | TTGTGTTTGA |
| 1751 | AACTATATCT | GAAGTATCAG | GGCAAGGAAT | GTGCATAGGG | ACTGTTCCTA |
| | TTGATATAGA | CTTCATAGTC | CCGTTCCTTA | CACGTATCCC | TGACAAGGAT |
| 1801 | AAACCCACCA | GGCTTTGTGC | AATAAGACAC | AACAGGGACA | TACAGGGGCG |
| | TTTGGGTGGT | CCGAAACACG | TTATTCTGTG | TTGTCCCTGT | ATGTCCCCGC |
| 1851 | CACTATCTAG | CCGCCCCCAA | CGGCACCTAT | TGGGCCTGTA | ACACTGGACT |
| | GTGATAGATC | GGCGGGGGTT | GCCGTGGATA | ACCCGGACAT | TGTGACCTGA |
| 1901 | CACCCCATGC | ATTTCCATGG | CGGTGCTCAA | TTGGACCTCT | GAATTCTGTG |
| | GTGGGGTACG | TAAAGGTACC | GCCACGAGTT | AACCTGGAGA | CTTAAGACAC |
| 1951 | TCTTAATCGA | ATTATGGCCC | AGAGTGACTT | ACCATCAACC | CGAATATGTG |
| | AGAATTAGCT | TAATACCGGG | TCTCACTGAA | TGGTAGTTGG | GCTTATACAC |
| 2001 | TACACACATT | TTGCCAAAGC | TGTCAGGTTC | CGAAGAGAAC | CAATATCACT |
| | ATGTGTGTAA | AACGGTTTCG | ACAGTCCAAG | GCTTCTCTTG | GTTATAGTGA |
| 2051 | AACGGTTGCC | CTTATGTTGG | GAGGACTTAC | TGTAGGGGGC | ATAGCCGCGG |
| | TTGCCAACGG | GAATACAACC | CTCCTGAATG | ACATCCCCCG | TATCGGCGCC |
| 2101 | GGGTCGGAAC | AGGGACTAAA | GCCCTCCTTG | AAACAGCCCA | GTTTAGACAA |
| | CCCAGCCTTG | TCCCTGATTT | CGGGAGGAAC | TTTGTCGGGT | CAAATCTGTT |
| 2151 | CTACAAATGG | CCATGCACAC | AGACATCCAG | GCCCTAGAAG | AATCAATTAG |
| | GATGTTTACC | GGTACGTGTG | TCTGTAGGTC | CGGGATCTTC | TTAGTTAATC |
| 2201 | TGCCTTAGAA | AAGTCCCTGA | CCTCCCTTTC | TGAAGTAGTC | TTACAAAACA |
| | ACGGAATCTT | TTCAGGGACT | GGAGGGAAAG | ACTTCATCAG | AATGTTTTGT |
| 2251 | GACGGGGCCT | AGATATTCTA | TTCTTACAAG | AGGGAGGGCT | CTGTGCCGCA |
| | CTGCCCCGGA | TCTATAAGAT | AAGAATGTTC | TCCCTCCCGA | GACACGGCGT |
| 2301 | TTGAAAGAAG | AATGTTGCTT | CTATGCGGAT | CACACCGGAC | TCGTCCGAGA |
| | AACTTTCTTC | TTACAACGAA | GATACGCCTA | GTGTGGCCTG | AGCAGGCTCT |
| 2351 | CAATATGGCC | AAATTAAGAG | AAAGACTAAA | ACAGCGGCAA | CAATTGTTTG |
| | GTTATACCGG | TTTAATTCTC | TTTCTGATTT | TGTCGCCGTT | GTTAACAAAC |
| 2401 | ACTCCCAACA | GGGATGGTTT | GAAGGATGGT | TCAACAAGTC | CCCCTGGTTT |
| | TGAGGGTTGT | CCCTACCAAA | CTTCCTACCA | AGTTGTTCAG | GGGGACCAAA |
| 2451 | ACAACCCTAA | TTTCCTCCAT | TATGGGCCCC | TTACTAATCC | TACTCCTAAT |
| | TGTTGGGATT | AAAGGAGGTA | ATACCCGGGG | AATGATTAGG | ATGAGGATTA |

Figure 18C

2501 TCTCCTCTTC GGCCCATGCA TCCTTAACCG ATTAGTACAA TTCGTAAAAG
AGAGGAGAAG CCGGGTACGT AGGAATTGGC TAATCATGTT AAGCATTTTC
2551 ACAGAATATC TGTGGTACAG GCTTTAATTT TAACCCAACA GTACCAACAG
TGTCTTATAG ACACCATGTC CGAAATTAAA ATTGGGTTGT CATGGTTGTC
2601 ATAAAGCAAT ACGATCCGGA CCGACCATGA TTTTTCTGGA TCCTTTTTAT
TATTTCGTTA TGCTAGGCCT GGCTGGTACT AAAAAGACCT AGGAAAAATA
2651 AGCTAATTAG TCACGTACCT TTGAGAGTAC CACTTCAGCT ACCTCTTTTG
TCGATTAATC AGTGCATGGA AACTCTCATG GTGAAGTCGA TGGAGAAAAC
2701 TGTCTCAGAG TAACTTTCTT TAATCAATTC CAAAACAGTA TATGATTTTC
ACAGAGTCTC ATTGAAAGAA ATTAGTTAAG GTTTTGTCAT ATACTAAAAG
2751 CATTTCTTTC AAAGATGTAG TTTACATCTG CTCCTTTGTT GAAAAGTAGC
GTAAAGAAAG TTTCTACATC AAATGTAGAC GAGGAAACAA CTTTTCATCG
2801 CTGAGCACTT CTTTTCTACC ATGAATTACA GCTGGCAAGA TCAATTTTTC
GACTCGTGAA GAAAAGATGG TACTTAATGT CGACCGTTCT AGTTAAAAAG
2851 CCAGTTCTGG ACATTTTATT TTTTTTAAGT AGTGTGCTAC ATATTTCAAT
GGTCAAGACC TGTAAAATAA AAAAAATTCA TCACACGATG TATAAAGTTA
2901 ATTTCCAGAT TGTACAGCGA TCATTAAAGG AGTACGTCCC ATGTTATCCA
TAAAGGTCTA ACATGTCGCT AGTAATTTCC TCATGCAGGG TACAATAGGT
2951 GCAAGTCAGT ATCAGCACCT TTGTTCAATA GAAGTTTAAC CATTGTTAAA
CGTTCAGTCA TAGTCGTGGA AACAAGTTAT CTTCAAATTG GTAACAATTT
3001 TTTTTATTTG ATACGGCTAT ATGTAGAGGA GTTAACCGAT CCGTGTTTGA
AAAAATAAAC TATGCCGATA TACATCTCCT CAATTGGCTA GGCACAAACT
3051 AATATCTACA TCCGCCGAAT GAGCCAATAG AAGTTTAACC AAATTAACTT
TTATAGATGT AGGCGGCTTA CTCGGTTATC TTCAAATTGG TTTAATTGAA
3101 TGTTAAGGTA AGCTGCCAAA CACAAAGGAG TAAAGCCTCC GCTGTAAAGA
ACAATTCCAT TCGACGGTTT GTGTTTCCTC ATTTCGGAGG CGACATTTCT
3151 ACATTGTTTA CATAGTTATT CTTCAACAGA TCTTTCACTA TTTTGTAGTC
TGTAACAAAT GTATCAATAA GAAGTTGTCT AGAAAGTGAT AAAACATCAG
3201 GTCTCTCAAC ACCGCATCAT GCAGACAAGA AGTTGTGCAT TCAGTAACTA
CAGAGAGTTG TGGCGTAGTA CGTCTGTTCT TCAACACGTA AGTCATTGAT
3251 CAGGTTTAGC TCCATACCTC ATCAAGATTT TTATAGCCTC GGTATTCTTG
GTCCAAATCG AGGTATGGAG TAGTTCTAAA AATATCGGAG CCATAAGAAC
3301 AACATTACAG CCATTTCAAG AGGAGATTGT AGAGTACCAT ATTCCGTGTT
TTGTAATGTC GGTAAAGTTC TCCTCTAACA TCTCATGGTA TAAGGCACAA
3351 AGGGTCGAAT CCATTGTCCA AAAACCTATT TAGAGATGCA TTGTCATTAT
TCCCAGCTTA GGTAACAGGT TTTTGGATAA ATCTCTACGT AACAGTAATA
3401 CCATGATAGC CTCACAGACG TATATGTAAG CCATCTTGAA TGTATAATTT
GGTACTATCG GAGTGTCTGC ATATACATTC GGTAGAACTT ACATATTAAA
3451 TGTTGTTTTC AACAACCGCT CGTGAACAGC TTCTATACTT TTTCATTTTC
ACAACAAAAG TTGTTGGCGA GCACTTGTCG AAGATATGAA AAAGTAAAAG
3501 TTCATGATTA ATATAGTTTA CGGAATATAA GTATACAAAA AGTTTATAGT
AAGTACTAAT TATATCAAAT GCCTTATATT CATATGTTTT TCAAATATCA
3551 AATCTCATAA TATCTGAAAC ACATACATAA AACATGGAAG AATTACACGA
TTAGAGTATT ATAGACTTTG TGTATGTATT TTGTACCTTC TTAATGTGCT
3601 TGTCGTTGAG ATAAATGGCT TTTTATTGTC ATAGTTTACA AATTCGCAGT
ACAGCAACTC TATTTACCGA AAAATAACAG TATCAAATGT TTAAGCGTCA
3651 AATCTTCATC TTTTACGAAT ATTGCAGAAT CTGTTTTATC CAACCAGTGA
TTAGAAGTAG AAAATGCTTA TAACGTCTTA GACAAAATAG GTTGGTCACT
3701 TTTTTGTATA ATATAACTGG TATCCTATCT TCCGATAGAA TGCTGTTATT
AAAAACATAT TATATTGACC ATAGGATAGA AGGCTATCTT ACGACAATAA
3751 TAACATTTTT GCACCTATTA AGTTACATCT GTCAAATCCA TCTTTCCAAC
ATTGTAAAAA CGTGGATAAT TCAATGTAGA CAGTTTAGGT AGAAAGGTTG

Figure 18D

3801 TGACTTTATG TAACGATGCG AAATAGCATT TATCACTATG TCGTACCCAA
ACTGAAATAC ATTGCTACGC TTTATCGTAA ATAGTGATAC AGCATGGGTT
3851 TTATCATGAC AAGATTCTCT TAAATACGTA ATCTTATTAT CTCTTGCATA
AATAGTACTG TTCTAAGAGA ATTTATGCAT TAGAATAATA GAGAACGTAT
3901 TTCGTAATAG TAATTGTAAA GAGTATACGA TAACAGTATA GATATACACG
AAGCATTATC ATTAACATTT CTCATATGCT ATTGTCATAT CTATATGTGC
3951 TGATATAAAT ATTTAACCCC ATTCCTGAGT AAAATAATTA CGATATTACA
ACTATATTTA TAAATTGGGG TAAGGACTCA TTTTATTAAT GCTATAATGT
4001 TTTCCTTTTA TTATTTTTAT GTTTTAGTTA TTTGTTAGGT TATACAAAAA
AAAGGAAAAT AATAAAAATA CAAAATCAAT AAACAATCCA ATATGTTTTT
4051 TTATGTTTAT TTGTGTATAT TTAAAGCGTC GTTAAGAATA AGCTTAGTTA
AATACAAATA AACACATATA AATTTCGCAG CAATTCTTAT TCGAATCAAT
4101 ACATATTATC GCTTAGGTTT TGTAGTATTT GAATCCTTTC TTTAAATGGA
TGTATAATAG CGAATCCAAA ACATCATAAA CTTAGGAAAG AAATTTACCT
4151 TTATTTTTCC AATGCATATT TATAGCTTCA TCCAAAGTAT AACATTTAAC
AATAAAAAGG TTACGTATAA ATATCGAAGT AGGTTTCATA TTGTAAATTG
4201 ATTCATTGCC ATAGTCAATA GTTCTCTCCT ACGAGAACCT ATATTTATAA
TAAGTAACGG TATCAGTTAT CAAGAGAGGA TGCTCTTGGA TATAAATATT
4251 TATCGTTCAT GCAATAACGG TACATAGTCA TTTTATCACG CGTCTCGATT
ATAGCAAGTA CGTTATTGCC ATGTATCAGT AAAATAGTGC GCAGAGCTAA
4301 AATTTATCCA AGTAACTAAC TAACAGATTC
TTAAATAGGT TCATTGATTG ATTGTCTAAG
~~~~~
~~~~~

Evolution of the mean proviremia per group after challenge

Evolution of the mean proviremia per group and p27 status after challenge

Proviremia in marrow function of p27 status

FeLV specific-IFNγ response on D35

FeLV specific (env peptide pool n°1) (IFNγ respone on D35)

FeLV specific (env peptide pools) IL-10 response on D35

FeLV specific (gag/pro peptide pools) – IL-20 response on D35

FeLV specific (env stimulation) – IFNγ/IL-10 ratio on D35

FeLV specific (env stimulation) – IFNγ/IL-10 ratio on D35

FeLV specific (gag/pro stimulation) – IFNγ response on D126

FeLV specific IFNγ/IL-10 ratio FeLV env and gag/pro peptide pools on D35

RECOMBINANT FELINE LEUKEMIA VIRUS VACCINE CONTAINING OPTIMIZED FELINE LEUKEMIA VIRUS ENVELOPE GENE

CROSS-REFERENCE TO RELATED APPLICATIONS

This application claims priority to U.S. provisional application 61/509,912 filed Jul. 20, 2011, and is a continuation-in-part of U.S. application Ser. No. 11/547,399 filed Mar. 30, 2005.

FIELD OF THE INVENTION

The present invention relates to compositions or vaccines for combating feline leukemia virus infections in animals. Specifically, the present invention provides vectors that contain and express in vivo or in vitro optimized feline leukemia virus envelope antigens that elicit an immune response in animals against feline leukemia virus, including compositions comprising said vectors, methods of vaccination against feline leukemia virus, and kits for use with such methods and compositions.

BACKGROUND OF THE INVENTION

Feline Leukemia Virus (FeLV) is a common cause of infection of domestic cats throughout the world and a cause of significant morbidity and mortality. The prevalence of antigenaemia may vary from 1 to 5 percent in healthy cats to 15 to 30 percent in sick cats (Hosie M. J. et al., Veterinary Records, 1989, 128, 293-297; Braley J., Feline Practice, 1994, 22, 25-29; Malik R. et al., Australian Veterinary Journal, 1997, 75, 323-327; Arjona A. et al., Journal of Clinical Microbiology, 2000, 38, 3448-3449). The virus may establish a life-long infection characterized by a persistent viraemia and a fatal outcome. Most FeLV-related diseases occur persistently in infected animals, and they are always serious and most likely fatal. Among the most frequently diagnosed conditions are lymphomas, myeloid leukaemias, immunodeficiency and non-regenerative anaemia. The infection can be controlled by the identification and isolation of persistently viraemic cats, which are the source of the infection. Vaccines have also helped to prevent the virus spreading. Several FeLV vaccines are available. Most of them contain either inactivated virus or recombinant subunits. Their efficacy is controversial (Sparkes A. H., Journal of Small Animal Practice, 1997, 38, 187-194). Vaccine breakdowns have been observed.

An alternative way would be to use recombinant viral vector. The canarypox virus vector and especially the ALVAC vector have been tested for the expression of FeLV genes (Tartaglia J. et al., Journal of Virology, 1993, 67, 2370-2375; Poulet H. et al., Veterinary Record, 2003, 153, 141-145). A commercial recombinant FeLV vaccine is also available (EURIFEL® FeLV, Merial).

The FeLV genome codes for three genes: a GAG gene coding for the major structural components of the virus, an ENV gene which codes for the envelope glycoprotein, and a POL gene cndoing the polymerase protein (Thomsen D. R., et al., Journal of General Virology, 73, 1819-1824, 1992). The FeLV envelope (ENV) gene encodes a gp85 precursor protein which is proteolytically processed by cellular enzymes(s) to yield the major envelope glycoprotein gp70 and the associated transmembrane protein p15E (DeNoronha, F., et al., 1978, Virology 85:617-621; Nunberg, J. H., et al., 1983, PNAS 81:3675-3679). The transmembrane protein p15E contains a sequence conserved among gammaretroviruses with immunosuppressive properties (Mathes, L. E. et al., 1978, Nature). FeLV envelope glycoprotein is one of the major immunogens and is the target of FeLV-specific cytotoxic T cell responses as well as neutralizing antibodies (Flynn, J. N., et al., 2002, J. Virol.). US patent application US 2008/0008683 discussed a polypeptide that is capable of modulating the immunosuppressive properties of a viral protein against the host in which it is expressed. The FeLV GAG gene encodes a precursor polyprotein which is cleaved by the protease (FeLV PRO gene) to generate the capsid proteins. The capsid proteins are also a major immunogen inducing FeLV-specific cytotoxic T cell responses as well as neutralizing antibodies (Flynn, J. N., et al., 2002, J. Virol.). The POL gene encodes three proteins: protease (PRO), reverse transcriptase and integrase. Autoprocessing by the protease portion of the gene gives rise to all three proteins of the POL region (Thomsen D. R., et al., 1992).

There is a general need for an improvement in efficacy and safety of the FeLV vaccines and for more effective protection in field conditions.

SUMMARY OF THE INVENTION

An object of this invention can be any one or all of providing recombinant vectors or viruses as well as methods for making such viruses, and providing compositions and/or vaccines as well as methods for treatment and prophylaxis of infection by FeLV.

The invention provides a recombinant vector, such as a recombinant virus, e.g., a recombinant poxvirus, that contains and expresses at least one exogenous nucleic acid molecule and, the at least one exogenous nucleic acid molecule may comprise a nucleic acid molecule encoding an immunogen or epitope of interest from FeLV proteins, such as FeLV ENV and/or FeLV GAG/PRO.

In particular, the present invention provides a recombinant vector, such as a recombinant virus, e.g., a recombinant poxvirus, that contains and expresses at least one exogenous nucleic acid molecule and, the at least one exogenous nucleic acid molecule may comprise FeLV polypeptides and/or variants or fragments thereof.

The invention further provides compositions or vaccine comprising such an expression vector or the expression product(s) of such an expression vector.

The invention further provides methods for inducing an immunological (or immunogenic) or protective response against FeLV, as well as methods for preventing FeLV or disease state(s) caused by FeLV, comprising administering the expression vector or an expression product of the expression vector, or a composition comprising the expression vector, or a composition comprising an expression product of the expression vector.

The invention also relates to expression products from the virus as well as antibodies generated from the expression products or the expression thereof in vivo and uses for such products and antibodies, e.g., in diagnostic applications.

These and other embodiments are disclosed or are obvious from and encompassed by, the following Detailed Description.

BRIEF DESCRIPTION OF DRAWINGS

The following detailed description, given by way of example, and which is not intended to limit the invention to specific embodiments described, may be understood in conjunction with the accompanying figures, incorporated herein by reference, in which:

FIG. 1 provides a table identifying the SEQ ID NO assigned to the polynucleotide and protein sequence.

FIG. 3 provides the sequences for plasmid pCXL208.2 (pH6C5env) fragment containing FeLV ENV DNA and left and right arms (SEQ ID NO:36) and FeLV ENV protein (SEQ ID NO:7) from plasmid pHCMV-ENV FeLV.

FIG. 10 provides the FeLV GAG-PRO protein sequence.

FIG. 11 shows the nucleotide sequence of the pJY1874.1 DNA fragment containing the arms and insert (SEQ ID NO:38).

FIG. 12 provides the cloning scheme for making vCP2294 plasmid.

FIG. 14 depicts the vCP2294 plasmid sequence (annotated).

FIG. 18 depicts the vCP2295 plasmid sequence.

DETAILED DESCRIPTION

Figure 2:
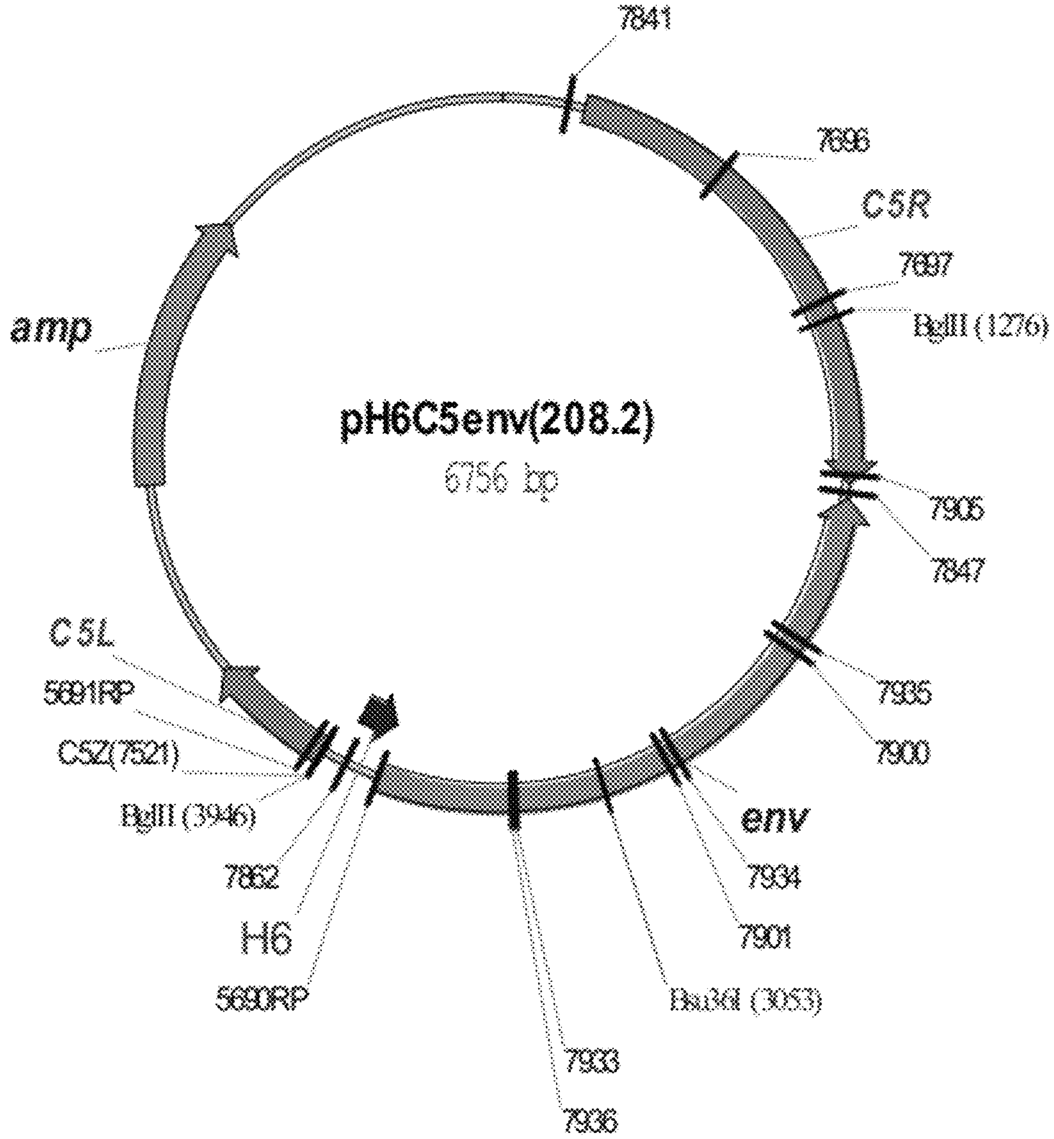
FIG. 2 depicts a plasmid map of pH6C5env (208.2).

It is noted that in this disclosure and particularly in the claims, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

Unless otherwise noted, technical terms are used according to conventional usage. Definitions of common terms in molecular biology may be found in Benjamin Lewin, Genes V. published by Oxford University Press, 1994 (ISBN 0-19-854287-9); Kendrew et al. (eds.), The Encyclopedia of Molecular Biology, published by Blackwell Science Ltd., 1994 (ISBN 0-632-02182-9); and Robert A. Meyers (ed.), Molecular Biology and Biotechnology: a Comprehensive Desk Reference, published by VCH Publishers, Inc., 1995 (ISBN 1-56081-569-8).

The singular terms "a," "an," and "the" include plural referents unless context clearly indicates otherwise. Similarly, the word "or" is intended to include "and" unless the context clearly indicate otherwise. The word "or" means any one member of a particular list and also includes any combination of members of that list.

The term "FeLV ENV polypeptide or DNA" refers to any native or optimized/mutated FeLV ENV polypeptide or DNA, and their derivatives and variants. For example, the optimized/mutated FeLV ENV DNA may be codon-optimized FeLV DNA, the FeLV ENV DNA may be optimized to produce a single amino acid mutation in the FeLV polypeptide. The optimized/mutated FeLV ENV polypeptide may comprise a single amino acid mutation, or a double amino acid mutation, or a multiple amino acid mutation.

The term "animal" is used herein to include all mammals, birds and fish. The animal as used herein may be selected from the group consisting of equine (e.g., horse), canine (e.g., dogs, wolves, foxes, coyotes, jackals), feline (e.g., lions, tigers, domestic cats, wild cats, other big cats, and other felines including cheetahs and lynx), bovine (e.g., cattle), porcine (e.g., pig), ovine (e.g., sheep, goats, lamas, bisons), avian (e.g., chicken, duck, goose, turkey, quail, pheasant, parrot, finches, hawk, crow, ostrich, emu and cassowary), primate (e.g., prosimian, tarsier, monkey, gibbon, ape), humans, and fish. The term "animal" also includes an individual animal in all stages of development, including embryonic and fetal stages.

The terms "polypeptide" and "protein" are used interchangeably herein to refer to a polymer of consecutive amino acid residues.

The term "nucleic acid", "nucleotide", and "polynucleotide" refers to RNA or DNA and derivatives thereof, such as those containing modified backbones. It should be appreciated that the invention provides polynucleotides comprising sequences complementary to those described herein. Polynucleotides according to the invention can be prepared in different ways (e.g. by chemical synthesis, by gene cloning etc.) and can take various forms (e.g. linear or branched, single or double stranded, or a hybrid thereof, primers, probes etc.).

The term "gene" is used broadly to refer to any segment of polynucleotide associated with a biological function. Thus, genes or polynucleotides include introns and exons as in genomic sequence, or just the coding sequences as in cDNAs, such as an open reading frame (ORF), starting from the start codon (methionine codon) and ending with a termination signal (stop codon). Genes and polynucleotides can also include regions that regulate their expression, such as transcription initiation, translation and transcription termination. Thus, also included are promoters and ribosome binding regions (in general these regulatory elements lie approximately between 60 and 250 nucleotides upstream of the start codon of the coding sequence or gene; Doree S M et al.;

Pandher K et al.; Chung J Y et al.), transcription terminators (in general the terminator is located within approximately 50 nucleotides downstream of the stop codon of the coding sequence or gene; Ward C K et al.). Gene or polynucleotide also refers to a nucleic acid fragment that expresses mRNA or functional RNA, or encodes a specific protein, and which includes regulatory sequences.

The term "immunogenic polypeptide" or "immunogenic fragment" as used herein refers to a polypeptide or a fragment of a polypeptide which comprises an allele-specific motif, an epitope or other sequence such that the polypeptide or the fragment will bind an MHC molecule and induce a cytotoxic T lymphocyte ("CTL") response, and/or a B cell response (for example, antibody production), and/or T-helper lymphocyte response, and/or a delayed type hypersensitivity (DTH) response against the antigen from which the immunogenic polypeptide or the immunogenic fragment is derived. A DTH response is an immune reaction in which T cell-dependent macrophage activation and inflammation cause tissue injury. A DTH reaction to the subcutaneous injection of antigen is often used as an assay for cell-mediated immunity.

By definition, an epitope is an antigenic determinant that is immunologically active in the sense that once administered to the host, it is able to evoke an immune response of the humoral (B cells) and/or cellular type (T cells). These are particular chemical groups or peptide sequences on a molecule that are antigenic. An antibody specifically binds a particular antigenic epitope on a polypeptide. Specific, non-limiting examples of an epitope include a tetra- to penta-peptide sequence in a polypeptide, a tri- to penta-glycoside sequence in a polysaccharide. In the animal most antigens will present several or even many antigenic determinants simultaneously. Such a polypeptide may also be qualified as an immunogenic polypeptide and the epitope may be identified as described further.

An "isolated" biological component (such as a nucleic acid or protein or organelle) refers to a component that has been substantially separated or purified away from other biological components in the cell of the organism in which the component naturally occurs, for instance, other chromosomal and extra-chromosomal DNA and RNA, proteins, and organelles. Nucleic acids and proteins that have been "isolated" include nucleic acids and proteins purified by standard purification methods. The term also embraces nucleic acids and proteins prepared by recombinant technology as well as chemical synthesis.

The term "purified" as used herein does not require absolute purity; rather, it is intended as a relative term. Thus, for example, a purified polypeptide preparation is one in which the polypeptide is more enriched than the polypeptide is in its natural environment. A polypeptide preparation is substantially purified such that the polypeptide represents several embodiments at least 60%, at least 70%, at least 80%, at least 90%, at least 95%, or at least 98%, of the total polypeptide content of the preparation. The same applies to polynucleotides. The polypeptides disclosed herein can be purified by any of the means known in the art.

A recombinant polynucleotide is one that has a sequence that is not naturally occurring or has a sequence that is made by an artificial combination of two otherwise separated segments of sequence. This artificial combination is often accomplished by chemical synthesis or, more commonly, by the artificial manipulation of isolated segments of nucleic acids, for example, by genetic engineering techniques. In one embodiment, a recombinant polynucleotide encodes a fusion protein.

In one aspect, the present invention provides optimized or mutated polypeptides from FeLV. In another aspect, the present invention provides optimized or mutated FeLV ENV polypeptides. In yet another aspect, the present invention provides an optimized FeLV ENV protein wherein a mutation occurs at, but not limited to, the amino acid position 527 of SEQ ID NOs: 2, 4, 6, 27, 28, 29, 30, 31, 32, 33, 34, or 43 or amino acid position 533 of SEQ ID NO:7. In yet another aspect, the mutation is a substitution of arginine (R), aspartic acid (D), or methionine (M) for glutamic acid (E) at amino acid position 527 of SEQ ID NOs: 2, 4, 6, 27, 28, 29, 30, 31, 32, 33, 34, or 43, or amino acid position 533 of SEQ ID NO:7. It is appreciated by a person skilled in the art that based on sequence alignment, the described mutation encompasses the mutation at the corresponding amino acid position in other FeLV ENV polypeptides which are not listed in the present application, wherein the corresponding amino acid position is equivalent to the amino acid position 527 of SEQ ID NOs: 2, 4, 6, 27, 28, 29, 30, 31, 32, 33, 34, or 43, or amino acid position 533 of SEQ ID NO:7. The protein sequence alignment of some of the FeLV ENV polypeptides is exemplified in FIG. 1*d*. In one embodiment, the optimized or mutated FeLV ENV polypeptide comprises an amino acid mutation at amino acid position 527 of SEQ ID NO:6 or at the corresponding amino acid position of FeLV ENV proteins. In yet another embodiment, the optimized or mutated FeLV ENV polypeptide comprises the amino acid substitution of R, D or M for E at amino acid position 527 of SEQ ID NO:6 or at the corresponding amino acid position of FeLV ENV polypeptide. In yet another embodiment, the optimized or mutated FeLV ENV polypeptide comprises the amino acid substitution of R for E at amino acid position 527 of SEQ ID NO:6 or at the corresponding amino acid position of FeLV ENV polypeptide. In yet another embodiment, the mutated FELV ENV polypeptide has the sequence as set forth in SEQ ID NO:2, 4, 7, or 43.

Moreover, homologs of polypeptides from FeLV are intended to be within the scope of the present invention. As used herein, the term "homologs" includes orthologs, analogs and paralogs. The term "anologs" refers to two polynucleotides or polypeptides that have the same or similar function, but that have evolved separately in unrelated organisms. The term "orthologs" refers to two polynucleotides or polypeptides from different species, but that have evolved from a common ancestral gene by speciation. Normally, orthologs encode polypeptides having the same or similar functions. The term "paralogs" refers to two polynucleotides or polypeptides that are related by duplication within a genome. Paralogs usually have different functions, but these functions may be related. Analogs, orthologs, and paralogs of a wild-type FeLV polypeptide can differ from the wild-type FeLV polypeptide by post-translational modifications, by amino acid sequence differences, or by both. In particular, homologs of the invention will generally exhibit at least 80-85%, 85-90%, 90-95%, or 95%, 96%, 97%, 98%, 99% sequence identity, with all or part of the wild-type FeLV polypeptide or polynucleotide sequences, and will exhibit a similar function.

In another aspect, the present invention provides an optimized or mutated FeLV ENV polypeptide having at least 70%, at least 75%, at least 80%, at least 85%, at least 90%, at least 95%, 96%, 97%, 98% or 99% sequence identity to a polypeptide having a sequence as set forth in SEQ ID NO: 2, 4, 6, 27, 28, 29, 30, 31, 32, 33, or 34.

In yet another aspect, the present invention provides fragments and variants of the optimized or mutated FeLV ENV polypeptides identified above, which may readily be prepared by one of skill in the art using well-known molecular biology techniques.

Variants are homologous polypeptides having an amino acid sequence at least 75%, 80%, 85%, 90%, 95%, 96%, 97%, 98%, or 99% identity to the amino acid sequence as set forth in SEQ ID NO: 2, 4, 6, 27, 28, 29, 30, 31, 32, 33, or 34.

Variants include allelic variants. The term "allelic variant" refers to a polynucleotide or a polypeptide containing polymorphisms that lead to changes in the amino acid sequences of a protein and that exist within a natural population (e.g., a virus species or variety). Such natural allelic variations can typically result in 1-5% variance in a polynucleotide or a polypeptide. Allelic variants can be identified by sequencing the nucleic acid sequence of interest in a number of different species, which can be readily carried out by using hybridization probes to identify the same gene genetic locus in those species. Any and all such nucleic acid variations and resulting amino acid polymorphisms or variations that are the result of natural allelic variation and that do not alter the functional activity of gene if interest, are intended to be within the scope of the invention.

As used herein, the term "derivative" or "variant" refers to a polypeptide, or a nucleic acid encoding a polypeptide, that has one or more conservative amino acid variations or other minor modifications such that (1) the corresponding polypeptide has substantially equivalent function when compared to the wild type polypeptide or (2) an antibody raised against the polypeptide is immunoreactive with the wild-type polypeptide. These variants or derivatives include polypeptides having minor modifications of the optimized or mutated FeLV ENV polypeptide primary amino acid sequences that may result in peptides which have substantially equivalent activity as compared to the unmodified counterpart polypeptide. Such modifications may be deliberate, as by site-directed mutagenesis, or may be spontaneous. The term "variant" further contemplates deletions, additions and substitutions to the sequence, so long as the polypeptide functions to produce an immunological response as defined herein. The modifications may be any amino acid change at amino acid positions other than position 527 of SEQ ID NOs: 2, 4, 6, 27, 28, 29, 30, 31, 32, 33, 34, or 43, or amino acid position 533 of SEQ ID NO:7.

The term "conservative variation" denotes the replacement of an amino acid residue by another biologically similar residue, or the replacement of a nucleotide in a nucleic acid sequence such that the encoded amino acid residue does not change or is another biologically similar residue. In this regard, particularly preferred substitutions will generally be conservative in nature, i.e., those substitutions that take place within a family of amino acids. For example, amino acids are generally divided into four families: (1) acidic—aspartate and glutamate; (2) basic—lysine, arginine, histidine; (3) non-polar—alanine, valine, leucine, isoleucine, proline, phenylalanine, methionine, tryptophan; and (4) uncharged polar—glycine, asparagine, glutamine, cysteine, serine, threonine, tyrosine. Phenylalanine, tryptophan, and tyrosine are sometimes classified as aromatic amino acids. Examples of conservative variations include the substitution of one hydrophobic residue such as isoleucine, valine, leucine or methionine for another hydrophobic residue, or the substitution of one polar residue for another polar residue, such as the substitution of arginine for lysine, glutamic acid for aspartic acid, or glutamine for asparagine, and the like; or a similar conservative replacement of an amino acid with a structurally related amino acid that will not have a major effect on the biological activity. Proteins having substantially the same amino acid sequence as the reference molecule but possessing minor amino acid substitutions that do not substantially affect the immunogenicity of the protein are, therefore, within the definition of the reference polypeptide. All of the polypeptides produced by these modifications are included herein. The term "conservative variation" also includes the use of a substituted amino acid in place of an unsubstituted parent amino acid provided that antibodies raised to the substituted polypeptide also immunoreact with the unsubstituted polypeptide.

An immunogenic fragment of an FeLV ENV polypeptide includes at least 8, 10, 15, or 20 consecutive amino acids, at least 21 amino acids, at least 23 amino acids, at least 25 amino acids, or at least 30 amino acids of an FeLV ENV polypeptide having a sequence as set forth in SEQ ID NO: 2, 4, 6, 7, 27, 28, 29, 30, 31, 32, 33, 34, or 43, or variants thereof. In another embodiment, a fragment of an FeLV ENV polypeptide includes a specific antigenic epitope found on a full-length FeLV ENV polypeptide.

Procedures to determine fragments of polypeptide and epitope such as, generating overlapping peptide libraries (Hemmer B. et al.), Pepscan (Geysen H. M. et al., 1984; Geysen H. M. et al., 1985; Van der Zee R. et al.; Geysen H. M.) and algorithms (De Groot A. et al.; Hoop T. et al.; Parker K. et al.), can be used in the practice of the invention, without undue experimentation. Generally, antibodies specifically bind a particular antigenic epitope. Specific, non-limiting examples of epitopes include a tetra- to penta-peptide sequence in a polypeptide, a tri- to penta glycoside sequence in a polysaccharide. In animals most antigens will present several or even many antigenic determinants simultaneously. Preferably wherein the epitope is a protein fragment of a larger molecule it will have substantially the same immunological activity as the total protein.

In one aspect, the present invention provides a polynucleotide encoding an FeLV ENV polypeptide. In another aspect, the present invention provides an FeLV ENV polynucleotide encoding an optimized or mutated FeLV ENV polypeptide, wherein the mutation occurs at the amino acid position 527 of SEQ ID NOs: 2, 4, 6, 27, 28, 29, 30, 31, 32, 33, 34, or 43, or amino acid position 533 of SEQ ID NO:7. In yet another aspect, the FeLV ENV polynucleotide encodes an optimized or mutated FeLV ENV polypeptide wherein the mutation is a substitution of arginine (R), aspartic acid (D), or methionine (M) for glutamic acid (E) at the amino acid position 527 of SEQ ID NOs: 2, 4, 6, 7, 28, 29, 30, 31, 32, 33, 34, or 43, or amino acid position 533 of SEQ ID NO:7. In yet another aspect, the FeLV ENV polynucleotide encodes an optimized or mutated FeLV ENV polypeptide having an amino acid mutation at amino acid position 527 of SEQ ID NO:6 or at the corresponding amino acid position of FeLV ENV proteins. In another aspect, the FeLV ENV polynucleotide encodes an optimized or mutated FeLV ENV polypeptide having the amino acid change of E to R, D or M at amino acid position 527 of SEQ ID NO:6 or at the corresponding amino acid position of FeLV ENV polypeptide. In yet another aspect, the FeLV ENV polynucleotide encodes an optimized or mutated FeLV ENV polypeptide having the amino acid change of E to R at amino acid position 527 of SEQ ID NO:6 or at the corresponding amino acid position of FeLV ENV polypeptide. In yet another embodiment, the FeLV ENV polynucleotide encodes an FeLV ENV polypeptide having the sequence as set forth in SEQ ID NO:2, 4, 7, or 43. In yet another embodiment, the FeLV ENV polynucleotide encodes an FeLV ENV polypeptide having at least 70%, at least 75%, at least 80%, at least 85%, at least 90%, at least 95%, 96%, 97%, 98% or 99% sequence identity to a polypeptide having a sequence as set forth in SEQ ID NO: 2, 4, 6, 7, 27, 28, 29, 30, 31, 32, 33, 34, or 43, or a conservative variant, an allelic variant, a homolog or an immunogenic fragment comprising at least eight or at east ten consecutive amino acids of one of these polypeptides, or a combination of these polypeptides.

In another aspect, the present invention provides an FeLV GAG-PRO polypeptide having at least 70%, at least 75%, at least 80%, at least 85%, at least 90%, at least 95%, 96%, 97%, 98% or 99% sequence identity to a polypeptide having a sequence as set forth in SEQ ID NO: 12.

In another aspect, the present invention provides an FeLV ENV polynucleotide having a nucleotide sequence as set forth in SEQ ID NO: 1, 3, or 5, or a variant thereof. In yet another aspect, the present invention provides an FeLV ENV polynucleotide having at least 70%, at least 75%, at least 80%, at least 85%, at least 90%, at least 95%, at least 95%, 96%, 97%, 98% or 99% sequence identity to a polynucleotide having a sequence as set forth in SEQ ID NO: 1, 3, or 5, or a variant thereof.

In yet another aspect, the present invention provides an FeLV GAG-PRO polynucleotide having at least 70%, at least 75%, at least 80%, at least 85%, at least 90%, at least 95%, at least 95%, 96%, 97%, 98% or 99% sequence identity to a polynucleotide having a sequence as set forth in SEQ ID NO: 10, or 11, or a variant thereof.

These polynucleotides may include DNA, cDNA, and RNA sequences that encode FeLV ENV or GAG-PRO polypeptides. It is understood that all polynucleotides encoding FeLV ENV or GAG-PRO polypeptides are also included herein, as long as they encode a polypeptide with the recognized activity, such as the binding to an antibody that recognizes the polypeptide, the induction of an immune response to the polypeptide, or an effect on survival of Leukemia disease when administered to a subject exposed to the parasite or who undergoes a decrease in a sign or a symptom of FeLV infection.

The polynucleotides of the disclosure include sequences that are degenerate as a result of the genetic code, e.g., optimized codon usage for a specific host. As used herein, "optimized" refers to a polynucleotide that is genetically engineered to increase its expression in a given species. To provide optimized polynucleotides coding for an FeLV ENV or GAG-PRO polypeptide, the DNA sequence of the FeLV ENV or GAG-PRO gene can be modified to 1) comprise codons preferred by highly expressed genes in a particular species; 2) comprise an A+T or G+C content in nucleotide base composition to that substantially found in said species; 3) form an initiation sequence of said species; or 4) eliminate sequences that cause destabilization, inappropriate polyadenylation, degradation and termination of RNA, or that form secondary structure hairpins or RNA splice sites. Increased expression of FeLV protein in said species can be achieved by utilizing the distribution frequency of codon usage in eukaryotes and prokaryotes, or in a particular species. The term "frequency of preferred codon usage" refers to the preference exhibited by a specific host cell in usage of nucleotide codons to specify a given amino acid. There are 20 natural amino acids, most of which are specified by more than one codon. Therefore, all degenerate nucleotide sequences are included in the disclosure as long as the amino acid sequence of the FeLV polypeptide encoded by the nucleotide sequence is functionally unchanged.

The sequence identity between two amino acid sequences may be established by the NCBI (National Center for Biotechnology Information) pairwise blast and the blosum62 matrix, using the standard parameters (see, e.g., the BLAST or BLASTX algorithm available on the "National Center for Biotechnology Information" (NCBI, Bethesda, Md., USA) server, as well as in Altschul et al.; and thus, this document speaks of using the algorithm or the BLAST or BLASTX and BLOSUM62 matrix by the term "blasts").

Sequence identity between two nucleotide sequences also may be determined using the "Align" program of Myers and Miller, ("Optimal Alignments in Linear Space", CABIOS 4, 11-17, 1988) and available at NCBI, as well as the same or other programs available via the Internet at sites thereon such as the NCBI site.

Alternatively or additionally, the term "identity", for instance, with respect to a nucleotide or amino acid sequence, may indicate a quantitative measure of homology between two sequences. The percent sequence homology may be calculated as:

$(N_{ref}-N_{dif})*100/N_{ref}$, wherein $N_{dif}$ is the total number of non-identical residues in the two sequences when aligned and wherein $N_{ref}$ is the number of residues in one of the sequences. Hence, the DNA sequence AGTCAGTC will have a sequence identity of 75% with the sequence AATCAATC ($N_{ref}$=8; $N_{dif}$=2).

Alternatively or additionally, "identity" with respect to sequences can refer to the number of positions with identical nucleotides or amino acids divided by the number of nucleotides or amino acids in the shorter of the two sequences wherein alignment of the two sequences can be determined in accordance with the Wilbur and Lipman algorithm (Wilbur and Lipman), for instance, using a window size of 20 nucleotides, a word length of 4 nucleotides, and a gap penalty of 4, and computer-assisted analysis and interpretation of the sequence data including alignment can be conveniently performed using commercially available programs (e.g., Intelligenetics™ Suite, Intelligenetics Inc. CA). When RNA sequences are said to be similar, or have a degree of sequence identity or homology with DNA sequences, thymidine (T) in the DNA sequence is considered equal to uracil (U) in the RNA sequence. Thus, RNA sequences are within the scope of the invention and can be derived from DNA sequences, by thymidine (T) in the DNA sequence being considered equal to uracil (U) in RNA sequences.

The sequence identity or sequence similarity of two amino acid sequences, or the sequence identity between two nucleotide sequences can be determined using Vector NTI software package (Invitrogen, 1600 Faraday Ave., Carlsbad, Calif.).

The FeLV ENV or GAG-PRO polynucleotides may include a recombinant DNA which is incorporated into a vector, into an autonomously replicating plasmid or virus, or into the genomic DNA of a prokaryote or eukaryote, or which exists as a separate molecule (for example, a cDNA) independent of other sequences.

Recombinant vectors disclosed herein may include a polynucleotide encoding a polypeptide, a variant thereof or a fragment thereof. Recombinant vectors may include plasmids and viral vectors and may be used for in vitro or in vivo expression. Recombinant vectors may include further a signal peptide. Signal peptides are short peptide chain (3-60 amino acids long) that direct the post-translational transport of a protein (which are synthesized in the cytosol) to certain organelles such as the nucleus, mitochondrial matrix, endoplasmic reticulum, chloroplast, apoplast and peroxisome. Typically, the naturally occurring FeLV ENV proteins may be translated as precursors, having an N-terminal signal peptide sequence and a "mature" protein domain. The signal peptide may be cleaved off rapidly upon translation. The signal sequence may be the natural sequence from the FeLV ENV protein or a peptide signal from a secreted protein e.g. the signal peptide from the tissue plasminogen activator protein (tPA), in particular the human tPA (S. Friezner Degen et al.; R.

Rickles et al.; D. Berg. et al.), or the signal peptide from the Insulin-like growth factor 1 (IGF1), in particular the equine IGF1 (K. Otte et al.), the canine IGF1 (P. Delafontaine et al.), the feline IGF1 (WO03/022886), the bovine IGF1 (S. Lien et al.), the porcine IGF1 (M. Muller et al.), the chicken IGF1 (Y. Kajimoto et al.), the turkey IGF1 (GenBank accession number AF074980). The signal peptide from IGF1 may be natural or optimized which may be achieved by removing cryptic splice sites and/or by adapting the codon usage. Upon translation, the unprocessed polypeptide may be cleaved at a cleavage site to lead to the mature polypeptide. The cleavage site may be predicted using the method of Von Heijne (1986).

A plasmid may include a DNA transcription unit, for instance a nucleic acid sequence that permits it to replicate in a host cell, such as an origin of replication (prokaryotic or eukaryotic). A plasmid may also include one or more selectable marker genes and other genetic elements known in the art. Circular and linear forms of plasmids are encompassed in the present disclosure.

In a further aspect, the present invention relates to an in vivo expression vector comprising a polynucleotide sequence, which contains and expresses in vivo in a host the optimized or mutated FeLV ENV polypeptides and/or variants or fragments thereof. The expression vector may further comprise a polynucleotide encoding an FeLV GAG-PRO polypeptide and/or variants or fragments thereof.

The in vivo expression vector may include any transcription unit containing a polynucleotide or a gene of interest and those essential elements for its in vivo expression. These expression vectors may be plasmids or recombinant viral vectors. For in vivo expression, the promoter may be of viral or cellular origin. In one embodiment, the promoter may be the cytomegalovirus (CMV) early promoter (CMV-IE promoter), the SV40 virus early or late promoter or the Rous Sarcoma virus LTR promoter, a promoter of a cytoskeleton gene, such as the desmin promoter (Kwissa M. et al.), or the actin promoter (Miyazaki J. et al.). When several genes are present in the same plasmid, they may be provided in the same transcription unit or in different units.

As used herein, the term "plasmid" may include any DNA transcription unit comprising a polynucleotide according to the invention and the elements necessary for its in vivo expression in a cell or cells of the desired host or target; and, in this regard, it is noted that a supercoiled or non-supercoiled, circular plasmid, as well as a linear form, are intended to be within the scope of the invention. The plasmids may also comprise other transcription-regulating elements such as, for example, stabilizing sequences of the intron type. In several embodiments, the plasmids may include the first intron of CMV-IE (WO 89/01036), the intron II of the rabbit beta-globin gene (van Ooyen et al.), the signal sequence of the protein encoded by the tissue plasminogen activator (tPA; Montgomery et al.), and/or a polyadenylation signal (polyA), in particular the polyA of the bovine growth hormone (bGH) gene (U.S. Pat. No. 5,122,458) or the polyA of the rabbit beta-globin gene or of SV40 virus.

In a further aspect, the present invention relates to a composition comprising: a) an in vivo expression vector, wherein the vector comprises a polynucleotide encoding one or more polypeptide selected from the group consisting of an FeLV ENV polypeptide, a variant or fragment of the FeLV ENV polypeptide, and a mixture thereof; and b) a pharmaceutically or veterinary acceptable vehicle, diluent or excipient.

In another aspect, the present invention relates to a composition comprising: a) an in vivo expression vector, wherein the vector comprises a polynucleotide encoding one or more polypeptide selected from the group consisting of an FeLV ENV polypeptide, an FeLV GAG/PRO polypeptide, a variant or fragment of the FeLV ENV polypeptide, and a mixture thereof; and b) a pharmaceutically or veterinary acceptable vehicle, diluent or excipient.

In yet another aspect, the present invention relates to a composition comprising: a) an in vivo expression vector, wherein the vector comprises a polynucleotide encoding an FeLV ENV polypeptide, an FeLV GAG/PRO polypeptide; and b) a pharmaceutically or veterinary acceptable vehicle, diluent or excipient.

The FeLV ENV and FeLV GAG/PRO polypeptides are described above.

In one embodiment, the present invention relates to a composition comprising: a) an in vivo expression vector, wherein the vector comprises a polynucleotide encoding an optimized or mutated FeLV ENV having the amino acid substitution of R, D or M for E at amino acid position 527 of SEQ ID NO:6 or at the corresponding amino acid position of FeLV polypeptide and a polynucleotide encoding an FeLV GAG/PRO polypeptide having at least 90% sequence identity to a polypeptide having the sequence as set forth in SEQ ID NO:12; and b) a pharmaceutically or veterinary acceptable vehicle, diluent or excipient.

The term "composition" comprises any vaccine or immunological composition, once it has been injected to a host, including canines, felines and humans, that induces an immune response in the host, and/or protects the host from leukemia, and/or which may prevent implantation of the parasite, and/or which may prevent disease progression in infected subjects, and/or which may limit the diffusion of runaway parasites to internal organs. This may be accomplished upon vaccination according to the present invention through the induction of cytokine secretion, notably IFN-gamma secretion (as example of a method of measurement of IFN-gamma secretion, the Quantikine® immunoassay from R&D Systems Inc. (catalog number# CAIF00) could be used (Djoba Siawaya J F et al.)).

The pharmaceutically acceptable vehicles or excipients of use are conventional. *Remington's Pharmaceutical Sciences*, by E. W. Martin, Mack Publishing Co., Easton, Pa., 15th Edition (1975), describes compositions and formulations suitable for pharmaceutical delivery of the polypeptides, plasmids, viral vectors herein disclosed. In general, the nature of the vehicle or excipient will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (for example, freeze-dried pastille, powder, pill, tablet, or capsule forms), conventional non-toxic solid vehicles or excipients can include, for example, pharmaceutical grades of mannitol, lactose, starch, or magnesium stearate. In addition to biologically neutral vehicles or excipients, immunogenic compositions to be administered can contain minor amounts of non-toxic auxiliary substances, such as wetting or emulsifying agents, preservatives, and pH buffering agents and the like, for example sodium acetate or sorbitan monolaurate.

The compositions or vaccines according to the instant invention may include vectors encoding any polynucleotide according to the present invention as described above.

Multiple insertions may be done in the same vector using different insertion sites or using the same insertion site. When the same insertion site is used, each polynucleotide insert, which may be any polynucleotide of the present invention aforementioned, may be inserted under the control of the same and/or different promoters. The insertion can be done tail-to-tail, head-to-head, tail-to-head, or head-to-tail. IRES elements (Internal Ribosome Entry Site, see EP 0803573) can also be used to separate and to express multiple inserts operably linked to the same and/or different promoters.

In one embodiment, the present invention relates to an expression vector comprising a polynucleotide aforementioned. The expression vector may be an in vivo expression vector, or an in vitro expression vector.

More generally, the present invention encompasses in vivo expression vectors including any plasmid (EP-A2-1001025; Chaudhuri P.) containing and expressing in vivo in a host the polynucleotide or gene of FeLV ENV polypeptide, variant thereof or fragment thereof and elements necessary for its in vivo expression.

In a specific, non-limiting example, the pVR1020 or pVR1012 plasmid (VICAL Inc.; Luke C. et al.; Hartikka J. et al.), pVR2001-TOPA (or pVR2001-TOPO) (Oliveira F. et al.) or pAB110 (U.S. Pat. No. 6,852,705) can be utilized as a vector for the insertion of a polynucleotide sequence. The pVR1020 plasmid is derived from pVR1012 and contains the human tPA signal sequence. The pVR1020 is a plasmid backbone available from Vical, Inc., (San Diego, Calif.) which has been previously used, see, e.g., U.S. Pat. Nos. 6,451,769 and 7,078,507. As described in Oliveira et al., plasmid pVR2001-TOPO (or pVR2001-TOPA) is pVR1020 modified by the addition of topoisomerases flanking the cloning site and containing coding for and expressing a signal secretory peptide, for example, tissue plasminogen activator signal peptide (tPA), that increases the likelihood of producing a secreted protein, (see FIG. 1 in Oliveira F. et al.).

Each plasmid may comprise or contain or consist essentially of, the polynucleotide according to the present invention, operably linked to a promoter or under the control of a promoter or dependent upon a promoter, wherein the promoter may be advantageously adjacent to the polynucleotide for which expression is desired. In general, it is advantageous to employ a strong promoter that is functional in eukaryotic cells. One example of a useful promoter may be the immediate early cytomegalovirus promoter (CMV-IE) of human or murine origin, or it may optionally have another origin such as from rat or guinea pig. The CMV-IE promoter may comprise the actual promoter part, which may or may not be associated with the enhancer part. Reference can be made to EP 260 148, EP 323 597, U.S. Pat. Nos. 5,168,062, 5,385,839, and 4,968,615, as well as to WO 87/03905. The CMV-IE promoter may advantageously be a human CMV-IE (Boshart M. et al.) or murine CMV-IE. In more general terms, the promoter may have either a viral or a cellular origin. A strong viral promoter other than CMV-IE that may be usefully employed in the practice of the invention is the early/late promoter of the SV40 virus or the LTR promoter of the Rous sarcoma virus. A strong cellular promoter that may be usefully employed in the practice of the invention is the promoter of a gene of the cytoskeleton, such as the desmin promoter (Kwissa M. et al.), or the actin promoter (Miyazaki J. et al.). Functional sub fragments of these promoters, i.e., portions of these promoters that maintain adequate promoter activity, are included within the present invention, e.g. truncated CMV-IE promoters according to WO 98/00166 or U.S. Pat. No. 6,156,567 and may be used in the practice of the invention. A promoter useful in the practice of the invention consequently may include derivatives and/or sub fragments of a full-length promoter that maintain adequate promoter activity and hence function as a promoter, and which may advantageously have promoter activity that is substantially similar to that of the actual or full-length promoter from which the derivative or sub fragment is derived, e.g., akin to the activity of the truncated CMV-IE promoters of U.S. Pat. No. 6,156,567 in comparison to the activity of full-length CMV-IE promoters. Thus, a CMV-IE promoter in the practice of the invention may comprise or consist essentially of or consist of the promoter portion of the full-length promoter and/or the enhancer portion of the full-length promoter, as well as derivatives and/or sub fragments thereof.

Advantageously, the plasmids comprise or consist essentially of other expression control elements. It is especially advantageous to incorporate stabilizing sequence(s), e.g., intron sequence(s), for example, the first intron of the hCMV-IE (WO 89/01036), the intron II of the rabbit β-globin gene (van Ooyen et al.). As to the polyadenylation signal (polyA) for the plasmids and viral vectors other than poxviruses, use can be made of the poly(A) signal of the bovine growth hormone (bGH) gene (see U.S. Pat. No. 5,122,458), or the poly(A) signal of the rabbit β-globin gene or the poly(A) signal of the SV40 virus.

More generally, the present invention encompasses in vivo expression vectors including any recombinant viral vector containing a polynucleotide or gene encoding one or more FeLV ENV and/or variants or fragments thereof, including any elements necessary for its in vivo expression.

Said recombinant viral vectors could be selected from, for example, the poxviruses, especially avipox viruses, such as fowlpox viruses or canarypox viruses. In one embodiment, the fowlpox virus is a TROVAC (see WO 96/40241). In another embodiment, the canarypox vector is an ALVAC. The use of these recombinant viral vectors and the insertion of polynucleotides or genes of interest are fully described in U.S. Pat. No. 5,174,993; U.S. Pat. No. 5,505,941 and U.S. Pat. No. 5,766,599 for fowlpox, and in U.S. Pat. No. 5,756,103 for canarypox. More than one insertion site inside the viral genome could be used for the insertion of multiple genes of interest.

In one embodiment the viral vector is an adenovirus, such as a human adenovirus (HAV) or a canine adenovirus (CAV).

In another embodiment the viral vector is a human adenovirus, specifically a serotype 5 adenovirus, rendered incompetent for replication by a deletion in the E1 region of the viral genome, especially from about nucleotide 459 to about nucleotide 3510 by reference to the sequence of the hAd5 disclosed in Genbank under the accession number M73260 and in the referenced publication Chroboczek et al, 1992. The deleted adenovirus is propagated in E1-expressing 293 (Graham et al., 1977) or PER cells, especially PER.C6 (Falloux et al., 1998). The human adenovirus can additionally or alternatively be deleted in the E3 region, especially from about nucleotide 28592 to about nucleotide 30470. The deletion in the E1 region can be done in combination with a deletion in the E3 region (see, e.g. Shriver et al.; Graham et al.; Ilan et al.; U.S. Pat. Nos. 6,133,028 and 6,692,956; Tripathy et al.; Tapnell; Danthinne et al.; Berkner; Berkner et al.; Chavier et al.). The insertion sites can be the E1 and/or E3 loci (region) eventually after a partial or complete deletion of the E1 and/or E3 regions. Advantageously, when the expression vector is an adenovirus, the polynucleotide to be expressed is inserted under the control of a promoter functional in eukaryotic cells, such as a strong promoter, advantageously a cytomegalovirus immediate-early gene promoter (CMV-IE promoter), especially the enhancer/promoter region from about nucleotide −734 to about nucleotide +7 in Boshart et al., or the enhancer/promoter region from the pCI vector from Promega Corp. The CMV-IE promoter is advantageously of murine or human origin. The promoter of the elongation factor 1α can also be used. A muscle specific promoter can also be used (Li et al.).

Strong promoters are also discussed herein in relation to plasmid vectors. In one embodiment, a splicing sequence can be located downstream of the enhancer/promoter region. For example, the intron 1 isolated from the CMV-IE gene (Stenberg et al.), the intron isolated from the rabbit or human β-globin gene, especially the intron 2 from the β-globin gene, the intron isolated from the immunoglobulin gene, a splicing sequence from the SV40 early gene or the chimeric intron sequence isolated from the pCI vector from Promege Corp. A poly(A) sequence and terminator sequence can be inserted downstream the polynucleotide to be expressed, e.g. a bovine growth hormone gene, especially from about nucleotide 2339 to about nucleotide 2550 of the sequence with GenBank accession No. BOVGHRH, a rabbit β-globin gene or a SV40 late gene polyadenylation signal.

In another embodiment the viral vector is a canine adenovirus, especially a CAV-2 (see, e.g. Fischer et al.; U.S. Pat. Nos. 5,529,780 and 5,688,920; WO 95/14102). For CAV, the insertion sites can be in the E3 region and/or in the region located between the E4 region and the right ITR region (see U.S. Pat. Nos. 6,090,393 and 6,156,567). In one embodiment the insert is under the control of a promoter, such as a cytomegalovirus immediate-early gene promoter (CMV-IE promoter) or a promoter already described for a human adenovirus vector. A poly(A) sequence and terminator sequence can be inserted downstream the polynucleotide to be expressed, e.g. a bovine growth hormone gene or a rabbit β-globin gene polyadenylation signal.

In another embodiment, the viral vector is a herpesvirus such as a feline herpesvirus (FHV). In one embodiment the polynucleotide to be expressed is inserted under the control of a promoter functional in eukaryotic cells, advantageously a CMV-IE promoter (murine or human). A poly(A) sequence and terminator sequence can be inserted downstream the polynucleotide to be expressed, e.g. bovine growth hormone or a rabbit β-globin gene polyadenylation signal.

For recombinant vectors based on a poxvirus vector, a vaccinia virus or an attenuated vaccinia virus, (for instance, MVA, a modified Ankara strain obtained after more than 570 passages of the Ankara vaccine strain on chicken embryo fibroblasts; see Stickl & Hochstein-Mintzel; Sutter et al.; available as ATCC VR-1508; or NYVAC, see U.S. Pat. No. 5,494,807, and U.S. Pat. No. 5,494,807 which discuss the construction of NYVAC, as well as variations of NYVAC with additional ORFs deleted from the Copenhagen strain vaccinia virus genome, as well as the insertion of heterologous coding nucleic acid molecules into sites of this recombinant, and also, the use of matched promoters; see also WO 96/40241), an avipox virus or an attenuated avipox virus (e.g., canarypox, fowlpox, dovepox, pigeonpox, quailpox, ALVAC or TROVAC; see, e.g., U.S. Pat. Nos. 5,505,941, 5,494,807) can be used. Attenuated canarypox viruses are described in U.S. Pat. No. 5,756,103 (ALVAC) and WO 01/05934. Reference is also made to U.S. Pat. No. 5,766,599 which pertains to the attenuated fowlpox strain TROVAC. Reference is made to the canarypox available from the ATCC under access number VR-111. Numerous fowlpox virus vaccination strains are also available, e.g. the DIFTOSEC CT strain marketed by MERIAL and the NOBILIS VARIOLE vaccine marketed by INTERVET. For information on the method used to generate recombinants thereof and how to administer recombinants thereof, the skilled artisan can refer documents cited herein and to WO 90/12882, e.g., as to vaccinia virus, mention is made of U.S. Pat. Nos. 4,769,330, 4,722,848, 4,603,112, 5,110,587, 5,494,807, and 5,762,938 inter alia; as to fowlpox, mention is made of U.S. Pat. Nos. 5,174,993, 5,505,941 and 5,766,599 inter alia; as to canarypox, mention is made of U.S. Pat. No. 5,756,103 inter alia. When the expression vector is a vaccinia virus, insertion site or sites for the polynucleotide or polynucleotides to be expressed are advantageously at the thymidine kinase (TK) gene or insertion site, the hemagglutinin (HA) gene or insertion site, the region encoding the inclusion body of the A type (ATI); see also documents cited herein, especially those pertaining to vaccinia virus. In the case of canarypox, advantageously the insertion site or sites are ORF(s) C3, C5 and/or C6; see also documents cited herein, especially those pertaining to canarypox virus. In the case of fowlpox, advantageously the insertion site or sites are ORFs F7 and/or F8; see also documents cited herein, especially those pertaining to fowlpox virus. The insertion site or sites for MVA virus are advantageously as in various publications, including Carroll M. W. et al.; Stittelaar K. J. et al.; Sutter G. et al.; and, in this regard it is also noted that the complete MVA genome is described in Antoine G., Virology, which enables the skilled artisan to use other insertion sites or other promoters. Advantageously, the polynucleotide to be expressed is inserted under the control of a specific poxvirus promoter, e.g., the vaccinia promoter 7.5 kDa (Cochran et al.), the vaccinia promoter I3L (Riviere et al.), the vaccinia promoter HA (Shida), the cowpox promoter ATI (Funahashi et al.), the vaccinia promoter H6 (Taylor J. et al.; Guo P. et al. J.; Perkus M. et al.), inter alia.

Any of the polynucleotides disclosed here may be expressed in vitro by DNA transfer or expression vectors into a suitable host cell. The host cell may be prokaryotic or eukaryotic. The term "host cell" also includes any progeny of the subject host cell. Methods of stable transfer, meaning that the foreign polynucleotide is continuously maintained in the host cell, are known in the art. Host cells may include bacteria (for example, *Escherichia coli*), yeast, insect cells, and vertebrate cells. Methods of expressing DNA sequences in eukaryotic cells are well known in the art. As a method for in vitro expression, recombinant Baculovirus vectors (for example, *Autographa* California Nuclear Polyhedrosis Virus (AcNPV)) may be used with the nucleic acids disclosed herein. For example, polyhedrin promoters may be utilized with insect cells (for example, *Spodoptera frugiperda* cells, like Sf9 cells available at the ATCC under the Accession number CRL 1711, or Sf21 cells) (see for example, Smith et al.; Pennock et al.; Vialard et al.; Verne A.; O'Reilly et al.; Kidd I. M. & Emery V. C.; EP 0370573; EP 0265785; U.S. Pat. No. 4,745,051). For expression, the BaculoGold Starter Package (Cat #21001K) from Pharmingen (Becton Dickinson) may be used. As a method for in vitro expression, recombinant *E. coli* may be used with a vector. For example, when cloning in bacterial systems, inducible promoters such as arabinose promoter, pL of bacteriophage lambda, plac, ptrp, ptac (ptrp-lac hybrid promoter), and the like may be used. Transformation of a host cell with recombinant DNA may be carried out by conventional techniques are well known to those skilled in the art. Where the host is prokaryotic, such as *E. coli*, competent cells which are capable of DNA uptake can be prepared from cells harvested after exponential growth phase and subsequently treated by the $CaCl_2$ method using procedures well known in the art. Alternatively, MgCl2 or RbCl can be used. Transformation can also be performed by electroporation. When the host is a eukaryote, such methods of transduction of DNA as calcium phosphate coprecipitates, conventional mechanical procedures such as microinjection, electroporation, insertion of a plasmid encased in liposomes, or virus vectors may be used. Eukaryotic cells may also be cotransformed with *L. longipalpis* polynucleotide sequences, and a second foreign DNA molecule encoding a selectable phenotype, such as the herpes simplex thymidine kinase gene. Another method is to use a eukaryotic viral vector (see above), such as a herpes virus or adenovirus (for example, canine adenovirus 2), to transiently transduce eukaryotic cells and express the protein (Gluzman EA). In addition, a transfection agent can be utilized, such as dioleoyl-phosphatidyl-ethanolamine (DOPE).

Isolation and purification of recombinantly expressed polypeptide may be carried out by conventional means including preparative chromatography (for example, size exclusion, ion exchange, affinity), selective precipitation and ultra-filtration. Examples of state of the art techniques that can be used, but not limited to, may be found in "Protein Purification Applications", Second Edition, Edited by Simon Roe and available at Oxford University Press. Such a recombinantly expressed polypeptide is part of the present disclosure. The methods for production of any polypeptide according to the present invention as described above are also encompassed, in particular the use of a recombinant expression vector comprising a polynucleotide according to the disclosure and of a host cell.

The vaccines containing recombinant viral vectors according to the invention may be freeze-dried, advantageously with a stabilizer. Freeze-drying can be done according to well-known standard freeze-drying procedures. The pharmaceutically or veterinary acceptable stabilizers may be carbohydrates (e.g. sorbitol, mannitol, lactose, sucrose, glucose, dextran, trehalose), sodium glutamate (Tsvetkov T et al.; Israeli E et al.), proteins such as peptone, albumin, lactalbumin or casein, protein containing agents such as skimmed milk (Mills C K et al.; Wolff E et al.), and buffers (e.g. phosphate buffer, alkaline metal phosphate buffer). An adjuvant may be used to make soluble the freeze-dried preparations.

Any vaccine composition according to the invention can also advantageously contain one or more adjuvant.

The plasmid-based vaccines may be formulated with cationic lipids, advantageously with DMRIE (N-(2-hydroxyethyl)-N,N-diméthyl-2,3-bis(tetradecyloxy)-1-propanammonium; WO96/34109), and advantageously in association with a neutral lipid, for example DOPE (dioleoyl-phosphatidyl-ethanolamine; Behr J. P.), in order to form DMRIE-DOPE. In one embodiment, the mixture is made extemporaneously, and before its administration it is advantageous to wait about 10 min to about 60 min, for example, about 30 min, for the appropriate mixture. When DOPE is used, the molar ratio of DMRIE/DOPE can be from 95/5 to 5/95 and is advantageously 1/1. The weight ratio plasmid/DMRIE or DMRIE-DOPE adjuvant is, for example, from 50/1 to 1/10, from 10/1 to 1/5 or from 1/1 to 1/2.

Optionally a cytokine may be added to the composition, especially GM-CSF or cytokines inducing Th1 (e.g. IL12). These cytokines can be added to the composition as a plasmid encoding the cytokine protein. In one embodiment, the cytokines are from canine origin, e.g. canine GM-CSF which gene sequence has been deposited at the GenBank database (accession number S49738). This sequence can be used to create said plasmid in a manner similar to what was made in WO 00/77210.

The recombinant viral vector-based vaccine may be combined with fMLP (N-formyl-methionyl-leucyl-phenylalanine; U.S. Pat. No. 6,017,537) and/or Carbomer adjuvant (Phameuropa Vol. 8, No. 2, June 1996). Persons skilled in the art can also refer to U.S. Pat. No. 2,909,462, which describes such acrylic polymers cross-linked with a polyhydroxylated compound having at least 3 hydroxyl groups, advantageously not more than 8, the hydrogen atoms of at least three hydroxyls being replaced by unsaturated aliphatic radicals having at least 2 carbon atoms. For example, the radicals are those containing from 2 to 4 carbon atoms, e.g. vinyls, allyls and other ethylenically unsaturated groups. The unsaturated radicals may themselves contain other substituents, such as methyl. The products sold under the name CARBOPOL® (BF Goodrich, Ohio, USA) are appropriate. The products are cross-linked with an allyl sucrose or with allyl pentaerythritol. Among them, there may be advantageously mentioned CARBOPOL® 974P, 934P and 971P.

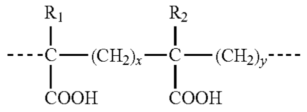

Among the copolymers of maleic anhydride and alkenyl derivative, the copolymers EMA® (Monsanto) which are copolymers of maleic anhydride and ethylene, linear or cross-linked, for example cross-linked with divinyl ether, are advantageous. Reference may be made to J. Fields et al.

The polymers of acrylic or methacrylic acid and the copolymers EMA® are formed, for example, of basic units of the following formula in which:

$R_1$ and $R_2$, which are identical or different, represent H or $CH_3$ x=0 or 1, preferably x=1 y=1 or 2, with x+y=2

For the copolymers EMA®, x=0 and y=2. For the carbomers, x=y=1.

The dissolution of these polymers in water leads to an acid solution, which is neutralized, advantageously to physiological pH, in order to provide the adjuvant solution into which the vaccine itself is incorporated. The carboxyl groups of the polymer are then partly in $COO^-$ form.

In one embodiment, a solution of adjuvant, especially of carbomer (*Pharmeuropa, vol.* 8, No. 2, June 1996), is prepared in distilled water, advantageously in the presence of sodium chloride, the solution obtained being at an acidic pH. This stock solution is diluted by adding it to the desired quantity (for obtaining the desired final concentration), or a substantial part thereof, of water charged with NaCl, advantageously physiological saline (NaCl9 g/l) all at once in several portions with concomitant or subsequent neutralization (pH 7.3 to 7.4), advantageously with NaOH. This solution at physiological pH is used for mixing with the vaccine, which may be especially stored in freeze-dried, liquid or frozen form.

The polymer concentration in the final vaccine composition can be from 0.01% to 2% w/v, from 0.06 to 1% w/v, or from 0.1 to 0.6% w/v.

The sub-unit vaccine may be combined with adjuvants, like oil-in-water, water-in-oil-in-water emulsions based on mineral oil and/or vegetable oil and non ionic surfactants such as block copolymers, TWEEN®, SPAN®. Such emulsions are notably those described in page 147 of "Vaccine Design—The Subunit and Adjuvant Approach", Pharmaceutical Biotechnology, 1995, or TS emulsions, notably the TS6 emulsion, and LF emulsions, notably LF2 emulsion (for both TS and LF emulsions, see WO 04/024027). Other suitable adjuvants are for example vitamin E, saponins, and CARBOPOL® (Noveon; see WO 99/51269; WO 99/44633), aluminium hydroxide or aluminium phosphate ("Vaccine Design, The subunit and adjuvant approach", Pharmaceutical Biotechnology, vol. 6, 1995), biological adjuvants (i.e. C4b, notably murine C4b (Ogata R T et al.) or equine C4b, GM- CSF, notably equine GM-CSF (U.S. Pat. No. 6,645,740)), toxins (i.e. cholera toxins CTA or CTB, *Escherichia coli* heat-labile toxins LTA or LTB (Olsen C W et al.; Fingerut E et al.; Zurbriggen R et al. Peppoloni S et al.), and CpG (i.e. CpG #2395 (see Jurk M et al.), CpG #2142 (see SEQ. ID. NO: 890 in EP 1,221,955).

The composition or vaccine may also contain or comprise one or more FeLV antigens, for example, ENV, or ENV and GAG, or ENV and GAG and PRO gene.

The composition or vaccine may also be associated with at least one FeLV antigen, for example inactivated FeLV. In a particular embodiment, the FeLV strain may be an FeLV type A strain, or a combination of FeLV type A and type B, or a combination of FeLV type A and type C, or a combination of type A, type B and type C strains. These strains of FeLV may be inactivated by chemical or physical methods. The chemical methods are notably BPL, formaldehyde. The physical methods may notably be sonication. One method for inactivating FeLV for use in a vaccine is described in R. Cordeiro Giunchetti et al., Vaccine, 2007. The inactivated FeLV vaccine may be combined with adjuvants, like those described previously for sub-unit vaccines.

Another aspect of the present invention relates to methods of vaccinating a host against FeLV using the vaccine compositions disclosed herein.

The host may be any one or all of felines (for example, domesticated cats, kittens, big cats and wild cats). In one embodiment, the host is a feline.

The routes of administration may be, for example, intramuscular (IM) or intradermal (ID) or transdermal (TD) or subcutaneous (SC). The means of administration may be, for example, a syringe with a needle, or needle free apparatus, or a syringe with a needle coupled to electrotransfer (ET) treatment, or needle free apparatus coupled to ET treatment.

Another aspect of the invention relates to the use of a plasmid-based vaccine according to the present invention for administration to a host, wherein this administration is coupled to ET treatment. The administration of a plasmid-based vaccine is advantageously intramuscular. The means of administration is, for example, a syringe and a needle. One or several injections may be administered successively. In the case of several injections, they may be carried out 2 to 6 weeks apart, for example, about 3 weeks apart. In one embodiment, a semi-annual booster or an annual booster is further administered.

For plasmid-based vaccines, advantageous routes of administration may be ID or IM. This administration may be through use of a syringe with a needle or with a needle free apparatus like Dermojet or Biojector (Bioject, Oregon, USA) or Vetjet™ (Merial) or Vitajet™ (Bioject Inc.), see US 2006/0034867. The dosage may be from 50 μg to 500 μg per plasmid. When DMRIE-DOPE is added, 100 μg per plasmid may be utilized. When GM-CSF or other cytokines are used, the plasmid encoding this protein may be present at a dosage of from about 200 μg to about 500 μg and may be 200 μg. The volume of doses can be between 0.01 ml and 0.5 ml, for example, 0.25 ml. Administration may be provided with multiple points of injection.

Alternatively, plasmid-based vaccines may be administered via the IM route coupled to electrotransfer (ET) treatment. The ET treatment may be performed using an apparatus for electrotransfer and the specifications of the manufacturer (i.e. Sphergen G250 generator (Sphergen SARL, Evry Genopole, France); MedPulser® DNA electroporation system (Innovio Biomedical Corporation, San Diego, Calif., USA)). In one embodiment, the apparatus for electrotransfer has a unipolar field. The field intensity may be from about 50 to about 250 V/cm, from about 50 to about 200 V/cm, or from about 50 to about 175 V/cm. The pulse duration may be from about 1 to about 50 msec, or from about 15 to about 25 msec. The frequency may be from about 1 to about 50 Hz, or from about 5 to about 15 Hz. The interpulse interval may be from about 1 to 1000 msec, or from about 1 to about 200 msec. The number of pulses may be from 1 to 20, or from 5 to 10. The intra tissular intensity may advantageously be up to about 2 Å. The distance between electrodes may be from about 0.2 to about 1 cm, or from about 0.2 to about 0.5 cm.

For recombinant viral vector-based vaccines, the routes of administration may advantageously be SC or IM or TD or ID. This administration may be made by a syringe with a needle or with a needle free apparatus like Dermojet or Biojector (Bioject, Oregon, USA) or Vetjet™ (Merial) or Vitajet™ (Bioject Inc.). The dosage may be from about $10^3$ pfu to about $10^9$ pfu per recombinant poxvirus vector. When the vector is a canarypox virus, the dosage may be, for example, from about $10^5$ pfu to about $10^9$ pfu, from about $10^6$ pfu to about $10^8$ pfu, or from about $10^6$ pfu to about $10^7$ pfu. The volume of doses may be from about 0.01 ml to 0.2 ml, and is advantageously 0.1 ml. Administration may comprise multiple points of injection.

For the IM route the volume of the vaccine provided may be from 0.2 to 2 ml, in particular from about 0.5 to 1 ml. The same dosages are utilized for any of the vectors of the present invention.

For sub-unit vaccines, the route of administration may advantageously be via SC or IM or TD or ID. This administration may be made by a syringe with a needle or with a needle free apparatus like Dermojet or Biojector (Bioject, Oregon, USA) or Vetjet™ (Merial) or Vitajet™ (Bioject Inc.). The dosage may be from about 50 to about 500 μg, in particular from about 50 to about 150 μg, and more particularly from about 50 to about 100 μg. The volume of the sub-unit vaccine provided is from 0.2 to 2 ml, in particular from about 0.5 to 1 ml.

In another aspect, the present invention relates to a vaccine strategy, which is based on a prime-boost administration regimen, where the primo-administration and the boost administration(s) utilize a composition comprising a pharmaceutically or veterinary acceptable excipient, diluent or vehicle and an in vivo expression vector comprising a polynucleotide sequence, that contains and expresses the FeLV polypeptide and/or variants or fragments thereof.

The present invention relates to the use of in vivo expression vectors in a prime-boost administration regimen, comprising a primo-administration of a vaccine comprising a pharmaceutically or veterinary acceptable vehicle, diluent or excipient, an in vivo expression vector containing a polynucleotide sequence for expressing, in vivo, FeLV polypeptides and/or variants or fragments thereof, followed by a boost administration of a vaccine comprising a pharmaceutically or veterinary acceptable vehicle or excipient, an in vivo expression vector containing a polynucleotide sequence for expressing, in vivo, FeLV polypeptides and/or variants or fragments thereof as described above, to protect a host from FeLV and/or to prevent disease progression in infected hosts.

A prime-boost regimen comprises at least one primo-administration and at least one boost administration using at least one common polypeptide and/or variants or fragments thereof. The vaccine used in primo-administration may be different in nature from those used as a later booster vaccine. The primo-administration may comprise one or more administrations. Similarly, the boost administration may comprise one or more administrations.

The routes of administration, doses and volumes are as previously disclosed herein.

The prime-boost administrations may be advantageously carried out 2 to 6 weeks apart, for example, about 3 weeks apart. According to one embodiment, a semi-annual booster or an annual booster, advantageously using the viral vector-based vaccine, is also envisaged. The animals may be at least 6 to 8 weeks old at the time of the first administration.

In one embodiment, the prime-boost administration regimen comprises at least one prime-administration of a plasmid-based vaccine according to the present invention and at least one boost-administration of a recombinant viral vector-based vaccine according to the present invention.

In another embodiment, the prime-boost administration regimen comprises at least one prime-administration of a recombinant viral vector-based vaccine according to the present invention and at least one boost-administration of a sub-unit vaccine according to the present invention.

In another embodiment, the prime-boost administration regimen comprises at least one prime-administration of a recombinant viral vector-based vaccine according to the present invention and at least one boost-administration of a plasmid-based vaccine according to the present invention.

In one embodiment, the present invention relates to a method of vaccinating a subject susceptible to FeLV comprising a prime-boost administration regimen wherein said regiment comprises a prime-administration of a vaccine or composition comprising, in a pharmaceutically or veterinary acceptable vehicle, diluent or excipient, a plasmid containing a polynucleotide for expressing, in vivo, an FeLV polypeptide, a variant or fragment of the FeLV polypeptide, or a mixture thereof, followed by a boost administration of a vaccine comprising, in a pharmaceutically or veterinary acceptable vehicle or excipient, a recombinant viral vector comprising a polynucleotide for expressing, in vivo, the same FeLV polypeptide(s), variant thereof, fragment thereof, to protect the subject from FeLV and/or to prevent disease progression in infected subject.

In another embodiment, the present invention relates to a method vaccinating a subject susceptible to FeLV comprising a prime-boost administration regimen wherein said regiment comprises a prime-administration of a vaccine or composition comprising, in a pharmaceutically or veterinary acceptable vehicle, diluent or excipient, a recombinant viral vector comprising a polynucleotide for expressing, in vivo, an FeLV polypeptide, a variant or fragment of the FeLV polypeptide, or a mixture thereof, followed by a boost administration of a vaccine comprising, in a pharmaceutically or veterinary acceptable vehicle or excipient, a plasmid containing a polynucleotide for expressing, in vivo, the FeLV polypeptide(s), variant thereof, fragment thereof, to protect the subject from FeLV and/or to prevent disease progression in infected subject.

In yet another embodiment, the present invention related to a method of vaccinating a subject susceptible to FeLV comprising a prime-boost administration regimen wherein said regiment comprises a prime-administration of a vaccine or composition comprising, in a pharmaceutically or veterinary acceptable vehicle, diluent or excipient, a recombinant viral vector comprising a polynucleotide for expressing, in vivo, a an FeLV polypeptide, a variant or fragment of the FeLV polypeptide, or a mixture thereof, followed by a boost administration of a vaccine comprising, in a pharmaceutically or veterinary acceptable vehicle or excipient, the same FeLV polypeptide(s), variant thereof, fragment thereof, to protect the subject from FeLV and/or to prevent disease progression in infected subject.

Another aspect of the present invention relates to a kit for prime-boost vaccination according to the present invention. The kit may comprise at least two vials: a first vial containing a vaccine for the prime-vaccination according to the present invention, and a second vial containing a vaccine for the boost-vaccination according to the present invention. The kit may advantageously contain additional first or second vials for additional prime-vaccinations or additional boost-vaccinations.

In one embodiment, the kit may comprise two vials, one containing a plasmid-based vaccine for the prime-vaccination according to the present invention, the other vial containing a recombinant viral vector-based vaccine for the boost-vaccination according to the present invention.

In another embodiment, the kit may comprise two vials, one containing a recombinant viral vector-based vaccine for the prime-vaccination according to the present invention, the other vial containing a sub-unit vaccine for the boost-vaccination according to the present invention.

In another embodiment, the kit may comprise two vials, one containing a recombinant viral vector-based vaccine for the prime-vaccination according to the present invention, the other vial containing a plasmid-based vaccine for the boost-vaccination according to the present invention.

The invention will now be further described by way of the following non-limiting examples.

EXAMPLES

Without further elaboration, it is believed that one skilled in the art can, using the preceding descriptions, practice the present invention to its fullest extent. The following detailed examples are to be construed as merely illustrative, and not limitations of the preceding disclosure in any way whatsoever. Those skilled in the art will promptly recognize appropriate variations from the procedures both as to reactants and as to reaction conditions and techniques.

Construction of DNA inserts, plasmids and recombinant viral vectors was carried out using the standard molecular biology techniques described by J. Sambrook et al. (Molecular Cloning: A Laboratory Manual, 2nd Edition, Cold Spring Harbor Laboratory, Cold Spring Harbor, N.Y., 1989). All the restriction fragments used for the present invention were isolated using the "Geneclean" kit (BIO 101 Inc., La Jolla, Calif.).

Example 1

Construction of pH6C5env Plasmid pPB713 Construction of pH6C5env-pCXL208.2, a C5 Insertion Plasmid for the Generation of FeLV-ENV/ALVAC(2) Recombinants An ALVAC(1) recombinant virus which contains FeLV ENV inserted at C5 locus and GAG/POL (+T5NT) inserted at C3 locus (Merial proprietary material) was used to amplify the FeLV ENV gene. Primers 7862CXL and 7847CXL were used for the PCR amplification.

```
7862CXL: ACG CCG CTC GAG CGG GGA TCT CTT TAT TCT ATA CTT A (SEQ ID NO: 25)
                  Xho I           H6 promoter 7847CXL: CTC GGA TCC AGAAAAA TCA TGG TCG GTC CGG ATC       (SEQ ID NO: 26)
             Bam HI   T5NT  stop
```

The amplified PCR fragment (2.1 Kb) contains the FeLV ENV gene, H6 promoter immediately upstream of the ENV and a T5NT sequence followed by stop codon of the ENV.

The PCR fragment was then digested with XhoI/BamHI and ligated to XhoI/BamHI digested pH6C5ALVAC donor plasmid (Merial proprietary material) to generate pCXL208.2, which was sequence confirmed.

The plasmid map of pCXL208.2 and its sequence are shown in FIGS. 2 and 3.

Construction of pH6C5env Plasmid pPB713

FeLV ENV is glycosylated and cleaved to produce glycoprotein gp70 ENV and p15E ENV. The protein sequence of mutated FeLV ENV gene of strain 82K is shown in FIG. 5. The mutation is the substitution of Arg for Glu at position 527 of the FeLV ENV gene.

Plasmid pHCMV-ENV FeLV was received from Institut Gustave-Roussy (Villejuif, France). The sequence of the mutated FeLV ENV fragment (SEQ ID NO:3) provided contains 5 mutations (in nucleotides) by comparison with the reference sequence (Glasgow, GenBank accession No. M12500, SEQ ID NO:35). Among the five nucleotide mutations, two mutations are silent mutations (no amino-acid change), but introduced a new restriction site (=FspI); three mutations introduced a mutation in the amino-acid sequence of FeLV ENV (Arg in place of Glu; as shown in FIG. 5, SEQ ID NO:4).

Figure 4:
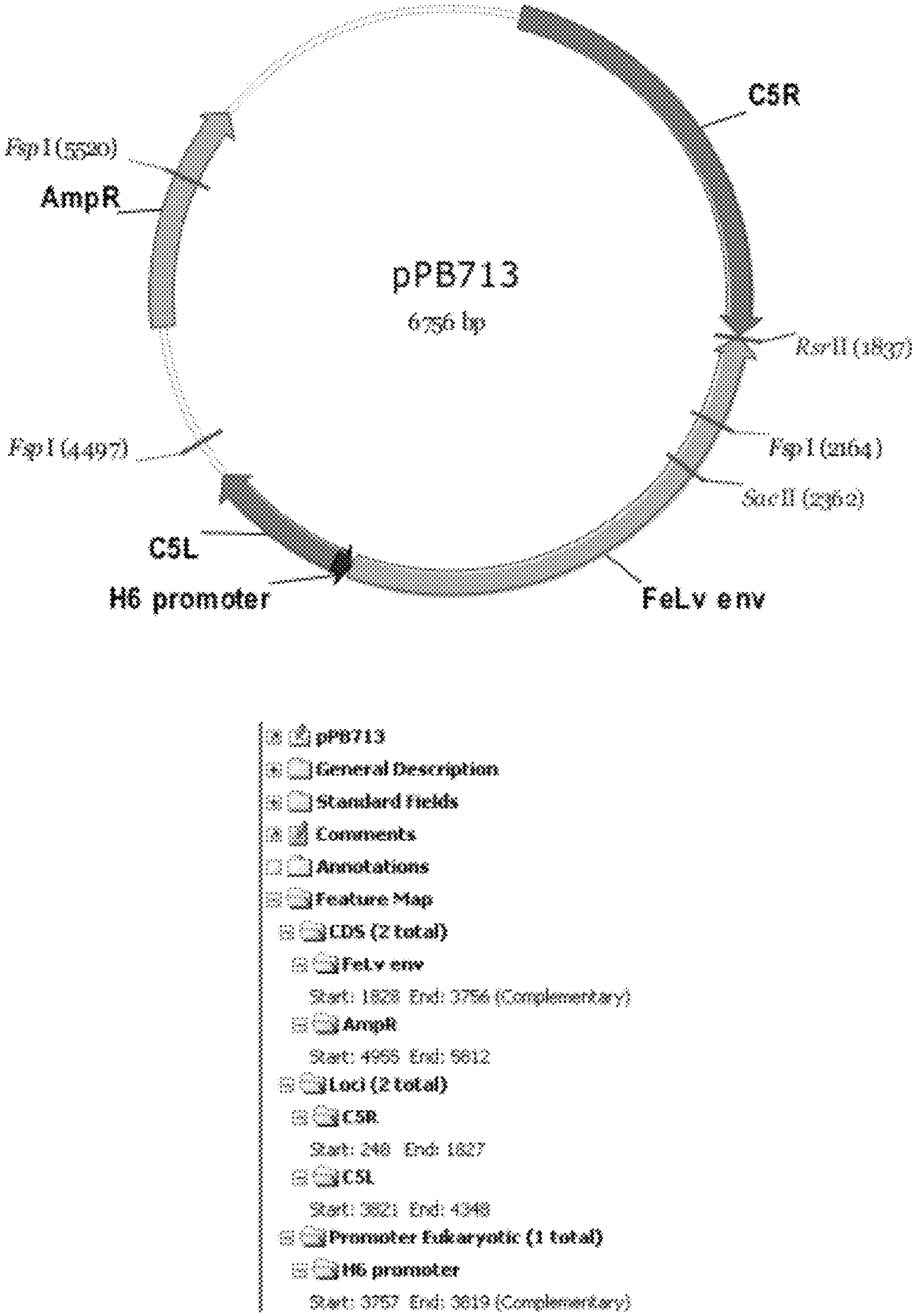
FIG. 4 provides the restriction map for plasmid pPB713.
Figure 5A:
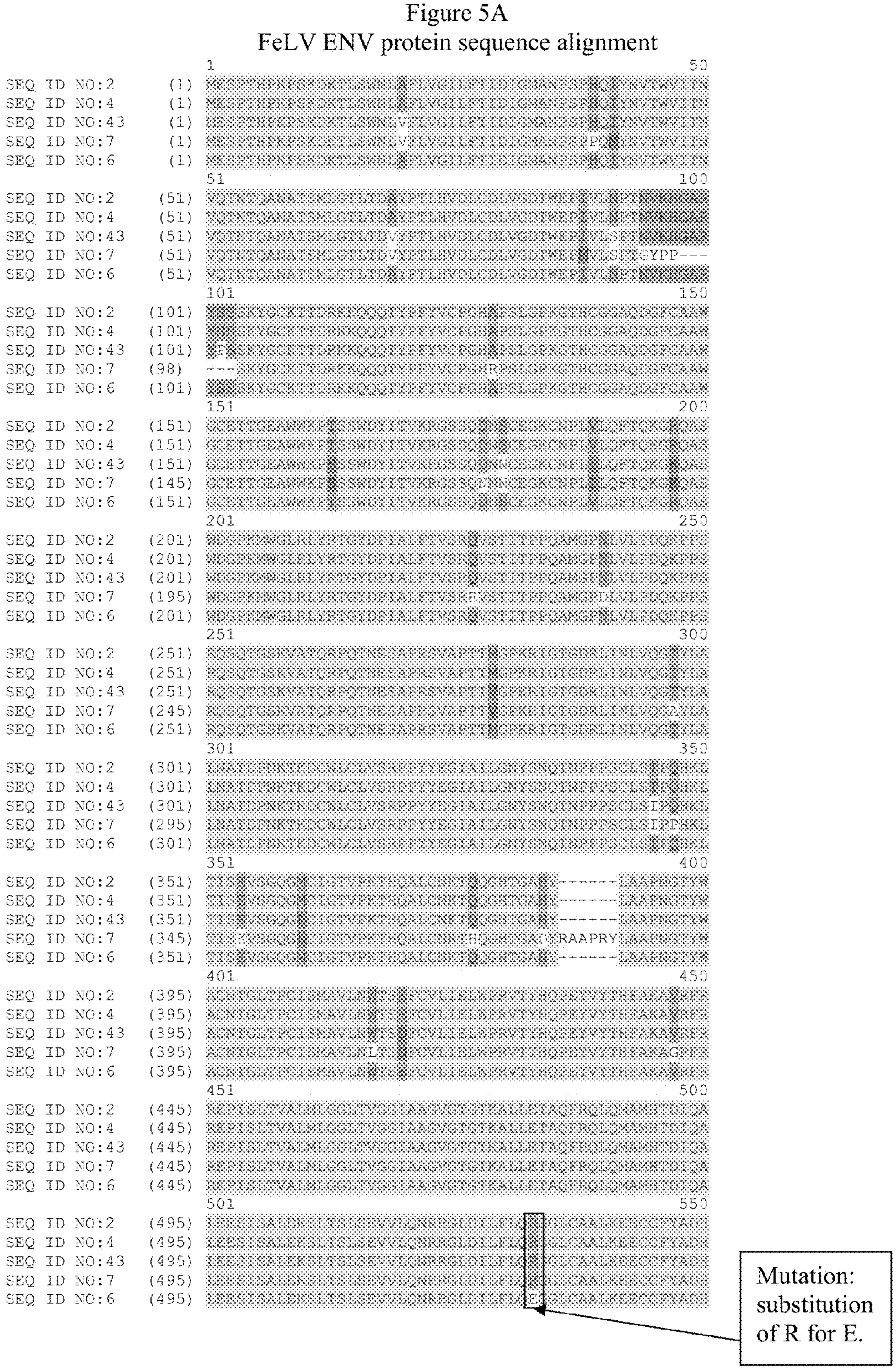
FIG. 5 provides the sequence alignments of the FeLV ENV DNA and proteins.
Figure 5C:
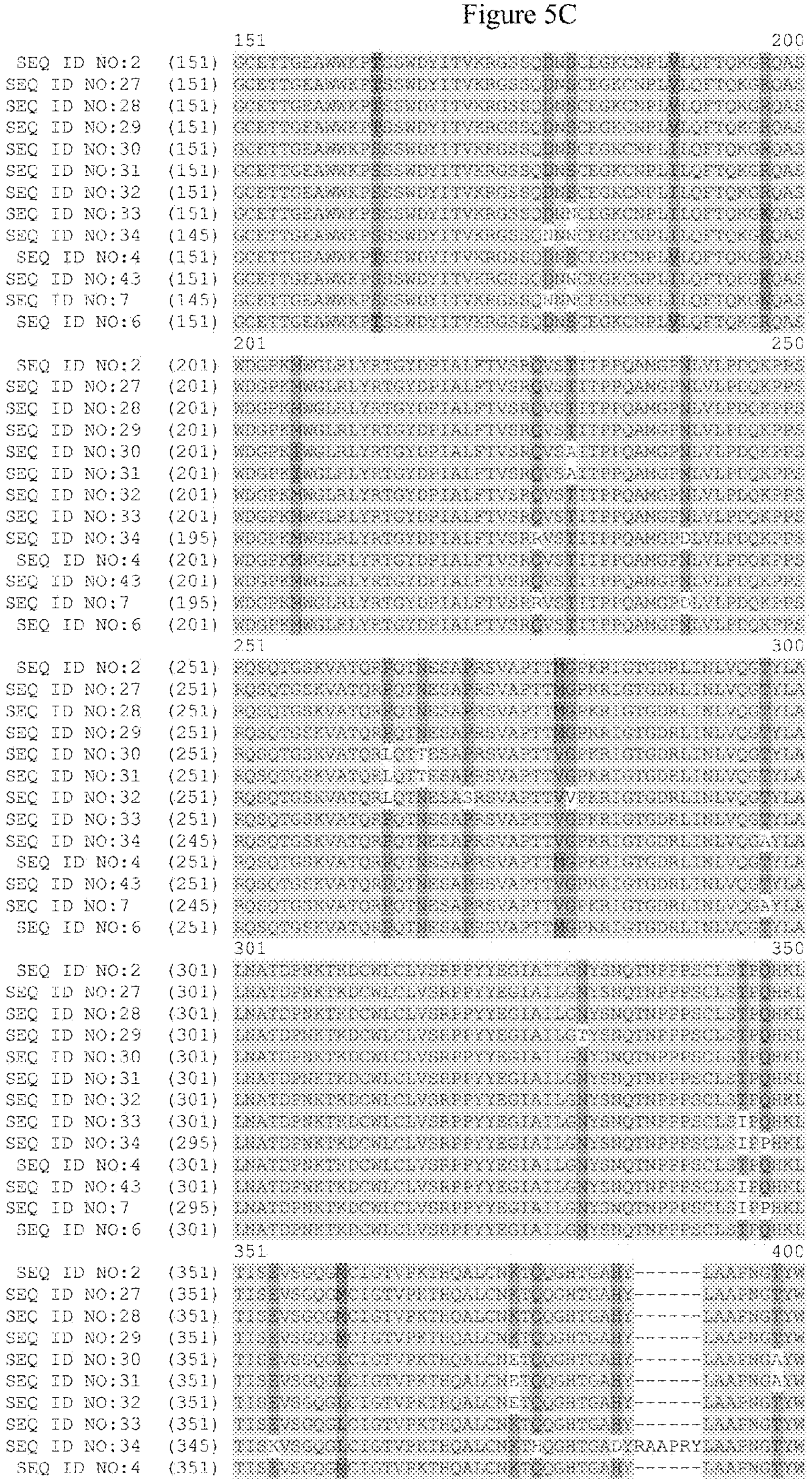
Figure 5D:
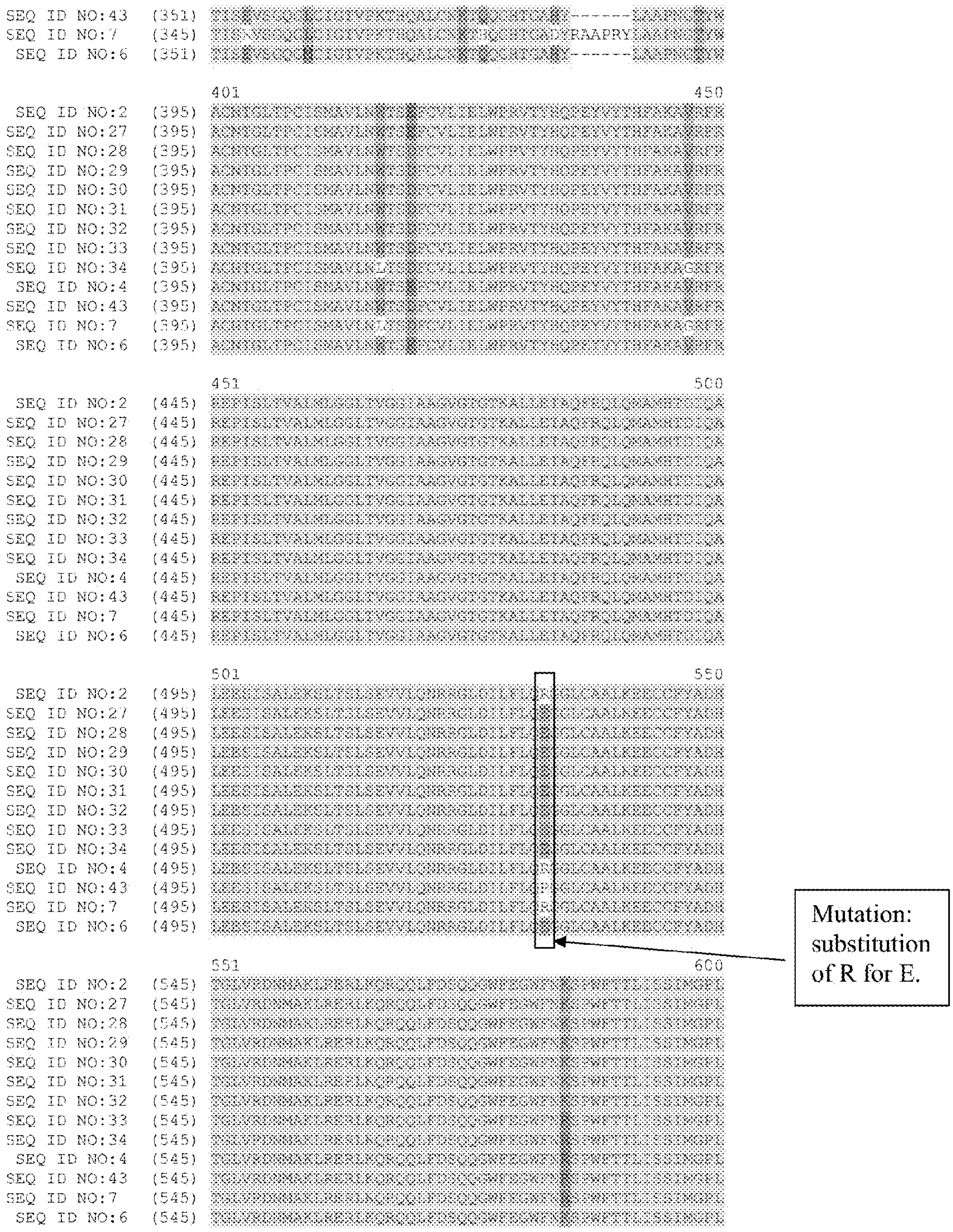
Figure 5H:
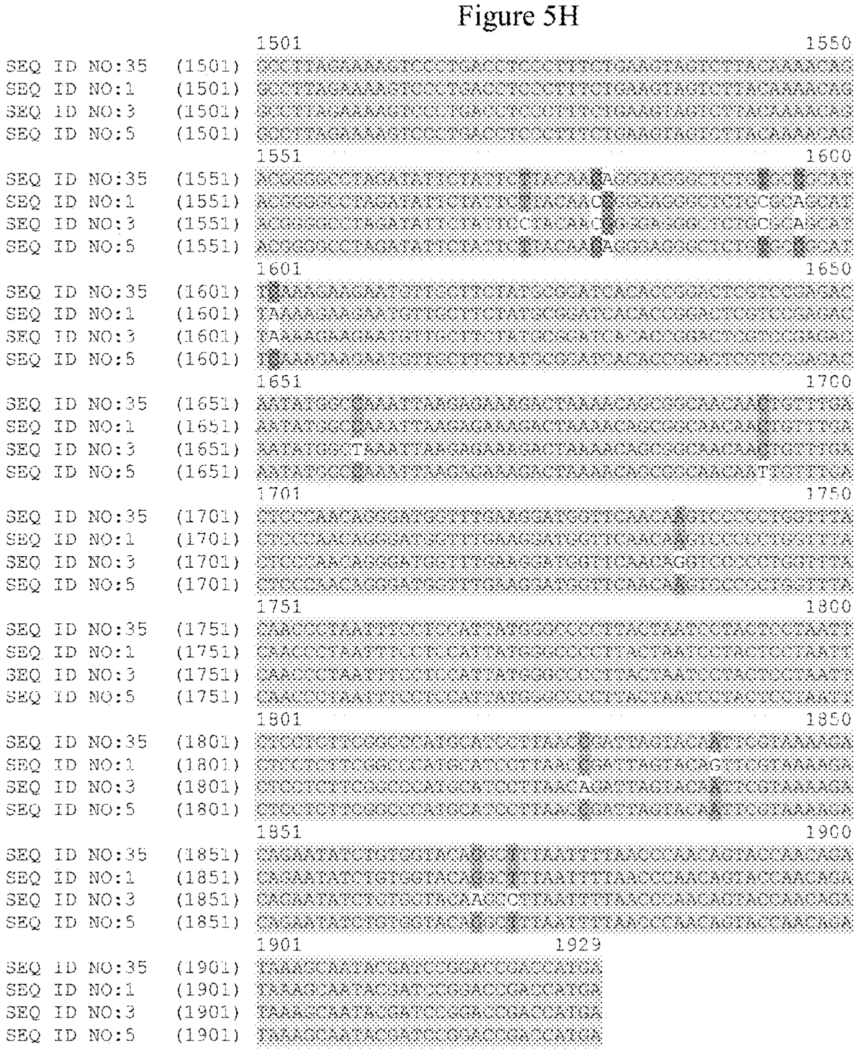
Figure 6:
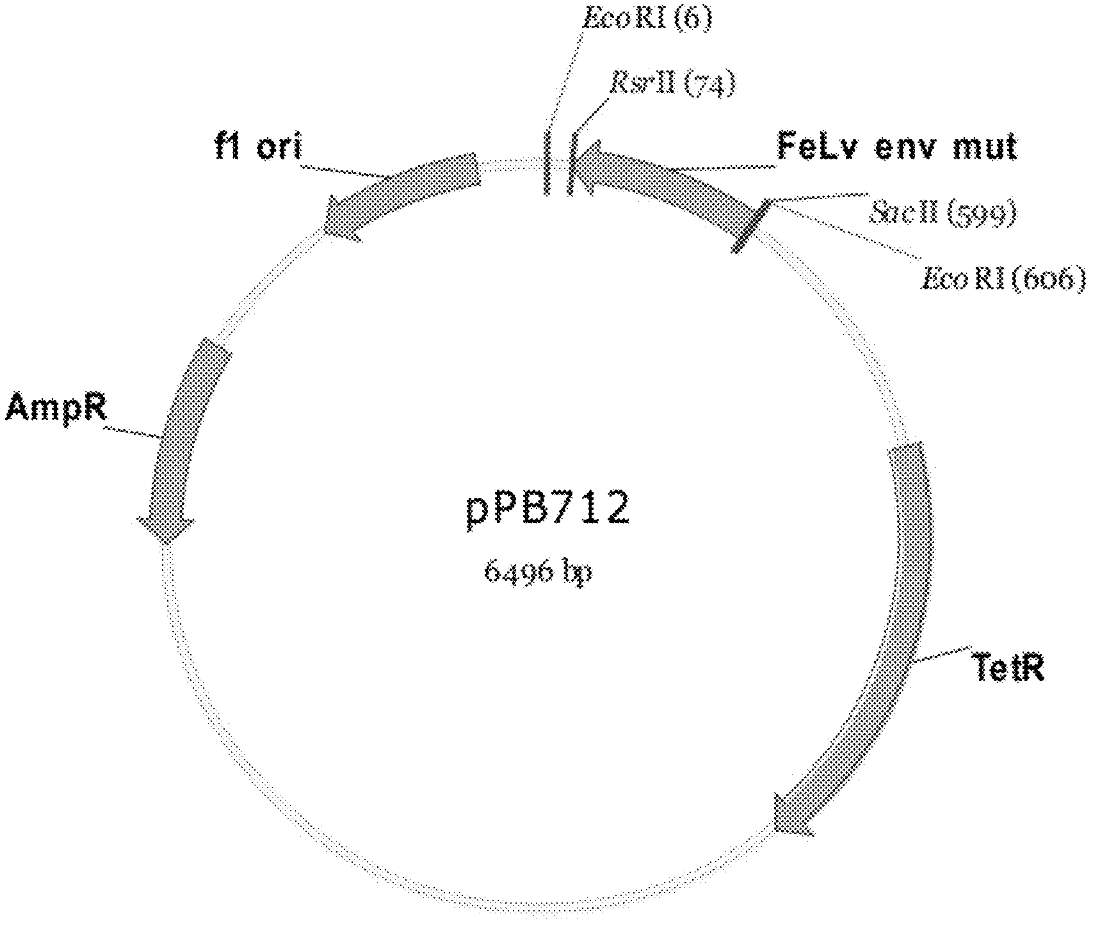
FIG. 6 provides the plasmid pPB712 restriction map.

Plasmid phCMV-ENV FeLV was digested with RsrII/SacII to generate an RsrII-SacII fragment (fragment B: 520 bp). Plasmid pCXL208.2 was digested with RsrII/SacII to generate a RsrII-SacII fragment (fragment A: 6231 bp). Fragments A and B were ligated to generate plasmid pPB713 (6756 bp). The identity of pPB713 was confirmed by an FspI digestion. The restriction map of pPB713 and the pPB713 sequences are shown in FIG. 4.

Construction of pH6C5env Plasmid pPB712

Plasmid PhCMV-ENV FeLV was digested with RsrII/SacII to generate an RsrII-SacII fragment (fragment A: 520 bp). Plasmid pPB575 (Merial proprietary material) was digested with RsrII/SacII to generate an RsrII-SacII fragment (fragment B: 5971 bp). Fragments A and B were ligated to generate plasmid pPB712 (6496 bp). The identity of pPB712 was confirmed by an EcoRI digestion. The sequence of the mutated region of FeLV present in pPB712 clone was controlled by DNA sequencing (Cogenics, France) with universal M13 primer and reverse M13 primer. Two candidates were selected (n° 1 and n° 2). The sequences of the 2 clones were identical but were different from SEQ ID NO:4 (single amino acid mutation Glu to Arg). There are eight nucleotide mutations, leading to only one amino acid change. The DNA and protein sequence comparisons between the mutated FeLV (SEQ ID NO:1) in pPB712 and the mutated FeLV (SEQ ID NO:3) in pHCMV-ENV FeLV are shown in FIG. 5. The sequence comparison of FeLV ENV proteins of different strains is shown in FIG. 5.

Example 2

Figure 7A:
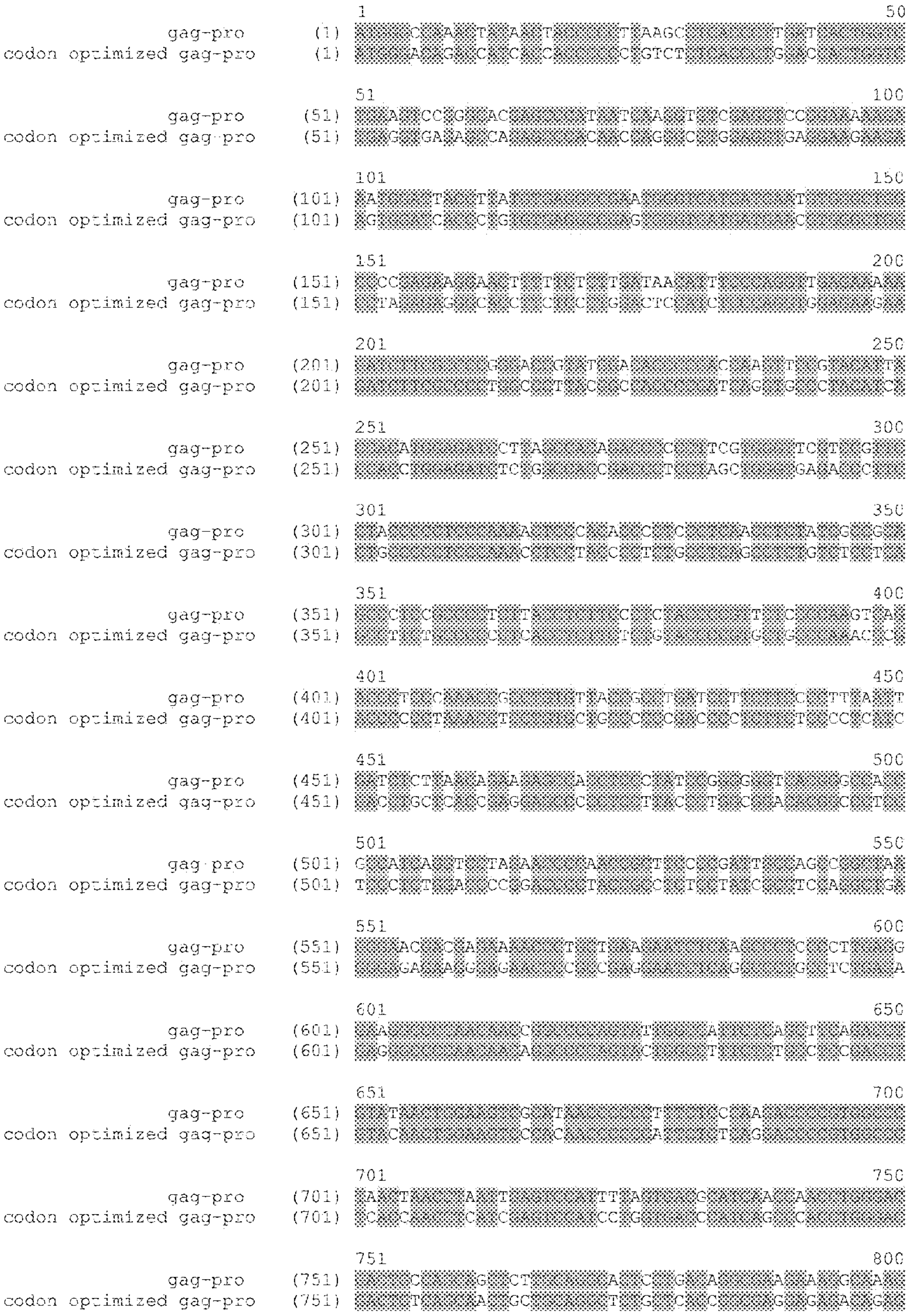
FIG. 7 shows the DNA sequence alignment between wild-type GAG/PRO DNA (SEQ ID NO:11) and codon-optimized GAG/PRO DNA (SEQ ID NO:10).
Figure 7B:
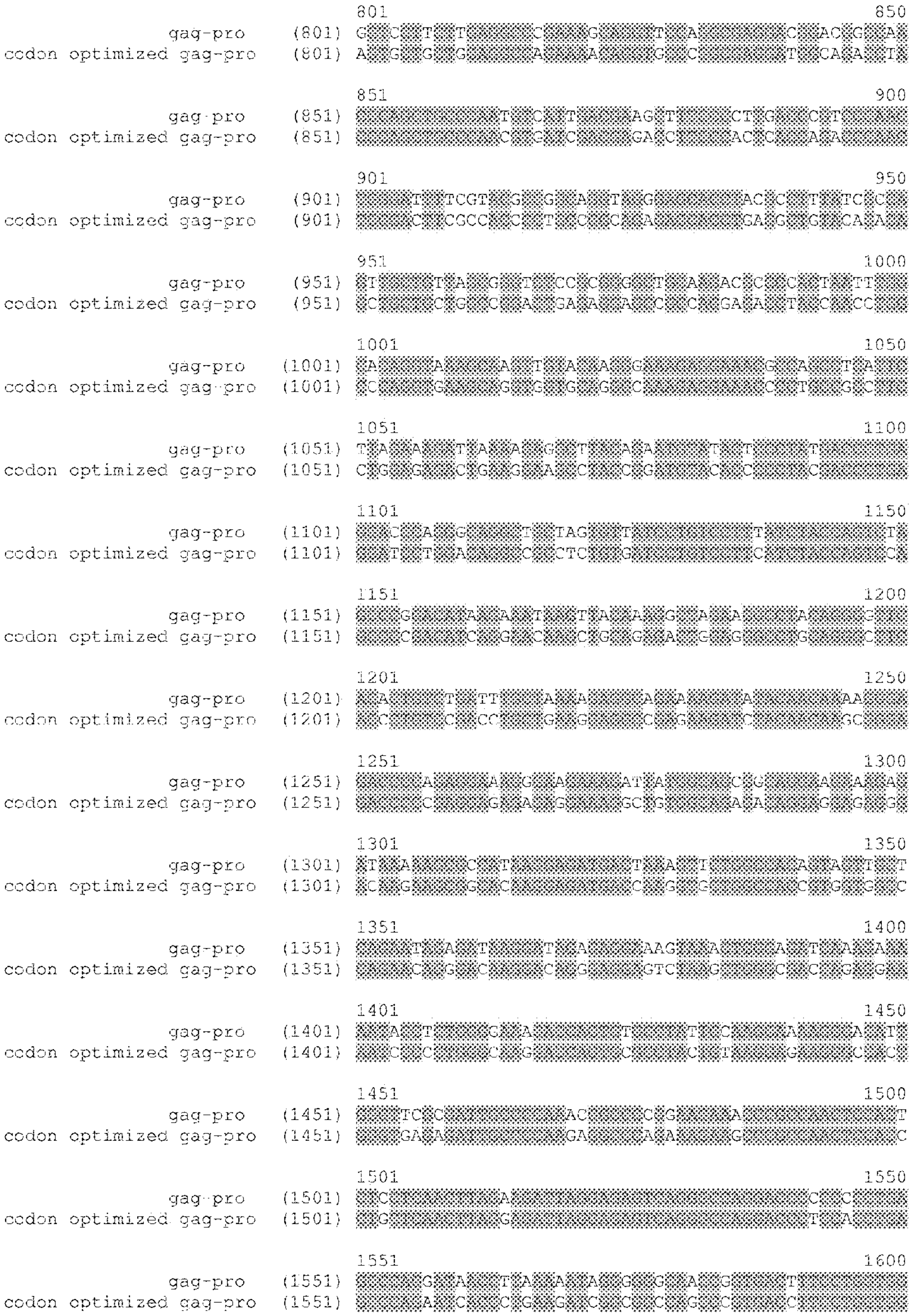
Figure 7C:
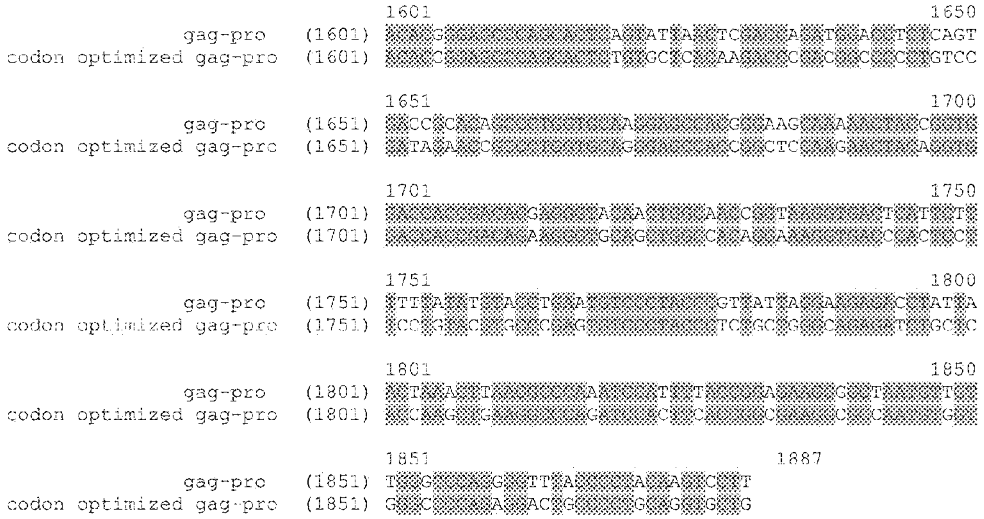

Construction of C3 ALVAC Donor Plasmid for Generation of an ALVAC Recombinant Expressing FeLV Codon Optimized GAG-PRO FeLV (Feline leukemia virus) codon optimized GAG-PRO gene was used in making the vCP2294. FeLV GAG-PRO gene was optimized for gene expression in mammalian cells. The sequence comparison at the DNA level between the codon-optimized GAG-PRO gene (SEQ ID NO:10) and the wild-type gap-pro gene (Genbank accession No. M18247, SEQ ID NO:11) is show in FIG. 7.

Figure 8A:
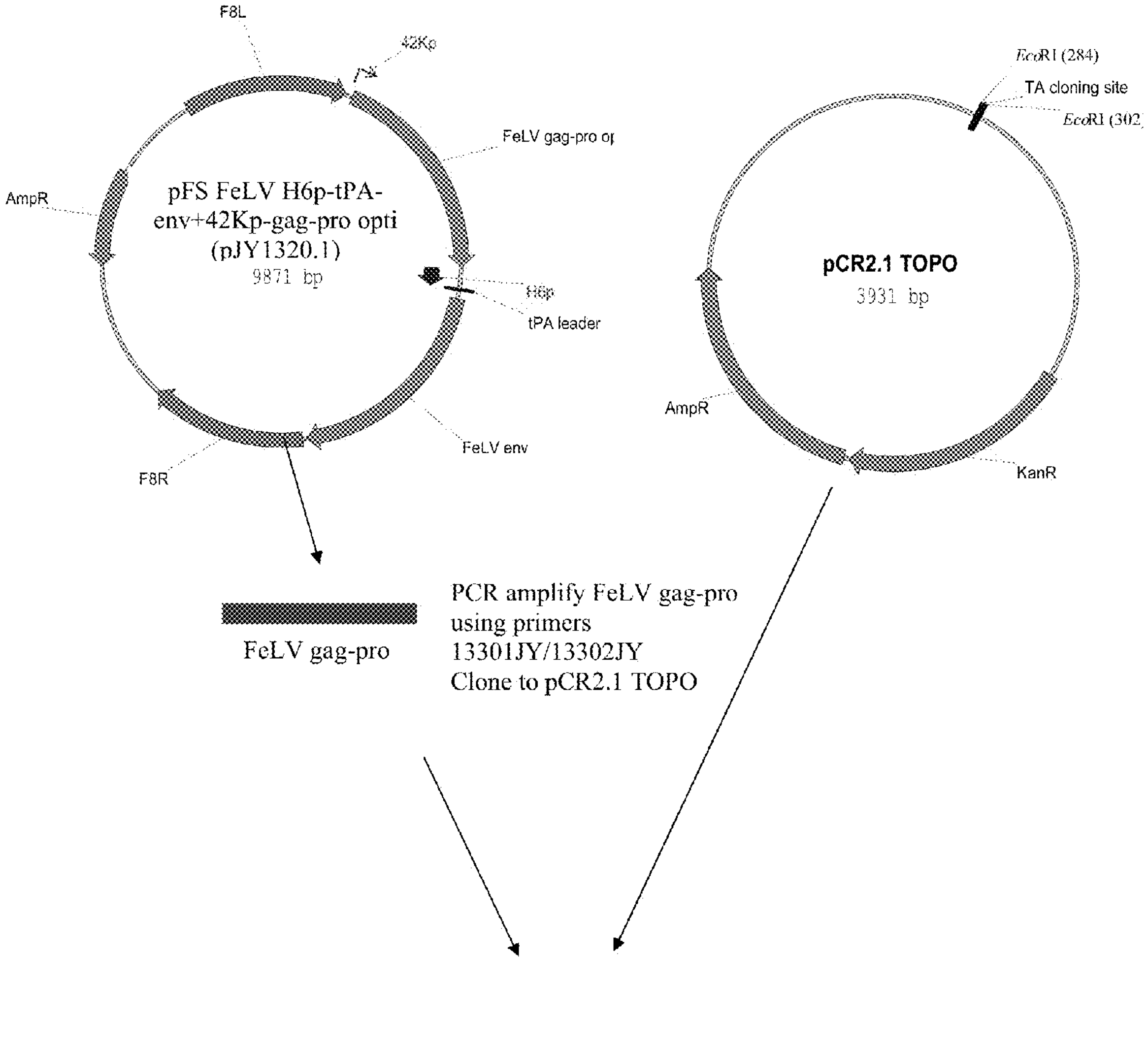
FIG. 8 provides the cloning scheme.
Figure 8B:
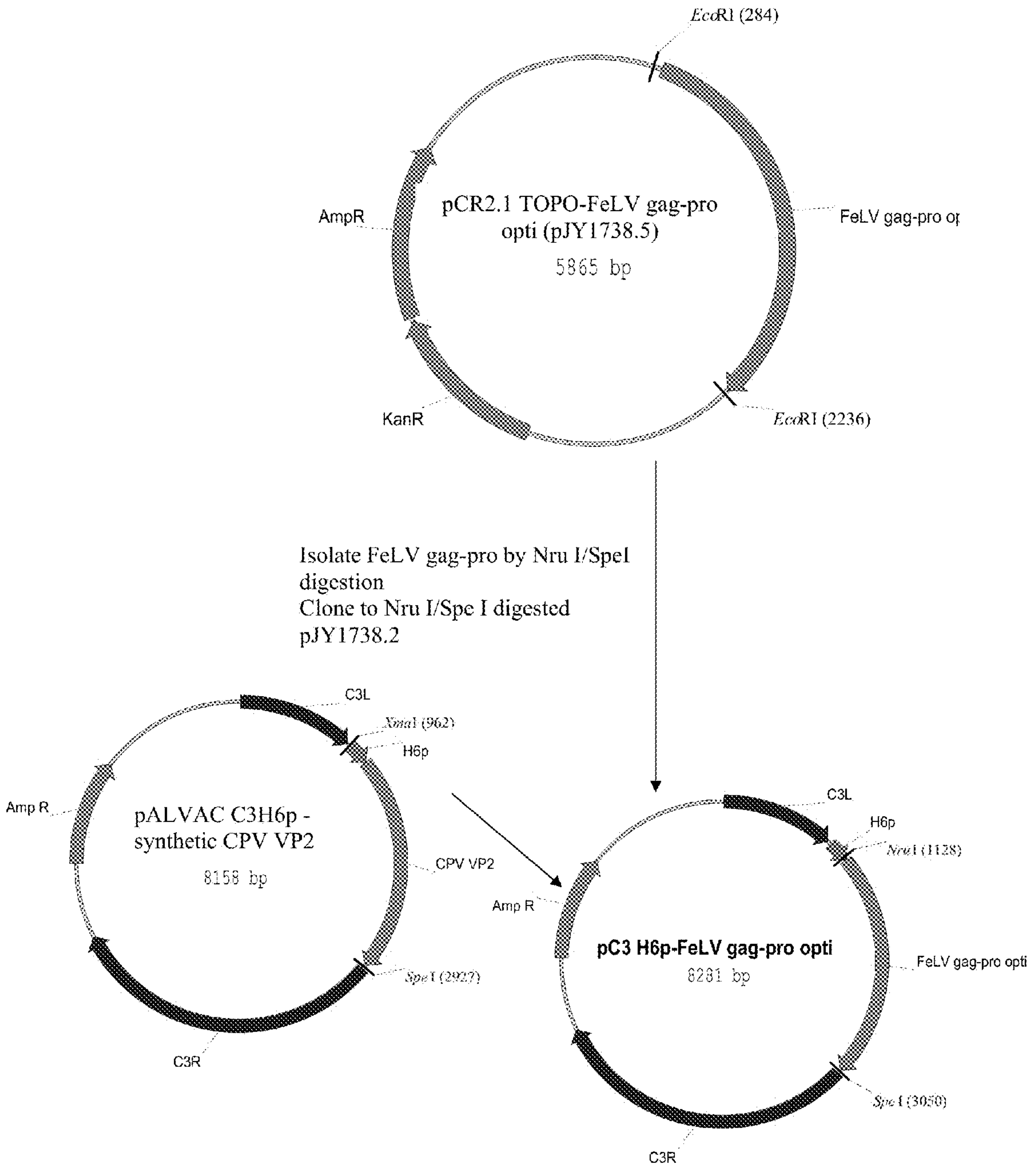
Figure 9:
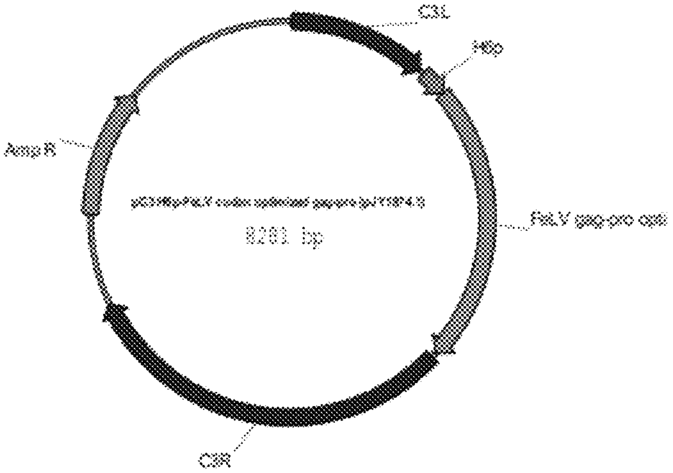
FIG. 9 provides the restriction map of plasmid pJY1874.1.

The construction scheme is outlined in FIG. 8. The plasmid pJY1320.1 (Merial proprietary material) containing H6p-FeLV codon optimized GAG-PRO cassette was used as a template for PCR amplification. H6p is Vaccinia virus H6 promoter. Primers 13301JY and 13302JY were used for the PCR amplification. The PCR fragment was cloned to a pCR2.1-TOPO vector. The resulting plasmid pJY1857.5 was sequenced and confirmed to have the correct sequences of H6p-FeLV GAG-PRO. In order to construct pC3 FeLV H6p-GAG-PRO, an NruI/SpeI DNA fragment, which contains 3'-partial H6 promoter and full-length GAG-PRO, was isolated from pJY1857.5 and ligated to Nru I/Spe I digested pJY1738.2 (Merial proprietary material) to create pJY1874.1 (as shown in FIGS. 9, 10 and 11), which was confirmed to have the correct sequences.

```
Primer forward 13301JY (SEQ ID NO: 13)

                                                            (SEQ ID NO: 15)
            Nru I  H6p
5' ATTA TCGCGA TATCCGTTAAGTTTGTATCGTA ATG GGA CAG ACC ATC ACC ACC

CCC CTG T

Primer reverse 13302JY (SEQ ID NO: 14)

            Spe I
5' ATTA ACTAGT CAAGAAAAA TCA TTA CAG CAC CTG CAG GGG CAG TCC TCT
```

In FeLV infected cells, GAG-PRO is produced by readthrough. GAG is further cleaved to MA (p15), CA (p30) and NC proteins during the later stage of virus assembly.

Example 3

Generation and Characterization of ALVAC Recombinant Containing H6p FeLV Codon Optimized GAG-PRO Inserted in C3 Locus of ALVAC (vFP2294)

The IVR (in vitro recombinant) was performed by transfection of Primary chicken embryo fibroblast cells (1°CEF) with 10 μg of Not I-linearized donor plasmid pJY1874.1 using FuGENE-6® reagent (Roche). The primary chicken embryo fibroblast cells (1°CEF) used for in vitro recombination were grown in 10% FBS (JRH: γ-irradiated #12107-500M), DMEM (BRL/Gibco#11960-051 or 11960-044) supplemented with 4 mM Glutamine (BRL/Gibco#25030-081) and 1 mM Sodium Pyruvate (BRL/Gibco#11360-070) in the presence of 1× antibiotics/antimycotics (P/S/A/A, BRL/Gibco#15240-062). The transfected cells were subsequently infected with ALVAC as rescue virus at MOI (multiplicity of infection) of 10 (ALVAC #HM1372 2007 Apr. 4). After 24 hours, the transfected-infected cells were harvested, sonicated and used for recombinant virus screening.

Recombinant plaques were screened based on the plaque lift hybridization method using a 1.4 kb FeLV GAG specific probe labeled with horse radish peroxidase (HRP) according to the manufacturer's protocol (Amersham Cat# RPN3001). After five sequential rounds of plaque purification, the recombinant designated as vCP2294.1.1.1.1.1 was generated and confirmed by hybridization as 100% positive for the FeLV GAG insert and 100% negative for the C3 ORF.

Single plaque was selected from the 5th round of plaque purification, and expanded to obtain P1 (1×T25 flask), P2 (1×T75 flask) and P3 (6× roller bottles). The infected cell culture fluid from the roller bottles was harvested and concentrated to produce a virus stock vCP2294.1.1.1.1.1.

The scheme to generate recombinant vCP2294 is depicted in FIG. 12.

Analysis of recombinant: the following analyses were performed on the P3 stocks.

Confirmation of Genetic Purity

The P3 stocks were re-confirmed by hybridization, as 100% positive for the FeLV GAG and 100% negative for the C3 ORF.

Genomic Analysis

Genomic DNA from vCP2294.1.1.1.1.1 was extracted, digested with BamHI, HindIII or Pst I and run on 0.8% agarose gel. The gel with BamHI, HindIII or PstI digested genomic DNA was transferred to a nylon membrane and Southern blot analysis was performed by probing with the 1.4 kb FeLV GAG probe. Multiple bands were observed at the expected sizes, indicating the correct insertion of FeLV GAG-PRO gene into the C3 locus.

| Restriction enzyme | Fragment (bp) |
|---|---|
| Bam HI | 4152 4885 13961 |
| Hind III | 17783 |
| Pst I | 681 2444 12041 |

Expression Analysis

1) Western Blot

Primary CEF cells were infected with the P3 stock of vCP2294.1.1.1.1.1 at MOI of 10 and incubated at 37° C. for 24 hrs. The culture supernatant and cells were then harvested. Cell pellet was lysed with Reporter Gene Assay Lysis Buffer manufactured by Roche (Cat. 1 897 675). Both Supernatant and lysate were prepared with the NuPage® System with antioxidant added. Proteins were separated on a NuPage® 10% Bis-Tris Pre-cast gel, and then transferred to a PVDF membrane. Anti FeLV GAG antibodies revealed a ~70 kDa protein detected in both supernatant and cell pellet, and a ~57 kDa protein, which was detected only in the cell pellet.

2) Immunoplaque Assay

The homogeneity of the population was 100% positive to the FeLV GAG protein for recombinant vCP2294.1.1.1.1.1 as evidenced by an immunoplaque assay, using anti-FeLV GAG antibodies.

Sequence Analysis

A more detailed analysis of the P3 stock genomic DNA was performed by PCR amplification and sequence analysis of the flanking arms of the C3 locus and the FeLV insert. Primers 8103JY and 8104JY, located beyond the arms of the C3 locus in the ALVAC genome were used to amplify the entire C3L-FeLV-C3R fragment. The results showed that the sequences of the FeLV insert and C3L and C3R of ALVAC are correct.

Primers for Amplifying the FeLV GAG Probe:

```
11369JY:
                                   (SEQ ID NO: 17)
5' ATGATGAACGTGGGCTGGCCT 3'

11377JY:
                                   (SEQ ID NO: 18)
5' TCTCCTAAGTTGAGCAGGGTG 3'
```

Primers for PCR Amplification of C3L-FeLV GAG-PRO Cassette-C3R:

```
8103JY:
                                   (SEQ ID NO: 19)
5' GAGGCATCCAACATATAAAGAAGACTAAAG 3'

8104JY:
                                   (SEQ ID NO: 20)
5' TAGTTAAATACTCATAACTCATATCTG 3'
```

Figure 13:
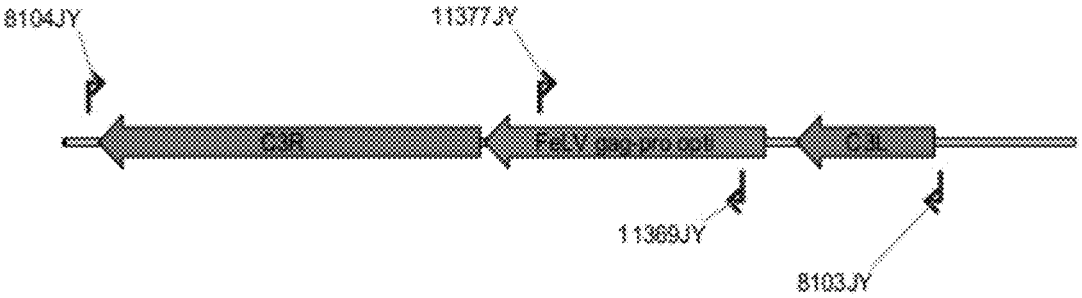
FIG. 13 shows the vCP2294 plasmid C3 region map with primer locations.

FIG. 13 shows the vCP2294 C3 region map showing primer locations. The vCP2294 sequence is depicted in FIG. 14.

Example 4

Generation and Characterization of ALVAC Recombinant Containing FeLV Modified ENV Gene Inserted at C5 Locus of vCP2294, ALVAC C3H6p FeLV Codon Optimized GAG-PRO-vCP2296

The IVR was performed by transfection of 1°CEF cells with 10 μg of Not I-linearized donor plasmid pPB713 using FuGENE-6® reagent (Roche). The transfected cells were subsequently infected with vCP2294 (ALVAC C3H6p FeLV codon optimized GAG-PRO, Example 2) as rescue virus at MOI of 10. After 24 hours, the transfected infected cells were harvested, sonicated and used for recombinant virus screening.

Recombinant plaques were screened based on the plaque lift hybridization method using a 503 by FeLV ENV specific probe labeled with horse radish peroxidase (HRP) according to the manufacturer's protocol (Amersham Cat# RPN3001). After four sequential rounds of plaque purification, the recombinant designated as vCP2296.6.1.1.2 was generated and confirmed by hybridization as 100% positive for the FeLV ENV insert and 100% negative for the empty C5 sites.

Single plaque was selected from the 4th round of plaque purification, and expanded to obtain P1 (1×T25 flask), P2 (1×T75 flask) and P3 (6× roller bottles) stocks. The infected cell culture fluid from the roller bottles was harvested and concentrated to produce a virus stock vCP2296.6.1.1.2.

Figure 15:
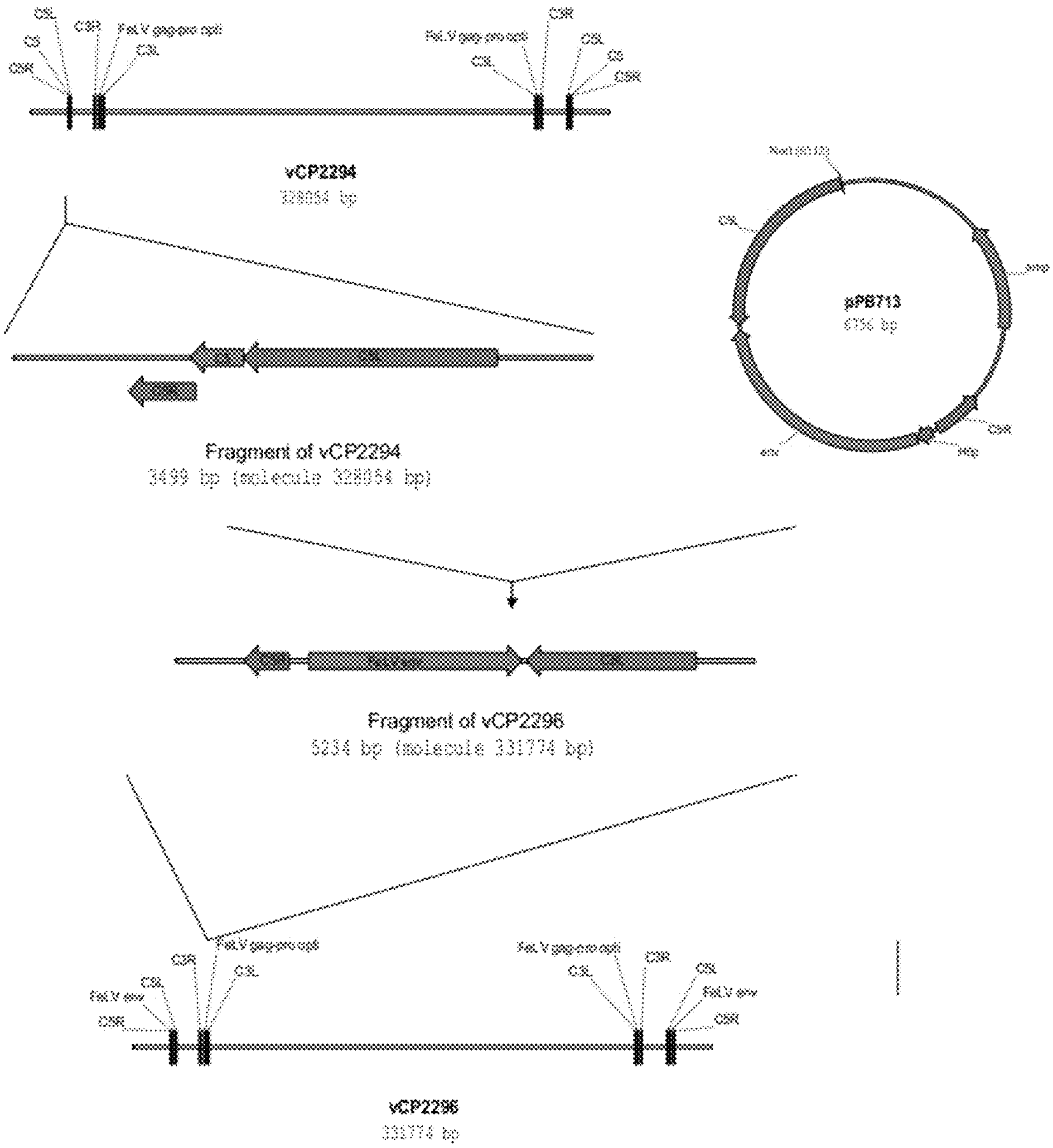
FIG. 15 provides the cloning scheme for making vCP2296 plasmid.

The construction of vCP2296 is depicted in FIG. 15.

Analysis of recombinant: the following analyses were performed on the P3 stocks.

Confirmation of Genetic Purity

The P3 stocks were re-confirmed by hybridization, as 100% positive for both FeLV GAG and FeLV ENV and 100% negative for both C3 and C5 ORF.

Expression Analysis

1) Western Blot:

Primary CEF cells were infected with the P3 stock of vCP2296.6.1.1.2 at MOI of 10 and incubated at 37° C. for 24 hrs. The culture supernatant and cells were then harvested.

Cell pellet was lysed with Reporter Gene Assay Lysis Buffer manufactured by Roche (Cat. 1 897 675). Both supernatant and lysate were prepared with the NuPage® System with antioxidant added. Proteins were separated on a NuPage® 10% Bis-Tris Pre-cast gel, and then transferred to a PVDF membrane. Anti FeLV GAG antibodies revealed a ~70 kDa protein detected in both supernatant and cell pellet, and a ~80 kDa protein was also expressed in both the supernatant and cell pellet by incubating with anti FeLV ENV antibody.

2) Immunoplaque Assay:

The homogeneity of the population was 100% positive to the FeLV ENV protein for recombinant vCP2296.1.1.2 as evidenced by an immunoplaque assay, using anti-FeLV ENV antibody (see IP confirmation scan picture in attachment vCP2296 Immunoplaque.doc).

Sequence Analysis

Figure 16:
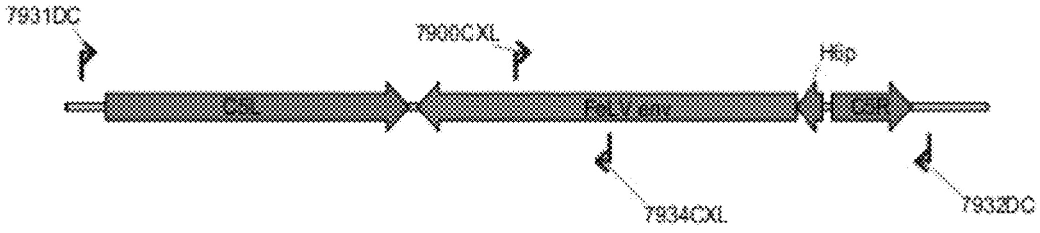
FIG. 16 shows the vCP2296 plasmid C5 region map with primer locations.

Insertion of the FeLV ENV gene at the C5 sites of vCP2296.6.1.1.2 was amplified by PCR. Primers 7931DC and 7932DC, located beyond the arms of the C5 locus in the ALVAC genome (see FIG. 16), were used to amplify the entire C5L-FeLV-C5R fragment.

Primers for Amplifying the FeLV ENV Probe:

```
7900CXL
                                    (SEQ ID NO: 21)
5'AGGAGGGCTTTAGTCCCTGTTCCGA 3'

7934CXL
                                    (SEQ ID NO: 22)
5'ACTAAAGACTGTTGGCTCTGCCTG 3'
```

Primers for PCR Amplification of C5L-FeLV ENV Cassette-05R:

```
7931DC
                                    (SEQ ID NO: 23)
5'GAATCTGTTAGTTAGTTACTTGGAT 3'

7932DC
                                    (SEQ ID NO: 24)
5'TGATTATAGCTATTATCACAGACTC 3'
```

Example 5

Generation and Characterization of ALVAC Recombinant Containing FeLV Native ENV Gene Inserted at C5 Locus of vCP2294, ALVAC C3H6p FeLV Codon Optimized GAG-PRO-vCP2295

The donor plasmid pCXL208.2 contains the native ENV gene (SEQ ID NO:5).

The IVR was performed by transfection of 1°CEF cells with 10 μg of Not I-linearized donor plasmid pCXL208.2 using FuGENE-6® reagent (Roche). The transfected cells were subsequently infected with vCP2294 (Example 2) as rescue virus at MOI of 10. After 24 hours, the transfected-infected cells were harvested, sonicated and used for recombinant virus screening.

Recombinant plaques were screened based on the plaque lift hybridization method using a 503 bp FeLV ENV specific probe labeled with horse radish peroxidase (HRP) according to the manufacturer's protocol (Amersham Cat# RPN3001). After four sequential rounds of plaque purification, the recombinant designated as vCP2295.2.2.2.1 was generated and confirmed by hybridization as 100% positive for the FeLV ENV insert and 100% negative for the empty C5 sites.

Figure 17:
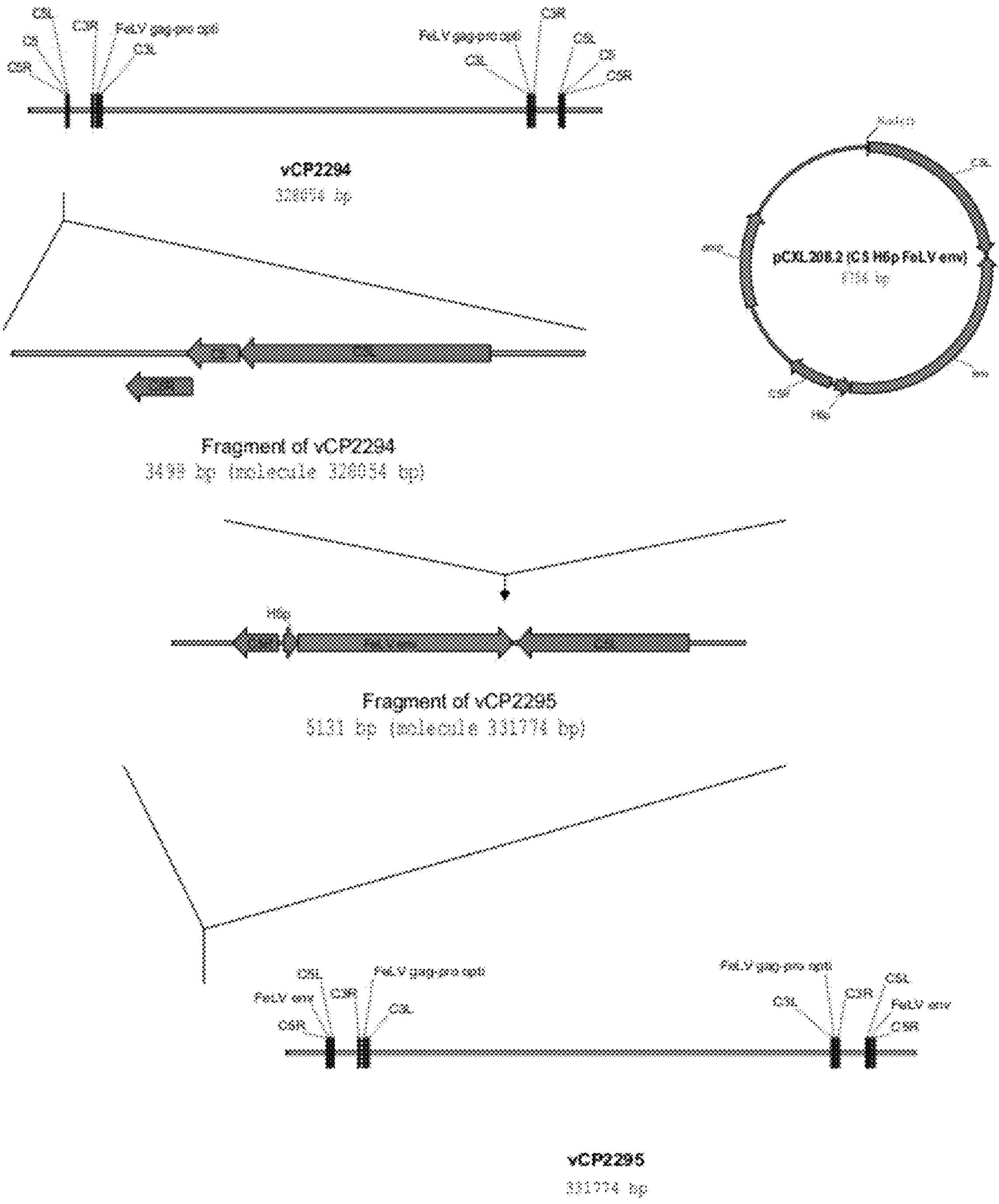
FIG. 17 provides the cloning scheme for making vCP2295 plasmid.

Single plaque was selected from the 4$^{th}$ round of plaque purification, and expanded to obtain P1 (1×T25 flask), P2 (1×T75 flask) and P3 (6× roller bottles). The infected cell culture fluid from the roller bottles was harvested and concentrated to produce a virus stock vCP2295.2.2.2.1. The scheme to generate recombinant vCP2295 is shown in FIG. 17.

Analysis of recombinant: the following analyses were performed on the P3 stocks.

Confirmation of Genetic Purity

The P3 stocks were re-confirmed by hybridization, as 100% positive for both FeLV GAG and FeLV ENV and 100% negative for both C3 and C5 ORF.

Expression Analysis

1) Western Blot

Primary CEF cells were infected with the P3 stock of vCP2295.2.2.2.1 at MOI of 10 and incubated at 37° C. for 24 hrs. The culture supernatant and cells were then harvested. Cell pellet was lysed with Reporter Gene Assay Lysis Buffer manufactured by Roche (Cat. 1 897 675). Both Supernatant and lysate were prepared with the NuPage® System with antioxidant added. Proteins were separated on a NuPage® 10% Bis-Tris Pre-cast gel, and then transferred to a PVDF membrane. Anti FeLV gag antibodies revealed a ~70 kDa protein detected in both supernatant and cell pellet, and a ~80 kDa protein was also expressed in both the supernatant and cell pellet by incubating with anti FeLV ENV antibody.

2) Immunoplaque Assay:

The homogeneity of the population was 100% positive to the FeLV ENV protein for recombinant vCP2295.2.2.2.1 as evidenced by an immunoplaque assay, using anti-FeLV ENV antibody.

Sequence Analysis

A detailed analysis of the P3 stock genomic DNA was performed by PCR amplification and sequence analysis of the flanking arms of the C5 locus and the FeLV insert. Primers 7931DC and 7932DC, located beyond the arms of the C5 locus in the ALVAC genome, were used to amplify the entire C5L-FeLV-C5R fragment. The results showed that the sequences of the FeLV insert and C5L and C5R of ALVAC are correct.

Recombinant vCP2295 sequence is depicted in FIG. 18.

Example 6

Efficacy Evaluation of Canarypox Vectored Vaccine (vCP2296, FeLV ENV)

Administered Subcutaneously Via a Vaccination/Challenge Model

Materials/Methods

Forty-four cats, male and female, between 57 and 63 days of age at first vaccination (average 58 days; standard deviation 1.3 days) were randomly allocated into two groups of twenty-two animals. Cats in Group 1 were vaccinated subcutaneously (SQ) on Days 0 and 21 with 1 ml of the FeLV-canarypox vector vaccine (vCP2296) at $10^{6.2}$ Tissue Culture Dose$_{50}$ (TCID$_{50}$)/ml. Cats in Group 2 received two doses of 1 ml of the Placebo Vaccine containing Sterile Physiological Saline Solution on Days 0 and 21 and served as negative controls. On Days 42 and 43 (3 weeks following the 2nd vaccination), all cats were challenged with 1 ml of a virulent strain of FeLV (61-E) suspension containing $10^{4.5}$ and $10^{4.7}$ TCID$_{50}$/ml; (Days 42 and 43 respectively) administered by the oro-nasal route. Blood samples were collected on Days −6, 42 (prior to challenge), and at approximately 3 weeks post-challenge and at weekly intervals for up to 12 consecutive weeks (Days 62-Day 146) and the sera tested for FeLV antigenemia (FeLV p27 protein).

Clinical evaluation was conducted starting 2 days prior to the 1st vaccination up to Day 42. Rectal temperature was recorded daily on Days −2-0 (prior to vaccination), 1-2, 19-21 (prior to vaccination) and 22-23. In addition, injection sites were assessed the first 2 days following each vaccination and at weekly intervals post-vaccination until the day of challenge and included the evaluation for swelling, redness and pain upon palpation.

Results: Persistence of FeLV p27 Antigenemia After Challenge

A cat was considered as having persistent FeLV p27 antigenemia when it was tested FeLV p27 positive for 3 consecutive weeks or 5 non-consecutive weeks. Nineteen out of 22 cats (86.4%) from the placebo group became persistently FeLV antigenemic in comparison to 5/21 (23.8%) of the vaccinated group. The incidence of cats with persistent FeLV antigenemia attributable to the FeLV challenge was significantly lower (p=0.00005) in the vaccinated group than in the placebo group. The estimated prevented fraction was 72.43% with a 95% confidence interval of 43.04% to 89.78%. Thus, there was a 72% reduction in the chance of an animal becoming persistent FeLV antigenemic in a vaccinated animal compared to that of a Placebo animal.

Conclusion

Two doses of Merial's FeLV-Canarypox Vectored Vaccine (vCP2296) administered by the SQ route were found to be efficacious against an FeLV challenge as evidenced by the following results:

1. Upon challenge, the test vaccine was shown to be effective in preventing persistent FeLV antigenemia in 16 out of the 21 (76.2%) vaccinated-challenged cats with a significantly lower number of vaccinated cats developing a persistent antigenemia as compared to controls (p=0.00005; prevented fraction 72%; primary efficacy variable).
2. An effective challenge was validated, as evidenced by the development of persistent FeLV antigenemia in 86% (19/22) of the control cats.
3. None of the vaccinated cats showed local or systemic reactions following vaccination.

Example 7

Comparison of the Efficacy of the Recombinant Canarypox-FeLV with Native ENV Gene (vCP2295) and the Recombinant Canarypox-FeLV with Optimized ENV Gene (vCP2296) by Challenge in Cats Materials/Methods Total of thirty SPF (specific pathogen free) kittens, 15 male and 15 female, aged between 8 and 12 weeks (9 weeks on average on D0), were randomly assigned to 3 groups of 10 kittens according to their sex, litter and age.

TABLE 1

Experimental design of the study

| Group | # of cats | Vaccination D0-D28 vaccine | Vaccination D0-D28 Target titre** | Vaccination D0-D28 Route volume | Challenge D44 |
|---|---|---|---|---|---|
| A | 10 | vCP2295 | 6.0 | SC** | FeLV-A- |
| B | 10 | vCP2296 | 6.0 | 1 mL | Glasgow-1 |
| C | 10* | Not vaccinated | | | Oro-Nasal route |

*group C: # of cats = 9 from D1 to the end due to the death of one cat on D1
**in log10CCID50/mL
SC: subcutaneous
BS: blood sampling On D0 and D28, prior to vaccination, all kittens were monitored for body condition. Cats from groups A and B were then vaccinated under general anesthesia by subcutaneous injection in inter-scapular area. On D44, the challenge strain was thawed at 37° C., 32 mL of strain were mixed with 8 mL of F15 medium with 10% foetal calf serum and kept on crushed ice before inoculation. All cats underwent general anesthesia. Then each cat was inoculated via the oro-nasal route with 1 mL of inoculum (0.25 mL in each nasal cavity) and 0.5 mL orally (tongue, pharynx and tonsil).

Results

Blood samplings were performed on vigil cats on D0, D5, D7, D15, D26, D35, D49, D70, D77, DB4, D91, D96, D105, D112, D133 and under general anesthesia (0.1 to 0.2 mL/kg of Zoletll" 50, Intramuscular route) on D44, D56, D63, D119, D126, D140 and D147.

1. Antigenemia Test Blood samples were collected in dry tubes on D0, before the vaccination, on D44 before the challenge and every week from the third week post challenge, i.e., on D63, D70, D77, D84, D91, D98, D105, D112, D119, D126, D133, D140 and D147 for FeLV p2 7 antigen titration with Witness FeLV kit (Synbiotics Corporation, MO, USA). The response was a binary one (presence/absence). Three categories of response were defined: a) 0: no antigenemia (all the tions were negative), b) 1: transient antigenemia (less than three positive consecutive ations and less than five positive titrations), c) 2: persistent antigenemia (positive on at least five occasions or at least three positive consecutive titrations).

In the vCP2295-vaccinated group (group A), 40% of cats were protected against persistent antigenemia: 4/10 cats were never found positive and 6/10 cats presented a persistent antigenemia. In the vCP2296-vaccinated group (group B), 60% of cats were protected against p27 persistent antigenemia. 5/10 were never found positive and 1/10 cat presented a transient antigenemia: p27 could be detected in the serum of this cat on D63 and D84. 4/10 cats presented a persistent antigenemia. In the control group (group C), 100% of cats had persistent antigenemia. The results are shown in Table 2.

TABLE 2 p27 antigenemia results (rates)

| Group | Persistent antigenemia | Transient antigenemia | No positive antigenemia | Protection* rate |
|---|---|---|---|---|
| A | 6/10** | 0/10 | 4/10 | 4/10 |
| vCP2295 vaccinated | 60% | 0% | 40% | 40% |
| B | 4/10 | 1/10 | 5/10 | 6/10 |
| vCP2296 vaccinated | 40% | 10% | 50% | 60% |
| C | 9/9 | 0/9 | 0/9 | NA |
| control | 100% | 0% | 0% | |

*Number of non persistently infected cats/Number of cats
**One cat which died during the study was found positive 4 consecutive times
NA: not applicable: control group The comparison of the 3 groups on the frequency of cats presenting no (antigenemia=0), transient (antigenemia=1) or persistent (antigenemia=2) antigenemy gave a significant p-value ("Fisher's exact test": p=0.028). A trend to the significance was evidenced between group B and group C (adjusted p-value with Bonferroni's method: A vs C: p=0.260, B vs C: p=0.056, A vs B: p=1).

2. Proviremia Test

Leukocyte counts were used to express proviremia in provirus copy number/50,000 WBC (white blood cell). Blood samples were collected in EDTA tubes on D44 before the challenge and every 3 weeks after the challenge, i.e., on D63, D84, D105, D126 and D147 for leukocyte count and FeLV proviremia monitoring on PBMC (peripheral blood mononucleated cells) using a quantitative PCR. Due to the repeated measurement nature of the criterion and the individual random effect, the proviremia data was analyzed using a mixed model with repeated measurements.

a) Proviremia in Blood

Figure 19:
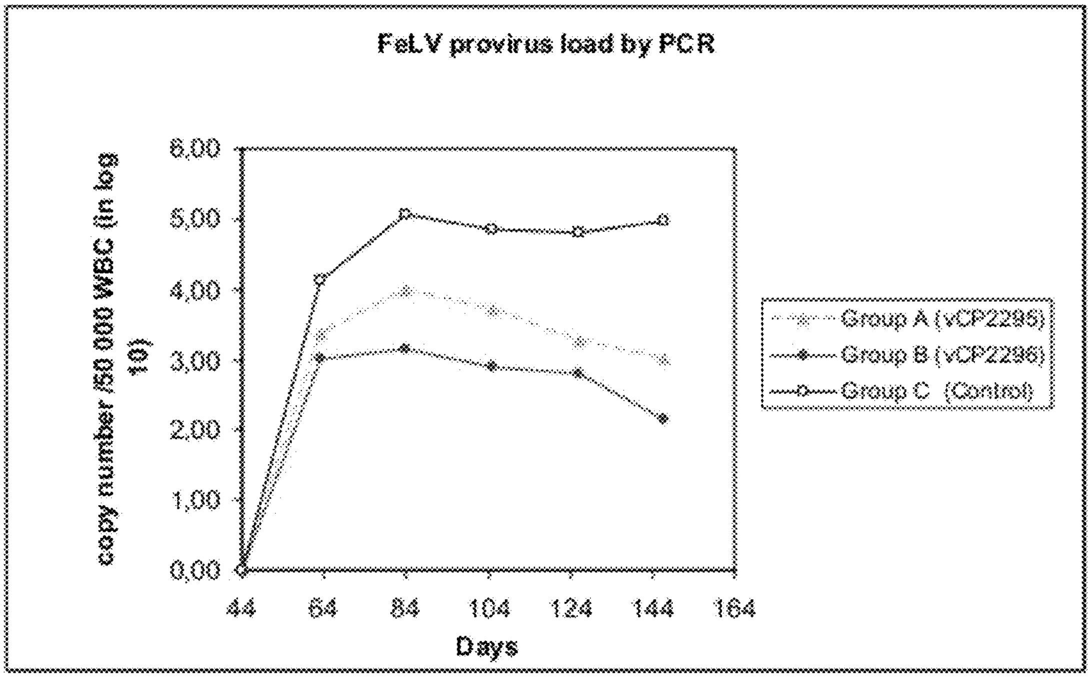
FIG. 19 is a graph showing the evolution of the mean proviremia per group after challenge.
Figure 20:
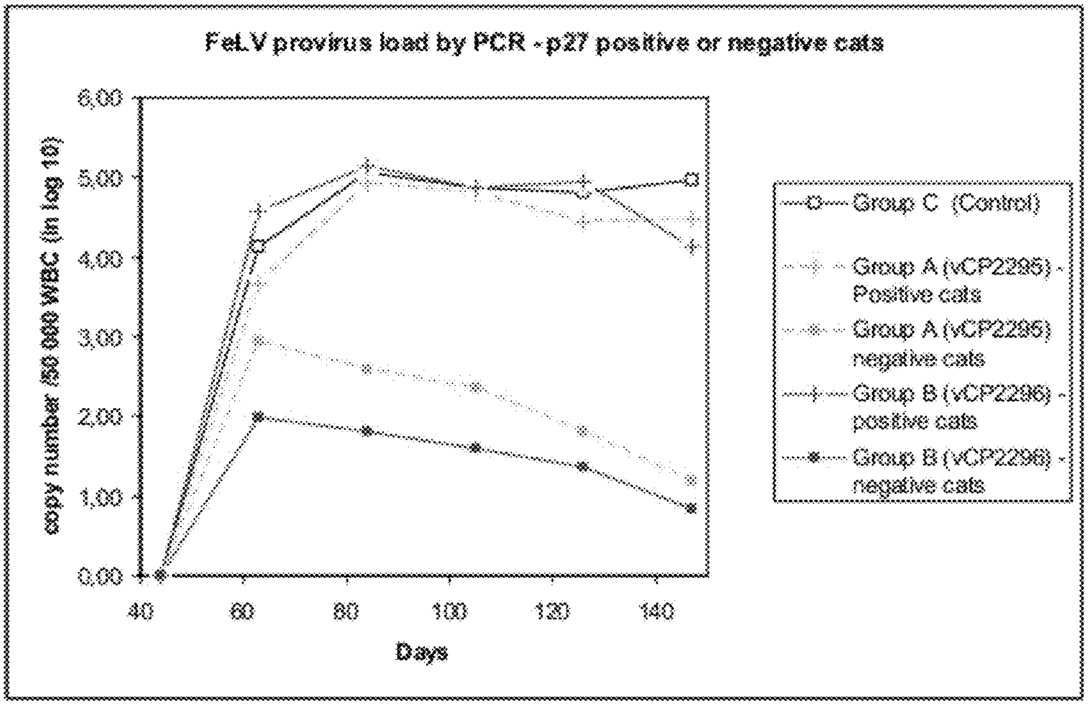
FIG. 20 is a graph showing the evolution of the mean proviremia per group and p27 status after challenge.

FIG. 19 displays the evolution of the mean proviremia per group after challenge. FIG. 17 displays the evolution of the mean proviremia per group and p27 antigenemia status after challenge. In both vaccinated groups, p27 antigenemia was well correlated to proviremia (FIG. 20).

b) proviremia in Marrow

Figure 21:
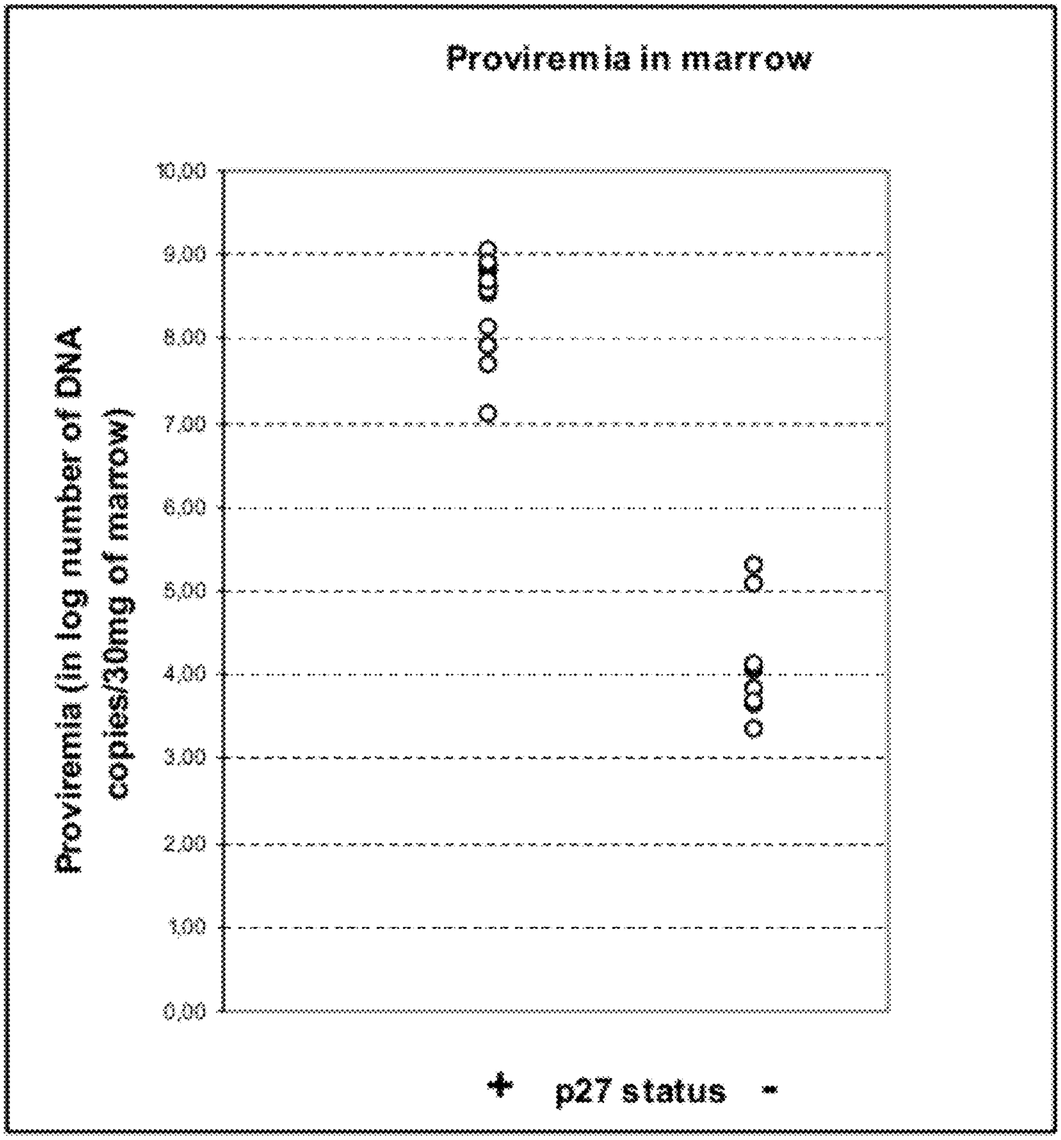
FIG. 21 is a graph showing the proviremia in marrow correlating to p27 status.

The level of proviremia in marrow of p27 negative cats was between 3 and 5 log 10 whereas it reached 8 to 9 log 10 in p27 positive cats. The level of proviremia was well correlated with the p27 antigenemia individual status and with individual blood proviremia (as shown in FIG. 21).

3. Cellular Immune Response

Blood samples were collected on heparin treated tubes on D5, D7, D15, D28, D35, D49, D56, D63, D119, and D126 for FeLV immunological monitoring. IFNγ-Cell Mediated Immune response was monitored by ELISpot after stimulation of PBMC by dendritic cells (DC) loaded with FeLV pools of peptides on D35 and D126. IL10 mediated Immunity was monitored by ELISpot after stimulation of PBMC by FeLV pools of peptides on D35, D63 and D126. Regulatory T cells were monitored on D5, D15, D35, D49, D63 and D126.

A) Methods a). Feline PBMCs Isolation

PBMCs were isolated by PANCOLL® density-gradient centrifugation (600 g for 30 minutes without brake). PBMCs were washed twice in sterile PBS (Phosphate-buffered saline) (centrifugation 400 g for 10 minutes) and subsequently counted with a robotized ABX Pentra 120 cell counter. The cells were washed one last time in PBS and resuspended at concentration of $5\cdot10^6$/ml in sterile complete RPMI (=RPMI+Penicillin-Streptomycine (PS)+βMercaptoethanol (βM))+10% of fetal calf serum (FCS).

b). Dendritic Cells Generation

Ficoll-Isolated PBMCs were cultivated during 20 hours in flat 6-wells plates. Non adherent cells were removed and fresh completed medium supplemented with feline IL-4 and feline GM-CSF was added to wells. The differentiation of monocytes into DC lasted 7 days.

c). IFNγ ELISpot Assay:

The intensity of FeLV-specific cellular immune responses in the different groups of animals was quantified by utilizing IFNγ ELISPOT assays. HA ELISPOT plates were coated overnight at +4° C. with 100 μl/well of purified Anti-canine IFNγ mAb diluted (1/25) in carbonate/bicarbonate buffer (0.2M, pH9.6). The coated plates were washed three times in sterile PBS and unoccupied sites were blocked with sterile complete RPMI 10% FCS for 2 h at Room Temperature (RT).

Dendritic cells were loaded with peptide pools encoding for FeLV ENV and GAG proteins at D+15, D+35 and D+126. Briefly, $100\cdot10^3$ DC were re-stimulated individually by peptide pools n°1 and 2 for FeLV ENV or peptide pools No. 2, 3, 6 and 8 FeLV GAG-PRO at 1 μg/ml in a final volume of 1000 completed RPMi 10% FCS. Loaded dendritic cells were transferred into ELISpot plates and $500\cdot10^3$ PBMCs were added into each well. Dendritic cells were loaded with an irrelevant peptide as a negative control. Cells were stimulated during 20-24 h at 37° C.+5% $CO_2$. Cells were then eliminated and to allow cellular lysis. Cold distilled water was added to each well (200 μl) for 5 min at RT. The plates were then washed three times in PBS-0.05% Tween and incubated at +4° C. with 100 μl of biotinylated Anti-feline γIFN MAb (diluted at 1/100 in PBS—0.05% Tween). The plates were then washed three times in PBS—0.05% Tween and 100 μl of diluted HRP-Streptavidine solution were added to each well for 1 h at 37° C. Plates were then washed three times in PBS—0.05% Tween and incubated for 15 minutes at RT in dark with the AEC substrate solution. The plates were extensively washed with tap water and dried. The spots were counted with a CCD camera system (Microvision, Redmond, Wash., USA). The frequency of peptide-specific IFNγ-spot forming cells (SFC) was calculated as follow: number of peptide-specific IFNγ SFC=number of IFNγ SFC upon individual FeLV peptide pool re-stimulation—number of IFNγ SFC upon irrelevant peptide pool re-stimulation. Results were expressed as the log 10.

d). IL-10 ELISpot Assay

The ELISpot IL-10 was performed according to the manufacturer Instructions (R&D systems, Minneapolis, Minn., USA). $500\cdot10^3$ purified PBMCs were directly re-stimulated using overlapping peptide pools encoding for FeLV ENV and GAG-PRO sequences, at μg/ml in a final volume of 200 μl completed RPMI 10% FCS, and set down in ELIspot IFNγ coated plates. $500\cdot10^3$ PBMCs were re-stimulated with an irrelevant peptide as a negative control. The frequency of peptide-specific IL-10 spot forming cells (SFC) was calculated as follow: number of peptide pool-specific IL-10 SFC=number of IL-10 SFC upon individual FeLV peptide pool re-stimulation−number of IL-10 SFC upon irrelevant peptide re-stimulation. Results were expressed as the log 10.

Figure 22:
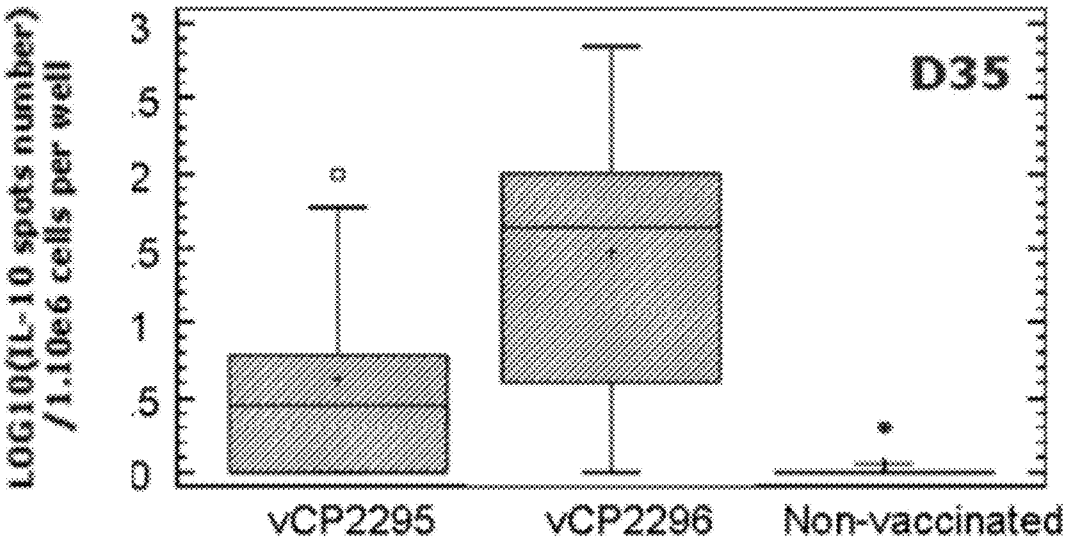
FIG. 22 shows the FeLV specific-IFNγ response on D35.

B) Results a) Cellular Immune Response after Vaccination i) Monitoring of FeLV-Specific IFNγ Secreting Cell Responses After Vaccination The ability of PBMCs to produce IFNγ In response to re-stimulation with FeLV ENV and GAG-PRO peptide pools-loaded DC was analyzed using an IFNγ-ELIspot assay. Analysis of the sum of $IFN\gamma^+$ SFC (spots forming cells) induced upon in vitro activation with dendritic cells loaded with peptide pools encoding for FeLV ENV and GAG-PRO sequences showed that vCP2296 vaccination induced a higher frequency of FeLV-specific IFNγ secreting cells at day 35 compared to vCP2295 vaccination. The non-vaccinated groups did not induce any IFNγ secreting cells (FIG. 22).

Figure 23:
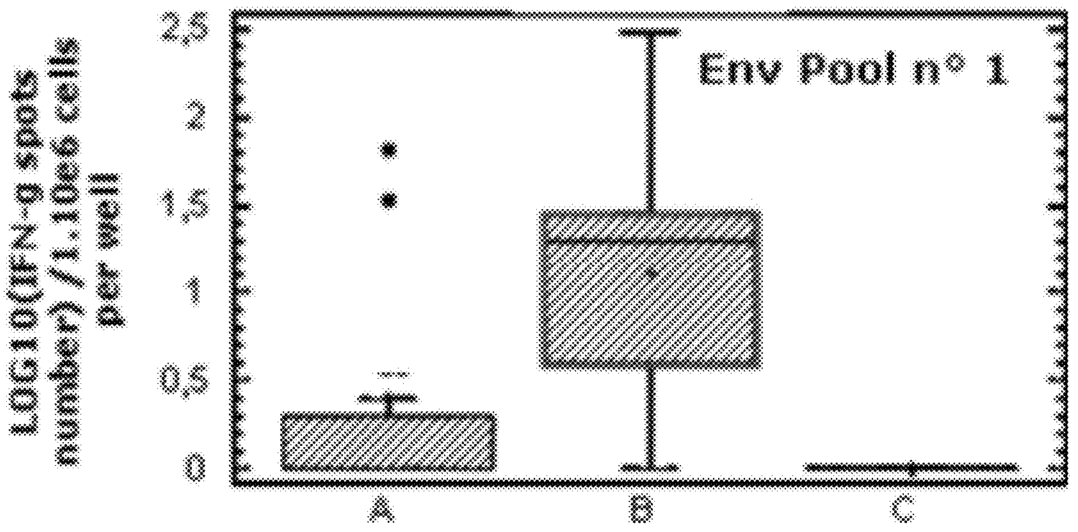
FIG. 23 shows the FeLV specific (ENV peptide pool No. 1) IFNγ response on D35.

The differences between vCP2295 and vCP2296 in their ability to induce IFNγ-producing cells were clearer when focusing on FeLV ENV pools No. 1 and No. 2 specific response. Analysis of the frequency of $IFN\gamma^+$ SFC within PBMCs upon in vitro activation with dendritic cells loaded with peptide pool No. 1 of FeLV ENV (encoding for the beginning of the FeLV ENV sequence) showed a difference between vCP2296 (group B) and vCP2295 vaccination (group A) at day 35, in blood. The non-vaccinated groups did not induce any IFNγ secreting cells (FIG. 23).

ii) Monitoring of FeLV-Specific IL-10 Secreting Cells After Vaccination

Figure 24:
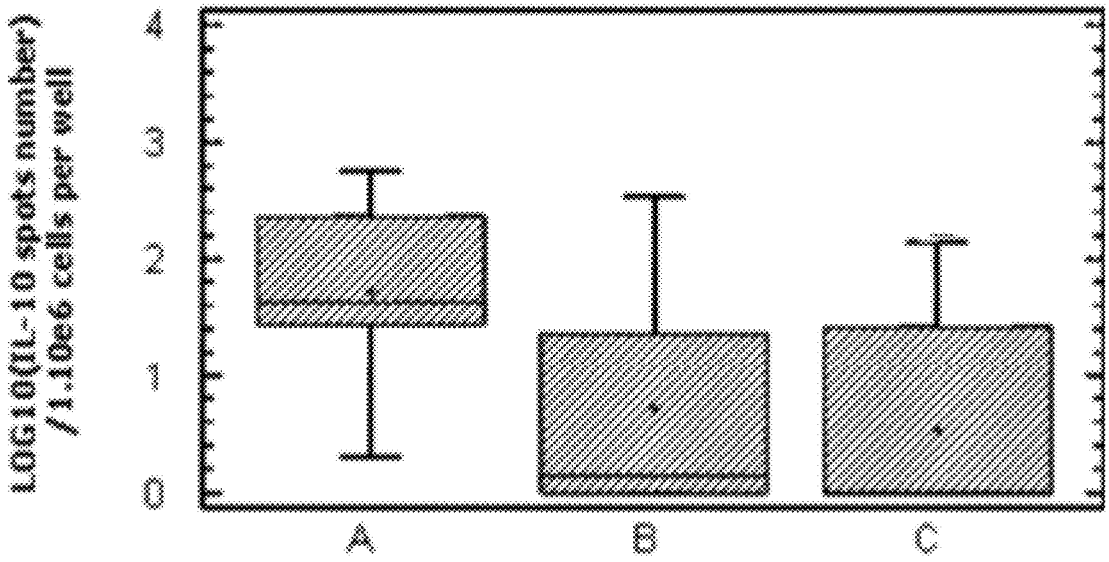
FIG. 24 shows the FeLV specific (ENV peptide pools) IL-10 response on D35.

FeLV-Specific IL-10 Secreting Cells Monitoring: Analysis of FeLV ENV-Specific Responses in Blood At day 35 post-vaccination, the ability of PBMCs to produce IL-10 in response to FeLV ENV peptide pools re-stimulation was analyzed using an IL-10 ELIspot assay. vCP2295 vaccination induced a higher frequency of FeLV ENV-specific IL-10 secreting cells in comparison to vCP2296 vaccination and control group (FIG. 24).

Figure 25:
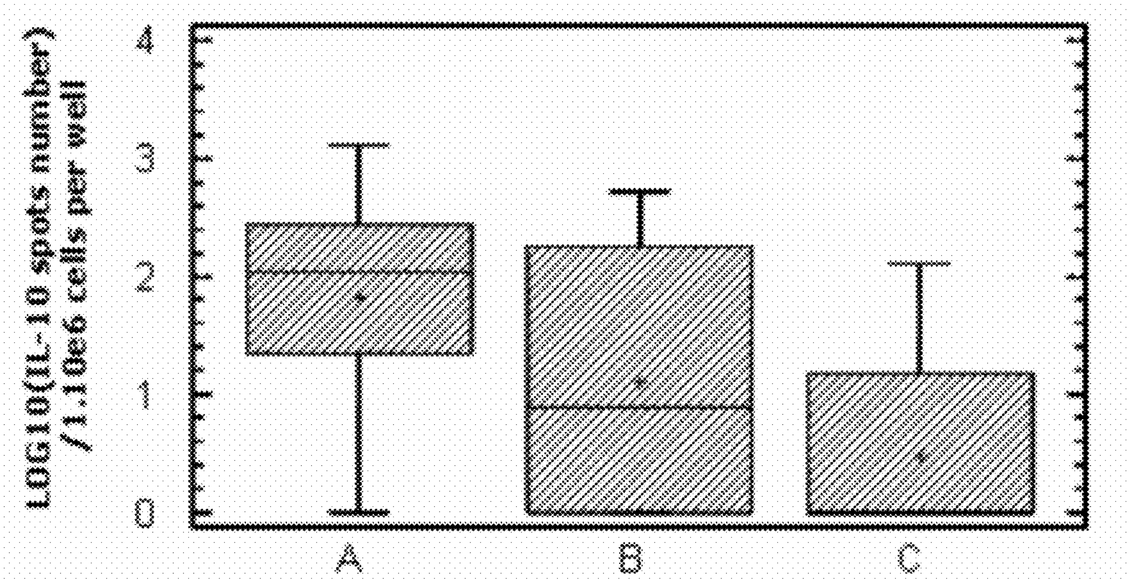
FIG. 25 shows the FeLV specific (GAG/PRO peptide pools)—IL-20 response on D35.

FeLV-specific IL-10 Secreting Cells Monitoring: Analysis of FeLV GAG-PRO Specific Responses in Blood At day 35 post-vaccination, the ability of PBMCs to produce IL-10 in response to FeLV GAG-PRO peptides pools re-stimulation was analyzed using an IL-10 ELIspot assay. vCP2295 vaccination tended to induce more FeLV GAG-PRO specific IL-10 secreting cells than vCP2296 vaccination (FIG. 25).

In conclusion, vCP2295 vaccination (group A) induced a higher frequency of FeLV specific IL-10 secreting cells in peripheral blood, in comparison to vCP2296 vaccination (group B) and control group (group C).

iii) FeLV-specific IFNγ and IL-10 Producing Cells Ratio After Vaccination.

Figure 26A:
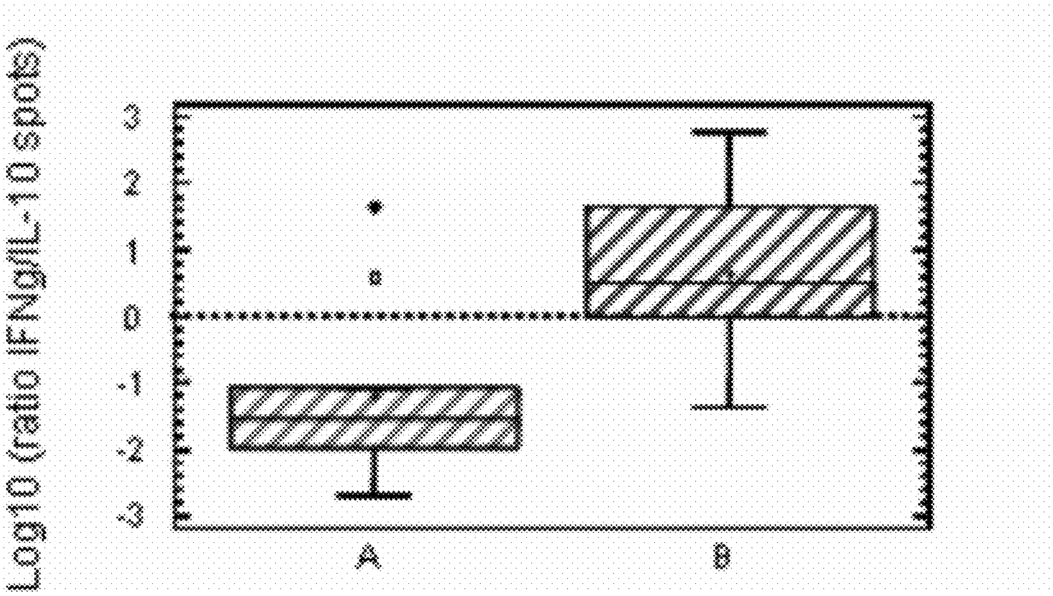
FIGS. 26*a-b* show the FeLV specific (ENV stimulation)—IFNγ/IL-10 ratio on D35.
Figure 26B:
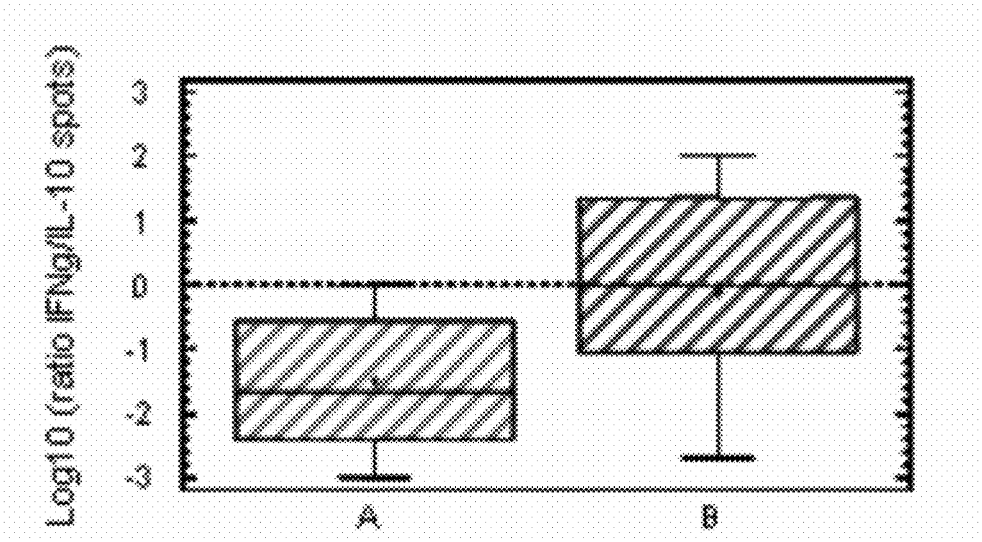
Figure 27:
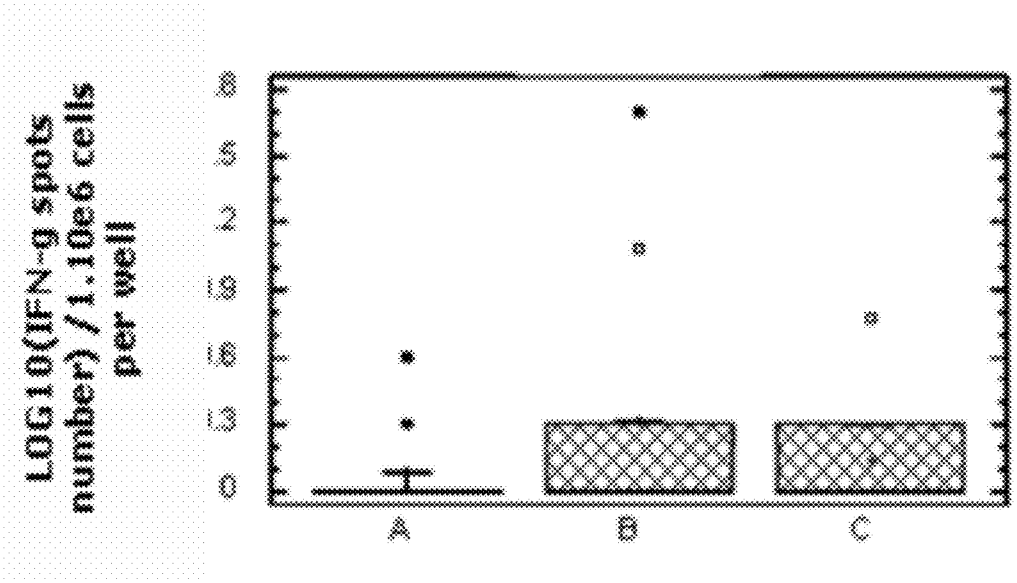
FIG. 27 shows the FeLV specific (GAG/PRO stimulation)—IFNγ response on D126.

In order to further evaluate the two recombinant vaccines and the balance between Th1 response and regulatory response, the ratio between the number of FeLV-specific IFNγ SFC and the number of FeLV specific IL-10 SFC after ENV or GAG-PRO in vitro re-stimulation for each vaccinated group was calculated. Comparison of the FeLV-specific IFNγ IL-10 SFC ratio for each group demonstrated that vCP2296 vaccination induced a more balanced response as compared to the immune response induced by vCP2295 vaccination which was biased toward IL-10 response. This difference was more apparent in response to FeLV ENV re-stimulation than to GAG-PRO re-stimulation (FIGS. 26*a* and 26*b*).

b) Cellular Immune Response Monitoring after Experimental Challenge i) Monitoring of FeLV-Specific IFNγ Secreting Cell Responses after Challenge After the challenge (D126) the ability of PBMCs to produce IFNγ in response to re-stimulation with FeV ENV and GAG-PRO peptide pools-loaded OC was analyzed using an IFNγ-ELIspot assay. vCP2296-vaccinated cats maintained a higher frequency of FeLV ENV-specific IFNγ secreting cells in PBMCs lately after the challenge (D126) as compared to vCP2295-vaccinated cats. No FeLV GAG-PRO-specific secreting cells could be observed at this time point, for any group (FIG. 27).

ii) Monitoring of FeLV-Specific IL-10 Secreting Cell Responses After Challenge

Figure 28A:
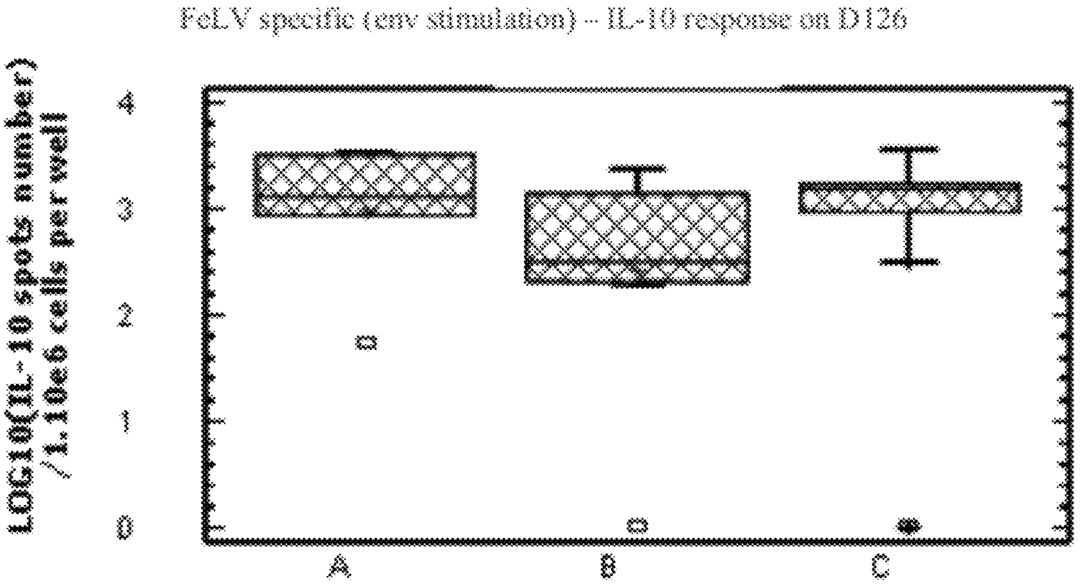
FIG. 28*a* shows the FeLV specific (ENV stimulation)—IL-10 response on D126.
Figure 28B:
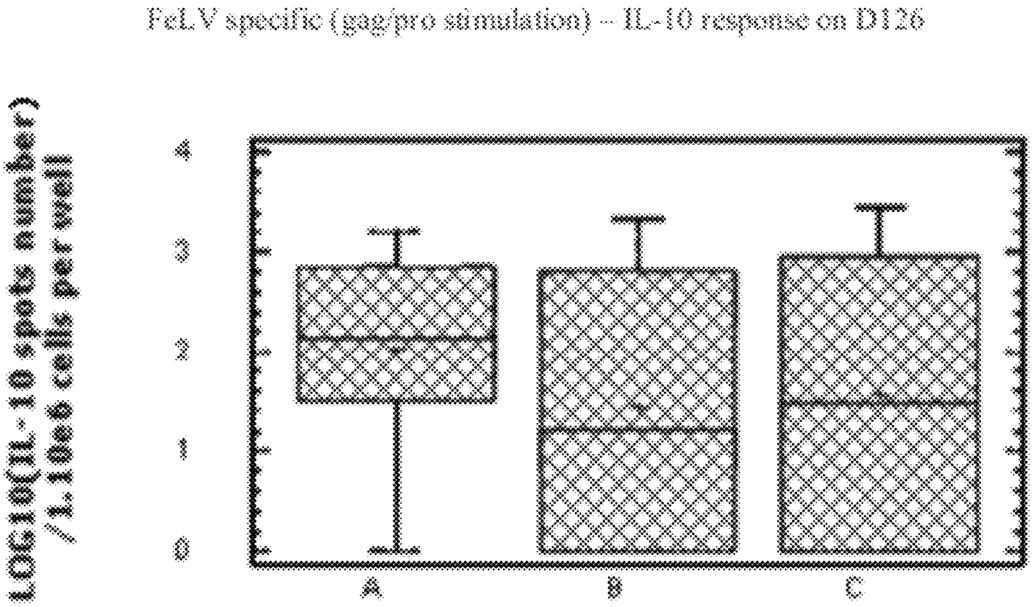
FIG. 28*b* shows the FeLV specific (GAG/PRO stimulation)—IL-10 response on D126.
Figure 29:
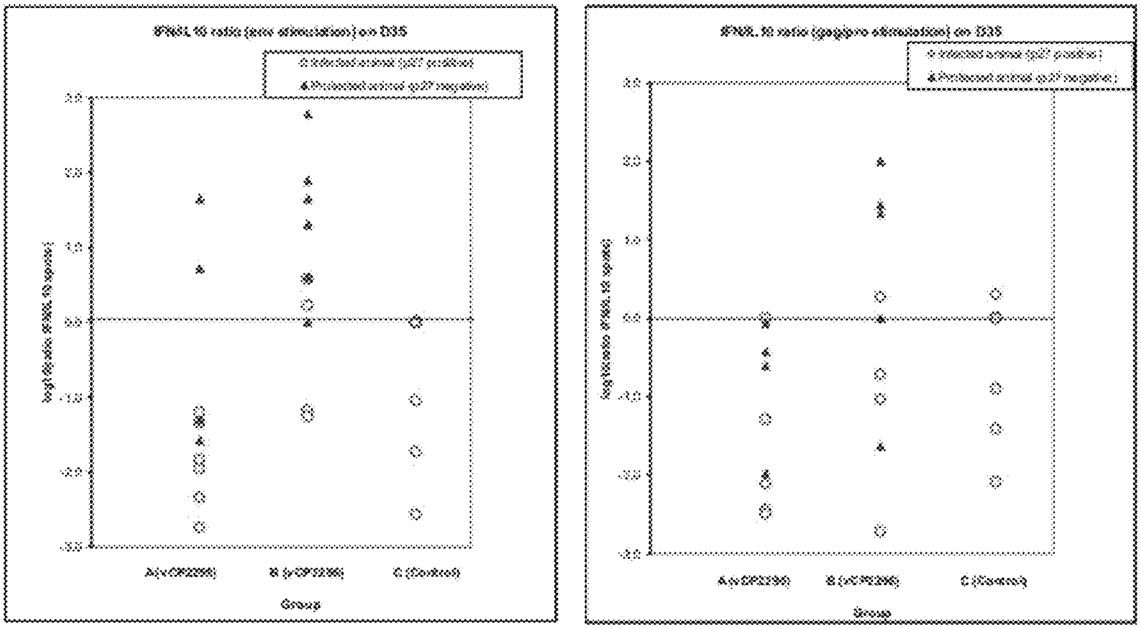
FIG. 29 shows the FeLV specific IFNγ/IL-10 ratio FeLV ENV and GAG/PRO peptide pools on D35.

After the challenge (D126), the ability of PBMCs to produce IL-10 in response to FeLV ENV or GAG-PRO peptides pools re-stimulation was analyzed using an IL-10 ELIspot assay. FeLV challenge specifically boosted the FeLV ENV-specific IL-10 cell response in all groups, as compared to the response at day 35, with no difference between the 3 groups (FIG. 28*a*). The challenge did not affect the antigen-specific response directed against FeLV GAG-PRO region, and vCP2295-vaccinated cats maintained their FeLV GAG-PRO-specific IL-10 response (FIG. 28*b*). After the challenge, vCP2295 vaccinated cats (group A) exhibited only a FeLV-specific IL-10 immune response whereas vCP2296-vaccinated cats (group B) developed a FeLV-specific IL-10 immune response but also maintained their FeLV-specific IFNγ response.

c) Frequency of FeLV-Specific IFNγ and IL-10 Producing Cells in Protected and Infected Animals Protected and Infected animals were identified according to p27 antigenemia results. Protected and infected animals were separated within each group (FIG. 29) and the IFNy/IL-10 ratio for each sub-group was calculated to evaluate if the IFNγ/IL-10 SFC ratio after the vaccination could be indicative of protection.

In the vCP2296 vaccinated group: four cats out of 10 presented a high IFNγ/IL-10 ratio related to a high IFNγ response and a low IL-10 response and were protected. Two cats out of 10 did not present any IFNγ or IL10 response and were protected. Four cats out of 10 presented a low IFNγ/IL-10 ratio related to a high IL-10 response. Three of these cats presented a high IFNγ response and one of them did not present any IFNγ response. These cats were not protected.

In the vCP2295 vaccinated group: eight cats out of 10 presented a low IFNγ/IL-10 ratio related to a high IL-10 response and a low IFNγ response. Six of them were infected and two of them were protected. Two cats out of 10 presented both IFNγ and IL-10 responses and a high IFNγ/IL-10 ratio. These cats were protected.

Protected cats either from vCP2295- or vCP2296-vaccinated group displayed a higher IFNγ/IL-10 ratio in blood (FIG. 26) as compared to infected cats. Moreover, protected cats from vCP2296-vaccinated group have a higher IFNγ/IL-10 SFC ratio as compared to protected cats from vCP2295-vaccinated group.

Protection was correlated with an increased IFNγ/IL-10 ratio and protected cats from vCP2296 vaccination developed a FeLV-specific cell mediated immunity biased toward IFNγ production as compared to vCP2295-vaccinated cats.

Conclusion

Sixty percent of cats vaccinated with vCP2296 (optimized ENV gene) were protected against persistent antigenemia and 40% of cats vaccinated with vCP2295 (native ENV gene) were protected against persistent antigenemia. The comparison of the three groups displayed a significant difference of protection between vaccinated and non-vaccinated groups and a trend to a significant difference between group B vaccinated with the optimized ENV gene (vCP2296) and group A vaccinated with the native ENV gene (vCP2295).

Proviremia and antigenemia results were well correlated: cats with persistent antigenemia had a strong and sustained proviremia until the end of the study. Non-antigenemic cats had lower and regressing proviremia. P27 negative cats were able to control the proviremia. Differences between vCP2295 and vCP2296 vaccination, according to the induction of FeLV specific IFNγ and IL-10 producing cells during the vaccination and challenge phases were evidenced. The induction of FeLV-specific IFNγ producing cells by FeLV canarypox vaccines especially when the ENV gene was mutated in its immunosuppressive sequence (vCP2296) was demonstrated. Interestingly, these IFNγ producing FeLV-specific cells induced by vCP2296 vaccination were still detected more than 100 days after challenge demonstrating that the vCP2296 vaccination induced the generation of FeLV-specific memory T cells. Conversely, vCP2295 was more potent to induce the differentiation of FeLV-specific IL-10-producing cells. The frequency of FeLV-specific IL-10 producing cells was higher in vCP2295 vaccinated cats as compared to vCP2296 and non-vaccinated control cats after the vaccination. IL-10 is known for its regulatory properties, participating either in the inhibition of the immune response or in its termination. The higher FeLV-specific IFNγ/IL-10 SFC ratio after the vaccination was correlated to protection (evaluated by antigenemia). All cats presenting a high IFNγ/IL-10 ratio and a low IL-10 response were protected. This observation was in line with the potentially immunosuppressive role of the IL-10-producing cells and with an anti-viral function of IFNγ-producing cells, Modification of the ENV gene in the vCP2296 vaccine decreased the immunosuppressive properties of the construct and provided an immunological advantage to this construct as compared to the native ENV gene in vCP2295.

This study showed that the modification of the ENV gene of FeLV resulted in a different quality of the immune response associated with a better protection against persistent antigenemia. The modification of the ENV gene of FeLV allows the canarypox-FeLV to work at lower dose than the same construct with native ENV FeLV gene.

It will be apparent that the precise details of the methods described may be varied or modified without departing from the spirit of the described disclosure. We claim all such modifications and variations that fall within the scope and spirit of the claims below.

All documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention.

What we claim is:

1. An isolated polypeptide comprising the amino acid sequence of SEQ ID NO:2 or SEQ ID NO:4.

2. A composition comprising the polypeptide of claim 1, and a pharmaceutically or veterinary acceptable vehicle, diluent or excipient.

3. The composition of claim 2, wherein the composition is capable of eliciting an immune response in a host.

4. The isolated polypeptide of claim 1 consisting of the amino acid sequence of SEQ ID NO:2 or SEQ ID NO:4.

5. An isolated polynucleotide coding for the polypeptide of claim 1.

6. The polynucleotide of claim 5 comprising the nucleic acid sequence of SEQ ID NO:1 or SEQ ID NO:3.

7. A vector comprising the polynucleotide of claim 5 or 6.

8. The vector of claim 7, wherein the vector is a plasmid, a phage, or a virus.

9. The vector of claim 8, wherein the vector is a viral vector.

10. The vector of claim 9, wherein the viral vector is an avipox vector.

11. An isolated transformed or transfected host cell comprising the polynucleotide of claim 5 or 6.

12. The host cell of claim 11, wherein the host cell comprises the vector of claim 6.

* * * * *

SEQUENCE LISTING

```
<160> NUMBER OF SEQ ID NOS: 43

<210> SEQ ID NO 1
<211> LENGTH: 1921
<212> TYPE: DNA
<213> ORGANISM: artificial sequence
<220> FEATURE:
<223> OTHER INFORMATION: FeLV ENV DNA with double mutations

<400> SEQUENCE: 1
atggaaagtc caacgcaccc aaaaccctct aaagataaga ctctctcgtg gaacttagcg     60
tttctggtgg ggatcttatt tacaatagac ataggaatgg ccaatcctag tccacaccaa    120
atatataatg taacttgggt aataaccaat gtacaaacta acacccaagc taacgccacc    180
tctatgttag gaaccttaac cgatgcctac cctaccctac atgttgactt atgtgaccta    240
gtgggagaca cctgggaacc tatagtccta aacccaacca atgtaaaaca cggggcacgt    300
tactcctcct caaaatatgg atgtaaaact acagatagaa aaaaacagca acagacatac    360
cccttttacg tctgccccgg acatgccccc tcgttggggc caaagggaac acattgtgga    420
ggggcacaag atgggttttg tgccgcatgg ggatgtgaga ccaccggaga agcttggtgg    480
aagcccacct cctcatggga ctatatcaca gtaaaaagag ggagtagtca ggacaatagc    540
tgtgagggaa aatgcaaccc cctggttttg cagttcaccc agaagggaag acaagcctct    600
tgggacggac ctaagatgtg gggattgcga ctataccgta caggatatga ccctatcgct    660
ttattcacgg tgtcccggca ggtatcaacc attacgccgc ctcaggcaat gggaccaaac    720
ctagtcttac ctgatcaaaa acccccatcc cgacaatctc aaacagggtc caaagtggcg    780
acccagaggc cccaaacgaa tgaaagcgcc ccaaggtctg ttgcccccac caccatgggt    840
cccaaacgga ttgggaccgg agataggtta ataaatttag tacaagggac atacctagcc    900
ttaaatgcca ccgaccccaa caaaactaaa gactgttggc tctgcctggt ttctcgacca    960
ccctattacg aagggattgc aatcttaggt aactacagca accaaacaaa cccccccca   1020 tcctgcctat ctactccgca acacaaacta actatatctg aagtatcagg gcaaggaatg   1080
tgcataggga ctgttcctaa aacccaccag gctttgtgca ataagacaca acagggacat   1140
acaggggcgc actatctagc cgcccccaac ggcacctatt gggcctgtaa cactggactc   1200
accccatgca tttccatggc ggtgctcaat tggacctctg aattctgtgt cttaatcgaa   1260
ttatggccca gagtgactta ccatcaaccc gaatatgtgt acacacattt tgccaaagct   1320
gtcaggttcc gaagagaacc aatatcacta acggttgccc ttatgttggg aggacttact   1380
gtagggggca tagccgcggg ggtcggaaca gggactaaag ccctccttga aacagcccag   1440
tttagacaac tacaaatggc catgcacaca gacatccagg ccctagaaga atcaattagt   1500
```

```
gccttagaaa agtccctgac ctccctttct gaagtagtct tacaaaacag acggggccta   1560

gatattctat tcttacaaga gggagggctc tgtgccgcat tgaaagaaga atgttgcttc   1620

tatgcggatc acaccggact cgtccgagac aatatggcca aattaagaga aagactaaaa   1680

cagcggcaac aattgtttga ctcccaacag ggatggtttg aaggatggtt caacaagtcc   1740

ccctggttta caaccctaat ttcctccatt atgggcccct tactaatcct actcctaatt   1800

ctcctcttcg gcccatgcat ccttaaccga ttagtacaat tcgtaaaaga cagaatatct   1860

gtggtacagg ctttaatttt aacccaacag taccaacaga taaagcaata cgatccggac   1920

c                                                                   1921
```

<210> SEQ ID NO 2
<211> LENGTH: 640
<212> TYPE: PRT
<213> ORGANISM: artificial sequence
<220> FEATURE:
<223> OTHER INFORMATION: FeLV ENV mutated protein (double mutations)

<400> SEQUENCE: 2

```
Met Glu Ser Pro Thr His Pro Lys Pro Ser Lys Asp Lys Thr Leu Ser
1               5                   10                  15

Trp Asn Leu Ala Phe Leu Val Gly Ile Leu Phe Thr Ile Asp Ile Gly
            20                  25                  30

Met Ala Asn Pro Ser Pro His Gln Ile Tyr Asn Val Thr Trp Val Ile
        35                  40                  45

Thr Asn Val Gln Thr Asn Thr Gln Ala Asn Ala Thr Ser Met Leu Gly
    50                  55                  60

Thr Leu Thr Asp Ala Tyr Pro Thr Leu His Val Asp Leu Cys Asp Leu
65                  70                  75                  80

Val Gly Asp Thr Trp Glu Pro Ile Val Leu Asn Pro Thr Asn Val Lys
                85                  90                  95

His Gly Ala Arg Tyr Ser Ser Ser Lys Tyr Gly Cys Lys Thr Thr Asp
            100                 105                 110

Arg Lys Lys Gln Gln Gln Thr Tyr Pro Phe Tyr Val Cys Pro Gly His
        115                 120                 125

Ala Pro Ser Leu Gly Pro Lys Gly Thr His Cys Gly Gly Ala Gln Asp
    130                 135                 140

Gly Phe Cys Ala Ala Trp Gly Cys Glu Thr Thr Gly Glu Ala Trp Trp
145                 150                 155                 160

Lys Pro Thr Ser Ser Trp Asp Tyr Ile Thr Val Lys Arg Gly Ser Ser
                165                 170                 175

Gln Asp Asn Ser Cys Glu Gly Lys Cys Asn Pro Leu Val Leu Gln Phe
            180                 185                 190

Thr Gln Lys Gly Arg Gln Ala Ser Trp Asp Gly Pro Lys Met Trp Gly
        195                 200                 205

Leu Arg Leu Tyr Arg Thr Gly Tyr Asp Pro Ile Ala Leu Phe Thr Val
    210                 215                 220

Ser Arg Gln Val Ser Thr Ile Thr Pro Pro Gln Ala Met Gly Pro Asn
225                 230                 235                 240

Leu Val Leu Pro Asp Gln Lys Pro Pro Ser Arg Gln Ser Gln Thr Gly
                245                 250                 255

Ser Lys Val Ala Thr Gln Arg Pro Gln Thr Asn Glu Ser Ala Pro Arg
            260                 265                 270

Ser Val Ala Pro Thr Thr Met Gly Pro Lys Arg Ile Gly Thr Gly Asp
```

-continued

```
        275                 280                 285

Arg Leu Ile Asn Leu Val Gln Gly Thr Tyr Leu Ala Leu Asn Ala Thr
    290                 295                 300

Asp Pro Asn Lys Thr Lys Asp Cys Trp Leu Cys Leu Val Ser Arg Pro
305                 310                 315                 320

Pro Tyr Tyr Glu Gly Ile Ala Ile Leu Gly Asn Tyr Ser Asn Gln Thr
                325                 330                 335

Asn Pro Pro Pro Ser Cys Leu Ser Thr Pro Gln His Lys Leu Thr Ile
            340                 345                 350

Ser Glu Val Ser Gly Gln Gly Met Cys Ile Gly Thr Val Pro Lys Thr
        355                 360                 365

His Gln Ala Leu Cys Asn Lys Thr Gln Gln Gly His Thr Gly Ala His
    370                 375                 380

Tyr Leu Ala Ala Pro Asn Gly Thr Tyr Trp Ala Cys Asn Thr Gly Leu
385                 390                 395                 400

Thr Pro Cys Ile Ser Met Ala Val Leu Asn Trp Thr Ser Glu Phe Cys
                405                 410                 415

Val Leu Ile Glu Leu Trp Pro Arg Val Thr Tyr His Gln Pro Glu Tyr
            420                 425                 430

Val Tyr Thr His Phe Ala Lys Ala Val Arg Phe Arg Arg Glu Pro Ile
        435                 440                 445

Ser Leu Thr Val Ala Leu Met Leu Gly Gly Leu Thr Val Gly Gly Ile
    450                 455                 460

Ala Ala Gly Val Gly Thr Gly Thr Lys Ala Leu Leu Glu Thr Ala Gln
465                 470                 475                 480

Phe Arg Gln Leu Gln Met Ala Met His Thr Asp Ile Gln Ala Leu Glu
                485                 490                 495

Glu Ser Ile Ser Ala Leu Glu Lys Ser Leu Thr Ser Leu Ser Glu Val
            500                 505                 510

Val Leu Gln Asn Arg Arg Gly Leu Asp Ile Leu Phe Leu Gln Arg Gly
        515                 520                 525

Gly Leu Cys Ala Ala Leu Lys Glu Glu Cys Cys Phe Tyr Ala Asp His
    530                 535                 540

Thr Gly Leu Val Arg Asp Asn Met Ala Lys Leu Arg Glu Arg Leu Lys
545                 550                 555                 560

Gln Arg Gln Gln Leu Phe Asp Ser Gln Gln Gly Trp Phe Glu Gly Trp
                565                 570                 575

Phe Asn Lys Ser Pro Trp Phe Thr Thr Leu Ile Ser Ser Ile Met Gly
            580                 585                 590

Pro Leu Leu Ile Leu Leu Leu Ile Leu Leu Phe Gly Pro Cys Ile Leu
        595                 600                 605

Asn Arg Leu Val Gln Phe Val Lys Asp Arg Ile Ser Val Val Gln Ala
    610                 615                 620

Leu Ile Leu Thr Gln Gln Tyr Gln Gln Ile Lys Gln Tyr Asp Pro Asp
625                 630                 635                 640
```

<210> SEQ ID NO 3
<211> LENGTH: 1921
<212> TYPE: DNA
<213> ORGANISM: artificial sequence
<220> FEATURE:
<223> OTHER INFORMATION: FeLV ENV DNA (1 mutation)

<400> SEQUENCE: 3
atggaaagtc caacgcaccc aaaaccctct aaagataaga ctctctcgtg gaacttagcg     60

-continued

```
tttctggtgg ggatcttatt tacaatagac ataggaatgg ccaatcctag tccacaccaa    120
atatataatg taacttgggt aataaccaat gtacaaacta acacccaagc taacgccacc    180
tctatgttag gaaccttaac cgatgcctac cctaccctac atgttgactt atgtgaccta    240
gtgggagaca cctgggaacc tatagtccta aacccaacca atgtaaaaca cggggcacgt    300
tactcctcct caaaatatgg atgtaaaact acagatagaa aaaaacagca acagacatac    360
cccttttacg tctgccccgg acatgccccc tcgttggggc caaagggaac acattgtgga    420
ggggcacaag atgggttttg tgccgcatgg ggatgtgaga ccaccggaga agcttggtgg    480
aagcccacct cctcatggga ctatatcaca gtaaaaagag ggagtagtca ggacaatagc    540
tgtgagggaa aatgcaaccc cctggttttg cagttcaccc agaagggaag acaagcctct    600
tgggacggac ctaagatgtg ggattgcga ctataccgta caggatatga ccctatcgct    660
ttattcacgg tgtcccggca ggtatcaacc attacgccgc ctcaggcaat gggaccaaac    720
ctagtcttac ctgatcaaaa acccccatcc cgacaatctc aaacagggtc caaagtggcg    780
acccagaggc cccaaacgaa tgaaagcgcc ccaaggtctg ttgcccccac caccatgggt    840
cccaaacgga ttgggaccgg agataggtta ataaatttag tacaagggac atacctagcc    900
ttaaatgcca ccgaccccaa caaaactaaa gactgttggc tctgcctggt ttctcgacca    960
ccctattacg aagggattgc aatcttaggt aactacagca accaaacaaa cccccccca   1020
tcctgcctat ctactccgca acacaaacta actatatctg aagtatcagg gcaaggaatg   1080
tgcataggga ctgttcctaa aacccaccag gctttgtgca ataagacaca acagggacat   1140
acaggggcgc actatctagc cgcccccaac ggcacctatt gggcctgtaa cactggactc   1200
accccatgca tttccatggc ggtgctcaat tggacctctg aattctgtgt cttaatcgaa   1260
ttatggccca gagtgactta ccatcaaccc gaatatgtgt acacacattt tgccaaagct   1320
gtcaggttcc gaagagaacc aatatcacta acggttgccc ttatgttggg aggacttact   1380
gtagggggca tagccgcggg ggtcggaaca gggactaaag ccctccttga aacagcccag   1440
ttcagacaac tacaaatggc catgcacaca gacatccagg ccctagaaga gtcaattagt   1500
gccttagaaa agtccctgac ctccctttct gaagtagtct tacaaaacag acggggccta   1560
gatattctat tcctacaacg gggagggctc tgcgcagcat taaaagaaga atgttgcttc   1620
tatgcggatc acaccggact cgtccgagac aatatggcta aattaagaga aagactaaaa   1680
cagcggcaac aactgtttga ctcccaacag ggatggtttg aaggatggtt caacaggtcc   1740
ccctggttta caaccctaat ttcctccatt atgggcccct tactaatcct actcctaatt   1800
ctcctcttcg gcccatgcat ccttaacaga ttagtacaat tcgtaaaaga cagaatatct   1860
gtggtacaag ccttaatttt aacccaacag taccaacaga taaagcaata cgatccggac   1920
c                                                                    1921
```

<210> SEQ ID NO 4
<211> LENGTH: 640
<212> TYPE: PRT
<213> ORGANISM: artificial sequence
<220> FEATURE:
<223> OTHER INFORMATION: FeLV ENV protein (1 mutation)

<400> SEQUENCE: 4

```
Met Glu Ser Pro Thr His Pro Lys Pro Ser Lys Asp Lys Thr Leu Ser
1               5                   10                  15

Trp Asn Leu Ala Phe Leu Val Gly Ile Leu Phe Thr Ile Asp Ile Gly
```

-continued

```
            20                  25                  30

Met Ala Asn Pro Ser Pro His Gln Ile Tyr Asn Val Thr Trp Val Ile
        35                  40                  45

Thr Asn Val Gln Thr Asn Thr Gln Ala Asn Ala Thr Ser Met Leu Gly
    50                  55                  60

Thr Leu Thr Asp Ala Tyr Pro Thr Leu His Val Asp Leu Cys Asp Leu
65                  70                  75                  80

Val Gly Asp Thr Trp Glu Pro Ile Val Leu Asn Pro Thr Asn Val Lys
                85                  90                  95

His Gly Ala Arg Tyr Ser Ser Ser Lys Tyr Gly Cys Lys Thr Thr Asp
            100                 105                 110

Arg Lys Lys Gln Gln Gln Thr Tyr Pro Phe Tyr Val Cys Pro Gly His
        115                 120                 125

Ala Pro Ser Leu Gly Pro Lys Gly Thr His Cys Gly Gly Ala Gln Asp
    130                 135                 140

Gly Phe Cys Ala Ala Trp Gly Cys Glu Thr Thr Gly Glu Ala Trp Trp
145                 150                 155                 160

Lys Pro Thr Ser Ser Trp Asp Tyr Ile Thr Val Lys Arg Gly Ser Ser
                165                 170                 175

Gln Asp Asn Ser Cys Glu Gly Lys Cys Asn Pro Leu Val Leu Gln Phe
            180                 185                 190

Thr Gln Lys Gly Arg Gln Ala Ser Trp Asp Gly Pro Lys Met Trp Gly
        195                 200                 205

Leu Arg Leu Tyr Arg Thr Gly Tyr Asp Pro Ile Ala Leu Phe Thr Val
    210                 215                 220

Ser Arg Gln Val Ser Thr Ile Thr Pro Pro Gln Ala Met Gly Pro Asn
225                 230                 235                 240

Leu Val Leu Pro Asp Gln Lys Pro Pro Ser Arg Gln Ser Gln Thr Gly
                245                 250                 255

Ser Lys Val Ala Thr Gln Arg Pro Gln Thr Asn Glu Ser Ala Pro Arg
            260                 265                 270

Ser Val Ala Pro Thr Thr Met Gly Pro Lys Arg Ile Gly Thr Gly Asp
        275                 280                 285

Arg Leu Ile Asn Leu Val Gln Gly Thr Tyr Leu Ala Leu Asn Ala Thr
    290                 295                 300

Asp Pro Asn Lys Thr Lys Asp Cys Trp Leu Cys Leu Val Ser Arg Pro
305                 310                 315                 320

Pro Tyr Tyr Glu Gly Ile Ala Ile Leu Gly Asn Tyr Ser Asn Gln Thr
                325                 330                 335

Asn Pro Pro Pro Ser Cys Leu Ser Thr Pro Gln His Lys Leu Thr Ile
            340                 345                 350

Ser Glu Val Ser Gly Gln Gly Met Cys Ile Gly Thr Val Pro Lys Thr
        355                 360                 365

His Gln Ala Leu Cys Asn Lys Thr Gln Gln Gly His Thr Gly Ala His
    370                 375                 380

Tyr Leu Ala Ala Pro Asn Gly Thr Tyr Trp Ala Cys Asn Thr Gly Leu
385                 390                 395                 400

Thr Pro Cys Ile Ser Met Ala Val Leu Asn Trp Thr Ser Glu Phe Cys
                405                 410                 415

Val Leu Ile Glu Leu Trp Pro Arg Val Thr Tyr His Gln Pro Glu Tyr
            420                 425                 430

Val Tyr Thr His Phe Ala Lys Ala Val Arg Phe Arg Arg Glu Pro Ile
        435                 440                 445
```

```
Ser Leu Thr Val Ala Leu Met Leu Gly Gly Leu Thr Val Gly Gly Ile
    450                 455                 460

Ala Ala Gly Val Gly Thr Gly Thr Lys Ala Leu Leu Glu Thr Ala Gln
465                 470                 475                 480

Phe Arg Gln Leu Gln Met Ala Met His Thr Asp Ile Gln Ala Leu Glu
                485                 490                 495

Glu Ser Ile Ser Ala Leu Glu Lys Ser Leu Thr Ser Leu Ser Glu Val
            500                 505                 510

Val Leu Gln Asn Arg Arg Gly Leu Asp Ile Leu Phe Leu Gln Arg Gly
        515                 520                 525

Gly Leu Cys Ala Ala Leu Lys Glu Glu Cys Cys Phe Tyr Ala Asp His
    530                 535                 540

Thr Gly Leu Val Arg Asp Asn Met Ala Lys Leu Arg Glu Arg Leu Lys
545                 550                 555                 560

Gln Arg Gln Gln Leu Phe Asp Ser Gln Gln Gly Trp Phe Glu Gly Trp
                565                 570                 575

Phe Asn Arg Ser Pro Trp Phe Thr Thr Leu Ile Ser Ser Ile Met Gly
            580                 585                 590

Pro Leu Leu Ile Leu Leu Leu Ile Leu Leu Phe Gly Pro Cys Ile Leu
        595                 600                 605

Asn Arg Leu Val Gln Phe Val Lys Asp Arg Ile Ser Val Val Gln Ala
    610                 615                 620

Leu Ile Leu Thr Gln Gln Tyr Gln Gln Ile Lys Gln Tyr Asp Pro Asp
625                 630                 635                 640

<210> SEQ ID NO 5
<211> LENGTH: 1929
<212> TYPE: DNA
<213> ORGANISM: artificial sequence
<220> FEATURE:
<223> OTHER INFORMATION: FeLV ENV DNA (wildtype, no mutation)

<400> SEQUENCE: 5
atggaaagtc caacgcaccc aaaaccctct aaagataaga ctctctcgtg gaacttagcg      60
tttctggtgg ggatcttatt tacaatagac ataggaatgg ccaatcctag tccacaccaa     120
atatataatg taacttgggt aataaccaat gtacaaacta acacccaagc taacgccacc     180
tctatgttag gaaccttaac cgatgcctac cctaccctac atgttgactt atgtgaccta     240
gtgggagaca cctgggaacc tatagtccta aacccaacca atgtaaaaca cggggcacgt     300
tactcctcct caaaatatgg atgtaaaact acagatagaa aaaaacagca acagacatac     360 ccctttttacg tctgccccgg acatgccccc tcgttggggc caaagggaac acattgtgga    420
ggggcacaag atgggttttg tgccgcatgg ggatgtgaga ccaccggaga agcttggtgg     480
aagcccacct cctcatggga ctatatcaca gtaaaaagag ggagtagtca ggacaatagc     540
tgtgagggaa aatgcaaccc cctggttttg cagttcaccc agaagggaag acaagcctct     600
tgggacggac ctaagatgtg gggattgcga ctataccgta caggatatga ccctatcgct     660
ttattcacgg tgtcccggca ggtatcaacc attacgccgc ctcaggcaat gggaccaaac     720
ctagtcttac ctgatcaaaa acccccatcc cgacaatctc aaacagggtc caaagtggcg     780
acccagaggc cccaaacgaa tgaaagcgcc ccaaggtctg ttgcccccac caccatgggt     840
cccaaacgga ttgggaccgg agataggtta ataaatttag tacaagggac atacctagcc     900
ttaaatgcca ccgaccccaa caaaactaaa gactgttggc tctgcctggt ttctcgacca     960
```

-continued

```
ccctattacg aagggattgc aatcttaggt aactacagca accaaacaaa ccccccccca   1020

tcctgcctat ctactccgca acacaaacta actatatctg aagtatcagg gcaaggaatg   1080

tgcataggga ctgttcctaa aacccaccag gctttgtgca ataagacaca acagggacat   1140

acaggggcgc actatctagc cgcccccaac ggcacctatt gggcctgtaa cactggactc   1200

accccatgca tttccatggc ggtgctcaat tggacctctg aattctgtgt cttaatcgaa   1260

ttatggccca gagtgactta ccatcaaccc gaatatgtgt acacacattt tgccaaagct   1320

gtcaggttcc gaagagaacc aatatcacta acggttgccc ttatgttggg aggacttact   1380

gtagggggca tagccgcggg ggtcggaaca gggactaaag ccctccttga aacagcccag   1440

tttagacaac tacaaatggc catgcacaca gacatccagg ccctagaaga atcaattagt   1500

gccttagaaa agtccctgac ctccctttct gaagtagtct tacaaaacag acggggccta   1560

gatattctat tcttacaaga gggagggctc tgtgccgcat tgaaagaaga atgttgcttc   1620

tatgcggatc acaccggact cgtccgagac aatatggcca aattaagaga aagactaaaa   1680

cagcggcaac aattgtttga ctcccaacag ggatggtttg aaggatggtt caacaagtcc   1740

ccctggttta caaccctaat ttcctccatt atgggcccct tactaatcct actcctaatt   1800

ctcctcttcg gcccatgcat ccttaaccga ttagtacaat tcgtaaaaga cagaatatct   1860

gtggtacagg ctttaatttt aacccaacag taccaacaga taaagcaata cgatccggac   1920

cgaccatga                                                           1929
```

<210> SEQ ID NO 6
<211> LENGTH: 642
<212> TYPE: PRT
<213> ORGANISM: artificial sequence
<220> FEATURE:
<223> OTHER INFORMATION: FeLV wildtype ENV protein

<400> SEQUENCE: 6

```
Met Glu Ser Pro Thr His Pro Lys Pro Ser Lys Asp Lys Thr Leu Ser
1               5                   10                  15

Trp Asn Leu Ala Phe Leu Val Gly Ile Leu Phe Thr Ile Asp Ile Gly
            20                  25                  30

Met Ala Asn Pro Ser Pro His Gln Ile Tyr Asn Val Thr Trp Val Ile
        35                  40                  45

Thr Asn Val Gln Thr Asn Thr Gln Ala Asn Ala Thr Ser Met Leu Gly
    50                  55                  60

Thr Leu Thr Asp Ala Tyr Pro Thr Leu His Val Asp Leu Cys Asp Leu
65                  70                  75                  80

Val Gly Asp Thr Trp Glu Pro Ile Val Leu Asn Pro Thr Asn Val Lys
                85                  90                  95

His Gly Ala Arg Tyr Ser Ser Ser Lys Tyr Gly Cys Lys Thr Thr Asp
            100                 105                 110

Arg Lys Lys Gln Gln Gln Thr Tyr Pro Phe Tyr Val Cys Pro Gly His
        115                 120                 125

Ala Pro Ser Leu Gly Pro Lys Gly Thr His Cys Gly Gly Ala Gln Asp
    130                 135                 140

Gly Phe Cys Ala Ala Trp Gly Cys Glu Thr Thr Gly Glu Ala Trp Trp
145                 150                 155                 160

Lys Pro Thr Ser Ser Trp Asp Tyr Ile Thr Val Lys Arg Gly Ser Ser
                165                 170                 175

Gln Asp Asn Ser Cys Glu Gly Lys Cys Asn Pro Leu Val Leu Gln Phe
            180                 185                 190
```

-continued

```
Thr Gln Lys Gly Arg Gln Ala Ser Trp Asp Gly Pro Lys Met Trp Gly
        195                 200                 205

Leu Arg Leu Tyr Arg Thr Gly Tyr Asp Pro Ile Ala Leu Phe Thr Val
    210                 215                 220

Ser Arg Gln Val Ser Thr Ile Thr Pro Pro Gln Ala Met Gly Pro Asn
225                 230                 235                 240

Leu Val Leu Pro Asp Gln Lys Pro Pro Ser Arg Gln Ser Gln Thr Gly
            245                 250                 255

Ser Lys Val Ala Thr Gln Arg Pro Gln Thr Asn Glu Ser Ala Pro Arg
            260                 265                 270

Ser Val Ala Pro Thr Thr Met Gly Pro Lys Arg Ile Gly Thr Gly Asp
        275                 280                 285

Arg Leu Ile Asn Leu Val Gln Gly Thr Tyr Leu Ala Leu Asn Ala Thr
    290                 295                 300

Asp Pro Asn Lys Thr Lys Asp Cys Trp Leu Cys Leu Val Ser Arg Pro
305                 310                 315                 320

Pro Tyr Tyr Glu Gly Ile Ala Ile Leu Gly Asn Tyr Ser Asn Gln Thr
            325                 330                 335

Asn Pro Pro Pro Ser Cys Leu Ser Thr Pro Gln His Lys Leu Thr Ile
            340                 345                 350

Ser Glu Val Ser Gly Gln Gly Met Cys Ile Gly Thr Val Pro Lys Thr
        355                 360                 365

His Gln Ala Leu Cys Asn Lys Thr Gln Gln Gly His Thr Gly Ala His
    370                 375                 380

Tyr Leu Ala Ala Pro Asn Gly Thr Tyr Trp Ala Cys Asn Thr Gly Leu
385                 390                 395                 400

Thr Pro Cys Ile Ser Met Ala Val Leu Asn Trp Thr Ser Glu Phe Cys
            405                 410                 415

Val Leu Ile Glu Leu Trp Pro Arg Val Thr Tyr His Gln Pro Glu Tyr
            420                 425                 430

Val Tyr Thr His Phe Ala Lys Ala Val Arg Phe Arg Arg Glu Pro Ile
        435                 440                 445

Ser Leu Thr Val Ala Leu Met Leu Gly Gly Leu Thr Val Gly Gly Ile
    450                 455                 460

Ala Ala Gly Val Gly Thr Gly Thr Lys Ala Leu Leu Glu Thr Ala Gln
465                 470                 475                 480

Phe Arg Gln Leu Gln Met Ala Met His Thr Asp Ile Gln Ala Leu Glu
            485                 490                 495

Glu Ser Ile Ser Ala Leu Glu Lys Ser Leu Thr Ser Leu Ser Glu Val
            500                 505                 510

Val Leu Gln Asn Arg Arg Gly Leu Asp Ile Leu Phe Leu Gln Glu Gly
        515                 520                 525

Gly Leu Cys Ala Ala Leu Lys Glu Glu Cys Cys Phe Tyr Ala Asp His
    530                 535                 540

Thr Gly Leu Val Arg Asp Asn Met Ala Lys Leu Arg Glu Arg Leu Lys
545                 550                 555                 560

Gln Arg Gln Gln Leu Phe Asp Ser Gln Gln Gly Trp Phe Glu Gly Trp
            565                 570                 575

Phe Asn Lys Ser Pro Trp Phe Thr Thr Leu Ile Ser Ser Ile Met Gly
            580                 585                 590

Pro Leu Leu Ile Leu Leu Leu Ile Leu Leu Phe Gly Pro Cys Ile Leu
        595                 600                 605
```

Asn Arg Leu Val Gln Phe Val Lys Asp Arg Ile Ser Val Val Gln Ala
    610                 615                 620

Leu Ile Leu Thr Gln Gln Tyr Gln Gln Ile Lys Gln Tyr Asp Pro Asp
625                 630                 635                 640

Arg Pro

<210> SEQ ID NO 7
<211> LENGTH: 642
<212> TYPE: PRT
<213> ORGANISM: artificial sequence
<220> FEATURE:
<223> OTHER INFORMATION: FeLV ENV mutant protein

<400> SEQUENCE: 7

Met Glu Ser Pro Thr His Pro Lys Pro Ser Lys Asp Lys Thr Leu Ser
1               5                   10                  15

Trp Asn Leu Val Phe Leu Val Gly Ile Leu Phe Thr Ile Asp Ile Gly
            20                  25                  30

Met Ala Asn Pro Ser Pro Pro Gln Met Tyr Asn Val Thr Trp Val Ile
        35                  40                  45

Thr Asn Val Gln Thr Asn Thr Gln Ala Asn Ala Thr Ser Met Leu Gly
    50                  55                  60

Thr Leu Thr Asp Val Tyr Pro Thr Leu His Val Asp Leu Cys Asp Leu
65                  70                  75                  80

Val Gly Asp Thr Trp Glu Pro Met Val Leu Ser Pro Thr Gly Tyr Pro
                85                  90                  95

Pro Ser Lys Tyr Gly Cys Lys Thr Thr Asp Arg Lys Lys Gln Gln Gln
            100                 105                 110

Thr Tyr Pro Phe Tyr Val Cys Pro Gly His Arg Pro Ser Leu Gly Pro
        115                 120                 125

Lys Gly Thr His Cys Gly Gly Ala Gln Asp Gly Phe Cys Ala Ala Trp
    130                 135                 140

Gly Cys Glu Thr Thr Gly Glu Ala Trp Trp Lys Pro Ser Ser Ser Trp
145                 150                 155                 160

Asp Tyr Ile Thr Val Lys Arg Gly Ser Ser Gln Asn Asn Asn Cys Glu
                165                 170                 175

Gly Lys Cys Asn Pro Leu Ile Leu Gln Phe Thr Gln Lys Gly Lys Gln
            180                 185                 190

Ala Ser Trp Asp Gly Pro Lys Met Trp Gly Leu Arg Leu Tyr Arg Thr
        195                 200                 205

Gly Tyr Asp Pro Ile Ala Leu Phe Thr Val Ser Arg Arg Val Ser Thr
    210                 215                 220

Ile Thr Pro Pro Gln Ala Met Gly Pro Asp Leu Val Leu Pro Asp Gln
225                 230                 235                 240

Lys Pro Pro Ser Arg Gln Ser Gln Thr Gly Ser Lys Val Ala Thr Gln
                245                 250                 255

Arg Pro Gln Thr Asn Glu Ser Ala Pro Arg Ser Val Ala Pro Thr Thr
            260                 265                 270

Val Gly Pro Lys Arg Ile Gly Thr Gly Asp Arg Leu Ile Asn Leu Val
        275                 280                 285

Gln Gly Ala Tyr Leu Ala Leu Asn Ala Thr Asp Pro Asn Lys Thr Lys
    290                 295                 300

Asp Cys Trp Leu Cys Leu Val Ser Arg Pro Pro Tyr Tyr Glu Gly Ile
305                 310                 315                 320

Ala Ile Leu Gly Asn Tyr Ser Asn Gln Thr Asn Pro Pro Pro Ser Cys

-continued

```
                325                 330                 335

Leu Ser Ile Pro Pro His Lys Leu Thr Ile Ser Lys Val Ser Gly Gln
            340                 345                 350

Gly Leu Cys Ile Gly Thr Val Pro Lys Thr His Gln Ala Leu Cys Asn
        355                 360                 365

Lys Thr His Gln Gly His Thr Gly Ala Asp Tyr Arg Ala Ala Pro Arg
    370                 375                 380

Tyr Leu Ala Ala Pro Asn Gly Thr Tyr Trp Ala Cys Asn Thr Gly Leu
385                 390                 395                 400

Thr Pro Cys Ile Ser Met Ala Val Leu Asn Leu Thr Ser Asp Phe Cys
                405                 410                 415

Val Leu Ile Glu Leu Trp Pro Arg Val Thr Tyr His Gln Pro Glu Tyr
            420                 425                 430

Val Tyr Thr His Phe Ala Lys Ala Gly Arg Phe Arg Arg Glu Pro Ile
        435                 440                 445

Ser Leu Thr Val Ala Leu Met Leu Gly Gly Leu Thr Val Gly Gly Ile
    450                 455                 460

Ala Ala Gly Val Gly Thr Gly Thr Lys Ala Leu Leu Glu Thr Ala Gln
465                 470                 475                 480

Phe Arg Gln Leu Gln Met Ala Met His Thr Asp Ile Gln Ala Leu Glu
                485                 490                 495

Glu Ser Ile Ser Ala Leu Glu Lys Ser Leu Thr Ser Leu Ser Glu Val
            500                 505                 510

Val Leu Gln Asn Arg Arg Gly Leu Asp Ile Leu Phe Leu Gln Arg Gly
        515                 520                 525

Gly Leu Cys Ala Ala Leu Lys Glu Glu Cys Cys Phe Tyr Ala Asp His
    530                 535                 540

Thr Gly Leu Val Arg Asp Asn Met Ala Lys Leu Arg Glu Arg Leu Lys
545                 550                 555                 560

Gln Arg Gln Gln Leu Phe Asp Ser Gln Gln Gly Trp Phe Glu Gly Trp
                565                 570                 575

Phe Asn Arg Ser Pro Trp Phe Thr Thr Leu Ile Ser Ser Ile Met Gly
            580                 585                 590

Pro Leu Leu Ile Leu Leu Leu Ile Leu Leu Phe Gly Pro Tyr Ile Leu
        595                 600                 605

Asn Arg Leu Val Gln Phe Val Lys Asp Arg Ile Ser Val Val Gln Ala
    610                 615                 620

Leu Ile Leu Thr Gln Gln Tyr Gln Gln Ile Lys Gln Tyr Asp Pro Asp
625                 630                 635                 640

Arg Pro
```

<210> SEQ ID NO 8
<211> LENGTH: 4330
<212> TYPE: DNA
<213> ORGANISM: artificial sequence
<220> FEATURE:
<223> OTHER INFORMATION: vCP2295 vector sequence

<400> SEQUENCE: 8

```
tgattatagc tattatcaca gactcattca atttcatctt attagcagag ttaacataat      60
cttctattat cgatatattt ttttcgtctt cagctgtaaa caaatataat gaaaagtatt     120
ctaaactagg aatagatgaa attatgtgca aaggagatac ctttagatat ggatctgatt     180
tatttggttt ttcataatca taatctaaca acattttcac tatactatac cttcttgcac     240
```

-continued

```
aagtcgccat tagtagtata gacttatact ttgtaaccat agtatacttt agcgcgtcat    300
cttcttcatc taaaacagat ttacaacaat aatcatcgtc gtcatcttca tcttcattaa    360
agttttcata ttcaataact ttcttttcta aaacatcatc tgaatcaata aacatagaac    420
ggtatagagc gttaatctcc attgtaaaat atactaacgc gttgctcatg atgtactttt    480
tttcattatt tagaaattat gcattttaga tctttataag cggccgtgat taactagtca    540
taaaaacccg ggatcgattc tagactcgag cggggatctc tttattctat acttaaaaag    600
tgaaaataaa tacaaaggtt cttgagggtt gtgttaaatt gaaagcgaga aataatcata    660
aattatttca ttatcgcgat atccgttaag tttgtatcgt aatggaaagt ccaacgcacc    720
caaaaccctc taaagataag actctctcgt ggaacttagc gtttctggtg gggatcttat    780
ttacaataga cataggaatg gccaatccta gtccacacca aatatataat gtaacttggg    840
taataaccaa tgtacaaact aacacccaag ctaacgccac ctctatgtta ggaaccttaa    900
ccgatgccta ccctacccta catgttgact tatgtgacct agtgggagac acctgggaac    960
ctatagtcct aaacccaacc aatgtaaaac acggggcacg ttactcctcc tcaaaatatg   1020
gatgtaaaac tacagataga aaaaaacagc aacagacata ccccttttac gtctgccccg   1080
gacatgcccc ctcgttgggg ccaaagggaa cacattgtgg aggggcacaa gatgggtttt   1140
gtgccgcatg gggatgtgag accaccggag aagcttggtg gaagcccacc tcctcatggg   1200
actatatcac agtaaaaaga gggagtagtc aggacaatag ctgtgaggga aaatgcaacc   1260
ccctggtttt gcagttcacc cagaagggaa gacaagcctc ttgggacgga cctaagatgt   1320
ggggattgcg actataccgt acaggatatg accctatcgc tttattcacg gtgtcccggc   1380
aggtatcaac cattacgccg cctcaggcaa tgggaccaaa cctagtctta cctgatcaaa   1440
aacccccatc ccgacaatct caaacagggt ccaaagtggc gacccagagg ccccaaacga   1500
atgaaagcgc cccaaggtct gttgccccca ccaccatggg tcccaaacgg attgggaccg   1560
gagataggtt aataaattta gtacaaggga catacctagc cttaaatgcc accgacccca   1620
acaaaactaa agactgttgg ctctgcctgg tttctcgacc accctattac gaagggattg   1680
caatcttagg taactacagc aaccaaacaa acccccccc atcctgccta tctactccgc   1740
aacacaaact aactatatct gaagtatcag ggcaaggaat gtgcataggg actgttccta   1800
aaacccacca ggctttgtgc aataagacac aacagggaca tacaggggcg cactatctag   1860
ccgcccccaa cggcacctat tgggcctgta acactggact caccccatgc atttccatgg   1920
cggtgctcaa ttggacctct gaattctgtg tcttaatcga attatggccc agagtgactt   1980
accatcaacc cgaatatgtg tacacacatt ttgccaaagc tgtcaggttc cgaagagaac   2040
caatatcact aacggttgcc cttatgttgg gaggacttac tgtagggggc atagccgcgg   2100
gggtcggaac agggactaaa gccctccttg aaacagccca gtttagacaa ctacaaatgg   2160
ccatgcacac agacatccag gccctagaag aatcaattag tgccttagaa aagtccctga   2220
cctccctttc tgaagtagtc ttacaaaaca gacggggcct agatattcta ttcttacaag   2280
agggagggct ctgtgccgca ttgaaagaag aatgttgctt ctatgcggat cacaccggac   2340
tcgtccgaga caatatggcc aaattaagag aaagactaaa acagcggcaa caattgtttg   2400
actcccaaca gggatggttt gaaggatggt tcaacaagtc cccctggttt acaaccctaa   2460
tttcctccat tatgggcccc ttactaatcc tactcctaat tctcctcttc ggcccatgca   2520
tccttaaccg attagtacaa ttcgtaaaag acagaatatc tgtggtacag gctttaattt   2580
taacccaaca gtaccaacag ataaagcaat acgatccgga ccgaccatga tttttctgga   2640
```

-continued tcctttttat agctaattag tcacgtacct ttgagagtac cacttcagct acctcttttg 2700
tgtctcagag taactttctt taatcaattc caaaacagta tatgattttc catttctttc 2760
aaagatgtag tttacatctg ctcctttgtt gaaaagtagc ctgagcactt cttttctacc 2820
atgaattaca gctggcaaga tcaatttttc ccagttctgg acattttatt ttttttaagt 2880
agtgtgctac atatttcaat atttccagat tgtacagcga tcattaaagg agtacgtccc 2940
atgttatcca gcaagtcagt atcagcacct ttgttcaata gaagtttaac cattgttaaa 3000
tttttatttg atacggctat atgtagagga gttaaccgat ccgtgtttga aatatctaca 3060
tccgccgaat gagccaatag aagtttaacc aaattaactt tgttaaggta agctgccaaa 3120
cacaaaggag taaagcctcc gctgtaaaga acattgttta catagttatt cttcaacaga 3180
tctttcacta ttttgtagtc gtctctcaac accgcatcat gcagacaaga agttgtgcat 3240
tcagtaacta caggtttagc tccatacctc atcaagattt ttatagcctc ggtattcttg 3300
aacattacag ccatttcaag aggagattgt agagtaccat attccgtgtt agggtcgaat 3360
ccattgtcca aaaacctatt tagagatgca ttgtcattat ccatgatagc ctcacagacg 3420
tatatgtaag ccatcttgaa tgtataattt tgttgttttc aacaaccgct cgtgaacagc 3480
ttctatactt tttcattttc ttcatgatta atatagttta cggaatataa gtatacaaaa 3540
agtttatagt aatctcataa tatctgaaac acatacataa aacatggaag aattacacga 3600
tgtcgttgag ataaatggct ttttattgtc atagtttaca aattcgcagt aatcttcatc 3660
ttttacgaat attgcagaat ctgttttatc caaccagtga tttttgtata atataactgg 3720
tatcctatct tccgatagaa tgctgttatt taacattttt gcacctatta agttacatct 3780
gtcaaatcca tctttccaac tgactttatg taacgatgcg aaatagcatt tatcactatg 3840
tcgtacccaa ttatcatgac aagattctct taaatacgta atcttattat ctcttgcata 3900
ttcgtaatag taattgtaaa gagtatacga taacagtata gatatacacg tgatataaat 3960
atttaacccc attcctgagt aaaataatta cgatattaca tttcctttta ttatttttat 4020
gttttagtta tttgttaggt tatacaaaaa ttatgtttat ttgtgtatat ttaaagcgtc 4080
gttaagaata agcttagtta acatattatc gcttaggttt tgtagtattt gaatcctttc 4140
tttaaatgga ttatttttcc aatgcatatt tatagcttca tccaaagtat aacatttaac 4200
attcattgcc atagtcaata gttctctcct acgagaacct atatttataa tatcgttcat 4260
gcaataacgg tacatagtca ttttatcacg cgtctcgatt aatttatcca agtaactaac 4320
taacagattc 4330

<210> SEQ ID NO 9
<211> LENGTH: 8281
<212> TYPE: DNA
<213> ORGANISM: artificial sequence
<220> FEATURE:
<223> OTHER INFORMATION: plasmid pJY1874.1 sequence

<400> SEQUENCE: 9
tgcggccgcg tcgacatgca ttgttagttc tgtagatcag taacgtatag catacgagta 60
taattatcgt aggtagtagg tatcctaaaa taaatctgat acagataata actttgtaaa 120
tcaattcagc aatttctcta ttatcatgat aatgattaat acacagcgtg tcgttatttt 180
ttgttacgat agtatttcta aagtaaagag caggaatccc tagtataata gaaataatcc 240
atatgaaaaa tatagtaatg tacatatttc taatgttaac atatttatag gtaaatccag 300

-continued

```
gaagggtaat ttttacatat ctatatacgc ttattacagt tattaaaaat atacttgcaa    360
acatgttaga agtaaaaaag aaagaactaa ttttacaaag tgctttacca aaatgccaat    420
ggaaattact tagtatgtat ataatgtata aaggtatgaa tatcacaaac agcaaatcgg    480
ctattcccaa gttgagaaac ggtataatag atatatttct agataccatt aataacctta    540
taagcttgac gtttcctata atgcctacta agaaaactag aagatacata catactaacg    600
ccatacgaga gtaactactc atcgtataac tactgttgct aacagtgaca ctgatgttat    660
aactcatctt tgatgtggta taaatgtata ataactatat tacactggta ttttatttca    720
gttatatact atatagtatt aaaaattata tttgtataat tatattatta tattcagtgt    780
agaaagtaaa atactataaa tatgtatctc ttatttataa cttattagta aagtatgtac    840
tattcagtta tattgtttta taaaagctaa atgctactag attgatataa atgaatatgt    900
aataaattag taatgtagta tactaatatt aactcacatt tgactaatta gctataaaaa    960
cccgggttaa ttaattagtc atcaggcagg gcgagaacga gactatctgc tcgttaatta   1020
attagagctt ctttattcta tacttaaaaa gtgaaaataa atacaaaggt tcttgagggt   1080
tgtgttaaat tgaaagcgag aaataatcat aaattatttc attatcgcga tatccgttaa   1140
gtttgtatcg taatgggaca gaccatcacc acccccctgt ctctcaccct ggaccactgg   1200
tctgaggtga gagccagagc ccacaaccag ggcgtggagg tgaggaagaa gaagtggatc   1260
accctgtgtg aggccgagtg ggtgatgatg aacgtgggct ggcctagaga gggcaccttc   1320
tccctggact ccatctccca ggtggagaag aagatcttcg cccctggccc ttacggccac   1380
cccgatcagg tgccctacat caccacctgg agatctctgg ccaccgaccc tcctagctgg   1440
gtgagaccct tcctgccccc tcccaaacct cctacccctc tgcctcagcc tctgtctcct   1500
cagccttctg ccccccctcac ctcttctctg taccccgtgc tgcccaaacc cgaccccct    1560
aaacctcctg tgctgccccc cgacccctct tctcccctca tcgacctgct caccgaggag   1620
ccccctcctt accctggcgg acacggccct cctccctctg gaccccggac ccctaccgcc   1680
tctcctatcg cctccaggct gagggagaga agggagaacc ccgccgagga atctcaggcc   1740
ctgcctctga gagagggccc caacaacagg ccccagtact ggcctttctc tgcctccgac   1800
ctgtacaact ggaagtccca caacccccca ttctctcagg accccgtggc cctcaccaac   1860
ctcatcgagt ccatcctggt gacccatcag cccacctggg acgactgtca gcaactgctg   1920
caggctctgc tcaccggcga ggagagacag agagtgctgc tggaggccag aaaacaggtg   1980
cccggcgagg atggcagacc tacccagctg cccaacgtga tcgacgagac cttcccactc   2040
accagaccca actgggactt cgccacccct gccggcagag agcacctgag gctgtacaga   2100
cagctgctgc tggccggact gagaggagcc gccaggagac ctaccaacct ggcccaggtg   2160
aagcaggtgg tgcagggcaa agaggaaacc cctgccgcct tcctggagag actgaaggaa   2220
gcctaccgga tgtacacccc ctacgaccct gaggatcctg gacaggccgc ctctgtgatc   2280
ctgtccttca tctaccagtc cagccccgac atcaggaaca agctgcagag actggagggc   2340
ctgcagggct tcaccctgtc cgacctgctg aaggaggccg agaagatcta caacaagcgg   2400
gagacccccg aggagagaga ggaaaggctg tggcagagac aggaggagag ggacaagaag   2460
cggcacaagg agatgaccaa ggtgctggcc accgtggtgg cccagaacag ggacaaggac   2520
agggaggagt ctaagctggg cgaccagagg aaaatccccc tgggcaagga ccagtgcgcc   2580
tactgtaagg agaagggcca ctgggtgaga gattgcccca agaggcccag aaagaagccc   2640
gccaactcca ccctgctcaa cttaggagat taggagagtc agggccagga ccctccacct   2700
```

-continued

```
gagcccagaa tcaccctgaa gatcggcggc cagcccgtga ccttcctggt ggacaccgga   2760
gcccagcact ctgtgctcac aagacccgac ggcccccctgt ccgatagaac cgccctggtg   2820
cagggagcca ccggctccaa gaactacagg tggaccaccg acagaagggt gcagctggcc   2880
acaggaaagg tgacccactc cttcctgtac gtgcccgagt gtccctaccc tctgctgggc   2940
agagatctgc tcaccaagct gaaggcccag atccacttca ccggcgaagg cgccaatgtg   3000
gtgggcccca gaggactgcc cctgcaggtg ctgtaatgat tttcttgac tagttaatca   3060
aataaaaagc atacaagcta ttgcttcgct atcgttacaa aatggcagga attttgtgta   3120
aactaagcca catacttgcc aatgaaaaaa atagtagaaa ggatactatt ttaatgggat   3180
tagatgttaa ggttccttgg gattatagta actgggcatc tgttaacttt tacgacgtta   3240
ggttagatac tgatgttaca gattataata atgttacaat aaaatacatg acaggatgtg   3300
atatttttcc tcatataact cttggaatag caaatatgga tcaatgtgat agatttgaaa   3360
atttcaaaaa gcaaataact gatcaagatt tacagactat ttctatagtc tgtaaagaag   3420
agatgtgttt tcctcagagt aacgcctcta aacagttggg agcgaaagga tgcgctgtag   3480
ttatgaaact ggaggtatct gatgaactta gagccctaag aaatgttctg ctgaatgcgg   3540
taccctgttc gaaggacgtg tttggtgata tcacagtaga taatccgtgg aatcctcaca   3600
taacagtagg atatgttaag gaggacgatg tcgaaaacaa gaaacgccta atggagtgca   3660
tgtccaagtt tagggggcaa gaaatacaag ttctaggatg gtattaataa gtatctaagt   3720
atttggtata atttattaaa tagtataatt ataacaaata ataaataaca tgataacggt   3780
ttttattaga ataaaataga gataatatca taatgatata taatacttca ttaccagaaa   3840
tgagtaatgg aagacttata aatgaactgc ataaagctat aaggtataga gatataaatt   3900
tagtaaggta tatacttaaa aaatgcaaat acaataacgt aaatatacta tcaacgtctt   3960
tgtatttagc cgtaagtatt tctgatatag aaatggtaaa attattacta gaacacggtg   4020
ccgatatttt aaaatgtaaa aatcctcctc ttcataaagc tgctagttta gataatacag   4080
aaattgctaa actactaata gattctggcg ctgacataga acagatacat tctggaaata   4140
gtccgttata tatttctgta tatagaaaca ataagtcatt aactagatat ttattaaaaa   4200
aaggtgttaa ttgtaataga ttctttctaa attattacga tgtactgtat gataagatat   4260
ctgatgatat gtataaaata tttatagatt ttaatattga tcttaatata caaactagaa   4320
attttgaaac tccgttacat tacgctataa agtataagaa tatagattta attaggatat   4380
tgttagataa tagtattaaa atagataaaa gtttattttt gcataaacag tatctcataa   4440
aggcacttaa aaataattgt agttacgata taatagcgtt acttataaat cacggagtgc   4500
ctataaacga acaagatgat ttaggtaaaa ccccattaca tcattcggta attaatagaa   4560
gaaaagatgt aacagcactt ctgttaaatc taggagctga tataaacgta atagatgact   4620
gtatgggcag tcccttacat tacgctgttt cacgtaacga tatcgaaaca acaaagacac   4680
ttttagaaag aggatctaat gttaatgtgg ttaataatca tatagatacc gttctaaata   4740
tagctgttgc atctaaaaac aaaactatag taaacttatt actgaagtac ggtactgata   4800
caaagttggt aggattagat aaacatgtta ttcacatagc tatagaaatg aaagatatta   4860
atatactgaa tgcgatctta ttatatggtt gctatgtaaa cgtctataat cataaaggtt   4920
tcactcctct atacatggca gttagttcta tgaaaacaga atttgttaaa ctcttacttg   4980
accacggtgc ttacgtaaat gctaaagcta agttatctgg aaatactcct ttacataaag   5040
```

```
ctatgttatc taatagtttt aataatataa aattactttt atcttataac gccgactata   5100
attctctaaa taatcacggt aatacgcctc taacttgtgt tagcttttta gatgacaaga   5160
tagctattat gataatatct aaaatgatgt tagaaatatc taaaaatcct gaaatagcta   5220
attcagaagg ttttatagta aacatggaac atataaacag taataaaaga ctactatcta   5280
taaaagaatc atgcgaaaaa gaactagatg ttataacaca tataaagtta aattctatat   5340
attcttttaa tatctttctt gacaataaca tagatcttat ggtaaagttc gtaactaatc   5400
ctagagttaa taagatacct gcatgtatac gtatatatag ggaattaata cggaaaaata   5460
aatcattagc ttttcataga catcagctaa tagttaaagc tgtaaaagag agtaagaatc   5520
taggaataat aggtaggtta cctatagata tcaaacatat aataatggaa ctattaagta   5580
ataatgattt acattctgtt atcaccagct gttgtaaccc agtagtataa agagctcgaa   5640
ttaattcact ggccgtcgtt ttacaacgtc gtgactggga aaaccctggc gttacccaac   5700
ttaatcgcct tgcagcacat ccccctttcg ccagctggcg taatagcgaa gaggcccgca   5760
ccgatcgccc ttcccaacag ttgcgcagcc tgaatggcga atggcgcctg atgcggtatt   5820
ttctccttac gcatctgtgc ggtatttcac accgcatatg gtgcactctc agtacaatct   5880
gctctgatgc cgcatagtta agccagcccc gacacccgcc aacacccgct gacgcgccct   5940
gacgggcttg tctgctcccg gcatccgctt acagacaagc tgtgaccgtc tccgggagct   6000
gcatgtgtca gaggttttca ccgtcatcac cgaaacgcgc gagacgaaag ggcctcgtga   6060
tacgcctatt tttataggtt aatgtcatga taataatggt ttcttagacg tcaggtggca   6120
cttttcgggg aaatgtgcgc ggaaccccta tttgtttatt tttctaaata cattcaaata   6180
tgtatccgct catgagacaa taaccctgat aaatgcttca ataatattga aaaaggaaga   6240
gtatgagtat tcaacatttc cgtgtcgccc ttattccctt ttttgcggca ttttgccttc   6300
ctgtttttgc tcacccagaa acgctggtga aagtaaaaga tgctgaagat cagttgggtg   6360
cacgagtggg ttacatcgaa ctggatctca acagcggtaa gatccttgag agttttcgcc   6420
ccgaagaacg ttttccaatg atgagcactt ttaaagttct gctatgtggc gcggtattat   6480
cccgtattga cgccgggcaa gagcaactcg gtcgccgcat acactattct cagaatgact   6540
tggttgagta ctcaccagtc acagaaaagc atcttacgga tggcatgaca gtaagagaat   6600
tatgcagtgc tgccataacc atgagtgata acactgcggc caacttactt ctgacaacga   6660
tcggaggacc gaaggagcta accgcttttt tgcacaacat gggggatcat gtaactcgcc   6720
ttgatcgttg ggaaccggag ctgaatgaag ccataccaaa cgacgagcgt gacaccacga   6780
tgcctgtagc aatggcaaca acgttgcgca aactattaac tggcgaacta cttactctag   6840
cttcccggca acaattaata gactggatgg aggcggataa agttgcagga ccacttctgc   6900
gctcggccct tccggctggc tggtttattg ctgataaatc tggagccggt gagcgtgggt   6960
ctcgcggtat cattgcagca ctggggccag atggtaagcc ctcccgtatc gtagttatct   7020
acacgacggg gagtcaggca actatggatg aacgaaatag acagatcgct gagataggtg   7080
cctcactgat taagcattgg taactgtcag accaagttta ctcatatata ctttagattg   7140
atttaaaact tcatttttaa tttaaaagga tctaggtgaa gatccttttt gataatctca   7200
tgaccaaaat cccttaacgt gagttttcgt tccactgagc gtcagacccc gtagaaaaga   7260
tcaaaggatc ttcttgagat cctttttttc tgcgcgtaat ctgctgcttg caaacaaaaa   7320
aaccaccgct accagcggtg gtttgtttgc cggatcaaga gctaccaact ctttttccga   7380
aggtaactgg cttcagcaga gcgcagatac caaatactgt ccttctagtg tagccgtagt   7440
```

```
taggccacca cttcaagaac tctgtagcac cgcctacata cctcgctctg ctaatcctgt   7500

taccagtggc tgctgccagt ggcgataagt cgtgtcttac cgggttggac tcaagacgat   7560

agttaccgga taaggcgcag cggtcgggct gaacgggggg ttcgtgcaca cagcccagct   7620

tggagcgaac gacctacacc gaactgagat acctacagcg tgagctatga gaaagcgcca   7680

cgcttcccga agggagaaag gcggacaggt atccggtaag cggcagggtc ggaacaggag   7740

agcgcacgag ggagcttcca gggggaaacg cctggtatct ttatagtcct gtcgggtttc   7800

gccacctctg acttgagcgt cgatttttgt gatgctcgtc aggggggcgg agcctatgga   7860

aaaacgccag caacgcggcc tttttacggt tcctggcctt ttgctggcct tttgctcaca   7920

tgttctttcc tgcgttatcc cctgattctg tggataaccg tattaccgcc tttgagtgag   7980

ctgataccgc tcgccgcagc cgaacgaccg agcgcagcga gtcagtgagc gaggaagcgg   8040

aagagcgccc aatacgcaaa ccgcctctcc ccgcgcgttg gccgattcat taatgcagct   8100

ggcacgacag gtttcccgac tggaaagcgg gcagtgagcg caacgcaatt aatgtgagtt   8160

agctcactca ttaggcaccc caggctttac actttatgct tccggctcgt atgttgtgtg   8220

gaattgtgag cggataacaa tttcacacag gaaacagcta tgaccatgat tacgccaagc   8280

t                                                                   8281
```

<210> SEQ ID NO 10
<211> LENGTH: 1881
<212> TYPE: DNA
<213> ORGANISM: artificial sequence
<220> FEATURE:
<223> OTHER INFORMATION: FeLV GAG-PRO codon-optimized DNA

<400> SEQUENCE: 10

```
atgggacaga ccatcaccac ccccctgtct ctcaccctgg accactggtc tgaggtgaga     60
gccagagccc acaaccaggg cgtggaggtg aggaagaaga agtggatcac cctgtgtgag    120
gccgagtggg tgatgatgaa cgtgggctgg cctagagagg gcaccttctc cctggactcc    180
atctcccagg tggagaagaa gatcttcgcc cctggccctt acggccaccc cgatcaggtg    240
ccctacatca ccacctggag atctctggcc accgaccctc ctagctgggt gagacccttc    300
ctgccccctc ccaaacctcc taccccctctg cctcagcctc tgtctcctca gccttctgcc    360
cccctcacct cttctctgta ccccgtgctg cccaaacccg acccccctaa acctcctgtg    420
ctgccccccg accccctcttc tcccctcatc gacctgctca ccgaggagcc ccctccttac    480
cctggcggac acggccctcc tccctctgga ccccggaccc ctaccgcctc tcctatcgcc    540
tccaggctga gggagagaag ggagaacccc gccgaggaat ctcaggccct gcctctgaga    600
gagggcccca acaacaggcc ccagtactgg cctttctctg cctccgacct gtacaactgg    660
aagtcccaca accccccatt ctctcaggac cccgtggccc tcaccaacct catcgagtcc    720
atcctggtga cccatcagcc cacctgggac gactgtcagc aactgctgca ggctctgctc    780
accggcgagg agagacagag agtgctgctg gaggccagaa aacaggtgcc cggcgaggat    840
ggcagaccta cccagctgcc caacgtgatc gacgagacct tcccactcac cagacccaac    900
tgggacttcg ccacccctgc cggcagagag cacctgaggc tgtacagaca gctgctgctg    960
gccggactga gaggagccgc caggagacct accaacctgg cccaggtgaa gcaggtggtg   1020
cagggcaaag aggaaacccc tgccgccttc ctggagagac tgaaggaagc ctaccggatg   1080 tacacccccct acgaccctga ggatcctgga caggccgcct ctgtgatcct gtccttcatc   1140
```

-continued

```
taccagtcca gccccgacat caggaacaag ctgcagagac tggagggcct gcagggcttc   1200

accctgtccg acctgctgaa ggaggccgag aagatctaca acaagcggga gacccccgag   1260

gagagagagg aaaggctgtg gcagagacag gaggagaggg acaagaagcg gcacaaggag   1320

atgaccaagg tgctggccac cgtggtggcc cagaacaggg acaaggacag ggaggagtct   1380

aagctgggcg accagaggaa aatccccctg ggcaaggacc agtgcgccta ctgtaaggag   1440

aagggccact gggtgagaga ttgccccaag aggcccagaa agaagcccgc caactccacc   1500

ctgctcaact taggagatta ggagagtcag ggccaggacc ctccacctga gcccagaatc   1560

accctgaaga tcggcggcca gcccgtgacc ttcctggtgg acaccggagc ccagcactct   1620

gtgctcacaa gacccgacgg cccccctgtcc gatagaaccg ccctggtgca gggagccacc   1680

ggctccaaga actacaggtg gaccaccgac agaagggtgc agctggccac aggaaaggtg   1740

acccactcct tcctgtacgt gcccgagtgt ccctaccctc tgctgggcag agatctgctc   1800

accaagctga aggcccagat ccacttcacc ggcgaaggcg ccaatgtggt gggccccaga   1860

ggactgcccc tgcaggtgct g                                             1881
```

<210> SEQ ID NO 11
<211> LENGTH: 1881
<212> TYPE: DNA
<213> ORGANISM: artificial sequence
<220> FEATURE:
<223> OTHER INFORMATION: FeLV GAG-PRO wildtype DNA

<400> SEQUENCE: 11

```
atgggccaaa ctataactac ccccttaagc ctcacccttg atcactggtc tgaagtccgg     60
gcacgagccc ataatcaagg tgtcgaggtc cggaaaaaga aatggattac cttatgtgag    120
gccgaatggg tgatgatgaa tgtgggctgg ccccgagaag gaactttttc tcttgataac    180
atttcccagg ttgagaaaaa gatcttcgcc ccgggaccgt atggacaccc cgaccaagtt    240
ccgtacatta ccacatggag atccttagcc acagaccccc cttcgtgggt tcgtccgttc    300 ctacccccctc ccaaaactcc cacacccctc cctcaacctc tatcgccgca gccctccgcc    360
cctcttacct cttccctcta ccccgttctc cccaagtcag accctcccaa accgcctgtg    420
ttaccgcctg atccttcttc ccctttaatt gatctcttaa cagaagagcc acctccctat    480 ccgggggggtc acgggccacc gccatcaggt cctagaaccc caaccgcttc cccgattgcc    540
agccggctaa gggaacgacg agaaaaccct gctgaagaat ctcaagccct cccccttgagg    600 gaaggcccca acaaccggcc ccagtattgg ccattctcag cttcagacct gtataactgg    660
aagtcgcata acccccccttt ctcccaagac cccgtggccc taactaacct aattgagtcc    720
attttagtga cgcatcaacc aacctgggac gactgccagc agctcttgca ggcactcctg    780
acaggcgaag aaaggcaaag ggtccttctt gaggcccgaa agcaggttcc aggcgaggac    840
ggacggccaa cccagctgcc caatgtcatt gacgaagctt tccccttgac ccgtcccaac    900
tgggattttc gtacgccggc aggtagggag cacctacgcc tttatcgcca gttgctgtta    960
gcgggtctcc gcggggctgc aagacgcccc actaatttgg cacaggtaaa gcaagttgta   1020
caagggaaag aggaaacgcc agcctcattc ttagaaagat taaaagaggc ttacagaatg   1080
tatactccct atgaccctga ggacccaggg caggctgcta gtgttatcct gtcctttatc   1140
taccagtcta gcccggacat aagaaataag ttacaaaggc tagaaggcct acaggggttc   1200
acactgtctg atttgctaaa agaggcagaa aagatataca acaaaaggga gaccccagag   1260
gaaagggaag aaagattatg gcagcggcag gaagaaagag ataaaaagcg ccataaggag   1320
```

```
atgactaaag ttctggccac agtagttgct cagaatagag ataaggatag agaggaaagt   1380

aaactgggag atcaaagaaa aatacctctg gggaaagacc agtgtgccta ttgcaaggaa   1440

aagggacatt gggttcgcga ttgccccaaa cggccccgga agaaacccgc caactccact   1500

ctcctcaact tagaagatta ggagagtcag ggccaggacc cccccctga gcccaggata   1560

accttaaaaa tagggggca accggtgact ttcctggtgg acacgggagc ccagcactca   1620

gtattaactc gaccagatgg acctctcagt gaccgcacag ccctggtgca aggagccacg   1680

ggaagcaaaa actaccggtg gaccaccgac aggagggtac aactggcaac cggtaaggtg   1740

actcattctt ttttatatgt acctgaatgt ccctacccgt tattaggaag agacctatta   1800

actaaactta aggcccaaat ccattttacc ggagaagggg ctaatgttgt tgggcccagg   1860

ggtttacccc tacaagtcct t                                              1881
```

```
<210> SEQ ID NO 12
<211> LENGTH: 626
<212> TYPE: PRT
<213> ORGANISM: artificial sequence
<220> FEATURE:
<223> OTHER INFORMATION: FeLV GAG-PRO protein

<400> SEQUENCE: 12

Met Gly Gln Thr Ile Thr Thr Pro Leu Ser Leu Thr Leu Asp His Trp
1               5                   10                  15

Ser Glu Val Arg Ala Arg Ala His Asn Gln Gly Val Glu Val Arg Lys
            20                  25                  30

Lys Lys Trp Ile Thr Leu Cys Glu Ala Glu Trp Val Met Met Asn Val
        35                  40                  45

Gly Trp Pro Arg Glu Gly Thr Phe Ser Leu Asp Ser Ile Ser Gln Val
    50                  55                  60

Glu Lys Lys Ile Phe Ala Pro Gly Pro Tyr Gly His Pro Asp Gln Val
65                  70                  75                  80

Pro Tyr Ile Thr Thr Trp Arg Ser Leu Ala Thr Asp Pro Pro Ser Trp
                85                  90                  95

Val Arg Pro Phe Leu Pro Pro Pro Lys Pro Pro Thr Pro Leu Pro Gln
            100                 105                 110

Pro Leu Ser Pro Gln Pro Ser Ala Pro Leu Thr Ser Ser Leu Tyr Pro
        115                 120                 125

Val Leu Pro Lys Pro Asp Pro Pro Lys Pro Pro Val Leu Pro Pro Asp
    130                 135                 140

Pro Ser Ser Pro Leu Ile Asp Leu Leu Thr Glu Glu Pro Pro Pro Tyr
145                 150                 155                 160

Pro Gly Gly His Gly Pro Pro Pro Ser Gly Pro Arg Thr Pro Thr Ala
                165                 170                 175

Ser Pro Ile Ala Ser Arg Leu Arg Glu Arg Arg Glu Asn Pro Ala Glu
            180                 185                 190

Glu Ser Gln Ala Leu Pro Leu Arg Glu Gly Pro Asn Asn Arg Pro Gln
        195                 200                 205

Tyr Trp Pro Phe Ser Ala Ser Asp Leu Tyr Asn Trp Lys Ser His Asn
    210                 215                 220

Pro Pro Phe Ser Gln Asp Pro Val Ala Leu Thr Asn Leu Ile Glu Ser
225                 230                 235                 240

Ile Leu Val Thr His Gln Pro Thr Trp Asp Asp Cys Gln Gln Leu Leu
                245                 250                 255
```

-continued

```
Gln Ala Leu Leu Thr Gly Glu Glu Arg Gln Arg Val Leu Leu Glu Ala
            260                 265                 270

Arg Lys Gln Val Pro Gly Glu Asp Gly Arg Pro Thr Gln Leu Pro Asn
        275                 280                 285

Val Ile Asp Glu Thr Phe Pro Leu Thr Arg Pro Asn Trp Asp Phe Ala
    290                 295                 300

Thr Pro Ala Gly Arg Glu His Leu Arg Leu Tyr Arg Gln Leu Leu Leu
305                 310                 315                 320

Ala Gly Leu Arg Gly Ala Ala Arg Arg Pro Thr Asn Leu Ala Gln Val
                325                 330                 335

Lys Gln Val Val Gln Gly Lys Glu Glu Thr Pro Ala Ala Phe Leu Glu
            340                 345                 350

Arg Leu Lys Glu Ala Tyr Arg Met Tyr Thr Pro Tyr Asp Pro Glu Asp
        355                 360                 365

Pro Gly Gln Ala Ala Ser Val Ile Leu Ser Phe Ile Tyr Gln Ser Ser
    370                 375                 380

Pro Asp Ile Arg Asn Lys Leu Gln Arg Leu Glu Gly Leu Gln Gly Phe
385                 390                 395                 400

Thr Leu Ser Asp Leu Leu Lys Glu Ala Glu Lys Ile Tyr Asn Lys Arg
                405                 410                 415

Glu Thr Pro Glu Glu Arg Glu Glu Arg Leu Trp Gln Arg Gln Glu Glu
            420                 425                 430

Arg Asp Lys Lys Arg His Lys Glu Met Thr Lys Val Leu Ala Thr Val
        435                 440                 445

Val Ala Gln Asn Arg Asp Lys Asp Arg Glu Glu Ser Lys Leu Gly Asp
    450                 455                 460

Gln Arg Lys Ile Pro Leu Gly Lys Asp Gln Cys Ala Tyr Cys Lys Glu
465                 470                 475                 480

Lys Gly His Trp Val Arg Asp Cys Pro Lys Arg Pro Arg Lys Lys Pro
                485                 490                 495

Ala Asn Ser Thr Leu Leu Asn Leu Gly Asp Glu Ser Gln Gly Gln Asp
            500                 505                 510

Pro Pro Pro Glu Pro Arg Ile Thr Leu Lys Ile Gly Gly Gln Pro Val
        515                 520                 525

Thr Phe Leu Val Asp Thr Gly Ala Gln His Ser Val Leu Thr Arg Pro
    530                 535                 540

Asp Gly Pro Leu Ser Asp Arg Thr Ala Leu Val Gln Gly Ala Thr Gly
545                 550                 555                 560

Ser Lys Asn Tyr Arg Trp Thr Thr Asp Arg Arg Val Gln Leu Ala Thr
                565                 570                 575

Gly Lys Val Thr His Ser Phe Leu Tyr Val Pro Glu Cys Pro Tyr Pro
            580                 585                 590

Leu Leu Gly Arg Asp Leu Leu Thr Lys Leu Lys Ala Gln Ile His Phe
        595                 600                 605

Thr Gly Glu Gly Ala Asn Val Val Gly Pro Arg Gly Leu Pro Leu Gln
    610                 615                 620

Val Leu
625

<210> SEQ ID NO 13
<211> LENGTH: 60
<212> TYPE: DNA
<213> ORGANISM: artificial sequence
<220> FEATURE:
<223> OTHER INFORMATION: primer 13301JY
```

<400> SEQUENCE: 13
attatcgcga tatccgttaa gtttgtatcg taatgggaca gaccatcacc acccccctgt 60

<210> SEQ ID NO 14
<211> LENGTH: 49
<212> TYPE: DNA
<213> ORGANISM: artificial sequence
<220> FEATURE:
<223> OTHER INFORMATION: primer 13302JY

<400> SEQUENCE: 14
attaactagt caagaaaaat cattacagca cctgcagggg cagtcctct 49

<210> SEQ ID NO 15
<211> LENGTH: 22
<212> TYPE: DNA
<213> ORGANISM: artificial sequence
<220> FEATURE:
<223> OTHER INFORMATION: H6P promoter

<400> SEQUENCE: 15
tatccgttaa gtttgtatcg ta 22

<210> SEQ ID NO 16
<211> LENGTH: 5757
<212> TYPE: DNA
<213> ORGANISM: artificial sequence
<220> FEATURE:
<223> OTHER INFORMATION: vCP2294 vector sequence

<400> SEQUENCE: 16
gaggcatcca acatataaag aagactaaag ctgtagaagc tgttatgaag aatatcttat 60
cagatatatt agatgcattg ttagttctgt agatcagtaa cgtatagcat acgagtataa 120
ttatcgtagg tagtaggtat cctaaaataa atctgataca gataataact ttgtaaatca 180
attcagcaat ttctctatta tcatgataat gattaataca cagcgtgtcg ttattttttg 240
ttacgatagt atttctaaag taaagagcag gaatccctag tataatagaa ataatccata 300
tgaaaaatat agtaatgtac atatttctaa tgttaacata tttataggta aatccaggaa 360
gggtaatttt tacatatcta tatacgctta ttacagttat taaaaatata cttgcaaaca 420
tgttagaagt aaaaaagaaa gaactaattt tacaaagtgc tttaccaaaa tgccaatgga 480
aattacttag tatgtatata atgtataaag gtatgaatat cacaaacagc aaatcggcta 540
ttcccaagtt gagaaacggt ataatagata tatttctaga taccattaat aaccttataa 600
gcttgacgtt tcctataatg cctactaaga aaactagaag atacatacat actaacgcca 660
tacgagagta actactcatc gtataactac tgttgctaac agtgacactg atgttataac 720
tcatctttga tgtggtataa atgtataata actatattac actggtattt tatttcagtt 780
atatactata tagtattaaa aattatattt gtataattat attattatat tcagtgtaga 840
aagtaaaata ctataaatat gtatctctta tttataactt attagtaaag tatgtactat 900
tcagttatat tgttttataa aagctaaatg ctactagatt gatataaatg aatatgtaat 960
aaattagtaa tgtagtatac taatattaac tcacatttga ctaattagct ataaaaaccc 1020
gggttaatta attagtcatc aggcagggcg agaacgagac tatctgctcg ttaattaatt 1080
agagcttctt tattctatac ttaaaaagtg aaaataaata caaaggttct tgagggttgt 1140
gttaaattga aagcgagaaa taatcataaa ttatttcatt atcgcgatat ccgttaagtt 1200

-continued

```
tgtatcgtaa tgggacagac catcaccacc cccctgtctc tcaccctgga ccactggtct   1260
gaggtgagag ccagagccca caaccagggc gtggaggtga ggaagaagaa gtggatcacc   1320
ctgtgtgagg ccgagtgggt gatgatgaac gtgggctggc ctagagaggg caccttctcc   1380
ctggactcca tctcccaggt ggagaagaag atcttcgccc ctggccctta cggccacccc   1440
gatcaggtgc cctacatcac cacctggaga tctctggcca ccgaccctcc tagctgggtg   1500
agacccttcc tgccccctcc caaacctcct acccctctgc ctcagcctct gtctcctcag   1560
ccttctgccc ccctcacctc ttctctgtac cccgtgctgc ccaaacccga ccccccctaaa   1620
cctcctgtgc tgccccccga cccctcttct cccctcatcg acctgctcac cgaggagccc   1680
cctccttacc ctggcggaca cggccctcct ccctctggac cccggacccc taccgcctct   1740
cctatcgcct ccaggctgag ggagagaagg gagaaccccg ccgaggaatc tcaggccctg   1800
cctctgagag agggccccaa caacaggccc cagtactggc ctttctctgc ctccgacctg   1860
tacaactgga agtcccacaa ccccccattc tctcaggacc ccgtggccct caccaacctc   1920
atcgagtcca tcctggtgac ccatcagccc acctgggacg actgtcagca actgctgcag   1980
gctctgctca ccggcgagga gagacagaga gtgctgctgg aggccagaaa acaggtgccc   2040
ggcgaggatg gcagacctac ccagctgccc aacgtgatcg acgagacctt cccactcacc   2100
agacccaact gggacttcgc cacccctgcc ggcagagagc acctgaggct gtacagacag   2160
ctgctgctgg ccggactgag aggagccgcc aggagaccta ccaacctggc ccaggtgaag   2220
caggtggtgc agggcaaaga ggaaacccct gccgccttcc tggagagact gaaggaagcc   2280
taccggatgt acacccccta cgaccctgag gatcctggac aggccgcctc tgtgatcctg   2340
tccttcatct accagtccag ccccgacatc aggaacaagc tgcagagact ggagggcctg   2400
cagggcttca ccctgtccga cctgctgaag gaggccgaga agatctacaa caagcgggag   2460
acccccgagg agagagagga aaggctgtgg cagagacagg aggagaggga caagaagcgg   2520
cacaaggaga tgaccaaggt gctggccacc gtggtggccc agaacaggga caaggacagg   2580
gaggagtcta agctgggcga ccagaggaaa atccccctgg gcaaggacca gtgcgcctac   2640
tgtaaggaga agggccactg ggtgagagat tgccccaaga ggcccagaaa gaagcccgcc   2700
aactccaccc tgctcaactt aggagattag gagagtcagg gccaggaccc tccacctgag   2760
cccagaatca ccctgaagat cggcggccag cccgtgacct tcctggtgga caccggagcc   2820
cagcactctg tgctcacaag acccgacggc cccctgtccg atagaaccgc cctggtgcag   2880
ggagccaccg gctccaagaa ctacaggtgg accaccgaca gaagggtgca gctggccaca   2940
ggaaaggtga cccactcctt cctgtacgtg cccgagtgtc cctaccctct gctgggcaga   3000
gatctgctca ccaagctgaa ggcccagatc cacttcaccg gcgaaggcgc caatgtggtg   3060
ggccccagag gactgcccct gcaggtgctg taatgatttt tcttgactag ttaatcaaat   3120
aaaaagcata caagctattg cttcgctatc gttacaaaat ggcaggaatt ttgtgtaaac   3180
taagccacat acttgccaat gaaaaaaata gtagaaagga tactatttta atgggattag   3240
atgttaaggt tccttgggat tatagtaact gggcatctgt taacttttac gacgttaggt   3300
tagatactga tgttacagat tataataatg ttacaataaa atacatgaca ggatgtgata   3360
tttttcctca tataactctt ggaatagcaa atatggatca atgtgataga tttgaaaatt   3420
tcaaaaagca aataactgat caagatttac agactatttc tatagtctgt aaagaagaga   3480
tgtgttttcc tcagagtaac gcctctaaac agttgggagc gaaaggatgc gctgtagtta   3540
tgaaactgga ggtatctgat gaacttagag ccctaagaaa tgttctgctg aatgcggtac   3600
```

```
cctgttcgaa ggacgtgttt ggtgatatca cagtagataa tccgtggaat cctcacataa   3660

cagtaggata tgttaaggag gacgatgtcg aaaacaagaa acgcctaatg gagtgcatgt   3720

ccaagtttag gggcaagaa atacaagttc taggatggta ttaataagta tctaagtatt   3780

tggtataatt tattaaatag tataattata acaaataata aataacatga taacggtttt   3840

tattagaata aaatagagat aatatcataa tgatatataa tacttcatta ccagaaatga   3900

gtaatggaag acttataaat gaactgcata aagctataag gtatagagat ataaatttag   3960

taaggtatat acttaaaaaa tgcaaataca ataacgtaaa tatactatca acgtctttgt   4020

atttagccgt aagtatttct gatatagaaa tggtaaaatt attactagaa cacggtgccg   4080

atattttaaa atgtaaaaat cctcctcttc ataaagctgc tagtttagat aatacagaaa   4140

ttgctaaact actaatagat tctggcgctg acatagaaca gatacattct ggaaatagtc   4200

cgttatatat ttctgtatat agaaacaata agtcattaac tagatattta ttaaaaaaag   4260

gtgttaattg taatagattc tttctaaatt attacgatgt actgtatgat aagatatctg   4320

atgatatgta taaaatattt atagatttta atattgatct taatatacaa actagaaatt   4380

ttgaaactcc gttacattac gctataaagt ataagaatat agatttaatt aggatattgt   4440

tagataatag tattaaaata gataaaagtt tatttttgca taaacagtat ctcataaagg   4500

cacttaaaaa taattgtagt tacgatataa tagcgttact tataaatcac ggagtgccta   4560

taaacgaaca agatgattta ggtaaaaccc cattacatca ttcggtaatt aatagaagaa   4620

aagatgtaac agcacttctg ttaaatctag gagctgatat aaacgtaata gatgactgta   4680

tgggcagtcc cttacattac gctgtttcac gtaacgatat cgaaacaaca aagacacttt   4740

tagaaagagg atctaatgtt aatgtggtta ataatcatat agataccgtt ctaaatatag   4800

ctgttgcatc taaaaacaaa actatagtaa acttattact gaagtacggt actgatacaa   4860

agttggtagg attagataaa catgttattc acatagctat agaaatgaaa gatattaata   4920

tactgaatgc gatcttatta tatggttgct atgtaaacgt ctataatcat aaaggtttca   4980

ctcctctata catggcagtt agttctatga aaacagaatt tgttaaactc ttacttgacc   5040

acggtgctta cgtaaatgct aaagctaagt tatctggaaa tactccttta cataaagcta   5100

tgttatctaa tagttttaat aatataaaat tacttttatc ttataacgcc gactataatt   5160

ctctaaataa tcacggtaat acgcctctaa cttgtgttag ctttttagat gacaagatag   5220

ctattatgat aatatctaaa atgatgttag aaatatctaa aaatcctgaa atagctaatt   5280

cagaaggttt tatagtaaac atggaacata taaacagtaa taaaagacta ctatctataa   5340

aagaatcatg cgaaaaagaa ctagatgtta taacacatat aaagttaaat tctatatatt   5400

cttttaatat ctttcttgac aataacatag atcttatggt aaagttcgta actaatccta   5460

gagttaataa gatacctgca tgtatacgta tatataggga attaatacgg aaaaataaat   5520

cattagcttt tcatagacat cagctaatag ttaaagctgt aaaagagagt aagaatctag   5580

gaataatagg taggttacct atagatatca aacatataat aatggaacta ttaagtaata   5640

atgatttaca ttctgttatc accagctgtt gtaacccagt agtataaagt gattttattc   5700

aattacgaag ataaacatta aatttgttaa cagatatgag ttatgagtat ttaacta      5757
```

<210> SEQ ID NO 17
<211> LENGTH: 21
<212> TYPE: DNA
<213> ORGANISM: artificial sequence
<220> FEATURE:

<223> OTHER INFORMATION: primer 11369JY

<400> SEQUENCE: 17
atgatgaacg tgggctggcc t 21

<210> SEQ ID NO 18
<211> LENGTH: 21
<212> TYPE: DNA
<213> ORGANISM: artificial sequence
<220> FEATURE:
<223> OTHER INFORMATION: primer 11377JY

<400> SEQUENCE: 18
tctcctaagt tgagcagggt g 21

<210> SEQ ID NO 19
<211> LENGTH: 30
<212> TYPE: DNA
<213> ORGANISM: artificial sequence
<220> FEATURE:
<223> OTHER INFORMATION: primer 8103JY

<400> SEQUENCE: 19
gaggcatcca acatataaag aagactaaag 30

<210> SEQ ID NO 20
<211> LENGTH: 27
<212> TYPE: DNA
<213> ORGANISM: artificial sequence
<220> FEATURE:
<223> OTHER INFORMATION: primer 8104JY

<400> SEQUENCE: 20
tagttaaata ctcataactc atatctg 27

<210> SEQ ID NO 21
<211> LENGTH: 25
<212> TYPE: DNA
<213> ORGANISM: artificial sequence
<220> FEATURE:
<223> OTHER INFORMATION: primer 7900CXL

<400> SEQUENCE: 21
aggagggctt tagtccctgt tccga 25

<210> SEQ ID NO 22
<211> LENGTH: 24
<212> TYPE: DNA
<213> ORGANISM: artificial sequence
<220> FEATURE:
<223> OTHER INFORMATION: primer 7934CXL

<400> SEQUENCE: 22
actaaagact gttggctctg cctg 24

<210> SEQ ID NO 23
<211> LENGTH: 25
<212> TYPE: DNA
<213> ORGANISM: artificial sequence
<220> FEATURE:
<223> OTHER INFORMATION: primer 7931DC

<400> SEQUENCE: 23
gaatctgtta gttagttact tggat 25

<210> SEQ ID NO 24
<211> LENGTH: 25
<212> TYPE: DNA
<213> ORGANISM: artificial sequence
<220> FEATURE:
<223> OTHER INFORMATION: primer 7932DC

<400> SEQUENCE: 24
tgattatagc tattatcaca gactc 25

<210> SEQ ID NO 25
<211> LENGTH: 37
<212> TYPE: DNA
<213> ORGANISM: artificial sequence
<220> FEATURE:
<223> OTHER INFORMATION: primer 7862CXL

<400> SEQUENCE: 25
acgccgctcg agcggggatc tctttattct atactta 37

<210> SEQ ID NO 26
<211> LENGTH: 34
<212> TYPE: DNA
<213> ORGANISM: artificial sequence
<220> FEATURE:
<223> OTHER INFORMATION: primer 7847CXL

<400> SEQUENCE: 26
ctcggatcca gaaaaatcat ggtcggtccg gatc 34

<210> SEQ ID NO 27
<211> LENGTH: 642
<212> TYPE: PRT
<213> ORGANISM: artificial sequence
<220> FEATURE:
<223> OTHER INFORMATION: FeLV ENV protein pPB179

<400> SEQUENCE: 27

```
Met Glu Ser Pro Thr His Pro Lys Pro Ser Lys Asp Lys Thr Leu Ser
1               5                   10                  15

Trp Asn Leu Ala Phe Leu Val Gly Ile Leu Phe Thr Ile Asp Ile Gly
            20                  25                  30

Met Ala Asn Pro Ser Pro His Gln Ile Tyr Asn Val Thr Trp Val Ile
        35                  40                  45

Thr Asn Val Gln Thr Asn Thr Gln Ala Asn Ala Thr Ser Met Leu Gly
    50                  55                  60

Thr Leu Thr Asp Ala Tyr Pro Thr Leu His Val Asp Leu Cys Asp Leu
65                  70                  75                  80

Val Gly Asp Thr Trp Glu Pro Ile Val Leu Asn Pro Thr Asn Val Lys
                85                  90                  95

His Gly Ala Arg Tyr Ser Ser Ser Lys Tyr Gly Cys Lys Thr Thr Asp
            100                 105                 110

Arg Lys Lys Gln Gln Gln Thr Tyr Pro Phe Tyr Val Cys Pro Gly His
        115                 120                 125

Ala Pro Ser Leu Gly Pro Lys Gly Thr His Cys Gly Gly Ala Gln Asp
    130                 135                 140

Gly Phe Cys Ala Ala Trp Gly Cys Glu Thr Thr Gly Glu Ala Trp Trp
145                 150                 155                 160

Lys Pro Thr Ser Ser Trp Asp Tyr Ile Thr Val Lys Arg Gly Ser Ser
                165                 170                 175

Gln Asp Asn Ser Cys Glu Gly Lys Cys Asn Pro Leu Val Leu Gln Phe
```

-continued

```
            180                 185                 190

Thr Gln Lys Gly Arg Gln Ala Ser Trp Asp Gly Pro Lys Met Trp Gly
        195                 200                 205

Leu Arg Leu Tyr Arg Thr Gly Tyr Asp Pro Ile Ala Leu Phe Thr Val
    210                 215                 220

Ser Arg Gln Val Ser Thr Ile Thr Pro Pro Gln Ala Met Gly Pro Asn
225                 230                 235                 240

Leu Val Leu Pro Asp Gln Lys Pro Pro Ser Arg Gln Ser Gln Thr Gly
                245                 250                 255

Ser Lys Val Ala Thr Gln Arg Pro Gln Thr Asn Glu Ser Ala Pro Arg
            260                 265                 270

Ser Val Ala Pro Thr Thr Met Gly Pro Lys Arg Ile Gly Thr Gly Asp
        275                 280                 285

Arg Leu Ile Asn Leu Val Gln Gly Thr Tyr Leu Ala Leu Asn Ala Thr
    290                 295                 300

Asp Pro Asn Lys Thr Lys Asp Cys Trp Leu Cys Leu Val Ser Arg Pro
305                 310                 315                 320

Pro Tyr Tyr Glu Gly Ile Ala Ile Leu Gly Asn Tyr Ser Asn Gln Thr
                325                 330                 335

Asn Pro Pro Pro Ser Cys Leu Ser Thr Pro Gln His Lys Leu Thr Ile
            340                 345                 350

Ser Glu Val Ser Gly Gln Gly Met Cys Ile Gly Thr Val Pro Lys Thr
        355                 360                 365

His Gln Ala Leu Cys Asn Lys Thr Gln Gln Gly His Thr Gly Ala His
    370                 375                 380

Tyr Leu Ala Ala Pro Asn Gly Thr Tyr Trp Ala Cys Asn Thr Gly Leu
385                 390                 395                 400

Thr Pro Cys Ile Ser Met Ala Val Leu Asn Trp Thr Ser Glu Phe Cys
                405                 410                 415

Val Leu Ile Glu Leu Trp Pro Arg Val Thr Tyr His Gln Pro Glu Tyr
            420                 425                 430

Val Tyr Thr His Phe Ala Lys Ala Val Arg Phe Arg Arg Glu Pro Ile
        435                 440                 445

Ser Leu Thr Val Ala Leu Met Leu Gly Gly Leu Thr Val Gly Gly Ile
    450                 455                 460

Ala Ala Gly Val Gly Thr Gly Thr Lys Ala Leu Leu Glu Thr Ala Gln
465                 470                 475                 480

Phe Arg Gln Leu Gln Met Ala Met His Thr Asp Ile Gln Ala Leu Glu
                485                 490                 495

Glu Ser Ile Ser Ala Leu Glu Lys Ser Leu Thr Ser Leu Ser Glu Val
            500                 505                 510

Val Leu Gln Asn Arg Arg Gly Leu Asp Ile Leu Phe Leu Gln Glu Gly
        515                 520                 525

Gly Leu Cys Ala Ala Leu Lys Glu Glu Cys Cys Phe Tyr Ala Asp His
    530                 535                 540

Thr Gly Leu Val Arg Asp Asn Met Ala Lys Leu Arg Glu Arg Leu Lys
545                 550                 555                 560

Gln Arg Gln Gln Leu Phe Asp Ser Gln Gln Gly Trp Phe Glu Gly Trp
                565                 570                 575

Phe Asn Lys Ser Pro Trp Phe Thr Thr Leu Ile Ser Ser Ile Met Gly
            580                 585                 590

Pro Leu Leu Ile Leu Leu Leu Ile Leu Leu Phe Gly Pro Cys Ile Leu
        595                 600                 605
```

Asn Arg Leu Val Gln Phe Val Lys Asp Arg Ile Ser Val Val Gln Ala
    610                 615                 620

Leu Ile Leu Thr Gln Gln Tyr Gln Gln Ile Lys Gln Tyr Asp Pro Asp
625                 630                 635                 640

Arg Pro

<210> SEQ ID NO 28
<211> LENGTH: 642
<212> TYPE: PRT
<213> ORGANISM: artificial sequence
<220> FEATURE:
<223> OTHER INFORMATION: FeLV ENV protein (1_Glasgow-1)

<400> SEQUENCE: 28

Met Glu Ser Pro Thr His Pro Lys Pro Ser Lys Asp Lys Thr Leu Ser
1               5                   10                  15

Trp Asn Leu Ala Phe Leu Val Gly Ile Leu Phe Thr Ile Asp Ile Gly
            20                  25                  30

Met Ala Asn Pro Ser Pro His Gln Ile Tyr Asn Val Thr Trp Val Ile
        35                  40                  45

Thr Asn Val Gln Thr Asn Thr Gln Ala Asn Ala Thr Ser Met Leu Gly
    50                  55                  60

Thr Leu Thr Asp Ala Tyr Pro Thr Leu His Val Asp Leu Cys Asp Leu
65                  70                  75                  80

Val Gly Asp Thr Trp Glu Pro Ile Val Leu Asn Pro Thr Asn Val Lys
                85                  90                  95

His Gly Ala Arg Tyr Ser Ser Ser Lys Tyr Gly Cys Lys Thr Thr Asp
            100                 105                 110

Arg Lys Lys Gln Gln Gln Thr Tyr Pro Phe Tyr Val Cys Pro Gly His
        115                 120                 125

Ala Pro Ser Leu Gly Pro Lys Gly Thr His Cys Gly Gly Ala Gln Asp
    130                 135                 140

Gly Phe Cys Ala Ala Trp Gly Cys Glu Thr Thr Gly Glu Ala Trp Trp
145                 150                 155                 160

Lys Pro Thr Ser Ser Trp Asp Tyr Ile Thr Val Lys Arg Gly Ser Ser
                165                 170                 175

Gln Asp Asn Ser Cys Glu Gly Lys Cys Asn Pro Leu Val Leu Gln Phe
            180                 185                 190

Thr Gln Lys Gly Arg Gln Ala Ser Trp Asp Gly Pro Lys Met Trp Gly
        195                 200                 205

Leu Arg Leu Tyr Arg Thr Gly Tyr Asp Pro Ile Ala Leu Phe Thr Val
    210                 215                 220

Ser Arg Gln Val Ser Thr Ile Thr Pro Pro Gln Ala Met Gly Pro Asn
225                 230                 235                 240

Leu Val Leu Pro Asp Gln Lys Pro Pro Ser Arg Gln Ser Gln Thr Gly
                245                 250                 255

Ser Lys Val Ala Thr Gln Arg Pro Gln Thr Asn Glu Ser Ala Pro Arg
            260                 265                 270

Ser Val Ala Pro Thr Thr Met Gly Pro Lys Arg Ile Gly Thr Gly Asp
        275                 280                 285

Arg Leu Ile Asn Leu Val Gln Gly Thr Tyr Leu Ala Leu Asn Ala Thr
    290                 295                 300

Asp Pro Asn Lys Thr Lys Asp Cys Trp Leu Cys Leu Val Ser Arg Pro
305                 310                 315                 320

Pro Tyr Tyr Glu Gly Ile Ala Ile Leu Gly Asn Tyr Ser Asn Gln Thr
325 330 335

Asn Pro Pro Pro Ser Cys Leu Ser Thr Pro Gln His Lys Leu Thr Ile
340 345 350

Ser Glu Val Ser Gly Gln Gly Met Cys Ile Gly Thr Val Pro Lys Thr
355 360 365

His Gln Ala Leu Cys Asn Lys Thr Gln Gln Gly His Thr Gly Ala His
370 375 380

Tyr Leu Ala Ala Pro Asn Gly Thr Tyr Trp Ala Cys Asn Thr Gly Leu
385 390 395 400

Thr Pro Cys Ile Ser Met Ala Val Leu Asn Trp Thr Ser Asp Phe Cys
405 410 415

Val Leu Ile Glu Leu Trp Pro Arg Val Thr Tyr His Gln Pro Glu Tyr
420 425 430

Val Tyr Thr His Phe Ala Lys Ala Val Arg Phe Arg Arg Glu Pro Ile
435 440 445

Ser Leu Thr Val Ala Leu Met Leu Gly Gly Leu Thr Val Gly Gly Ile
450 455 460

Ala Ala Gly Val Gly Thr Gly Thr Lys Ala Leu Leu Glu Thr Ala Gln
465 470 475 480

Phe Arg Gln Leu Gln Met Ala Met His Thr Asp Ile Gln Ala Leu Glu
485 490 495

Glu Ser Ile Ser Ala Leu Glu Lys Ser Leu Thr Ser Leu Ser Glu Val
500 505 510

Val Leu Gln Asn Arg Arg Gly Leu Asp Ile Leu Phe Leu Gln Glu Gly
515 520 525

Gly Leu Cys Ala Ala Leu Lys Glu Glu Cys Cys Phe Tyr Ala Asp His
530 535 540

Thr Gly Leu Val Arg Asp Asn Met Ala Lys Leu Arg Glu Arg Leu Lys
545 550 555 560

Gln Arg Gln Gln Leu Phe Asp Ser Gln Gln Gly Trp Phe Glu Gly Trp
565 570 575

Phe Asn Lys Ser Pro Trp Phe Thr Thr Leu Ile Ser Ser Ile Met Gly
580 585 590

Pro Leu Leu Ile Leu Leu Leu Ile Leu Leu Phe Gly Pro Cys Ile Leu
595 600 605

Asn Arg Leu Val Gln Phe Val Lys Asp Arg Ile Ser Val Val Gln Ala
610 615 620

Leu Ile Leu Thr Gln Gln Tyr Gln Gln Ile Lys Gln Tyr Asp Pro Asp
625 630 635 640

Arg Pro

<210> SEQ ID NO 29
<211> LENGTH: 642
<212> TYPE: PRT
<213> ORGANISM: artificial sequence
<220> FEATURE:
<223> OTHER INFORMATION: ENV protein (3_Glasgow-1)

<400> SEQUENCE: 29

Met Glu Ser Pro Thr His Pro Lys Pro Ser Lys Asp Lys Thr Leu Ser
1 5 10 15

Trp Asn Leu Ala Phe Leu Val Gly Ile Leu Phe Thr Ile Asp Ile Gly
20 25 30

Met Ala Asn Pro Ser Pro His Gln Ile Tyr Asn Val Thr Trp Val Ile

-continued

```
        35                  40                  45

Thr Asn Val Gln Thr Asn Thr Gln Ala Asn Ala Thr Ser Met Leu Gly
    50                  55                  60

Thr Leu Thr Asp Ala Tyr Pro Thr Leu His Val Asp Leu Cys Asp Leu
65                  70                  75                  80

Val Gly Asp Thr Trp Glu Pro Ile Val Leu Asn Pro Thr Asn Val Lys
                85                  90                  95

His Gly Ala Arg Tyr Ser Ser Ser Lys Tyr Gly Cys Lys Thr Thr Asp
            100                 105                 110

Arg Lys Lys Gln Gln Gln Thr Tyr Pro Phe Tyr Val Cys Pro Gly His
        115                 120                 125

Ala Pro Ser Leu Gly Pro Lys Gly Thr His Cys Gly Gly Ala Gln Asp
    130                 135                 140

Gly Phe Cys Ala Ala Trp Gly Cys Glu Thr Thr Gly Glu Ala Trp Trp
145                 150                 155                 160

Lys Pro Thr Ser Ser Trp Asp Tyr Ile Thr Val Lys Arg Gly Ser Ser
                165                 170                 175

Gln Asp Asn Ser Cys Glu Gly Lys Cys Asn Pro Leu Val Leu Gln Phe
            180                 185                 190

Thr Gln Lys Gly Arg Gln Ala Ser Trp Asp Gly Pro Lys Met Trp Gly
        195                 200                 205

Leu Arg Leu Tyr Arg Thr Gly Tyr Asp Pro Ile Ala Leu Phe Thr Val
    210                 215                 220

Ser Arg Gln Val Ser Thr Ile Thr Pro Pro Gln Ala Met Gly Pro Asn
225                 230                 235                 240

Leu Val Leu Pro Asp Gln Lys Pro Pro Ser Arg Gln Ser Gln Thr Gly
                245                 250                 255

Ser Lys Val Ala Thr Gln Arg Pro Gln Thr Asn Glu Ser Ala Pro Arg
            260                 265                 270

Ser Val Ala Pro Thr Thr Met Gly Pro Lys Arg Ile Gly Thr Gly Asp
        275                 280                 285

Arg Leu Ile Asn Leu Val Gln Gly Thr Tyr Leu Ala Leu Asn Ala Thr
    290                 295                 300

Asp Pro Asn Lys Thr Lys Asp Cys Trp Leu Cys Leu Val Ser Arg Pro
305                 310                 315                 320

Pro Tyr Tyr Glu Gly Ile Ala Ile Leu Gly Thr Tyr Ser Asn Gln Thr
                325                 330                 335

Asn Pro Pro Pro Ser Cys Leu Ser Thr Pro Gln His Lys Leu Thr Ile
            340                 345                 350

Ser Glu Val Ser Gly Gln Gly Met Cys Ile Gly Thr Val Pro Lys Thr
        355                 360                 365

His Gln Ala Leu Cys Asn Lys Thr Gln Gln Gly His Thr Gly Ala His
    370                 375                 380

Tyr Leu Ala Ala Pro Asn Gly Thr Tyr Trp Ala Cys Asn Thr Gly Leu
385                 390                 395                 400

Thr Pro Cys Ile Ser Met Ala Val Leu Asn Trp Thr Ser Asp Phe Cys
                405                 410                 415

Val Leu Ile Glu Leu Trp Pro Arg Val Thr Tyr His Gln Pro Glu Tyr
            420                 425                 430

Val Tyr Thr His Phe Ala Lys Ala Val Arg Phe Arg Arg Glu Pro Ile
        435                 440                 445

Ser Leu Thr Val Ala Leu Met Leu Gly Gly Leu Thr Val Gly Gly Ile
    450                 455                 460
```

```
Ala Ala Gly Val Gly Thr Gly Thr Lys Ala Leu Leu Glu Thr Ala Gln
465                 470                 475                 480

Phe Arg Gln Leu Gln Met Ala Met His Thr Asp Ile Gln Ala Leu Glu
                485                 490                 495

Glu Ser Ile Ser Ala Leu Glu Lys Ser Leu Thr Ser Leu Ser Glu Val
            500                 505                 510

Val Leu Gln Asn Arg Arg Gly Leu Asp Ile Leu Phe Leu Gln Glu Gly
        515                 520                 525

Gly Leu Cys Ala Ala Leu Lys Glu Glu Cys Cys Phe Tyr Ala Asp His
    530                 535                 540

Thr Gly Leu Val Arg Asp Asn Met Ala Lys Leu Arg Glu Arg Leu Lys
545                 550                 555                 560

Gln Arg Gln Gln Leu Phe Asp Ser Gln Gln Gly Trp Phe Glu Gly Trp
                565                 570                 575

Phe Asn Lys Ser Pro Trp Phe Thr Thr Leu Ile Ser Ser Ile Met Gly
            580                 585                 590

Pro Leu Leu Ile Leu Leu Leu Ile Leu Leu Phe Gly Pro Cys Ile Leu
        595                 600                 605

Asn Arg Leu Val Gln Phe Val Lys Asp Arg Ile Ser Val Val Gln Ala
    610                 615                 620

Leu Ile Leu Thr Gln Gln Tyr Gln Gln Ile Lys Gln Tyr Asp Pro Asp
625                 630                 635                 640

Arg Pro

<210> SEQ ID NO 30
<211> LENGTH: 642
<212> TYPE: PRT
<213> ORGANISM: artificial sequence
<220> FEATURE:
<223> OTHER INFORMATION: ENV protein (Rickard, NP_047256)

<400> SEQUENCE: 30

Met Glu Ser Pro Thr His Pro Lys Pro Ser Lys Asp Lys Thr Leu Ser
1               5                   10                  15

Trp Asn Leu Ala Phe Leu Val Gly Ile Leu Phe Thr Ile Asp Ile Gly
            20                  25                  30

Met Ala Asn Pro Ser Pro His Gln Ile Tyr Asn Val Thr Trp Val Ile
        35                  40                  45

Thr Asn Met Gln Thr Asn Thr Gln Ala Asn Ala Thr Ser Met Leu Gly
    50                  55                  60

Thr Leu Thr Asp Ala Tyr Pro Thr Leu His Val Asp Leu Cys Asp Leu
65                  70                  75                  80

Val Gly Asp Thr Trp Glu Pro Ile Val Leu Asp Pro Thr Asn Val Lys
                85                  90                  95

His Gly Ala Arg Tyr Ser Ser Ser Lys Tyr Gly Cys Lys Thr Thr Asp
            100                 105                 110

Arg Lys Lys Gln Gln Gln Thr Tyr Pro Phe Tyr Val Cys Pro Gly His
        115                 120                 125

Ala Pro Ser Leu Gly Pro Lys Gly Thr His Cys Gly Gly Ala Gln Asp
    130                 135                 140

Gly Phe Cys Ala Ala Trp Gly Cys Glu Thr Thr Gly Glu Ala Trp Trp
145                 150                 155                 160

Lys Pro Ser Ser Ser Trp Asp Tyr Ile Thr Val Lys Arg Gly Ser Ser
                165                 170                 175
```

-continued

```
Gln Asp Asn Ser Cys Glu Gly Lys Cys Asn Pro Leu Ile Leu Gln Phe
            180                 185                 190

Thr Gln Lys Gly Arg Gln Ala Ser Trp Asp Gly Pro Lys Ile Trp Gly
        195                 200                 205

Leu Arg Leu Tyr Arg Thr Gly Tyr Asp Pro Ile Ala Leu Phe Thr Val
    210                 215                 220

Ser Arg Gln Val Ser Ala Ile Thr Pro Pro Gln Ala Met Gly Pro Asn
225                 230                 235                 240

Leu Val Leu Pro Asp Gln Lys Pro Pro Ser Arg Gln Ser Gln Thr Gly
                245                 250                 255

Ser Lys Val Ala Thr Gln Arg Leu Gln Thr Thr Glu Ser Ala Pro Arg
            260                 265                 270

Ser Val Ala Pro Thr Thr Val Gly Pro Lys Arg Ile Gly Thr Gly Asp
        275                 280                 285

Arg Leu Ile Asn Leu Val Gln Gly Thr Tyr Leu Ala Leu Asn Ala Thr
    290                 295                 300

Asp Pro Asn Lys Thr Lys Asp Cys Trp Leu Cys Leu Val Ser Arg Pro
305                 310                 315                 320

Pro Tyr Tyr Glu Gly Ile Ala Ile Leu Gly Asn Tyr Ser Asn Gln Thr
                325                 330                 335

Asn Pro Pro Pro Ser Cys Leu Ser Thr Pro Gln His Lys Leu Thr Ile
            340                 345                 350

Ser Glu Val Ser Gly Gln Gly Leu Cys Ile Gly Thr Val Pro Lys Thr
        355                 360                 365

His Gln Ala Leu Cys Asn Glu Thr Gln Gln Gly His Thr Gly Ala His
    370                 375                 380

Tyr Leu Ala Ala Pro Asn Gly Ala Tyr Trp Ala Cys Asn Thr Gly Leu
385                 390                 395                 400

Thr Pro Cys Ile Ser Met Ala Val Leu Asn Trp Thr Ser Asp Phe Cys
                405                 410                 415

Val Leu Ile Glu Leu Trp Pro Arg Val Thr Tyr His Gln Pro Glu Tyr
            420                 425                 430

Val Tyr Thr His Phe Ala Lys Ala Val Arg Phe Arg Arg Glu Pro Ile
        435                 440                 445

Ser Leu Thr Val Ala Leu Met Leu Gly Gly Leu Thr Val Gly Gly Ile
    450                 455                 460

Ala Ala Gly Val Gly Thr Gly Thr Lys Ala Leu Leu Glu Thr Ala Gln
465                 470                 475                 480

Phe Arg Gln Leu Gln Met Ala Met His Thr Asp Ile Gln Ala Leu Glu
                485                 490                 495

Glu Ser Ile Ser Ala Leu Glu Lys Ser Leu Thr Ser Leu Ser Glu Val
            500                 505                 510

Val Leu Gln Asn Arg Arg Gly Leu Asp Ile Leu Phe Leu Gln Glu Gly
        515                 520                 525

Gly Leu Cys Ala Ala Leu Lys Glu Glu Cys Cys Phe Tyr Ala Asp His
    530                 535                 540

Thr Gly Leu Val Arg Asp Asn Met Ala Lys Leu Arg Glu Arg Leu Lys
545                 550                 555                 560

Gln Arg Gln Gln Leu Phe Asp Ser Gln Gln Gly Trp Phe Glu Gly Trp
                565                 570                 575

Phe Asn Lys Ser Pro Trp Phe Thr Thr Leu Ile Ser Ser Ile Met Gly
            580                 585                 590

Pro Leu Leu Ile Leu Leu Leu Ile Leu Leu Phe Gly Pro Cys Ile Leu
```

595 600 605

Asn Arg Leu Val Gln Phe Val Lys Asp Arg Ile Ser Val Val Gln Ala
610 615 620

Leu Ile Leu Thr Gln Gln Tyr Gln Gln Ile Lys Gln Tyr Asp Pro Asp
625 630 635 640

Arg Pro

<210> SEQ ID NO 31
<211> LENGTH: 642
<212> TYPE: PRT
<213> ORGANISM: artificial sequence
<220> FEATURE:
<223> OTHER INFORMATION: ENV protein (NP_047256)

<400> SEQUENCE: 31

Met Glu Ser Pro Thr His Pro Lys Pro Ser Lys Asp Lys Thr Leu Ser
1 5 10 15

Trp Asn Leu Ala Phe Leu Val Gly Ile Leu Phe Thr Ile Asp Ile Gly
20 25 30

Met Ala Asn Pro Ser Pro His Gln Ile Tyr Asn Val Thr Trp Val Ile
35 40 45

Thr Asn Met Gln Thr Asn Thr Gln Ala Asn Ala Thr Ser Met Leu Gly
50 55 60

Thr Leu Thr Asp Ala Tyr Pro Thr Leu His Val Asp Leu Cys Asp Leu
65 70 75 80

Val Gly Asp Thr Trp Glu Pro Ile Val Leu Asp Pro Thr Asn Val Lys
85 90 95

His Gly Ala Arg Tyr Ser Ser Ser Lys Tyr Gly Cys Lys Thr Thr Asp
100 105 110

Arg Lys Lys Gln Gln Gln Thr Tyr Pro Phe Tyr Val Cys Pro Gly His
115 120 125

Ala Pro Ser Leu Gly Pro Lys Gly Thr His Cys Gly Gly Ala Gln Asp
130 135 140

Gly Phe Cys Ala Ala Trp Gly Cys Glu Thr Thr Gly Glu Ala Trp Trp
145 150 155 160

Lys Pro Ser Ser Ser Trp Asp Tyr Ile Thr Val Lys Arg Gly Ser Ser
165 170 175

Gln Asp Asn Ser Cys Glu Gly Lys Cys Asn Pro Leu Ile Leu Gln Phe
180 185 190

Thr Gln Lys Gly Arg Gln Ala Ser Trp Asp Gly Pro Lys Ile Trp Gly
195 200 205

Leu Arg Leu Tyr Arg Thr Gly Tyr Asp Pro Ile Ala Leu Phe Thr Val
210 215 220

Ser Arg Gln Val Ser Ala Ile Thr Pro Pro Gln Ala Met Gly Pro Asn
225 230 235 240

Leu Val Leu Pro Asp Gln Lys Pro Pro Ser Arg Gln Ser Gln Thr Gly
245 250 255

Ser Lys Val Ala Thr Gln Arg Leu Gln Thr Thr Glu Ser Ala Pro Arg
260 265 270

Ser Val Ala Pro Thr Thr Val Gly Pro Lys Arg Ile Gly Thr Gly Asp
275 280 285

Arg Leu Ile Asn Leu Val Gln Gly Thr Tyr Leu Ala Leu Asn Ala Thr
290 295 300

Asp Pro Asn Lys Thr Lys Asp Cys Trp Leu Cys Leu Val Ser Arg Pro
305 310 315 320

Pro Tyr Tyr Glu Gly Ile Ala Ile Leu Gly Asn Tyr Ser Asn Gln Thr
325 330 335

Asn Pro Pro Pro Ser Cys Leu Ser Thr Pro Gln His Lys Leu Thr Ile
340 345 350

Ser Glu Val Ser Gly Gln Gly Leu Cys Ile Gly Thr Val Pro Lys Thr
355 360 365

His Gln Ala Leu Cys Asn Glu Thr Gln Gln Gly His Thr Gly Ala His
370 375 380

Tyr Leu Ala Ala Pro Asn Gly Ala Tyr Trp Ala Cys Asn Thr Gly Leu
385 390 395 400

Thr Pro Cys Ile Ser Met Ala Val Leu Asn Trp Thr Ser Asp Phe Cys
405 410 415

Val Leu Ile Glu Leu Trp Pro Arg Val Thr Tyr His Gln Pro Glu Tyr
420 425 430

Val Tyr Thr His Phe Ala Lys Ala Val Arg Phe Arg Arg Glu Pro Ile
435 440 445

Ser Leu Thr Val Ala Leu Met Leu Gly Gly Leu Thr Val Gly Gly Ile
450 455 460

Ala Ala Gly Val Gly Thr Gly Thr Lys Ala Leu Leu Glu Thr Ala Gln
465 470 475 480

Phe Arg Gln Leu Gln Met Ala Met His Thr Asp Ile Gln Ala Leu Glu
485 490 495

Glu Ser Ile Ser Ala Leu Glu Lys Ser Leu Thr Ser Leu Ser Glu Val
500 505 510

Val Leu Gln Asn Arg Arg Gly Leu Asp Ile Leu Phe Leu Gln Glu Gly
515 520 525

Gly Leu Cys Ala Ala Leu Lys Glu Glu Cys Cys Phe Tyr Ala Asp His
530 535 540

Thr Gly Leu Val Arg Asp Asn Met Ala Lys Leu Arg Glu Arg Leu Lys
545 550 555 560

Gln Arg Gln Gln Leu Phe Asp Ser Gln Gln Gly Trp Phe Glu Gly Trp
565 570 575

Phe Asn Lys Ser Pro Trp Phe Thr Thr Leu Ile Ser Ser Ile Met Gly
580 585 590

Pro Leu Leu Ile Leu Leu Leu Ile Leu Leu Phe Gly Pro Cys Ile Leu
595 600 605

Asn Arg Leu Val Gln Phe Val Lys Asp Arg Ile Ser Val Val Gln Ala
610 615 620

Leu Ile Leu Thr Gln Gln Tyr Gln Gln Ile Lys Gln Tyr Asp Pro Asp
625 630 635 640

Arg Pro

<210> SEQ ID NO 32
<211> LENGTH: 642
<212> TYPE: PRT
<213> ORGANISM: artificial sequence
<220> FEATURE:
<223> OTHER INFORMATION: ENV protein (AAA43051)

<400> SEQUENCE: 32

Met Glu Ser Pro Thr His Pro Lys Pro Ser Lys Asp Lys Thr Leu Ser
1 5 10 15

Trp Asn Leu Val Phe Leu Val Gly Ile Leu Phe Thr Ile Asp Ile Gly
20 25 30

-continued

```
Met Ala Asn Pro Ser Pro His Gln Ile Tyr Asn Val Thr Trp Val Ile
        35                  40                  45

Thr Asn Val Gln Thr Asn Thr Gln Ala Asn Ala Thr Ser Met Leu Gly
    50                  55                  60

Thr Leu Thr Asp Ala Tyr Pro Thr Leu His Val Asp Leu Cys Asp Leu
65                  70                  75                  80

Val Gly Asn Thr Trp Glu Pro Ile Val Leu Asp Pro Thr Asn Val Lys
                85                  90                  95

His Gly Ala Arg Tyr Ser Ser Ser Lys Tyr Gly Cys Lys Thr Thr Asp
            100                 105                 110

Arg Lys Lys Gln Gln Gln Thr Tyr Pro Phe Tyr Val Cys Pro Gly His
        115                 120                 125

Ala Pro Ser Leu Gly Pro Lys Gly Thr His Cys Gly Gly Ala Gln Asp
    130                 135                 140

Gly Phe Cys Ala Ala Trp Gly Cys Glu Thr Thr Gly Glu Ala Trp Trp
145                 150                 155                 160

Lys Pro Ser Ser Ser Trp Asp Tyr Ile Thr Val Lys Arg Gly Ser Ser
                165                 170                 175

Gln Asp Asn Ser Cys Glu Gly Lys Cys Asn Pro Leu Ile Leu Gln Phe
            180                 185                 190

Thr Gln Lys Gly Arg Gln Ala Ser Trp Asp Gly Pro Lys Met Trp Gly
        195                 200                 205

Leu Arg Leu Tyr Arg Thr Gly Tyr Asp Pro Ile Ala Leu Phe Thr Val
    210                 215                 220

Ser Arg Gln Val Ser Thr Ile Thr Pro Pro Gln Ala Met Gly Pro Asn
225                 230                 235                 240

Leu Val Leu Pro Asp Gln Lys Pro Pro Ser Arg Gln Ser Gln Thr Gly
                245                 250                 255

Ser Lys Val Ala Thr Gln Arg Leu Gln Thr Asn Glu Ser Ala Ser Arg
            260                 265                 270

Ser Val Ala Pro Thr Thr Val Val Pro Lys Arg Ile Gly Thr Gly Asp
        275                 280                 285

Arg Leu Ile Asn Leu Val Gln Gly Thr Tyr Leu Ala Leu Asn Ala Thr
    290                 295                 300

Asp Pro Asn Lys Thr Lys Asp Cys Trp Leu Cys Leu Val Ser Arg Pro
305                 310                 315                 320

Pro Tyr Tyr Glu Gly Ile Ala Ile Leu Gly Asn Tyr Ser Asn Gln Thr
                325                 330                 335

Asn Pro Pro Pro Ser Cys Leu Ser Thr Pro Gln His Lys Leu Thr Ile
            340                 345                 350

Ser Glu Val Ser Gly Gln Gly Leu Cys Ile Gly Thr Val Pro Lys Thr
        355                 360                 365

His Gln Ala Leu Cys Asn Glu Thr Gln Gln Gly His Thr Gly Ala His
    370                 375                 380

Tyr Leu Ala Ala Pro Asn Gly Thr Tyr Trp Ala Cys Asn Thr Gly Leu
385                 390                 395                 400

Thr Pro Cys Ile Ser Met Ala Val Leu Asn Trp Thr Ser Asp Phe Cys
                405                 410                 415

Val Leu Ile Glu Leu Trp Pro Arg Val Thr Tyr His Gln Pro Glu Tyr
            420                 425                 430

Val Tyr Thr His Phe Ala Lys Ala Val Arg Phe Arg Arg Glu Pro Ile
        435                 440                 445

Ser Leu Thr Val Ala Leu Met Leu Gly Gly Leu Thr Val Gly Gly Ile
```

```
    450                 455                 460

Ala Ala Gly Val Gly Thr Gly Thr Lys Ala Leu Leu Glu Thr Ala Gln
465                 470                 475                 480

Phe Arg Gln Leu Gln Met Ala Met His Thr Asp Ile Gln Ala Leu Glu
                485                 490                 495

Glu Ser Ile Ser Ala Leu Glu Lys Ser Leu Thr Ser Leu Ser Glu Val
            500                 505                 510

Val Leu Gln Asn Arg Arg Gly Leu Asp Ile Leu Phe Leu Gln Glu Gly
        515                 520                 525

Gly Leu Cys Ala Ala Leu Lys Glu Glu Cys Cys Phe Tyr Ala Asp His
    530                 535                 540

Thr Gly Leu Val Arg Asp Asn Met Ala Lys Leu Arg Glu Arg Leu Lys
545                 550                 555                 560

Gln Arg Gln Gln Leu Phe Asp Ser Gln Gln Gly Trp Phe Glu Gly Trp
                565                 570                 575

Phe Asn Lys Ser Pro Trp Phe Thr Thr Leu Ile Ser Ser Ile Met Gly
            580                 585                 590

Pro Leu Leu Ile Leu Leu Leu Ile Leu Leu Phe Gly Pro Cys Ile Leu
        595                 600                 605

Asn Arg Leu Val Gln Phe Val Lys Asp Arg Ile Ser Val Val Gln Ala
    610                 615                 620

Leu Ile Leu Thr Gln Gln Tyr Gln Gln Ile Lys Gln Tyr Asp Pro Asp
625                 630                 635                 640

Arg Pro

<210> SEQ ID NO 33
<211> LENGTH: 642
<212> TYPE: PRT
<213> ORGANISM: artificial sequence
<220> FEATURE:
<223> OTHER INFORMATION: ENV protein (AAA93093)

<400> SEQUENCE: 33

Met Glu Ser Pro Thr His Pro Lys Pro Ser Lys Asp Lys Thr Leu Ser
1               5                   10                  15

Trp Asn Leu Val Phe Leu Val Gly Ile Leu Phe Thr Ile Asp Ile Gly
            20                  25                  30

Met Ala Asn Pro Ser Pro His Gln Ile Tyr Asn Val Thr Trp Val Ile
        35                  40                  45

Thr Asn Val Gln Thr Asn Thr Gln Ala Asn Ala Thr Ser Met Leu Gly
    50                  55                  60

Thr Leu Thr Asp Val Tyr Pro Thr Leu His Val Asp Leu Cys Asp Leu
65                  70                  75                  80

Val Gly Asp Thr Trp Glu Pro Ile Val Leu Ser Pro Thr Asn Val Lys
                85                  90                  95

His Gly Ala Arg Tyr Pro Ser Ser Lys Tyr Gly Cys Lys Thr Thr Asp
            100                 105                 110

Arg Lys Lys Gln Gln Gln Thr Tyr Pro Phe Tyr Val Cys Pro Gly His
        115                 120                 125

Ala Pro Ser Leu Gly Pro Lys Gly Thr His Cys Gly Gly Ala Gln Asp
    130                 135                 140

Gly Phe Cys Ala Ala Trp Gly Cys Glu Thr Thr Gly Glu Ala Trp Trp
145                 150                 155                 160

Lys Pro Ser Ser Ser Trp Asp Tyr Ile Thr Val Lys Arg Gly Ser Ser
                165                 170                 175
```

```
Gln Asp Asn Asn Cys Glu Gly Lys Cys Asn Pro Leu Ile Leu Gln Phe
            180                 185                 190

Thr Gln Lys Gly Lys Gln Ala Ser Trp Asp Gly Pro Lys Met Trp Gly
        195                 200                 205

Leu Arg Leu Tyr Arg Thr Gly Tyr Asp Pro Ile Ala Leu Phe Thr Val
    210                 215                 220

Ser Arg Gln Val Ser Thr Ile Thr Pro Pro Gln Ala Met Gly Pro Asn
225                 230                 235                 240

Leu Val Leu Pro Asp Gln Lys Pro Pro Ser Arg Gln Ser Gln Thr Gly
                245                 250                 255

Ser Lys Val Ala Thr Gln Arg Pro Gln Thr Asn Glu Ser Ala Pro Arg
            260                 265                 270

Ser Val Ala Pro Thr Thr Val Gly Pro Lys Arg Ile Gly Thr Gly Asp
        275                 280                 285

Arg Leu Ile Asn Leu Val Gln Gly Thr Tyr Leu Ala Leu Asn Ala Thr
    290                 295                 300

Asp Pro Asn Lys Thr Lys Asp Cys Trp Leu Cys Leu Val Ser Arg Pro
305                 310                 315                 320

Pro Tyr Tyr Glu Gly Ile Ala Ile Leu Gly Asn Tyr Ser Asn Gln Thr
                325                 330                 335

Asn Pro Pro Pro Ser Cys Leu Ser Ile Pro Gln His Lys Leu Thr Ile
            340                 345                 350

Ser Glu Val Ser Gly Gln Gly Leu Cys Ile Gly Thr Val Pro Lys Thr
        355                 360                 365

His Gln Ala Leu Cys Asn Lys Thr Gln Gln Gly His Thr Gly Ala His
    370                 375                 380

Tyr Leu Ala Ala Pro Asn Gly Thr Tyr Trp Ala Cys Asn Thr Gly Leu
385                 390                 395                 400

Thr Pro Cys Ile Ser Met Ala Val Leu Asn Trp Thr Ser Asp Phe Cys
                405                 410                 415

Val Leu Ile Glu Leu Trp Pro Arg Val Thr Tyr His Gln Pro Glu Tyr
            420                 425                 430

Val Tyr Thr His Phe Ala Lys Ala Val Arg Phe Arg Arg Glu Pro Ile
        435                 440                 445

Ser Leu Thr Val Ala Leu Met Leu Gly Gly Leu Thr Val Gly Gly Ile
    450                 455                 460

Ala Ala Gly Val Gly Thr Gly Thr Lys Ala Leu Leu Glu Thr Ala Gln
465                 470                 475                 480

Phe Arg Gln Leu Gln Met Ala Met His Thr Asp Ile Gln Ala Leu Glu
                485                 490                 495

Glu Ser Ile Ser Ala Leu Glu Lys Ser Leu Thr Ser Leu Ser Glu Val
            500                 505                 510

Val Leu Gln Asn Arg Arg Gly Leu Asp Ile Leu Phe Leu Gln Glu Gly
        515                 520                 525

Gly Leu Cys Ala Ala Leu Lys Glu Glu Cys Cys Phe Tyr Ala Asp His
    530                 535                 540

Thr Gly Leu Val Arg Asp Asn Met Ala Lys Leu Arg Glu Arg Leu Lys
545                 550                 555                 560

Gln Arg Gln Gln Leu Phe Asp Ser Gln Gln Gly Trp Phe Glu Gly Trp
                565                 570                 575

Phe Asn Arg Ser Pro Trp Phe Thr Thr Leu Ile Ser Ser Ile Met Gly
            580                 585                 590
```

```
Pro Leu Leu Ile Leu Leu Leu Ile Leu Leu Phe Gly Pro Cys Ile Leu
        595                 600                 605

Asn Arg Leu Val Gln Phe Val Lys Asp Arg Ile Ser Val Val Gln Ala
    610                 615                 620

Leu Ile Leu Thr Gln Gln Tyr Gln Gln Ile Lys Gln Tyr Asp Pro Asp
625                 630                 635                 640

Arg Pro

<210> SEQ ID NO 34
<211> LENGTH: 642
<212> TYPE: PRT
<213> ORGANISM: artificial sequence
<220> FEATURE:
<223> OTHER INFORMATION: ENV protein (AAA43050)

<400> SEQUENCE: 34

Met Glu Ser Pro Thr His Pro Lys Pro Ser Lys Asp Lys Thr Leu Ser
1               5                   10                  15

Trp Asn Leu Val Phe Leu Val Gly Ile Leu Phe Thr Ile Asp Ile Gly
            20                  25                  30

Met Ala Asn Pro Ser Pro Pro Gln Met Tyr Asn Val Thr Trp Val Ile
        35                  40                  45

Thr Asn Val Gln Thr Asn Thr Gln Ala Asn Ala Thr Ser Met Leu Gly
    50                  55                  60

Thr Leu Thr Asp Val Tyr Pro Thr Leu His Val Asp Leu Cys Asp Leu
65                  70                  75                  80

Val Gly Asp Thr Trp Glu Pro Met Val Leu Ser Pro Thr Gly Tyr Pro
                85                  90                  95

Pro Ser Lys Tyr Gly Cys Lys Thr Thr Asp Arg Lys Lys Gln Gln Gln
            100                 105                 110

Thr Tyr Pro Phe Tyr Val Cys Pro Gly His Arg Pro Ser Leu Gly Pro
        115                 120                 125

Lys Gly Thr His Cys Gly Gly Ala Gln Asp Gly Phe Cys Ala Ala Trp
    130                 135                 140

Gly Cys Glu Thr Thr Gly Glu Ala Trp Trp Lys Pro Ser Ser Ser Trp
145                 150                 155                 160

Asp Tyr Ile Thr Val Lys Arg Gly Ser Ser Gln Asn Asn Asn Cys Glu
                165                 170                 175

Gly Lys Cys Asn Pro Leu Ile Leu Gln Phe Thr Gln Lys Gly Lys Gln
            180                 185                 190

Ala Ser Trp Asp Gly Pro Lys Met Trp Gly Leu Arg Leu Tyr Arg Thr
        195                 200                 205

Gly Tyr Asp Pro Ile Ala Leu Phe Thr Val Ser Arg Arg Val Ser Thr
    210                 215                 220

Ile Thr Pro Pro Gln Ala Met Gly Pro Asp Leu Val Leu Pro Asp Gln
225                 230                 235                 240

Lys Pro Pro Ser Arg Gln Ser Gln Thr Gly Ser Lys Val Ala Thr Gln
                245                 250                 255

Arg Pro Gln Thr Asn Glu Ser Ala Pro Arg Ser Val Ala Pro Thr Thr
            260                 265                 270

Val Gly Pro Lys Arg Ile Gly Thr Gly Asp Arg Leu Ile Asn Leu Val
        275                 280                 285

Gln Gly Ala Tyr Leu Ala Leu Asn Ala Thr Asp Pro Asn Lys Thr Lys
    290                 295                 300

Asp Cys Trp Leu Cys Leu Val Ser Arg Pro Pro Tyr Tyr Glu Gly Ile
```

```
305                 310                 315                 320

Ala Ile Leu Gly Asn Tyr Ser Asn Gln Thr Asn Pro Pro Pro Ser Cys
                325                 330                 335

Leu Ser Ile Pro Pro His Lys Leu Thr Ile Ser Lys Val Ser Gly Gln
            340                 345                 350

Gly Leu Cys Ile Gly Thr Val Pro Lys Thr His Gln Ala Leu Cys Asn
        355                 360                 365

Lys Thr His Gln Gly His Thr Gly Ala Asp Tyr Arg Ala Ala Pro Arg
    370                 375                 380

Tyr Leu Ala Ala Pro Asn Gly Thr Tyr Trp Ala Cys Asn Thr Gly Leu
385                 390                 395                 400

Thr Pro Cys Ile Ser Met Ala Val Leu Asn Leu Thr Ser Asp Phe Cys
                405                 410                 415

Val Leu Ile Glu Leu Trp Pro Arg Val Thr Tyr His Gln Pro Glu Tyr
            420                 425                 430

Val Tyr Thr His Phe Ala Lys Ala Gly Arg Phe Arg Arg Glu Pro Ile
        435                 440                 445

Ser Leu Thr Val Ala Leu Met Leu Gly Gly Leu Thr Val Gly Gly Ile
    450                 455                 460

Ala Ala Gly Val Gly Thr Gly Thr Lys Ala Leu Leu Glu Thr Ala Gln
465                 470                 475                 480

Phe Arg Gln Leu Gln Met Ala Met His Thr Asp Ile Gln Ala Leu Glu
                485                 490                 495

Glu Ser Ile Ser Ala Leu Glu Lys Ser Leu Thr Ser Leu Ser Glu Val
            500                 505                 510

Val Leu Gln Asn Arg Arg Gly Leu Asp Ile Leu Phe Leu Gln Glu Gly
        515                 520                 525

Gly Leu Cys Ala Ala Leu Lys Glu Glu Cys Cys Phe Tyr Ala Asp His
    530                 535                 540

Thr Gly Leu Val Arg Asp Asn Met Ala Lys Leu Arg Glu Arg Leu Lys
545                 550                 555                 560

Gln Arg Gln Gln Leu Phe Asp Ser Gln Gln Gly Trp Phe Glu Gly Trp
                565                 570                 575

Phe Asn Arg Ser Pro Trp Phe Thr Thr Leu Ile Ser Ser Ile Met Gly
            580                 585                 590

Pro Leu Leu Ile Leu Leu Leu Ile Leu Leu Phe Gly Pro Tyr Ile Leu
        595                 600                 605

Asn Arg Leu Val Gln Phe Val Lys Asp Arg Ile Ser Val Val Gln Ala
    610                 615                 620

Leu Ile Leu Thr Gln Gln Tyr Gln Gln Ile Lys Gln Tyr Asp Pro Asp
625                 630                 635                 640

Arg Pro
```

<210> SEQ ID NO 35
<211> LENGTH: 1929
<212> TYPE: DNA
<213> ORGANISM: artificial sequence
<220> FEATURE:
<223> OTHER INFORMATION: FeLV ENV DNA (M12500)

<400> SEQUENCE: 35

```
atggaaagtc caacgcaccc aaaaccctct aaagataaga ctctctcgtg gaacttagcg     60
tttctggtgg ggatcttatt tacaatagac ataggaatgg ccaatcctag tccacaccaa    120
atatataatg taacttgggt aataaccaat gtacaaacta acacccaagc taacgccacc    180
```
tctatgttag gaaccttaac cgatgcctac cctaccctac atgttgactt atgtgaccta 240
gtgggagaca cctgggaacc tatagtccta aacccaacca atgtaaaaca cggggcacgt 300
tactcctcct caaaatatgg atgtaaaact acagatagaa aaaaacagca acagacatac 360
cccttttacg tctgccccgg acatgccccc tcgttggggc caaagggaac acattgtgga 420
ggggcacaag atgggttttg tgccgcatgg ggatgtgaga ccaccggaga agcttggtgg 480
aagcccacct cctcatggga ctatatcaca gtaaaaagag ggagtagtca ggacaatagc 540
tgtgagggaa aatgcaaccc cctggttttg cagttcaccc agaagggaag acaagcctct 600
tgggacggac ctaagatgtg ggggattgcga ctataccgta caggatatga ccctatcgct 660
ttattcacgg tgtcccggca ggtatcaacc attacgccgc ctcaggcaat gggaccaaac 720
ctagtcttac ctgatcaaaa acccccatcc cgacaatctc aaacagggtc caaagtggcg 780
acccagaggc cccaaacgaa tgaaagcgcc ccaaggtctg ttgcccccac caccatgggt 840
cccaaacgga ttgggaccgg agataggtta ataaatttag tacaagggac atacctagcc 900
ttaaatgcca ccgaccccaa caaaactaaa gactgttggc tctgcctggt ttctcgacca 960
ccctattacg aagggattgc aatcttaggt aactacagca accaaacaaa cccccccca 1020 tcctgcctat ctactccgca acacaaacta actatatctg aagtatcagg gcaaggaatg 1080
tgcataggga ctgttcctaa aacccaccag gctttgtgca ataagacaca acagggacat 1140
acaggggcgc actatctagc cgcccccaac ggcacctatt gggcctgtaa cactggactc 1200
accccatgca tttccatggc ggtgctcaat tggacctctg atttttgtgt cttaatcgaa 1260
ttatggccca gagtgactta ccatcaaccc gaatatgtgt acacacattt tgccaaagct 1320
gtcaggttcc gaagagaacc aatatcacta acggttgccc ttatgttggg aggacttact 1380
gtagggggca tagccgcggg ggtcggaaca gggactaaag ccctccttga aacagcccag 1440
ttcagacaac tacaaatggc catgcacaca gacatccagg ccctagaaga atcaattagt 1500
gccttagaaa agtccctgac ctccctttct gaagtagtct tacaaaacag acggggccta 1560
gatattctat tcttacaaga gggagggctc tgtgccgcat tgaaagaaga atgttgcttc 1620
tatgcggatc acaccggact cgtccgagac aatatggcca aattaagaga aagactaaaa 1680
cagcggcaac aactgtttga ctcccaacag ggatggtttg aaggatggtt caacaagtcc 1740
ccctggttta caaccctaat ttcctccatt atgggcccct tactaatcct actcctaatt 1800
ctcctcttcg gcccatgcat ccttaaccga ttagtacaat tcgtaaaaga cagaatatct 1860
gtggtacagg ctttaatttt aacccaacag taccaacaga taaagcaata cgatccggac 1920
cgaccatga 1929

<210> SEQ ID NO 36
<211> LENGTH: 4111
<212> TYPE: DNA
<213> ORGANISM: artificial sequence
<220> FEATURE:
<223> OTHER INFORMATION: plasmid pCXL208.2

<400> SEQUENCE: 36
ggctgcaggt attctaaact aggaatagat gaaattatgt gcaaaggaga tacctttaga 60
tatggatctg atttatttgg tttttcataa tcataatcta acaacatttt cactatacta 120
taccttcttg cacaagtcgc cattagtagt atagacttat actttgtaac catagtatac 180
tttagcgcgt catcttcttc atctaaaaca gatttacaac aataatcatc gtcgtcatct 240

-continued

```
tcatcttcat taaagttttc atattcaata actttctttt ctaaaacatc atctgaatca    300
ataaacatag aacggtatag agcgttaatc tccattgtaa aatatactaa cgcgttgctc    360
atgatgtact ttttttcatt atttagaaat tatgcatttt agatctttat aagcggccgt    420
gattaactag tcataaaaac ccgggatcga ttctagactc gagcggggat ctctttattc    480
tatacttaaa aagtgaaaat aaatacaaag gttcttgagg gttgtgttaa attgaaagcg    540
agaaataatc ataaattatt tcattatcgc gatatccgtt aagtttgtat cgtaatggaa    600
agtccaacgc acccaaaacc ctctaaagat aagactctct cgtggaactt agcgtttctg    660
gtggggatct tatttacaat agacatagga atggccaatc ctagtccaca ccaaatatat    720
aatgtaactt gggtaataac caatgtacaa actaacaccc aagctaacgc cacctctatg    780
ttaggaacct taaccgatgc ctaccctacc ctacatgttg acttatgtga cctagtggga    840
gacacctggg aacctatagt cctaaaccca accaatgtaa aacacggggc acgttactcc    900
tcctcaaaat atggatgtaa aactacagat agaaaaaaac agcaacagac ataccccttt    960
tacgtctgcc ccggacatgc cccctcgttg gggccaaagg gaacacattg tggaggggca   1020
caagatgggt tttgtgccgc atggggatgt gagaccaccg gagaagcttg gtggaagccc   1080
acctcctcat gggactatat cacagtaaaa agagggagta gtcaggacaa tagctgtgag   1140
ggaaaatgca acccctggt tttgcagttc acccagaagg gaagacaagc ctcttgggac   1200
ggacctaaga tgtggggatt gcgactatac cgtacaggat atgaccctat cgctttattc   1260
acggtgtccc ggcaggtatc aaccattacg ccgcctcagg caatgggacc aaacctagtc   1320
ttacctgatc aaaaaccccc atcccgacaa tctcaaacag ggtccaaagt ggcgacccag   1380
aggccccaaa cgaatgaaag cgccccaagg tctgttgccc ccaccaccat gggtcccaaa   1440
cggattggga ccggagatag gttaataaat ttagtacaag ggacatacct agccttaaat   1500
gccaccgacc ccaacaaaac taaagactgt tggctctgcc tggtttctcg accaccctat   1560
tacgaaggga ttgcaatctt aggtaactac agcaaccaaa caaacccccc cccatcctgc   1620
ctatctactc cgcaacacaa actaactata tctgaagtat cagggcaagg aatgtgcata   1680
gggactgttc ctaaaaccca ccaggctttg tgcaataaga cacaacaggg acatacaggg   1740
gcgcactatc tagccgcccc caacggcacc tattgggcct gtaacactgg actcacccca   1800
tgcatttcca tggcggtgct caattggacc tctgaattct gtgtcttaat cgaattatgg   1860
cccagagtga cttaccatca acccgaatat gtgtacacac attttgccaa agctgtcagg   1920
ttccgaagag aaccaatatc actaacggtt gcccttatgt tgggaggact tactgtaggg   1980
ggcatagccg cgggggtcgg aacagggact aaagccctcc ttgaaacagc ccagtttaga   2040
caactacaaa tggccatgca cacagacatc caggccctag aagaatcaat tagtgcctta   2100
gaaaagtccc tgacctccct ttctgaagta gtcttacaaa acagacgggg cctagatatt   2160
ctattcttac aagagggagg gctctgtgcc gcattgaaag aagaatgttg cttctatgcg   2220
gatcacaccg gactcgtccg agacaatatg gccaaattaa gagaaagact aaaacagcgg   2280
caacaattgt ttgactccca acagggatgg tttgaaggat ggttcaacaa gtcccccctgg   2340
tttacaaccc taatttcctc cattatgggc cccttactaa tcctactcct aattctcctc   2400
ttcggcccat gcatccttaa ccgattagta caattcgtaa aagacagaat atctgtggta   2460
caggctttaa ttttaaccca acagtaccaa cagataaagc aatacgatcc ggaccgacca   2520
tgatttttct ggatcctttt tatagctaat tagtcacgta cctttgagag taccacttca   2580
gctacctctt ttgtgtctca gagtaacttt ctttaatcaa ttccaaaaca gtatatgatt   2640
```

-continued ttccatttct ttcaaagatg tagtttacat ctgctccttt gttgaaaagt agcctgagca 2700
cttcttttct accatgaatt acagctggca agatcaattt ttcccagttc tggacatttt 2760 attttttta agtagtgtgc tacatatttc aatatttcca gattgtacag cgatcattaa 2820
aggagtacgt cccatgttat ccagcaagtc agtatcagca cctttgttca atagaagttt 2880
aaccattgtt aaatttttat ttgatacggc tatatgtaga ggagttaacc gatccgtgtt 2940
tgaaatatct acatccgccg aatgagccaa tagaagttta accaaattaa ctttgttaag 3000
gtaagctgcc aaacacaaag gagtaaagcc tccgctgtaa agaacattgt ttacatagtt 3060
attcttcaac agatctttca ctattttgta gtcgtctctc aacaccgcat catgcagaca 3120
agaagttgtg cattcagtaa ctacaggttt agctccatac ctcatcaaga tttttatagc 3180
ctcggtattc ttgaacatta cagccatttc aagaggagat tgtagagtac catattccgt 3240
gttagggtcg aatccattgt ccaaaaacct atttagagat gcattgtcat tatccatgat 3300
agcctcacag acgtatatgt aagccatctt gaatgtataa ttttgttgtt ttcaacaacc 3360
gctcgtgaac agcttctata ctttttcatt ttcttcatga ttaatatagt ttacggaata 3420
taagtataca aaaagtttat agtaatctca taatatctga aacacataca taaaacatgg 3480
aagaattaca cgatgtcgtt gagataaatg gctttttatt gtcatagttt acaaattcgc 3540
agtaatcttc atcttttacg aatattgcag aatctgtttt atccaaccag tgatttttgt 3600
ataatataac tggtatccta tcttccgata gaatgctgtt atttaacatt tttgcaccta 3660
ttaagttaca tctgtcaaat ccatctttcc aactgacttt atgtaacgat gcgaaatagc 3720
atttatcact atgtcgtacc caattatcat gacaagattc tcttaaatac gtaatcttat 3780
tatctcttgc atattcgtaa tagtaattgt aaagagtata cgataacagt atagatatac 3840
acgtgatata aatatttaac cccattcctg agtaaaataa ttacgatatt acatttcctt 3900
ttattatttt tatgttttag ttatttgtta ggttatacaa aaattatgtt tatttgtgta 3960
tatttaaagc gtcgttaaga ataagcttag ttaacatatt atcgcttagg ttttgtagta 4020
tttgaatcct ttctttaaat ggattatttt tccaatgcat atttatagct tcatccaaag 4080
tataacattt aacattcaga attgcggccg c 4111

<210> SEQ ID NO 37
<211> LENGTH: 6756
<212> TYPE: DNA
<213> ORGANISM: artificial sequence
<220> FEATURE:
<223> OTHER INFORMATION: plasmid pPB713

<400> SEQUENCE: 37
tcttccgctt cctcgctcac tgactcgctg cgctcggtcg ttcggctgcg gcgagcggta 60
tcagctcact caaaggcggt aatacggtta tccacagaat caggggataa cgcaggaaag 120
aacatgtgag caaaaggcca gcaaaaggcc aggaaccgta aaaaggccgc gttgctggcg 180
tttttccata ggctccgccc ccctgacgag catcacaaaa atcgacgctc aagtcagagg 240
tggcgaaacc cgacaggact ataaagatac caggcgtttc cccctggaag ctccctcgtg 300
cgctctcctg ttccgaccct gccgcttacc ggatacctgt ccgcctttct cccttcggga 360
agcgtggcgc tttctcatag ctcacgctgt aggtatctca gttcggtgta ggtcgttcgc 420
tccaagctgg gctgtgtgca cgaacccccc gttcagcccg accgctgcgc cttatccggt 480
aactatcgtc ttgagtccaa cccggtaaga cacgacttat cgccactggc agcagccact 540

-continued

```
ggtaacagga ttagcagagc gaggtatgta ggcggtgcta cagagttctt gaagtggtgg    600
cctaactacg gctacactag aaggacagta tttggtatct gcgctctgct gaagccagtt    660
accttcggaa aaagagttgg tagctcttga tccggcaaac aaaccaccgc tggtagcggt    720
ggtttttttg tttgcaagca gcagattacg cgcagaaaaa aaggatctca agaagatcct    780
ttgatctttt ctacggggtc tgacgctcag tggaacgaaa actcacgtta agggattttg    840
gtcatgagat tatcaaaaag gatcttcacc tagatccttt taaattaaaa atgaagtttt    900
aaatcaatct aaagtatata tgagtaaact tggtctgaca gttaccaatg cttaatcagt    960
gaggcaccta tctcagcgat ctgtctattt cgttcatcca tagttgcctg actccccgtc   1020
gtgtagataa ctacgatacg ggagggctta ccatctggcc ccagtgctgc aatgataccg   1080
cgagacccac gctcaccggc tccagattta tcagcaataa accagccagc cggaagggcc   1140
gagcgcagaa gtggtcctgc aactttatcc gcctccatcc agtctattaa ttgttgccgg   1200
gaagctagag taagtagttc gccagttaat agtttgcgca acgttgttgc cattgctaca   1260
ggcatcgtgg tgtcacgctc gtcgtttggt atggcttcat tcagctccgg ttcccaacga   1320
tcaaggcgag ttacatgatc ccccatgttg tgcaaaaaag cggttagctc cttcggtcct   1380
ccgatcgttg tcagaagtaa gttggccgca gtgttatcac tcatggttat ggcagcactg   1440
cataattctc ttactgtcat gccatccgta agatgctttt ctgtgactgg tgagtactca   1500
accaagtcat tctgagaata gtgtatgcgg cgaccgagtt gctcttgccc ggcgtcaata   1560
cgggataata ccgcgccaca tagcagaact ttaaaagtgc tcatcattgg aaaacgttct   1620
tcggggcgaa aactctcaag gatcttaccg ctgttgagat ccagttcgat gtaacccact   1680
cgtgcaccca actgatcttc agcatctttt actttcacca gcgtttctgg gtgagcaaaa   1740
acaggaaggc aaaatgccgc aaaaaaggga ataagggcga cacggaaatg ttgaatactc   1800
atactcttcc tttttcaata ttattgaagc atttatcagg gttattgtct catgagcgga   1860
tacatatttg aatgtattta gaaaaataaa caaatagggg ttccgcgcac atttccccga   1920
aaagtgccac ctgacgtcta agaaaccatt attatcatga cattaaccta taaaaatagg   1980
cgtatcacga ggccctttcg tctcgcgcgt ttcggtgatg acggtgaaaa cctctgacac   2040
atgcagctcc cggagacggt cacagcttgt ctgtaagcgg atgccgggag cagacaagcc   2100
cgtcagggcg cgtcagcggg tgttggcggg tgtcggggct ggcttaacta tgcggcatca   2160
gagcagattg tactgagagt gcaccatatg cggtgtgaaa taccgcacag atgcgtaagg   2220
agaaaatacc gcatcaggcg ccattcgcca ttcaggctgc gcaactgttg ggaagggcga   2280
tcggtgcggg cctcttcgct attacgccag ctggcgaaag ggggatgtgc tgcaaggcga   2340
ttaagttggg taacgccagg gttttcccag tcacgacgtt gtaaaacgac ggccagtgcc   2400
aagcttggct gcaggtattc taaactagga atagatgaaa ttatgtgcaa aggagatacc   2460
tttagatatg gatctgattt atttggtttt tcataatcat aatctaacaa cattttcact   2520
atactatacc ttcttgcaca agtcgccatt agtagtatag acttatactt tgtaaccata   2580
gtatacttta gcgcgtcatc ttcttcatct aaaacagatt tacaacaata atcatcgtcg   2640
tcatcttcat cttcattaaa gttttcatat tcaataactt tcttttctaa aacatcatct   2700
gaatcaataa acatagaacg gtatagagcg ttaatctcca ttgtaaaata tactaacgcg   2760
ttgctcatga tgtacttttt ttcattattt agaaattatg cattttagat ctttataagc   2820
ggccgtgatt aactagtcat aaaaacccgg gatcgattct agactcgagc ggggatctct   2880
ttattctata cttaaaaagt gaaaataaat acaaaggttc ttgagggttg tgttaaattg   2940
```

-continued

```
aaagcgagaa ataatcataa attatttcat tatcgcgata tccgttaagt ttgtatcgta   3000
atggaaagtc caacgcaccc aaaaccctct aaagataaga ctctctcgtg gaacttagcg   3060
tttctggtgg ggatcttatt tacaatagac ataggaatgg ccaatcctag tccacaccaa   3120
atatataatg taacttgggt aataaccaat gtacaaacta acacccaagc taacgccacc   3180
tctatgttag gaaccttaac cgatgcctac cctaccctac atgttgactt atgtgaccta   3240
gtgggagaca cctgggaacc tatagtccta aacccaacca atgtaaaaca cggggcacgt   3300
tactcctcct caaaatatgg atgtaaaact acagatagaa aaaaacagca acagacatac   3360
ccccttttacg tctgccccgg acatgccccc tcgttggggc caaagggaac acattgtgga   3420
ggggcacaag atgggttttg tgccgcatgg ggatgtgaga ccaccggaga agcttggtgg   3480
aagcccacct cctcatggga ctatatcaca gtaaaaagag ggagtagtca ggacaatagc   3540
tgtgagggaa aatgcaaccc cctggttttg cagttcaccc agaagggaag acaagcctct   3600
tgggacggac ctaagatgtg ggattgcga ctataccgta caggatatga ccctatcgct   3660
ttattcacgg tgtcccggca ggtatcaacc attacgccgc ctcaggcaat gggaccaaac   3720
ctagtcttac ctgatcaaaa acccccatcc cgacaatctc aaacagggtc caaagtggcg   3780
acccagaggc cccaaacgaa tgaaagcgcc ccaaggtctg ttgccccccac caccatgggt   3840
cccaaacgga ttgggaccgg agataggtta ataaatttag tacaagggac atacctagcc   3900
ttaaatgcca ccgaccccaa caaaactaaa gactgttggc tctgcctggt ttctcgacca   3960
ccctattacg aagggattgc aatcttaggt aactacagca accaaacaaa cccccccca   4020
tcctgcctat ctactccgca acacaaacta actatatctg aagtatcagg gcaaggaatg   4080
tgcataggga ctgttcctaa aacccaccag gctttgtgca ataagacaca acagggacat   4140
acaggggcgc actatctagc cgcccccaac ggcacctatt gggcctgtaa cactggactc   4200
accccatgca tttccatggc ggtgctcaat tggacctctg aattctgtgt cttaatcgaa   4260
ttatggccca gagtgactta ccatcaaccc gaatatgtgt acacacattt tgccaaagct   4320
gtcaggttcc gaagagaacc aatatcacta acggttgccc ttatgttggg aggacttact   4380
gtagggggca tagccgcggg ggtcggaaca gggactaaag ccctccttga aacagcccag   4440
ttcagacaac tacaaatggc catgcacaca gacatccagg ccctagaaga atcaattagt   4500
gccttagaaa agtccctgac ctccctttct gaagtagtct tacaaaacag acggggccta   4560
gatattctat tcttacaacg ggagggctc tgcgcagcat taaaagaaga atgttgcttc   4620
tatgcggatc acaccggact cgtccgagac aatatggcca aattaagaga aagactaaaa   4680
cagcggcaac aactgtttga ctcccaacag ggatggtttg aaggatggtt caacaagtcc   4740
ccctggttta caaccctaat ttcctccatt atgggcccct tactaatcct actcctaatt   4800
ctcctcttcg gcccatgcat ccttaaccga ttagtacagt tcgtaaaaga cagaatatct   4860
gtggtacagg ctttaatttt aacccaacag taccaacaga taaagcaata cgatccggac   4920
cgaccatgat tttctggat cctttttata gctaattagt cacgtacctt tgagagtacc   4980
acttcagcta cctcttttgt gtctcagagt aactttcttt aatcaattcc aaaacagtat   5040
atgattttcc atttctttca aagatgtagt ttacatctgc tcctttgttg aaaagtagcc   5100
tgagcacttc ttttctacca tgaattacag ctggcaagat caatttttcc cagttctgga   5160
cattttattt tttttaagta gtgtgctaca tatttcaata tttccagatt gtacagcgat   5220
cattaaagga gtacgtccca tgttatccag caagtcagta tcagcacctt tgttcaatag   5280
```

-continued

```
aagtttaacc attgttaaat ttttatttga tacggctata tgtagaggag ttaaccgatc   5340
cgtgtttgaa atatctacat ccgccgaatg agccaataga agtttaacca aattaacttt   5400
gttaaggtaa gctgccaaac acaaaggagt aaagcctccg ctgtaaagaa cattgtttac   5460
atagttattc ttcaacagat ctttcactat tttgtagtcg tctctcaaca ccgcatcatg   5520
cagacaagaa gttgtgcatt cagtaactac aggtttagct ccatacctca tcaagatttt   5580
tatagcctcg gtattcttga acattacagc catttcaaga ggagattgta gagtaccata   5640
ttccgtgtta gggtcgaatc cattgtccaa aaacctattt agagatgcat tgtcattatc   5700
catgatagcc tcacagacgt atatgtaagc catcttgaat gtataatttt gttgttttca   5760
acaaccgctc gtgaacagct tctatacttt ttcattttct tcatgattaa tatagtttac   5820
ggaatataag tatacaaaaa gtttatagta atctcataat atctgaaaca catacataaa   5880
acatggaaga attacacgat gtcgttgaga taaatggctt tttattgtca tagtttacaa   5940
attcgcagta atcttcatct tttacgaata ttgcagaatc tgttttatcc aaccagtgat   6000
ttttgtataa tataactggt atcctatctt ccgatagaat gctgttattt aacatttttg   6060
cacctattaa gttacatctg tcaaatccat ctttccaact gactttatgt aacgatgcga   6120
aatagcattt atcactatgt cgtacccaat tatcatgaca agattctctt aaatacgtaa   6180
tcttattatc tcttgcatat tcgtaatagt aattgtaaag agtatacgat aacagtatag   6240
atatacacgt gatataaata tttaacccca ttcctgagta aaataattac gatattacat   6300
ttccttttat tatttttatg ttttagttat ttgttaggtt atacaaaaat tatgtttatt   6360
tgtgtatatt taaagcgtcg ttaagaataa gcttagttaa catattatcg cttaggtttt   6420
gtagtatttg aatcctttct ttaaatggat tatttttcca atgcatattt atagcttcat   6480
ccaaagtata acatttaaca ttcagaattg cggccgcaat tcaattcgta atcatggtca   6540
tagctgtttc ctgtgtgaaa ttgttatccg ctcacaattc cacacaacat acgagccgga   6600
agcataaagt gtaaagcctg gggtgcctaa tgagtgagct aactcacatt aattgcgttg   6660
cgctcactgc ccgctttcca gtcgggaaac ctgtcgtgcc agctgcatta atgaatcggc   6720
caacgcgcgg ggagaggcgg tttgcgtatt gggcgc                             6756
```

<210> SEQ ID NO 38
<211> LENGTH: 5632
<212> TYPE: DNA
<213> ORGANISM: artificial sequence
<220> FEATURE:
<223> OTHER INFORMATION: plasmid pJY1874.1

<400> SEQUENCE: 38

```
tgcggccgcg tcgacatgca ttgttagttc tgtagatcag taacgtatag catacgagta     60
taattatcgt aggtagtagg tatcctaaaa taaatctgat acagataata actttgtaaa    120
tcaattcagc aatttctcta ttatcatgat aatgattaat acacagcgtg tcgttatttt    180
ttgttacgat agtatttcta aagtaaagag caggaatccc tagtataata gaaataatcc    240
atatgaaaaa tatagtaatg tacatatttc taatgttaac atatttatag gtaaatccag    300
gaagggtaat ttttacatat ctatatacgc ttattacagt tattaaaaat atacttgcaa    360
acatgttaga agtaaaaaag aaagaactaa ttttacaaag tgctttacca aaatgccaat    420
ggaaattact tagtatgtat ataatgtata aaggtatgaa tatcacaaac agcaaatcgg    480
ctattcccaa gttgagaaac ggtataatag atatatttct agataccatt aataacctta    540
taagcttgac gtttcctata atgcctacta agaaaactag aagatacata catactaacg    600
```

```
ccatacgaga gtaactactc atcgtataac tactgttgct aacagtgaca ctgatgttat    660
aactcatctt tgatgtggta taaatgtata ataactatat tacactggta ttttatttca    720
gttatatact atatagtatt aaaaattata tttgtataat tatattatta tattcagtgt    780
agaaagtaaa atactataaa tatgtatctc ttatttataa cttattagta aagtatgtac    840
tattcagtta tattgtttta taaaagctaa atgctactag attgatataa atgaatatgt    900
aataaattag taatgtagta tactaatatt aactcacatt tgactaatta gctataaaaa    960
cccgggttaa ttaattagtc atcaggcagg gcgagaacga gactatctgc tcgttaatta   1020
attagagctt ctttattcta tacttaaaaa gtgaaaataa atacaaaggt tcttgagggt   1080
tgtgttaaat tgaaagcgag aaataatcat aaattatttc attatcgcga tatccgttaa   1140
gtttgtatcg taatgggaca gaccatcacc accccccctgt ctctcaccct ggaccactgg   1200
tctgaggtga gagccagagc ccacaaccag ggcgtggagg tgaggaagaa gaagtggatc   1260
accctgtgtg aggccgagtg ggtgatgatg aacgtgggct ggcctagaga gggcaccttc   1320
tccctggact ccatctccca ggtggagaag aagatcttcg cccctggccc ttacggccac   1380
cccgatcagg tgccctacat caccacctgg agatctctgg ccaccgaccc tcctagctgg   1440
gtgagaccct tcctgccccc tcccaaacct cctacccctc tgcctcagcc tctgtctcct   1500
cagccttctg ccccccctcac ctcttctctg taccccgtgc tgcccaaacc cgaccccccct   1560
aaacctcctg tgctgccccc cgacccctct tctcccctca tcgacctgct caccgaggag   1620
ccccctcctt accctggcgg acacggccct cctccctctg gaccccggac ccctaccgcc   1680
tctcctatcg cctccaggct gagggagaga agggagaacc ccgccgagga atctcaggcc   1740
ctgcctctga gagagggccc caacaacagg ccccagtact ggcctttctc tgcctccgac   1800
ctgtacaact ggaagtccca caacccccca ttctctcagg accccgtggc cctcaccaac   1860
ctcatcgagt ccatcctggt gacccatcag cccacctggg acgactgtca gcaactgctg   1920
caggctctgc tcaccggcga ggagagacag agagtgctgc tggaggccag aaaacaggtg   1980
cccggcgagg atggcagacc tacccagctg cccaacgtga tcgacgagac cttcccactc   2040
accagaccca actgggactt cgccacccct gccggcagag agcacctgag gctgtacaga   2100
cagctgctgc tggccggact gagaggagcc gccaggagac ctaccaacct ggcccaggtg   2160
aagcaggtgg tgcagggcaa agaggaaacc cctgccgcct tcctggagag actgaaggaa   2220
gcctaccgga tgtacacccc ctacgaccct gaggatcctg gacaggccgc ctctgtgatc   2280
ctgtccttca tctaccagtc cagccccgac atcaggaaca agctgcagag actggagggc   2340
ctgcagggct tcaccctgtc cgacctgctg aaggaggccg agaagatcta caacaagcgg   2400
gagacccccg aggagagaga ggaaaggctg tggcagagac aggaggagag ggacaagaag   2460
cggcacaagg agatgaccaa ggtgctggcc accgtggtgg cccagaacag ggacaaggac   2520
agggaggagt ctaagctggg cgaccagagg aaaatccccc tgggcaagga ccagtgcgcc   2580
tactgtaagg agaagggcca ctgggtgaga gattgcccca agaggcccag aaagaagccc   2640
gccaactcca ccctgctcaa cttaggagat taggagagtc agggccagga ccctccacct   2700
gagcccagaa tcaccctgaa gatcggcggc cagcccgtga ccttcctggt ggacaccgga   2760
gcccagcact ctgtgctcac aagacccgac ggcccccctgt ccgatagaac cgccctggtg   2820
cagggagcca ccggctccaa gaactacagg tggaccaccg acagaagggt gcagctggcc   2880
acaggaaagg tgacccactc cttcctgtac gtgcccgagt gtccctaccc tctgctgggc   2940
```

-continued agagatctgc tcaccaagct gaaggcccag atccacttca ccggcgaagg cgccaatgtg 3000
gtgggcccca gaggactgcc cctgcaggtg ctgtaatgat tttcttgac tagttaatca 3060 aataaaaagc atacaagcta ttgcttcgct atcgttacaa aatggcagga attttgtgta 3120
aactaagcca catacttgcc aatgaaaaaa atagtagaaa ggatactatt ttaatgggat 3180
tagatgttaa ggttccttgg gattatagta actgggcatc tgttaacttt tacgacgtta 3240
ggttagatac tgatgttaca gattataata atgttacaat aaaatacatg acaggatgtg 3300
atatttttcc tcatataact cttggaatag caaatatgga tcaatgtgat agatttgaaa 3360
atttcaaaaa gcaaataact gatcaagatt tacagactat ttctatagtc tgtaaagaag 3420
agatgtgttt tcctcagagt aacgcctcta aacagttggg agcgaaagga tgcgctgtag 3480
ttatgaaact ggaggtatct gatgaactta gagccctaag aaatgttctg ctgaatgcgg 3540
taccctgttc gaaggacgtg tttggtgata tcacagtaga taatccgtgg aatcctcaca 3600
taacagtagg atatgttaag gaggacgatg tcgaaaacaa gaaacgccta atggagtgca 3660
tgtccaagtt tagggggcaa gaaatacaag ttctaggatg gtattaataa gtatctaagt 3720
atttggtata atttattaaa tagtataatt ataacaaata ataaataaca tgataacggt 3780
ttttattaga ataaaataga gataatatca taatgatata taatacttca ttaccagaaa 3840
tgagtaatgg aagacttata aatgaactgc ataaagctat aaggtataga gatataaatt 3900
tagtaaggta tatacttaaa aaatgcaaat acaataacgt aaatatacta tcaacgtctt 3960
tgtatttagc cgtaagtatt tctgatatag aaatggtaaa attattacta gaacacggtg 4020
ccgatatttt aaaatgtaaa aatcctcctc ttcataaagc tgctagttta gataatacag 4080
aaattgctaa actactaata gattctggcg ctgacataga acagatacat tctggaaata 4140
gtccgttata tatttctgta tatagaaaca ataagtcatt aactagatat ttattaaaaa 4200
aaggtgttaa ttgtaataga ttctttctaa attattacga tgtactgtat gataagatat 4260
ctgatgatat gtataaaata tttatagatt ttaatattga tcttaatata caaactagaa 4320
attttgaaac tccgttacat tacgctataa agtataagaa tatagattta attaggatat 4380
tgttagataa tagtattaaa atagataaaa gtttattttt gcataaacag tatctcataa 4440
aggcacttaa aaataattgt agttacgata taatagcgtt acttataaat cacggagtgc 4500
ctataaacga acaagatgat ttaggtaaaa ccccattaca tcattcggta attaatagaa 4560
gaaaagatgt aacagcactt ctgttaaatc taggagctga tataaacgta atagatgact 4620
gtatgggcag tcccttacat tacgctgttt cacgtaacga tatcgaaaca acaaagacac 4680
ttttagaaag aggatctaat gttaatgtgg ttaataatca tatagatacc gttctaaata 4740
tagctgttgc atctaaaaac aaaactatag taaacttatt actgaagtac ggtactgata 4800
caaagttggt aggattagat aaacatgtta ttcacatagc tatagaaatg aaagatatta 4860
atatactgaa tgcgatctta ttatatggtt gctatgtaaa cgtctataat cataaaggtt 4920
tcactcctct atacatggca gttagttcta tgaaaacaga atttgttaaa ctcttacttg 4980
accacggtgc ttacgtaaat gctaaagcta agttatctgg aaatactcct ttacataaag 5040
ctatgttatc taatagtttt aataatataa aattactttt atcttataac gccgactata 5100
attctctaaa taatcacggt aatacgcctc taacttgtgt tagcttttta gatgacaaga 5160
tagctattat gataatatct aaaatgatgt tagaaatatc taaaaatcct gaaatagcta 5220
attcagaagg ttttatagta aacatggaac atataaacag taataaaaga ctactatcta 5280
taaaagaatc atgcgaaaaa gaactagatg ttataacaca tataaagtta aattctatat 5340

-continued attcttttaa tatctttctt gacaataaca tagatcttat ggtaaagttc gtaactaatc 5400
ctagagttaa taagatacct gcatgtatac gtatatatag ggaattaata cggaaaaata 5460
aatcattagc ttttcataga catcagctaa tagttaaagc tgtaaaagag agtaagaatc 5520
taggaataat aggtaggtta cctatagata tcaaacatat aataatggaa ctattaagta 5580
ataatgattt acattctgtt atcaccagct gttgtaaccc agtagtataa ag 5632

<210> SEQ ID NO 39
<211> LENGTH: 529
<212> TYPE: DNA
<213> ORGANISM: artificial sequence
<220> FEATURE:
<223> OTHER INFORMATION: FeLV ENV DNA 3' end (double mutations)

<400> SEQUENCE: 39
ccgcgggggt cggaacaggg actaaagccc tccttgaaac agcccagttc agacaactac 60
aaatggccat gcacacagac atccaggccc tagaagaatc aattagtgcc ttagaaaagt 120
ccctgacctc cctttctgaa gtagtcttac aaaacagacg gggcctagat attctattct 180
tacaacgggg agggctctgc gcagcattaa aagaagaatg ttgcttctat gcggatcaca 240
ccggactcgt ccgagacaat atggccaaat taagagaaag actaaaacag cggcaacaac 300
tgtttgactc ccaacaggga tggtttgaag gatggttcaa caagtccccc tggtttacaa 360
ccctaatttc ctccattatg ggcccccttac taatcctact cctaattctc ctcttcggcc 420
catgcatcct taaccgatta gtacagttcg taaaagacag aatatctgtg gtacaggctt 480
taattttaac ccaacagtac caacagataa agcaatacga tccggaccg 529

<210> SEQ ID NO 40
<211> LENGTH: 175
<212> TYPE: PRT
<213> ORGANISM: artificial sequence
<220> FEATURE:
<223> OTHER INFORMATION: FeLV ENV C-terminus (2 mutations)

<400> SEQUENCE: 40

Ala Gly Val Gly Thr Gly Thr Lys Ala Leu Leu Glu Thr Ala Gln Phe
1 5 10 15

Arg Gln Leu Gln Met Ala Met His Thr Asp Ile Gln Ala Leu Glu Glu
20 25 30

Ser Ile Ser Ala Leu Glu Lys Ser Leu Thr Ser Leu Ser Glu Val Val
35 40 45

Leu Gln Asn Arg Arg Gly Leu Asp Ile Leu Phe Leu Gln Arg Gly Gly
50 55 60

Leu Cys Ala Ala Leu Lys Glu Glu Cys Cys Phe Tyr Ala Asp His Thr
65 70 75 80

Gly Leu Val Arg Asp Asn Met Ala Lys Leu Arg Glu Arg Leu Lys Gln
85 90 95

Arg Gln Gln Leu Phe Asp Ser Gln Gln Gly Trp Phe Glu Gly Trp Phe
100 105 110

Asn Lys Ser Pro Trp Phe Thr Thr Leu Ile Ser Ser Ile Met Gly Pro
115 120 125

Leu Leu Ile Leu Leu Leu Ile Leu Leu Phe Gly Pro Cys Ile Leu Asn
130 135 140

Arg Leu Val Gln Phe Val Lys Asp Arg Ile Ser Val Val Gln Ala Leu
145 150 155 160

```
Ile Leu Thr Gln Gln Tyr Gln Gln Ile Lys Gln Tyr Asp Pro Asp
                165                 170                 175
```

<210> SEQ ID NO 41
<211> LENGTH: 529
<212> TYPE: DNA
<213> ORGANISM: artificial sequence
<220> FEATURE:
<223> OTHER INFORMATION: FeLV ENV DNA 3' end (one mutation)

<400> SEQUENCE: 41

```
ccgcgggggt cggaacaggg actaaagccc tccttgaaac agcccagttc agacaactac     60

aaatggccat gcacacagac atccaggccc tagaagagtc aattagtgcc ttagaaaagt    120

ccctgacctc cctttctgaa gtagtcttac aaaacagacg gggcctagat attctattcc    180

tacaacgggg agggctctgc gcagcattaa aagaagaatg ttgcttctat gcggatcaca    240

ccggactcgt ccgagacaat atggctaaat taagagaaag actaaaacag cggcaacaac    300

tgtttgactc ccaacaggga tggtttgaag gatggttcaa caggtccccc tggtttacaa    360

ccctaatttc ctccattatg ggcccttac taatcctact cctaattctc ctcttcggcc    420

catgcatcct taacagatta gtacaattcg taaaagacag aatatctgtg gtacaagcct    480

taattttaac ccaacagtac caacagataa agcaatacga tccggaccg                529
```

<210> SEQ ID NO 42
<211> LENGTH: 175
<212> TYPE: PRT
<213> ORGANISM: artificial sequence
<220> FEATURE:
<223> OTHER INFORMATION: FeLV ENV protein C-terminus (one mutation)

<400> SEQUENCE: 42

```
Ala Gly Val Gly Thr Gly Thr Lys Ala Leu Leu Glu Thr Ala Gln Phe
1               5                   10                  15

Arg Gln Leu Gln Met Ala Met His Thr Asp Ile Gln Ala Leu Glu Glu
            20                  25                  30

Ser Ile Ser Ala Leu Glu Lys Ser Leu Thr Ser Leu Ser Glu Val Val
        35                  40                  45

Leu Gln Asn Arg Arg Gly Leu Asp Ile Leu Phe Leu Gln Arg Gly Gly
    50                  55                  60

Leu Cys Ala Ala Leu Lys Glu Glu Cys Cys Phe Tyr Ala Asp His Thr
65                  70                  75                  80

Gly Leu Val Arg Asp Asn Met Ala Lys Leu Arg Glu Arg Leu Lys Gln
                85                  90                  95

Arg Gln Gln Leu Phe Asp Ser Gln Gln Gly Trp Phe Glu Gly Trp Phe
            100                 105                 110

Asn Arg Ser Pro Trp Phe Thr Thr Leu Ile Ser Ser Ile Met Gly Pro
        115                 120                 125

Leu Leu Ile Leu Leu Leu Ile Leu Leu Phe Gly Pro Cys Ile Leu Asn
    130                 135                 140

Arg Leu Val Gln Phe Val Lys Asp Arg Ile Ser Val Val Gln Ala Leu
145                 150                 155                 160

Ile Leu Thr Gln Gln Tyr Gln Gln Ile Lys Gln Tyr Asp Pro Asp
                165                 170                 175
```

<210> SEQ ID NO 43
<211> LENGTH: 640
<212> TYPE: PRT
<213> ORGANISM: artificial sequence
<220> FEATURE:
<223> OTHER INFORMATION: FeLV ENV full-length protein

<400> SEQUENCE: 43

```
Met Glu Ser Pro Thr His Pro Lys Pro Ser Lys Asp Lys Thr Leu Ser
1               5                   10                  15

Trp Asn Leu Val Phe Leu Val Gly Ile Leu Phe Thr Ile Asp Ile Gly
            20                  25                  30

Met Ala Asn Pro Ser Pro His Gln Ile Tyr Asn Val Thr Trp Val Ile
        35                  40                  45

Thr Asn Val Gln Thr Asn Thr Gln Ala Asn Ala Thr Ser Met Leu Gly
    50                  55                  60

Thr Leu Thr Asp Val Tyr Pro Thr Leu His Val Asp Leu Cys Asp Leu
65                  70                  75                  80

Val Gly Asp Thr Trp Glu Pro Ile Val Leu Ser Pro Thr Asn Val Lys
                85                  90                  95

His Gly Ala Arg Tyr Pro Ser Ser Lys Tyr Gly Cys Lys Thr Thr Asp
            100                 105                 110

Arg Lys Lys Gln Gln Gln Thr Tyr Pro Phe Tyr Val Cys Pro Gly His
        115                 120                 125

Ala Pro Ser Leu Gly Pro Lys Gly Thr His Cys Gly Gly Ala Gln Asp
    130                 135                 140

Gly Phe Cys Ala Ala Trp Gly Cys Glu Thr Thr Gly Glu Ala Trp Trp
145                 150                 155                 160

Lys Pro Ser Ser Ser Trp Asp Tyr Ile Thr Val Lys Arg Gly Ser Ser
                165                 170                 175

Gln Asp Asn Asn Cys Glu Gly Lys Cys Asn Pro Leu Ile Leu Gln Phe
            180                 185                 190

Thr Gln Lys Gly Lys Gln Ala Ser Trp Asp Gly Pro Lys Met Trp Gly
        195                 200                 205

Leu Arg Leu Tyr Arg Thr Gly Tyr Asp Pro Ile Ala Leu Phe Thr Val
    210                 215                 220

Ser Arg Gln Val Ser Thr Ile Thr Pro Pro Gln Ala Met Gly Pro Asn
225                 230                 235                 240

Leu Val Leu Pro Asp Gln Lys Pro Pro Ser Arg Gln Ser Gln Thr Gly
                245                 250                 255

Ser Lys Val Ala Thr Gln Arg Pro Gln Thr Asn Glu Ser Ala Pro Arg
            260                 265                 270

Ser Val Ala Pro Thr Thr Val Gly Pro Lys Arg Ile Gly Thr Gly Asp
        275                 280                 285

Arg Leu Ile Asn Leu Val Gln Gly Thr Tyr Leu Ala Leu Asn Ala Thr
    290                 295                 300

Asp Pro Asn Lys Thr Lys Asp Cys Trp Leu Cys Leu Val Ser Arg Pro
305                 310                 315                 320

Pro Tyr Tyr Glu Gly Ile Ala Ile Leu Gly Asn Tyr Ser Asn Gln Thr
                325                 330                 335

Asn Pro Pro Pro Ser Cys Leu Ser Ile Pro Gln His Lys Leu Thr Ile
            340                 345                 350

Ser Glu Val Ser Gly Gln Gly Leu Cys Ile Gly Thr Val Pro Lys Thr
        355                 360                 365

His Gln Ala Leu Cys Asn Lys Thr Gln Gln Gly His Thr Gly Ala His
    370                 375                 380

Tyr Leu Ala Ala Pro Asn Gly Thr Tyr Trp Ala Cys Asn Thr Gly Leu
385                 390                 395                 400
```

-continued

```
Thr Pro Cys Ile Ser Met Ala Val Leu Asn Trp Thr Ser Asp Phe Cys
                405                 410                 415

Val Leu Ile Glu Leu Trp Pro Arg Val Thr Tyr His Gln Pro Glu Tyr
            420                 425                 430

Val Tyr Thr His Phe Ala Lys Ala Val Arg Phe Arg Arg Glu Pro Ile
        435                 440                 445

Ser Leu Thr Val Ala Leu Met Leu Gly Gly Leu Thr Val Gly Gly Ile
    450                 455                 460

Ala Ala Gly Val Gly Thr Gly Thr Lys Ala Leu Leu Glu Thr Ala Gln
465                 470                 475                 480

Phe Arg Gln Leu Gln Met Ala Met His Thr Asp Ile Gln Ala Leu Glu
                485                 490                 495

Glu Ser Ile Ser Ala Leu Glu Lys Ser Leu Thr Ser Leu Ser Glu Val
            500                 505                 510

Val Leu Gln Asn Arg Arg Gly Leu Asp Ile Leu Phe Leu Gln Arg Gly
        515                 520                 525

Gly Leu Cys Ala Ala Leu Lys Glu Glu Cys Cys Phe Tyr Ala Asp His
    530                 535                 540

Thr Gly Leu Val Arg Asp Asn Met Ala Lys Leu Arg Glu Arg Leu Lys
545                 550                 555                 560

Gln Arg Gln Gln Leu Phe Asp Ser Gln Gln Gly Trp Phe Glu Gly Trp
                565                 570                 575

Phe Asn Arg Ser Pro Trp Phe Thr Thr Leu Ile Ser Ser Ile Met Gly
            580                 585                 590

Pro Leu Leu Ile Leu Leu Leu Ile Leu Leu Phe Gly Pro Cys Ile Leu
        595                 600                 605

Asn Arg Leu Val Gln Phe Val Lys Asp Arg Ile Ser Val Val Gln Ala
    610                 615                 620

Leu Ile Leu Thr Gln Gln Tyr Gln Gln Ile Lys Gln Tyr Asp Pro Asp
625                 630                 635                 640
```